US011927591B2

(12) United States Patent
Wellstein

(10) Patent No.: US 11,927,591 B2
(45) Date of Patent: Mar. 12, 2024

(54) METHODS OF IDENTIFYING NOVEL PROTEINS AND ANTIGENS IN CANCER CELLS

(71) Applicant: Georgetown University, Washington, DC (US)

(72) Inventor: Anton Wellstein, Washington, DC (US)

(73) Assignee: Georgetown University, Washington, DC (US)

( * ) Notice: Subject to any disclaimer, the term of this patent is extended or adjusted under 35 U.S.C. 154(b) by 245 days.

(21) Appl. No.: 16/322,824

(22) PCT Filed: Aug. 2, 2017

(86) PCT No.: PCT/US2017/045057
§ 371 (c)(1),
(2) Date: Feb. 1, 2019

(87) PCT Pub. No.: WO2018/026896
PCT Pub. Date: Feb. 8, 2018

(65) Prior Publication Data
US 2019/0204327 A1 Jul. 4, 2019

Related U.S. Application Data

(60) Provisional application No. 62/370,020, filed on Aug. 2, 2016.

(51) Int. Cl.
*G01N 33/574* (2006.01)
*C12Q 1/68* (2018.01)
*C12Q 1/6886* (2018.01)
*G01N 33/68* (2006.01)

(52) U.S. Cl.
CPC ......... *G01N 33/57492* (2013.01); *C12Q 1/68* (2013.01); *C12Q 1/6886* (2013.01); *G01N 33/57484* (2013.01); *G01N 33/6848* (2013.01)

(58) Field of Classification Search
CPC ........ C12Q 1/68; C12Q 1/6886; G01N 33/53; G01N 33/6848; G01N 33/57492
See application file for complete search history.

(56) References Cited

U.S. PATENT DOCUMENTS

| 7,883,896 | B2 | 2/2011 | Coy et al. | |
|---|---|---|---|---|
| 2016/0069895 | A1 | 3/2016 | Delamarre et al. | |
| 2017/0199961 | A1* | 7/2017 | Yelensky | A61P 35/02 |
| 2018/0172689 | A1* | 6/2018 | Liao | C07K 14/705 |
| 2019/0292600 | A1* | 9/2019 | Spira | C12Q 1/6886 |

FOREIGN PATENT DOCUMENTS

| EP | 1 426 422 A1 | 6/2004 | |
|---|---|---|---|
| WO | WO 2004/047863 A2 | 6/2004 | |
| WO | WO-2015179404 A1 * | 11/2015 | ........... C12Q 1/6886 |

OTHER PUBLICATIONS

Menon et al, Cancer Res. 70 (9), 3440-3449 (2012).*
Cabellero et al.,"Alternative spliced transcripts as cancer markers" Disease Markers 17(2) :67-75 (2001) . . . (Year: 2001).*
Cho et al., High-Resolution Transcriptome Analysis with Long-Read RNA Sequencing. PLOS One 9(9) : e108095 (Year: 2014).*
Domon et al., Mass Spectrometry and Protein Analysis. Science 312:212 (Year: 2006).*
Fackenthal et al., Aberrant RNA splicing and its functional consequences in cancer cells. Disease Models & Mechanisms 1 :37-42 (Year: 2008).*
Hartung et al., RNA blood levels of osteopontin splice variants are cancer markers. SpringerPlus 2:110 (Year: 2013).*
Hofmann et al., Cancer Rersearch 51 : 5292-5297 (Year: 1991).*
Klinck et al., Multiple Alternative Splicing Markers for Ovarian Cancer. Cancer Rersearch 68(3) : 657: 5292-5297 (Year: 2008).*
Levin et al., Targeted next-generation sequencing of a cancer transcriptome enhances detection of sequence variants and novel fusion transcripts. Genome Biology 10R115 (Year: 2009).*
Lu et al., Cancer Research 56:4578 (Year: 1996).*
Ozsolak et al., RNA sequencing: advances, challenges and opportunities. Nature Reviews|Genetics 12 :87 (Year: 2011).*
Pampalakis et al., Novel splice variants of prostate-specific antigen and applications in diagnosis of prostate cancer. Chemical Biochemistry 41 :591-597 (Year: 2008).*
Pretto et al., Differential increases of specific FMR1 mRNA isoforms in premutation carriers. J. Medical Gentics 52: 42-52 (Year: 2015).*
Ramskold et al., Full-length mRNA-Seq from single-cell levels of RNA and individual circulating tumor cells. Nature Biotechnology 30(8) : 777 (Year: 2012).*
Shendrue et al., Next-generation DNA Sequencing. Nature Biotechnology 26(10) : 1135 (Year: 2008).*
Stephens et al., Analysis of mRNA Partitioning Between the Cytosol and Endoplasmic Reticulum Compartments of Mammalian Cells. Methods in Molecular Biology 419, Ch. 14 in Post Transcriptional Gene RegulationEdited by Wilusz Humana Press Totowa, NJ (20.*
Brinkman, B.M.N., Review : Splice variants as cancer biomarkers. Clinical Biochemistry 37:584-594 (Year: 2004).*
Hatakeyama et al., Identification of a novel protein isoform derived from cancer-related splicing variants using combined analysis of transcriptome and proteome. Proteomics 11: 2275-2282 (Year: 2011).*

(Continued)

*Primary Examiner* — Ethan C Whisenant
(74) *Attorney, Agent, or Firm* — Grimes & Yvon LLP

(57) ABSTRACT

The present invention provides methods of identifying neopeptides in abnormal cells, with the methods comprising sequencing long-read messenger RNA (mRNA) isolated from the abnormal cells, identifying splice variants that could be generated from the sequenced long-read mRNA, determining if the abnormal cells contain neopeptides that correlate with the identified splice variants. The methods may also comprise identifying at least one neoantigen on the neopeptides that are present in the abnormal cells.

10 Claims, 35 Drawing Sheets
Specification includes a Sequence Listing.

(56) References Cited

OTHER PUBLICATIONS

Rapin et al., Comparing cancer vs normal gene expression profiles identifies new disease entities and common transcriptional programs in AML patients. Blood 123(6) : 894-904 (Year: 2014).*
Li et al., Cancer Research 66(4) :1990 (Year: 2006).*
Wang et al. Molecular & Cellular Proteomics 7: 1639 (Year: 2008).*
Grimes et al. Zebrafish models of idiopathic scoliosis link cerebrospinal fluid flow defects to spine curvature. Science 352:1341 (Year: 2016).*
Joyce et al. T cell exclusion, immune privilege, and the tumor microenvironment. Science 348 :74 (Year: 2015).*
Mashamaite et al., Microbial diversity in Antarctic Dry Valley soils across an altitudinal gradient. Frontiers in Microbiology 14: 1203216 (Year: 2023).*
Schumacher et al. Neoantigens in cancer imunotherapy. Science 348:69 (Year: 2015).*
Stronen et al. Targeting of cancer neoantigens with donor-derived T cell receptor repertoires. Science 352:1337 (Year: 2016).*
Tilgner et al.,Accurate identification and analysis of human mRNA isoforms using deep long read sequencing. Genes |Genomes|Genetics 3:387 (Year: 2013).*
Juan Diez et al., "Differential Splicing of the IA-2 mRNA in Pancreas and Lymphoid Organs as a Permissive Genetic Mechanism for Autoimmunity against the IA-2 Type 1 Diabetes Autoantigen," Diabetes, Apr. 1, 2001 (Apr. 1, 2001), pp. 895-900, XP055674499, United States.
Shangxi Xiao et al., "Low molecular weight species of TDP-43 generated by abnormal splicing form inclusions in amyotrophic lateral sclerosis and result in motor neuron death," Acta Neuropathologica, vol. 130, No. 1, Mar. 19, 2015 (Mar. 19, 2015), pp. 49-61, XP055674494, Berlin, Germany.
Extended European Search Report and Search Opinion dated Mar. 16, 2020 in corresponding European Application No. 17837591.1.
Routh et al., ClickSeq: Fragmentation-free next generation sequencing via click-ligation of adaptors to stochastically terminated 3'-azido cDNAs. J Mol Biol, Aug. 14, 2015, vol. 427, No. 16, pp. 2610-2616.
International Search Report and Written Opinion dated Oct. 31, 2017 in corresponding International Application No. PCT/US2017/045057.

* cited by examiner

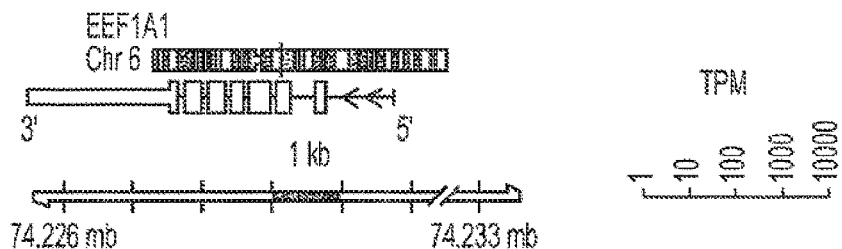
FIG. 2A
FIG. 2B
FIG. 2D
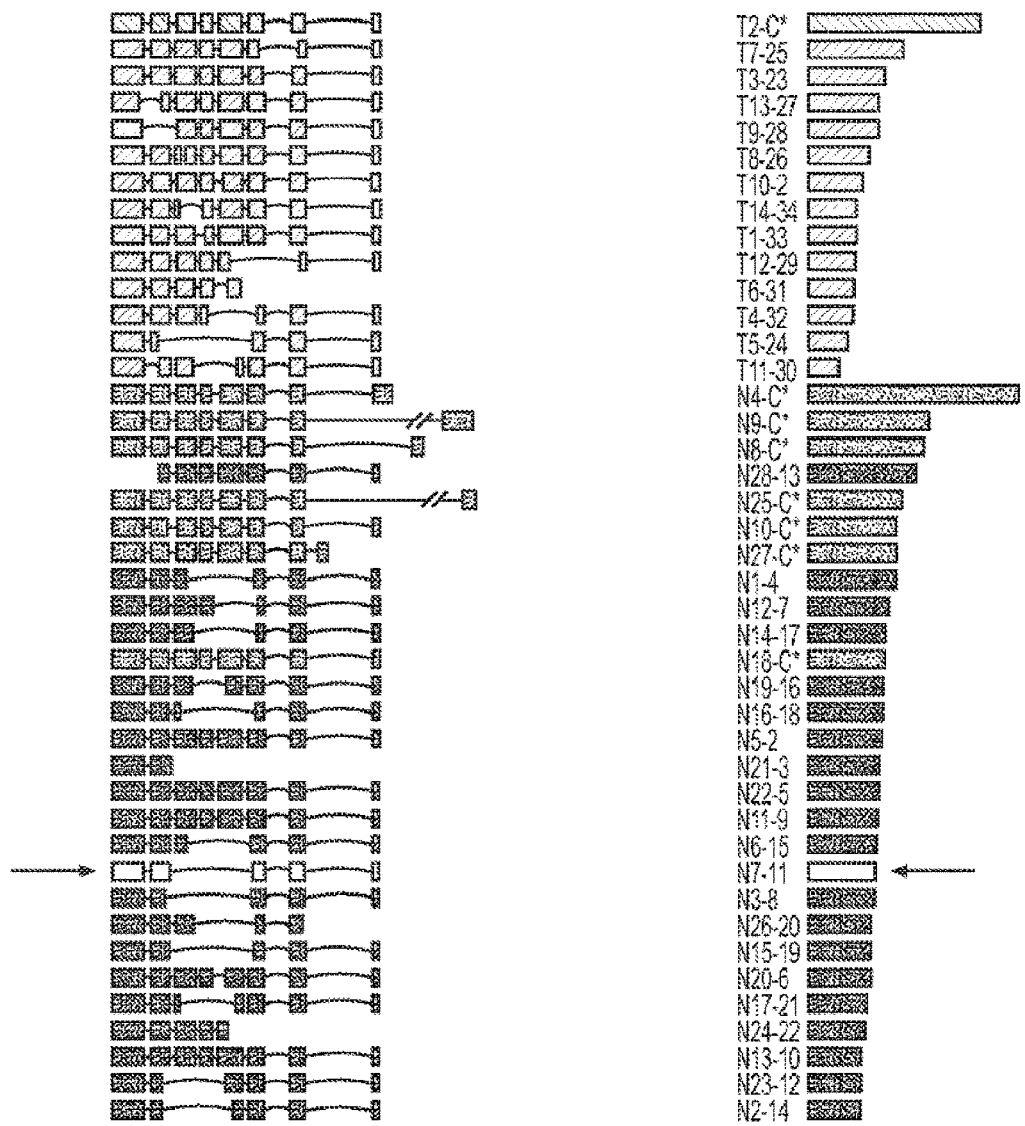
FIG. 2C
FIG. 2E

LEGEND FOR FIG. 3

RED (D,E) = ITALICS

YELLOW (G) = BOLD

BLUE (K,R) = SINGLE UNDERLINE

LIGHT BLUE (S,T) = REGULAR

TEAL (A,F,Y) = BOLD ITALICS

GREEN (M,L,V,I) = DOUBLE UNDERLINE

PURPLE (H) = BOLD UNDERLINE

LAVENDAR (Q,N) = DOTTED UNDERLINE

LIGHT GREEN (W) = SINGLE SQUIGGLE UNDERLINE

BURGANDY (C) = DOUBLE SQUIGGLE UNDERLINE

GRAY (P) = BOLD ITALICS UNDERLINE

```
                    0         10        20        30        40        50
                    ....|....|....|....|....|....|....|....|....|....|....|
        T14-34      MGKEKTHINIVVIGHVDSGKSTTTGHLIYKCGGIDKRTIEKFEKEAAEMG
        T1-33       MGKEKTHINIVVIGHVDSGKSTTTGHLIYKCGGIDKRTIEKFEKEAAEMG
        T4-32       MGKEKTHINIVVIGHVDSGKSTTTGHLIYKCGGIDKRTIEKFEKEAAEMG                TO
        T6-31       ~~~~~~~~~~~~~~~~~~~~~~~~~~~~~~~~~~~~~~~~~~~~~~~~~                FIG. 3A
        T11-30      MGKEKTHINIVVIGHVDSGKSTTTGHLIYKCGGIDKRTIEKFEKEAAEMG                (CONT. 1)
        T12-29      MGK-----------------------------------------------                ───►
        T9-28       MGKEKTHINIVVIGHVDSGKSTTTGHLIYKCGGIDKRTIEKFEKEAAEMG
        T13-27      MGKEKTHINIVVIGHVDSGKSTTTGHLIYKCGGIDKRTIEKFEKEAAEMG
        T8-26       MGKEKTHINIVVIGHVDSGKSTTTGHLIYKCGGIDKRTIEKFEKEAAEMG
        T7-25       MGKEKTH-------------------------------------------
        T5-24       MGKEKTHINIVVIGHVDSGKSTTTGHLIYKCGGIDKRTIEKFEKEAAEMG
        T3-23       MGKEKTHINIVVIGHVDSGKSTTTGHLIYKCGGIDK---------------
        T10-2       MGKEKTHINIVVIGHVDSGKSTTTGHLIYKCGGIDKRTIEKFEKEAAEMG
        ST2-C*      MGKEKTHINIVVIGHVDSGKSTTTGHLIYKCGGIDKRTIEKFEKEAAEMG
        T2-C*       MGKEKTHINIVVIGHVDSGKSTTTGHLIYKCGGIDKRTIEKFEKEAAEMG
        P68104      MGKEKTHINIVVIGHVDSGKSTTTGHLIYKCGGIDKRTIEKFEKEAAEMG
        GTP-EFTU    ~~~~~~~~~~~GHVDSGKSTTTGHLIYKCGGIDKRTIEKFEKEAAEMG
        GTP-EFTU-D2 ~~~~~~~~~~~~~~~~~~~~~~~~~~~~~~~~~~~~~~~~~~~~~~~~~
        GTP-EFTU-D3 ~~~~~~~~~~~~~~~~~~~~~~~~~~~~~~~~~~~~~~~~~~~~~~~~~
        N4-C*       MGKEKTHINIVVIGHVDSGKSTTTGHLIYKCGGIDKRTIEKFEKEAAEMG
        N8-C*       MGKEKTHINIVVIGHVDSGKSTTTGHLIYKCGGIDKRTIEKFEKEAAEMG
        N9-C*       MGKEKTHINIVVIGHVDSGKSTTTGHLIYKCGGIDKRTIEKFEKEAAEMG
        N10-C*      MGKEKTHINIVVIGHVDSGKSTTTGHLIYKCGGIDKRTIEKFEKEAAEMG
        N18-C*      MGKEKTHINIVVIGHVDSGKSTTTGHLIYKCGGIDKRTIEKFEKEAAEMG
        N25-C*      MGKEKTHINIVVIGHVDSGKSTTTGHLIYKCGGIDKRTIEKFEKEAAEMG
        N27-C*      MGKEKTHINIVVIGHVDSGKSTTTGHLIYKCGGIDKRTIEKFEKEAAEMG
        N5-2        MGKEKTHINIVVIGHVDSGKSTTTGHLIYKCGGIDKRTIEKFEKEAAEMG
        SN2-3       ~~~~~~~~~~~~~~~~~~~~~~~~~~~~~~~~~~~~~~~~~~~~~~~~~
        N21-3       ~~~~~~~~~~~~~~~~~~~~~~~~~~~~~~~~~~~~~~~~~~~~~~~~~
        N1-4        MGKEKTHINIVVIGHVDSGKSTTTGHLIYKCGGIDKRTIEKFEKEAAEMG
        N22-5       MGKEKTHINIVVIGHVDSGKSTTTGHLIYKCGGIDKRTIEKFEKEAAEMG
        N20-6       MGKEKTHINIVVIGHVDSGKSTTTGHLIYKCGGIDKRTIEKFEKEAAEMG
        N12-7       MGKEKTHINIVVIGHVDSGKSTTTGHLIYKCGGIDKRTIEKFEKE-----
        N3-8        MGKEKTHINIVVIGHVDSGKSTTTGHLIYKCGGIDKRTIEKFEKEAAEMG
        N11-9       MGKEKTHINIVVIGHVDSGKSTTTGHLIYKCGGIDKRTIEKFEKEAAEMG
        N13-10      MGKEKTHINIVVIGHVDSGKSTTTGHLIYKCGGIDKRTIEKFEKEAAEMG
        N7-11       MGKEKTHINIVVIGHVDSGKSTTTGHLIYKCGGIDKRTIEKFEKEAAEMG                TO
        N23-12      MGKEKTHINIVVIGHVDSGKSTTTGHLIYKCGGIDKRTIEKFEKEAAEMG                FIG. 3A
        N28-13      MGKEKTHINIVVIGHVDSGKSTTTGHLIYKCGGIDKRTIEKFEKEAAEMG                (CONT. 1)
        N2-14       MGKEKTHINIVVIGHVDSGKSTTTGHLIYKCGGIDKRTIEKFEKEAAEMG                ───►
        N6-15       MGKGKDSYQHCRHWTRRFGQVHHYWPSDL*~~~~~~~~~~~~~~~~~~~~
        N19-16      MGKEKTHINIVVIGHVDSGKSTTTGHLIYKCGGIDKRTIEKFEKEAAEMG
        N14-17      MGKEKTHINIVVIGHVDSGKSTTTGHLIYKCGGIDKRTIEKFEKEAAEMG
        N16-18      MGKEKTHINIVVIGHVDSGKSTTTGHLIYKCGGIDKRTIEKFEKEAAEMG
        N15-19      MGKEKTHINIVVIGHVDSGKSTTTGHLIYKCGGIDKRTIEKFEKEAAEMG
        N26-20      ~~~~~~~~~~~~~~~~~~~~~~~~~~~~~~~~~~~~~~~~~~~~~~~MG
        N17-21      ~~~~~~~~~~~~~~~~~~~~~~~~~~~~~~~~~~~~~~~~~~~~~~~~~
        N24-22      ~~~~~~~~~~~~~~~~~~~~~~~~~~~~~~~~~~~~~~~~~~~~~~~~~
```

*FIG. 3A*

```
                   60        70        80        90       100
           ....|....|....|....|....|....|....|....|....|....|....|
           KGSFKYAWVLDKLKAERERGITIDISLWKFETSKYYVTIIDAPGHRDFIK
           KGSFKYAWVLDKLKAERERGITIDISLWKFETSKYYVTIIDAPGHRDFIK
           KGSFKYAWVLDKL-------------------------------------
           ~~~~~~~~~~~~~~~~~~~~~~~~~~~~~~~~~~~~~~~~~~~~~~~~~
           KGSFKYAWVLDKLKAERERGITIDISLWKFETSKYYVTIIDAPGHRDFIK
           --------------------------------------------------
           KGSFKYAWVLDKLKAERERGITIDISLWKFETSKYYVTIIDAPGHRDFIK
           KGSFKYAWVLDKLKAERERGITIDISLWKFETSKYYVTIIDAPGHRDFIK
           KGSFKYAWVLDKLKAERERGITIDISLWKFETSKYYVTIIDAPGHRDFIK
           -----------------ITIDISLWKFETSKYYVTIIDAPGHRDFIK
           KGSFKYAWVLDKLKAERERGITIDISLWKFETSKYYVTIID---------
           -----SSLAWIN*~~~~~~~~~~~~~~~~~~~~~~~~~~~~~~~~~~~~
           KGSFKYAWSWIN*~~~~~~~~~~~~~~~~~~~~~~~~~~~~~~~~~~~~
           KGSFKYAWVLDKLKAERERGITIDISLWKFETSKYYVTIIDAPGHRDFIK
           KGSFKYAWVLDKLKAERERGITIDISLWKFETSKYYVTIIDAPGHRDFIK
           KGSFKYAWVLDKLKAERERGITIDISLWKFETSKYYVTIIDAPGHRDFIK
           KGSFKYAWVLDKLKAERERGITIDISLWKFETSKYYVTIIDAPGHRDFIK
           ~~~~~~~~~~~~~~~~~~~~~~~~~~~~~~~~~~~~~~~~~~~~~~~~~

KGSFKYAWVLDKLKAERERGITIDISLWKFETSKYYVTIIDAPGHRDFIK
           KGSFKYAWVLDKLKAERERGITIDISLWKFETSKYYVTIIDAPGHRDFIK
           KGSFKYAWVLDKLKAERERGITIDISLWKFETSKYYVTIIDAPGHRDFIK
           KGSFKYAWVLDKLKAERERGITIDISLWKFETSKYYVTIIDAPGHRDFIK
           KGSFKYAWVLDKLKAERERGITIDISLWKFETSKYYVTIIDAPGHRDFIK
           KGSFKYAWVLDKLKAERERGITIDISLWKFETSKYYVTIIDAPGHRDFIK
           KGSFKYAWVLDKLKAERERGITIDISLWKFETSKYYVTIIDAPGHRDFIK
           KGSFKYAWVWIN*
           ~~~~~~~~~~~~~~~~~~~~~~~~~~~~~~~~~~~~~~~~~~~~~~~~~
           ~~~~~~~~~~~~~~~~~~~~~~~~~~~~~~~~~~~~~~~~~~~~~~~~~
           KGSFKYAWVLDKLKAECVNVVRSINQLINLLSVVGNFE*
           KGSFKYAWVLDKLKAERERGITIDISLWKFETSKYYVTIIDAPGHRDFIK
           KGSFKYAWVLDKLKAERERGITIDISLWKFETSKYYVTIIDAPGHRDFIK

KGSFKYSWVLDKLKAERERGITIDISLWKFETSKYYVTIIDAPG------
           KGSFKYAWVLDKLKAERERGITIDISLWKFETSKYYVTIIDAPGHRDFIK
           KGSFKYAWVLDKLKAERERGITIDISLWKFETSKYYVT----------IK
           KGSFKYAWVLDKLKAERERGITIDISLWKFETSKYY--------------
           KGSFKYAWVLDKLKAERERGITIDISLWKFETSKYYVTIIDAPGHRDFIK
           KGSFKYAWVLDKLKAERERGITIDISLWKFETSKYYVTIIDAPGHRDFIK
           KGSFKYAWVLDKLKAERERGITIDISLWKFETSKYYVTIIDAPGHRDFIK
           ~~~~~~~~~~~~~~~~~~~~~~~~~~~~~~~~~~~~~~~~~~~~~~~~~
           KGSFKYAWVLDKLKAERERGITIDISLWKFETSKYYVTIIDAQDTETLSK
           KGSFKYAWVLDKLK------------------------------------
           KGSFKYAWVLDKLKAERERGITIDISLWKQLASLLR*
           KGSFKYAWVLDKLKAERERGITIDISLWKFETK*
           KGSFKYAWVLDKLKAERER-------------------------------
           ~~~~~~~~~~~~~~~~~~~~~~~~~~~~~~~~~~~~~~~~~~~~~~~~~
           ~~~~~~~~~~~~~~~~~~~~~~~~~~~~~~~~~~~~~~~~~~~~~~~~~
                                    [TYR] 86 ──→ YY
```

*FIG. 3A*
*(CONT. 1)*

```
                        110       120       130       140       150
                ....|....|....|....|....|....|....|....|....|....|
                NMITGTSQADCAVLIVAAGVGEFEAGISKNGQTREHALLAYTLGVKQLIV
                NMITGTSQADCAVLIVAAGVGEFEAGISKNGQTREHALLAYTLGVKQLIV
                ─────────────────────────────────────────────────
                ~~~~~~~~~~~~~~~~~~~~~~~~~~~~~~~~~~~~~~~~~~~~~~~~~
                NMITGTSQADCAVLIVAAGV──────────────────────────────
                ─────────────────────────────────────────────────
                NMITGTSQADCAVLIVAAGVGEFEAGISKNGQTREHALLAYTLGVKQLIV
                NMITGTSQADCAVLIVAAGVGEFEAGISKNGQTREHALLAYTLGVKQLIV
                NMITGTSQADCAVLIVAAGVGEFEAGISKNGQTREHALLAYTLGVKQLIV
                NMITGTSQADCAVLIVAAGVGEFEAGISKNGQTREHALLAYTLGVKQLIV
                ─────────────────────────────────────────────────
                ~~~~~~~~~~~~~~~~~~~~~~~~~~~~~~~~~~~~~~~~~~~~~~~~~
                ~~~~~~~~~~~~~~~~~~~~~~~~~~~~~~~~~~~~~~~~~~~~~~~~~
                NMITGTSQADCAVLIVAAGVGEFEAGISKNGQTREHALLAYTLGVKQLIV
                NMITGTSQADCAVLIVAAGVGEFEAGISKNGQTREHALLAYTLGVKQLIV
                NMITGTSQADCAVLIVAAGVGEFEAGISKNGQTREHALLAYTLGVKQLIV
                NMITGTSQADCAVLIVAAGVGEFEAGISKNGQTREHALLAYTLGVKQLIV
                ~~~~~~~~~~~~~~~~~~~~~~~~~~~~~~~~~~~~~~~~~~~~~~~~~
                NMITGTSQADCAVLIVAAGVGEFEAGISKNGQTREHALLAYTLGVKQLIV
                NMITGTSQADCAVLIVAAGVGEFEAGISKNGQTREHALLAYTLGVKQLIV
                NMITGTSQADCAVLIVAAGVGEFEAGISKNGQTREHALLAYTLGVKQLIV
                NMITGTSQADCAVLIVAAGVGEFEAGISKNGQTREHALLAYTLGVKQLIV
                NMITGTSQADCAVLIVAAGVGEFEAGISKNGQTREHALLAYTLGVKQLIV
                NMITGTSQADCAVLIVAAGVGEFEAGISKNGQTREHALLAYTLGVKQLIV
                NMITGTSQADCAVLIVAAGVGEFEAGISKNGQTREHALLAYTLGVKQLIV
                ~~~~~~~~~~~~~~~~~~~~~~~~~~~~~~~~~~~~~~~~~~~~~~~~~
                ~~~~~~~~~~~~~~~~~~~~~~~~~~~~~~~~~~~~~~~~~~~~~~~~~
                ~~~~~~~~~~~~~~~~~~~~~~~~~~~~~~~~~~~~~~~~~~~~~~~~~
                NMITGTSQADCAVLIVAAGVGEFEAGISKNGQTREHALLAYTLGVKQLIV
                NMITGTSQADCAVLIVAAGVGEFEAGISKNGQTREHALLAYTLGVKQLIV
                ─────────────────────────────────────LL───────────
                ─────────────────────────────────────────────────
                NMITGTSQADCAVLIVAAGVGEFEAGISKNGQTREHALLAYTLGVKQLIV
                NMITGTSQADCAVLIVAAGVGEFEAGISKNGQTREHALLAYTLGVKQLIV
                NMITGTSQADCAVLIVAAGVGEFEAGISKNGQTREHALLAYTLGVKQLIV
                NMITGTSQADCAVLIVAAGVGEFEAGISKNGQTREHALLAYTLGVKQLIV
                NMITGTSQADCAVLIVAAGVGEFEAGISKNGQTREHALNS*~~~~~~~~~
                ~~~~~~~~~~~~~~~~~~~~~~~~~~~~~~~~~~~~~~~~~~~~~~~~~
                HDYRDISG~~~~~~~~~~~~~~~~~~~~~~~~~~~~~~~~~~~~~~~~~
                ─────────────────────────────────────────────────
                ~~~~~~~~~~~~~~~~~~~~~~~~~~~~~~~~~~~~~~~~~~~~~~~~~
                ~~~~~~~~~~~~~~~~~~~~~~~~~~~~~~~~~~~~~~~~~~~~~~~~~
                ─────────────────────────────────────────────────
                ~MITGTSQADCAVLIVAAGVGEF──────────────────────────
                ~~~~~~~~~~~~~~~~~~~~~~~~~~~~~~~~~~~~~~~~~~~~~~~~~
```

*FIG. 3A*
*(CONT. 2)*

```
                    160        170        180        190        200
          ....|....|....|....|....|....|....|....|....|....|
          GVNKMDSTEPPYSQKRYEEIVKEVSTYIKKIGYNPDTVAFVPISGWNGDK
          GVNKMDSTEPPYSQKRYEEIVKEVSTYIKKIGYNPDTVAFVPISGWNGDN
          ~~~~MDSTEPPYSQKRYE-------------------------------
          ------------------------------------------------
          --------------------EIVKEVSTYIKKIGYNPDTVAFVPISGWNGDN
          GVNKMDSTEPPYSQKRYEEIVKEVSTYIKKIGYNPDTVAFVPISGWNGDN
          GVNKMDSTEPPYSQKRYEEIVKEVSTYIKKIGYNPDTVAFVPISGWNGDN
          GVNKMDSTEPPYSQKRYEEIVKEVSTYIKKIGYNPDTVAFVPISGWNGDN
          GVNKMDSTEPPYSQKRYEEIVKEVSTYIKKIGYNPDTVAFVPISGWNGDN
          ------------------------------------------------
          ~~~~~~~~~~~~~~~~~~~~~~~~~~~~~~~~~~~~~~~~~~~~~~~~
          ~~~~~~~~~~~~~~~~~~~~~~~~~~~~~~~~~~~~~~~~~~~~~~~~
          GVNKMDSTEPPYSQKRYEEIVKEVSTYIKKIGYNPDTVAFVPISGWNGDN
          GVNKMDSTEPPYSQKRYEEIVKEVSTYIKKIGYNPDTVAFVPISGWNGDN
          GVNKMDSTEPPYSQKRYEEIVKEVSTYIKKIGYNPDTVAFVPISGWNGDN
          GVNKMDSTEPPYSQKRYEEIVKEVSTYIKKIGYNPDTVAFVPISGWNGDN
          ~~~~~~~~~~~~~~~~~~~~~~~~~~~~~~~~~~~~~~~~~~~~~~~~
          ~~~~~~~~~~~~~~~~~~~~~~~~~~~~~~~~~~~~~~~~~~~~~~~~
          GVNKMDSTEPPYSQKRYEEIVKEVSTYIKKIGYNPDTVAFVPISGWNGDN
          GVNKMDSTEPPYSQKRYEEIVKEVSTYIKKIGYNPDTVAFVPISGWNGDN
          GVNKMDSTEPPYSQKRYEEIVKEVSTYIKKIGYNPDTVAFVPISGWNGDN
          GVNKMDSTEPPYSQKRYEEIVKEVSTYIKKIGYNPDTVAFVPISGWNGDN
          GVNKMDSTEPPYSQKRYEEIVKEVSTYIKKIGYNPDTVAFVPISGWNGDN
          GVNKMDSTEPPYSQKRYEEIVKEVSTYIKKIGYNPDTVAFVPISGWNGDN
          GVNKMDSTEPPYSQKRYEEIVKEVSTYIKKIGYNPDTVAFVPISGWNGDN
          ~~~~~~~~~~~~~~~~~~~~~~~~~~~~~~~~~~~~~~~~~~~~~~~~
          ~~~~~~~~~~~~~~~~~~~~~~~~~~~~~~~~~~~~~~~~~~~~~~~~
          ~~~~~~~~~~~~~~~~~~~~~~~~~~~~~~~~~~~~~~~~~~~~~~~~
          GVNKMDSTEPPYSQKRYEEIVKEVSTYIKKIGYNPDTVAFVPISGWNGDN
          GVNKMDSTEPPYSQKRYEEIVK---------------------------
          ----------RWE---------------------RA--PSS--------
          GVNKMDSTEPPYSQKRYEEIVKEVSTYIKKIGYNPDTVAFVPISGWNGDN
          GVNKMDSTEPPYSQKRYEEIVKEVSTYIKKIGYNPDTVAFVPISGWNGDN
          GVNKMDSTEPPYSQKRYEEIVKEKIDRRSGKKLEDGPKFLKSGDAAIVDM
          GVNKMDSTEPPYSQKRYEEIVKEVSTYIKKIGYNPDTVAFVPISGWNGDN
          ~~~~~~~~~~~~~~~~~~~~~~~~~~~~~~~~~~~~~~~~~~~~~~~~
          ------------------------------------------------
          ------------------------------------------------
          ------------------------------------------------
          ------------------------------------------------
          ~~~~~~~~~~~~~~~~~~~~~~~~~~~~~~~~~~~~~~~~~~~~~~~~
```

HAGAKC*~~~~~~~~~~~~~~~~~~~~~~~~~~~~~~~~~~~~~~~~~~~~~~~~~~~
MLEPSANMPWFKGWKVTRKDGNASGTTLLEALDWCSQTRYGGHLCSSQRY
-----------------------------------------TSPCACLS
----------------------DGNASGTTLLEALDCILHQLVQLTSPCACLS
MLEPSANMPWFKGWKVTRKDGNASGTTLLEALDCILPPTRPTDKPLRLPL
MLEPSANMPWFKGWKVTRKDGNASGTTLLEALDCILPPTRPTDKPLRLPL
MLEPSANMPWFKGWKVTRKDGNASGTTLLEALDCILPPTRPTDKPLRLPL
MLEPSANMPWFKGWKVTRKDGNASGTTLLEALDCILPPTRPTDKPLRLPL
MLEPSANMPWFKGWKVTRKDGNASGTTLLEALDCILPPTRPTDKPLRLPL

~~~~~~~~~~~~~~~~~~~~~~~~~~~~~~~~~~~~~~~~~~~~~~~~~~
~~~~~~~~~~~~~~~~~~~~~~~~~~~~~~~~~~~~~~~~~~~~~~~~~~

MLEPSANMPWFKGWKVTRKDGNASGTTLLEALDCILPPTRPTDKPLRLPL
MLEPSANMPWFKGWKVTRKDGNASGTTLLEALDCILPPTRPTDKPLRLPL
MLEPSANMPWFKGWKVTRKDGNASGTTLLEALDCILPPTRPTDKPLRLPL
MLEPSANMPWFKGWKVTRKDGNASGTTLLEALDCILPP~~~~~~~~~~~~
~~~~~~~~~~~~~~~~~~~~~~~~~~~~~~~~~~~~~~~~~~~~~~~~~~

MLEPSANMPWFKGWKVTRKDGNASGTTLLEALDCILPPTRPTDKPLRLPL
MLEPSANMPWFKGWKVTRKDGNASGTTLLEALDCILPPTRPTDKPLRLPL
MLEPSANMPWFKGWKVTRKDGNASGTTLLEALDCILPPTRPTDKPLRLPL
MLEPSANMPWFKGWKVTRKDGNASGTTLLEALDCILPPTRPTDKPLRLPL
MLEPSANMPWFKGWKVTRKDGNASGTTLLEALDCILPPTRPTDKPLRLPL
MLEPSANMPWFKGWKVTRKDGNASGTTLLEALDCILPPTRPTDKPLRLPL
MLEPSANMPWFKGWKVTRKDGNASGTTLLEALDCILPPTRPTDKPLRLPL
~~~~~~~~~~~~~~~~~~~~~~~~~~~~~~~~~~~~~~~~~~~~~~~~~~
~~~~~~~~~~~~~~~~~~~~~~~~~~~~~~~~~~~~~~~~~~~~~~~~~~
~~~~~~~~~~~~~~~~~~~~~~~~~~~~~~~~~~~~~~~~~~~~~~~~~~

--------MPWFKGWKVTRKDGNASGTTLLEALDCILPPTRPTDKPLRLPL
--------------DGNASGTTLLEALDCILPPTRPTDKPLRLPL
--------MPWFKGWKVTRKDGNASGTTLLEALDCILPPTRPTDKPLRLPL
MLEPSANMPWFKGWKVTRKDGNASGTTLLEALTASYTNSSTDNLAPASPG
MLEPSANMPWFKGWKVTVRMAMPVEPRCLRLWTASYHQLVQLTSPCACLS
VSWQAHVC*~~~~~~~~~~~~~~~~~~~~~~~~~~~~~~~~~~~~~~~~~
MLEPSANMPWFKGWKVTRKDGNASGTTLLEALDCILPPTRPTDKPLRLPL
~~~~~~~~~~~~~~~~~~~~~~~~~~~~~~~~~~~~~~~~~~~~~~~~~~
~~~~~~~~~~~~~~~~~~~~~~~~~~~~~~~~~~~~~~~~~~~~~~~~~~
~~~~~~~~~~~~~~~~~~~~~~~~~~~~~~~~~~~~~~~~~~~~~~~~~~
-----------------------------TRYGGHLCSSQRY
~~~~~~~~~~~~~~~~~~~~~~~~~~~~~~~~~~~~~~~~~~~~~~~~~~
~~~~~~~~~~~~~~~~~~~~~~~~~~~~~~~~~~~~~~~~~~~~~~~~~~

MLEPSANMPWFKGWKVTVRMAMPVEPRCLRLWTASYHQLVQLTSLAPASP
```

~~~~~~~~~~~~~~~~~~~~~~~~~~~~~~~~~~~~~~~~~~~~~~~~~~
                  NGSKICRNAP*
   TO             RMSTKLVVLVLFLLAEWRLVFSNPVWWSPLLQSTLQRK*~~~~~~~~~~~              TO
  FIG. 3A         RMSTKLVVLVLFLLAEWRLVFSNRYGGHLCSSQRYN~EVKSVEMHHEALS            FIG. 3A
 (CONT. 4)        --------------------GVLKPGMVVTFAPVNVTTEVKSVEMHHEALS          (CONT. 6)
                  QDVYKIGGIGTVPVGRVETGVLKPGMVVTFAPVNVTTEVKSVEMHHEALS
                  QDVYKIGGIGTVPVGRVETGVLKPGMVVTFAPVNVTTEVKSVEMHHEALS
                  QDVYKIGGIGTVPVGRVETGVLKPGMVVTFAPVNVTTEVKSVEMHHEALS
                  QDVYKIGGIGTVPVGRVETGVLKPGMVVTFAPVNVTTEVKSVE--------
                  QDVYKIGGIGTVPVGRVETGVLKPGMVVTFAPVNVTTEVKSVEMHHEALS

~~~~~~~~~~~~~~~~~~~~~~~~~~~~~~~~~~~~~~~~~~~~~~~~~~
                  ~~~~~~~~~~~~~~~~~~~~~~~~~~~~~~~~~~~~~~~~~~~~~~~~~~
                  QDVYKIGGIGTVPVGRVETGVLKPGMVVTFAPVNVTTEVKSVEMHHEALS
                  QDVYKIGGIGTVPVGRVETGVLKPGMVVTFAPVNVTTEVKSVEMHHEALS
                  QDVYKIGGIGTVPVGRVETGVLKPGMVVTFAPVNVTTEVKSVEMHHEALS
                  ~~~~~~~GTVPVGRVETGVLKPGMVVTFAPVNVTTEVKSVEMHHEALSE
                  ~~~~~~~~~~~~~~~~~~~~~~~~~~~~~~~~~~~~~~~~~~~~~~~~~~
                  QDVYKIGGIGTVPVGRVETGVLKPGMVVTFAPVNVTTEVKSVEMHHEALS
                  QDVYKIGGIGTVPVGRVETGVLKPGMVVTFAPVNVTTEVKSVEMHHEALS
                  QDVYKIGGIGTVPVGRVETGVLKPGMVVTFAPVNVTTEVKSVEMHHEALS
                  QDVYKIGGIGTVPVGRVETGVLKPGMVVTFAPVNVTTEVKSVEMHHEALS
                  QDVYKIGGIGTVPVGRVETGVLKPGMVVTFAPVNVTTEVKSVEMHHEALS
                  QDVYKIGGIGTVPVGRVETGVLKPGMVVTFAPVNVTTEVKSVEMHHEALS
                  QDVYKIGGIGTVPVGRVETGVLKPGMVVTFAPVNVTTEVKSVEMHHEALS
                  ~~~~~~~~~~~~~~~~~~~~~~~~~~~~~~~~~~~~~~~~~~~~~~~~~~
                  ~~~~~~~~~~~~~~~~~~~~~~~~~~~~~~~~~~~~~~~~~~~~~~~~~~
                  ~~~~~~~~~~~~~~~~~~~~~~~~~~~~~~~~~~~~~~~~~~~~~~~~~~
                  QDVYKIGGIGTVPVGRVETGVLKPGMVVTFAPVNVTTEVKSVEMHHEALS
                  QDVYKIGGIGTVPVGRVETGVLKPGMVVTFAPVNVTTEVKSVEMHHEALS
                  QDVYKIGGIGTVPVGRVETGVLKPGMVVTFAPVNVTTEVKSVEMHHEALS
                  ---------------------------------------------------
                  CLQNVYWY---CSCWPSETGVLKPGMVVTFAPVNVTTEVKSVEMHHEALS
                  RMSTKLVVLVLFLLAEWRLVFSNPVWWSPLLQSTLQCGLQCQECVCQGCS
   TO                                                                            TO
  FIG. 3A         ~~~~~~~~~~~~~~~~~~~~~~~~~~~~~~~~~~~~~~~~~~~~~~~~~~            FIG. 3A
 (CONT. 4)        QDVYKIGGIGTVPVGRVETGVLKPGMVVTFAPVNVTTEVKSVEMHHEALS            (CONT. 6)
                  ~~~~~~~~~~~~~~~~~~~~~~~~~~~~~~~~~~~~~~~~~~~~~~~~~~
                  ~~~~~~~~~~~~~~~~~~~~~~~~~~~~~~~~~~~~~~~~~~~~~~~~~~
                  ~~~~~~~~~~~~~~~~~~~~~~~~~~~~~~~~~~~~~~~~~~~~~~~~~~
                  NGSKICRNAP*~~~~~~~~~~~~~~~~~~~~~~~~~~~~~~~~~~~~~~~
                  ~~~~~~~~~~~~~~~~~~~~~~~~~~~~~~~~~~~~~~~~~~~~~~~~~~
                  --------------------GVLKPGMVVTFAPVNVTTEVKSVEMHHEALS
                  ---------------------------------------------------
                  GCLQNLVFSNPVWWSPLLQSTLQRK*~~~~~~~~~~~~~~~~~~~~~~~~~
```

~~~~~~~~~~~~~~~~~~~~~~~~~~~~~~~~~~~~~~~~
          ~~~~~~~~~~~~~~~~~~~~~~~~~~~~~~~~~~~~~~~~
          ~~~~~~~~~~~~~~~~~~~~~~~~~~~~~~~~~~~~~~~~
          EALPGDNVGFNVKNVSVKDVRRGNVAGDSKNDHQWKQLAS
          EALPGDNVGFNVKNVSVKDVRRGNVAGDSKNDPPMEAAGF
          EALPGDNVGFNVKNVSVKDVRRGNVAGDSKNDPPMEAAGF
          EALPGDNVGFNVKNVSVKDVRRGNVAGDSKNDPPMEA---
          EALPGDNVGFNVKNVSVKDVRRGNVAGDSKNDPPMEAAGF
          ------------------------------NDPPMEAAGF
          EALPGDNVGFNVKNVSVKDVRRGNVAGDSKNDPPMEAAGF
          ----------------------------------------
          ~~~~~~~~~~~~~~~~~~~~~~~~~~~~~~~~~~~~~~~~
          ~~~~~~~~~~~~~~~~~~~~~~~~~~~~~~~~~~~~~~~~
          EALPGDNVGFNVKNVSVKDVRRGNVAGDSKNDPPMEAAGF
          EALPGDNVGFNVKNVSVKDVRRGNVAGDSKNDPPMEAAGF
          EALPGDNVGFNVKNVSVKDVRRGNVAGDSKNDPPMEAAGF
          ~~~~~~~~~~~~~~~~~~~~~~~~~~~~~~~~~~~~~~~~
          ALPGDNVGFNVKNVSVKDVRRGNVAGDS~~~~~~~~~~~~
          ~~~~~~~~~~~~~~~~~~~~~~~~~~~~~PPMEAAGF
          EALPGDNVGFNVKNVSVKDVRRGNVAGDSKNDPPMEAAGF
          EALPGDNVGFNVKNVSVKDVRRGNVAGDSKNDPPMEAAGF
          EALPGDNVGFNVKNVSVKDVRRGNVAGDSKNDPPMEAAGF
          EALPGDNVGFNVKNVSVKDVRRGNVAGDSKNDPPMEAAGF
          EALPGDNVGFNVKNVSVKDVRRGNVAGDSKNDPPMEAAGF
          EALPGDNVGFNVKNVSVKDVRRGNVAGDSKNDPPMEAAGF
          EALPGDNVGFNVKNVSVKDVRRGNVAGDSKNDPPMEAAGF
          ~~~~~~~~~~~~~~~~~~~~~~~~~~~~~~~~~~~~~~~~
          ~~~~~~~~~~~~~~~~~~~~~~~~~~~~~~~~~~~~~~~~
          ~~~~~~~~~~~~~~~~~~~~~~~~~~~~~~~~~~~~~~~~
          EALPGDNVGFNVKNVSVKDVRRGNVAGDSKNDPPMEAAGF
          EALPGDNVGFNVKNVSVKDVRRGNVAGDSKNDPPMEAAGF
          EALPGDNVGFNVKNVSVKDVRRGNVAGDSKNDPPMEAAGF
          ----------------------------------------
          EALPGDNVGFNVKNVSVKDVRRGNVAGDSKNDPPMEAAGF
          SWQRCW*~~~~~~~~~~~~~~~~~~~~~~~~~~~~~~~~~
          ----------------------------------------
          ~~~~~~~~~~~~~~~~~~~~~~~~~~~~~~~~~~~~~~~~
          EALPGDNVGFNVKNVSVKDVRRGNVAGDSKNDPPMEAAGF
          ~~~~~~~~~~~~~~~~~~~~~~~~~~~~~~~~~~~~~~~~
          ~~~~~~~~~~~~~~~~~~~~~~~~~~~~~~~~~~~~~~~~
          ~~~~~~~~~~~~~~~~~~~~~~~~~~~~~~~~~~~~~~~~
          ~~~~~~~~~~~~~~~~~~~~~~~~~~~~~~~~~~~~~~~~
          ~~~~~~~~~~~~~~~~~~~~~~~~~~~~~~~~~~~~~~~~
          EALPGDNVGFNVKNVSVKDVRRGNVAGDSKNDPPMEAAGF
          -----------------------------------EAAGF
          ~~~~~~~~~~~~~~~~~~~~~~~~~~~~~~~~~~~~~~~~
```

```
                350       360       370       380       390
         ....|....|....|....|....|....|....|....|....|....|
         ~~~~~~~~~~~~~~~~~~~~~~~~~~~~~~~~~~~~~~~~~~~~~~~~~~
         ~~~~~~~~~~~~~~~~~~~~~~~~~~~~~~~~~~~~~~~~~~~~~~~~~~
         LLR*~~~~~~~~~~~~~~~~~~~~~~~~~~~~~~~~~~~~~~~~~~~~~~
         TAQVIILNHPGQISAGYAPVLDCHTAHIACKFAELKEKIDRCS*~~~~~~
         TAQVIILNHPGQISAGYAPVLDCHTAHIACKFAELKEKIDRRSGKKLEDG
         ──────────────────────────────────────────────────
         TAQVIILNHPGQISAGYAPVLDCHTAHIACK───────────────────
         TAQVIILNHPGQISAGYAPVLDCHTAHIACKFAELKEKIDRRSGKKLEDG
         TAQVIILNHPGQISAGYAPVLDCHTAHIACKFAELKEKIDRRSGKKLEDG
         ──────────────────────────────────────────────────
         ~~~~~~~~~~~~~~~~~~~~~~~~~~~~~~~~~~~~~~~~~~~~~~~~~
         TAQVIILNHPGQISAGYAPVLDCHTAHIACKFAELKEKIDRRSGKKLEDG
         TAQVIILNHPGQISAGYAPVLDCHTAHIACKFAELKEKIDRRSGKKLEDG
         TAQVIILNHPGQISAGYAPVLDCHTAHIACKFAELKEKIDRRSGKKLEDG
         ~~~~~~~~~~~~~~~~~~~~~~~~~~~~~~~~~~~~~~~~~~~~~~~~~
         TAQVIILNHPGQISAGYAPVLDCHTAHIACKFAELKEKIDRRSGKKLEDG
         TAQVIILNHPGQISAGYAPVLDCHTAHIACKFAELKEKIDRRSGKKLEDG
         TAQVIILNHPGQISAGYAPVLDCHTAHIACKFAELKEKIDRRSGKKLEDG
         TAQVIILNHPGQISAGYAPVLDCHTAHIACKFAELKEKIDRRSGKKLEDG
         TAQVIILNHPGQISAGYAPVLDCHTAHIACKFAELKEKIDRRSGKKLEDG
         TAQVIILNHPGQISAGYAPVLDCHTAHIACKFAELKEKIDRRSGKKLEDG
         TAQVIILNHPGQISAGYAPVLDCHTAHIACKFAELKEKIDRRSGKKLEDG
         TAQVIILNHPGQISAGYAPVLDCHTAHIACKFAELKEKIDRRSGKKLEDG
         ~~~~~~~~~~~~~~~~~~~~~~~~~~~~~~~~~~~~~~~~~~~~~~~~~
         ~~~~~~~~~~~~~~~~~~~~~~~~~~~~~~~~~~~~~~~~~~~~~~~~~
         ~~~~~~~~~~~~~~~~~~~~~~~~~~~~~~~~~~~~~~~~~~~~~~~~~
         TAQVIILNHPGQISAGYAPVLDCHTAHIACKFAELKEKIDRRSGKKLEDG
         TAQVIILNHPGQISAGYAPVLDCHTAHIACKFAELKEKIDRRSGKKLEDG
         TAQVIILNHPGQISAGYALYWIATRLTLHASLLS*~~~~~~~~~~~~~~~
         ─────────────────────────HIACKFAELKEKIDRRSGKKLEDG
         TAQVIILNHPGQISAGYAPVLDCHTAHIACKFAELKEKIDRRSGKKLEDG
         ~~~~~~~~~~~~~~~~~~~~~~~~~~~~~~~~~~~~~~~~~~~~~~~~~
         ───VIILNHPGQISAGYAPVLDCHTAHIACKFAELKEKIDRRSGKKLEDG
         ~~~~~~~~~~~~~~~~~~~~~~~~~~~~~~~~~~~~~~~~~~~~~~~~~
         TAQVIILNHPGQISAGYAPVLDCHTAHIACKFAEL~~~~~~~~~~~~~~
         ~~~~~~~~~~~~~~~~~~~~~~~~~~~~~~~~~~~~~~~~~~~~~~~~~
         ~~~~~~~~~~~~~~~~~~~~~~~~~~~~~~~~~~~~~~~~~~~~~~~~~
         ~~~~~~~~~~~~~~~~~~~~~~~~~~~~~~~~~~~~~~~~~~~~~~~~~
         ~~~~~~~~~~~~~~~~~~~~~~~~~~~~~~~~~~~~~~~~~~~~~~~~~
         TAQVIILNHPGQISAGYAPVLDCHTAHIACKFAELKEKIDRRSGKKLEDG
         TAQVIILNHPGQISAGYAPVLDCHTAHIACKFAELKEKIDRRSGKKLEDG
         ~~~~~~~~~~~~~~~~~~~~~~~~~~~~~~~~~~~~~~~~~~~~~~~~~

[VAL] 345 → VIILNHPGQISAGYAPVLDCHTAHIACK
```

```
                         400       410       420       430       440
                    ....|....|....|....|....|....|....|....|....|....|
                    ~~~~~~~~~~~~~~~~~~~~~~~~~~~~~~~~~~~~~~~~~~~~~~~~~~
                    ~~~~~~~~~~~~~~~~~~~~~~~~~~~~~~~~~~~~~~~~~~~~~~~~~~
                    ~~~~~~~~~~~~~~~~~~~~~~~~~~~~~~~~~~~~~~~~~~~~~~~~~~
                    ~~~~~~~~~~~~~~~~~~~~~~~~~~~~~~~~~~~~~~~~~~~~~~~~~~
                    PKFLKSGDAAIVDMVPGKPMCVESFSDYPPLGRFAVRDMRQTVAVVVIKA

PKFLKSGDAAIVDMVPGKPMCVESFSDYPPLGRFAVRDMRQTVAVGVIKA
                    PKFLKSGDAAIVDMVPGKPMCVESFSDYPPLGRFAVRDMRQTVAVGVIKA
                    --------AAIVDMVPGKPMCVESFSDYPPLGRFAVRDMRQTVAVGVIKA
                    ~~~~~~~~~~~~~~~~~~~~~~~~~~~~~~~~~~~~~~~~~~~~~~~~~
                    PKFLKSGDAAIVDMVPGKPMCVESFSDYPPLGRFAVRDMRQTVAVGVIKA
                    PKFLKSGDAAIVDMVPGKPMCVESFSDYPPLGRFAVRDMRQTVAVGVIKA
                    PKFLKSGDAAIVDMVPGKPMCVESFSDYPPLGRFAVRDMRQTVAVGVIKA
                    ~~~~~~~~~~~~~~~~~~~~~~~~~~~~~~~~~~~~~~~~~~~~~~~~~
                    PKFLKSGDAAIVDMVPGKPMCVESFSDYPPLG~~~~~~~~~~~~~~~~~~
                    PKFLKSGDAAIVDMVPGKPMCVESFSDYPPLGRFAVRDMRQTVAVGVIKA
                    PKFLKSGDAAIVDMVPGKPMCVESFSDYPPLGRFAVRDMRQTVAVGVIKA
                    PKFLKSGDAAIVDMVPGKPMCVESFSDYPPLGRFAVRDMRQTVAVGVIKA
                    PKFLKSGDAAIVDMVPGKPMCVESFSDYPPLGRFAVRDMRQTVAVGVIKA
                    PKFLKSGDAAIVDMVPGKPMCVESFSDYPPLGRFAVRDMRQTVAVGVIKA
                    PKFLKSGDAAIVDMVPGKPMCVESFSDYPPLGRFAVRDMRQTVAVGVIKA
                    ~~~~~~~~~~~~~~~~~~~~~~~~~~~~~~~~~~~~~~~~~~~~~~~~~
                    ~~~~~~~~~~~MVPGKPMCVESFSDYPPLGRFAVRDMRQTVAVGVIKA
                    ~~~~~~~~~~~MVPGKPMCVESFSDYPPLGRFAVRDMRQTVAVGVIKA
                    ~~~~~~~~~~~~~~~~~~~~~~~~~~~~~~~~~~~~~~~~~~~~~~~~~
                    PKFLKSGDAAIVDMVPGKPMCVESFSDYPPLGRFAVRDMRQTVAVGVIKA
                    PKFLKSGDAAIVDMVPGKPMCVESFSDYPPLGRFAVRDMRQTVAVGVIKA
                    ~~~~~~~~~~~~~~~~~~~~~~~~~~~~~~~~~~~~~~~~~~~~~~~~~
                    PKFLKSGDAAIVDMVPGKPMCVESFSDYPPLGRFAVRDMRQTVAVGVIKA
                    PKFLKSGDAAIVDMVPGKPMCVESFSDYPPLGRFAVRDMRQTVAVGVIKA
                    ~~~~~~~~~~~~~~~~~~~~~~~~~~~~~~~~~~~~~~~~~~~~~~~~~
                    PKFLKSGDAAIVDMVPGKPMCVESFSDYPPLGRFAVRDMRQTVAVGVIKA
                    ~~~~~~~~~~~~~~~~~~~~~~~~~~~~~~~~~~~~~~~~~~~~~~~~~
                    ~~~~~~~~~~~~~~~~~~~~~~~~~~~~~~~~~~~~~~~~~~~~~~~~~
                    ~~~~~~~~~~~~~~~~~~~~~~~~~~~~~~~~~~~~~~~~~~~~~~~~~
                    ~~~~~~~~~~~~~~~~~~~~~~~~~~~~~~~~~~~~~~~~~~~~~~~~~
                    ~~~~~~~~~~~~~~~~~~~~~~~~~~~~~~~~~~~~~~~~~~~~~~~~~
                    ~~~~~~~~~~~~~~~~~~~~~~~~~~~~~~~~~~~~~~~~~~~~~~~~~
                    ~~~~~~~~~~~~~~~~~~~~~~~~~~~~~~~~~~~~~~~~~~~~~~~~~
                    PKFLKSGDAAIVDMVPGKPMCVESFSDYPPLGRFAVRDMRQTVAVGVIKA
                    PKFLKSGDAAIVDMVPGKPMCVESFSDYPPLGRFAVRDMRQTVAVGVIKA
                    ~~~~~~~~~~~~~~~~~~~~~~~~~~~~~~~~~~~~~~~~~~~~~~~~~
```

*FIG. 3A*
*(CONT. 8)*

```
                        450        460
                   ....|....|....|....|....|..
                   ~~~~~~~~~~~~~~~~~~~~~~~~
                   ~~~~~~~~~~~~~~~~~~~~~~~~
TO                 ~~~~~~~~~~~~~~~~~~~~~~~~
FIG. 3A            ~~~~~~~~~~~~~~~~~~~~~~~~
(CONT. 8)          ~~~~~~~~~~~~~~~~~~~~~~~~
←                  VDKKAAGAGKVTKSAQKAQKAK*~~
                   VDKKAAGAGKVTKSAQKAQKAK*~~
                   --------------SAQKAQKAK*~~
                   VDKKAAGAGKVTKSAQKAQKAK*~~
                   VDKKAAGAGKVTKSAQKAQKAK*~~
                   VDKKAAGAGKVTKSAQKAQKAK*~~
                   ~~~~~~~~~~~~~~~~~~~~~~~~
                   ~~~~~~~~~~~~~~~~~~~~~~~~
                   VDKKAAGAGKVTKSAQKAQKAK*~~
                   VDKKAAGAGKVTKSAQKAQKAK*~~
                   VDKKAAGAGKVTKSAQKAQKAK*~~
                   ~~~~~~~~~~~~~~~~~~~~~~~~
                   ~~~~~~~~~~~~~~~~~~~~~~~~
                   VDKKAAGAGKVTKSAQKAQKAK*~~
                   VDKKAAGAGKVTKSAQKAQKAK*~~
                   VDKKAAGAGKVTKSAQKAQKAK*~~
                   VDKKAAGAGKVTKSAQKAQKAK*~~
                   VDKKAAGAGKVTKSAQKAQKAK*~~
                   VDKKAAGAGKVTKSAQKAQKAK*~~
                   VDKKAAGAGKVTKSAQKAQKAK*~~
                   ~~~~~~~~~~~~~~~~~~~~~~~~
                   VDKKAAGAGKVTKSAQKAQKAK*~~
                   VDKKAAGAGKVTKSAQKAQKAK*~~
                   ~~~~~~~~~~~~~~~~~~~~~~~~
                   VDKKAAGAGKVTKSAQKAQKAK*~~
                   VDKKAAGAGKVTKSAQKAQKAK*~~
                   ~~~~~~~~~~~~~~~~~~~~~~~~
                   VDKKAAGAGKVTKSAQKAQKAK*~~
                   VDKKAAGAGKVTKSAQKAQKAK*~~
                   ~~~~~~~~~~~~~~~~~~~~~~~~
TO                 VDKKAAGAGKVTKSAQKAQKAK*~~
FIG. 3A            ~~~~~~~~~~~~~~~~~~~~~~~~
(CONT. 8)          ~~~~~~~~~~~~~~~~~~~~~~~~
←                  ~~~~~~~~~~~~~~~~~~~~~~~~
                   ~~~~~~~~~~~~~~~~~~~~~~~~
                   ~~~~~~~~~~~~~~~~~~~~~~~~
                   ~~~~~~~~~~~~~~~~~~~~~~~~
                   ~~~~~~~~~~~~~~~~~~~~~~~~
                   VDKKAAGAGKVTKSARKLRRLNEYYP*
                   VDKKAAGAGKVTKSAQKAQKAK*~~
                   ~~~~~~~~~~~~~~~~~~~~~~~~
```

*FIG. 3A*
*(CONT. 9)*

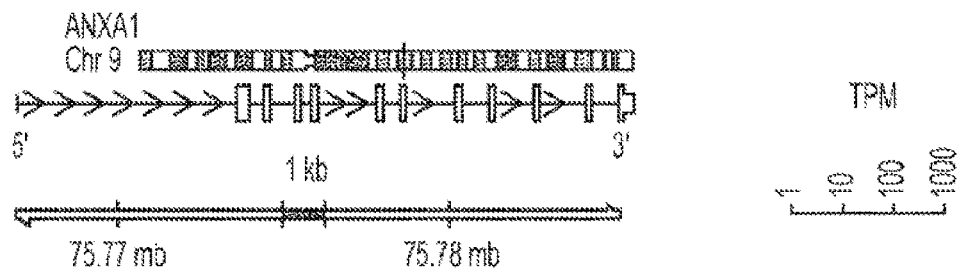
FIG. 4A
FIG. 4B                FIG. 4D
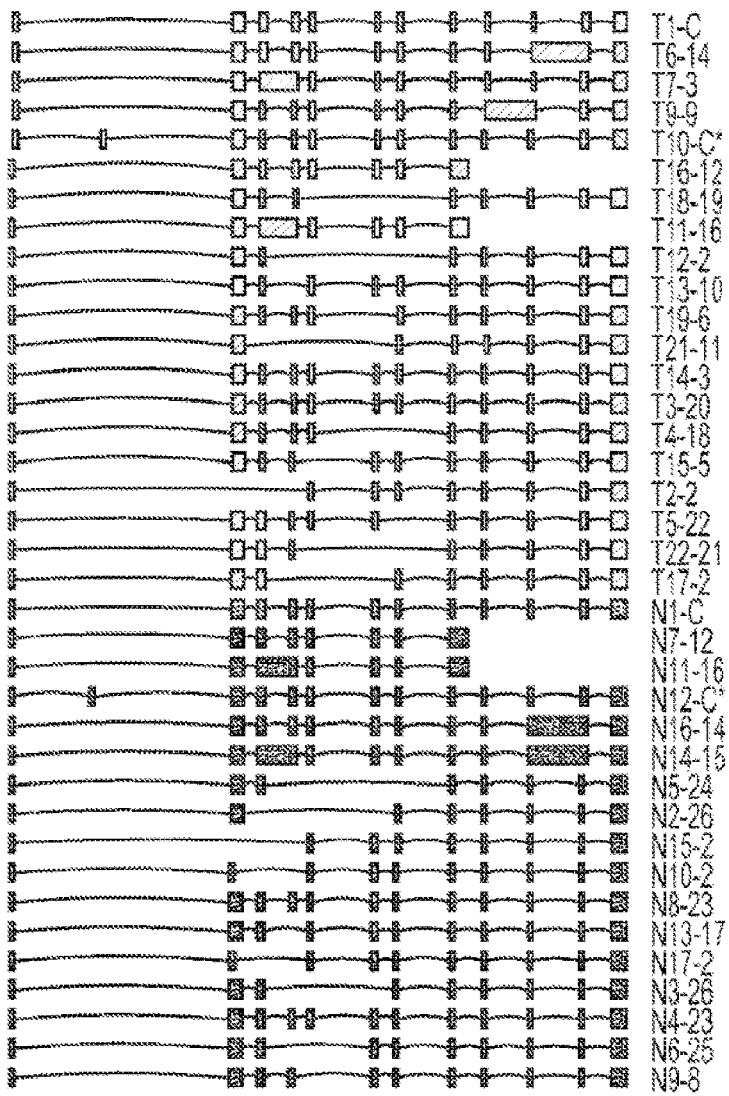
FIG. 4C                FIG. 4E

LEGEND FOR FIGS. 6A, 7, AND 8

RED (D,E) = ITALICS

YELLOW (G) = BOLD

BLUE (K,R) = SINGLE UNDERLINE

LIGHT BLUE (S,T) = REGULAR

TEAL (A,F,Y) = BOLD ITALICS

GREEN (M,L,V,I) = DOUBLE UNDERLINE

PURPLE (H) = DOUBLE DOTTED UNDERLINE

LAVENDAR (Q,N) = DOTTED UNDERLINE

LIGHT GREEN (W) = SINGLE SQUIGGLE UNDERLINE

BURGANDY (C) = DOUBLE SQUIGGLE UNDERLINE

GRAY (P) = BOLD ITALICS UNDERLINE

KPAFFAEKLHQAMKVCTILLICPA*

KPAFFAEKLHQAMKGVGTRHKALRIMVSRSEIDMNDIKAFYQKMYGISLCQAILDETKGDYEKILVAL
KPAFFAEKLHQAMKGVGTRHKALRIMVSRSEIDMNDIKAFYQKMYGISLCQAILDETKGDYEKILVAL

KPAFFAEKLHQAMKGVGTRHKALRIMVSRSEIDMNDIKAFYQKMYGISLCQAILDETKGDYEKILVAL
KPAFFAEKLHQAMKGVGTRHKALRIMVSRSEIDMNDIKAFYQKMYGISLCQAILDETKGDYEKILVAL
KPAFFAEKLHQAMKGVGTRHKALRIMVSRSEIDMNDIKAFYQKMYGISLCQAILDETKGDYEKILVAL
KPAFFAEKLHQAMKGVGTRHKALRIMVSRSEIDMNDIKAFYQKMYGISLCQAILDETKGDYEKILVAL
KPAFFAEKLHQAMKGVGTRHKALRIMVSRSEIDMNDIKAFYQKMYGISLCQAILDETKGDYEKILVAL
KPAFFAEKLHQAMKGVGTRHKALRIMVSRSEIDMNDIKAFYQKMYGISLCQAILDETKGDYEKILVAL

KPAFFAEKLHQAMKGVGTRHKALRIMVSRSEIDMNDIKAFYQKMYGISLCQAILDETKGDYEKILVAL
KPAFFAEKLHQAMKGVGTRHKALRIMVSRSEIDMNDIKAFYQKMYGISLCQAILDETKGDYEKILVAL

-----LHQAMKGVGTRHKALRIMVSRSEIDMNDIKAFYQKMYGISLCQAILDETKGDYEKILVAL
KPAFFAEKLHQAMKGVGTRHKALRIMVSRSEIDMNDIKAFYQKMYGISLCQAILDETKGDYEKILVAL

KPAFFAEKLHQAMKGVGTRHKALRIMVSRSEIDMNDIKAFYQKMYGISLCQAILDETKGDYEKILVAL
KPAFFAEKLHQAMKGVGTRHKALRIMVSRSEIDMNDIKAFYQKMYGISLCQAILDETKGDYEKILVAL

KPAFFAEKLHQAMKGVGTRHKALRIMVSRSEIDMNDIKAFYQKMYGISLCQAILDETKGDYEKILVAL
KPAFFAEKLHQAMKGVGTRHKALRIMVSRSEIDMNDIKAFYQKMYGISLCQAILDETKGDYEKILVAL
KPAFFAEKLHQAMKGVGTRHKALRIMVSRSEIDMNDIKAFYQKMYGISLCQAILDETKGDYEKILVAL
KPAFFAEKLHQAMKGVGTRHKALRIMVSRSEIDMNDIKAFYQKMYGISLCQAILDETKGDYEKILVAL

KPAFFAEKLHQAMKVCTILLICPA*
KPAFFAEKLHQAMKVCTILLICPA*

EPSSQPTIPIVGIIAGLVLFGAVITGAVVAAVMWRRKSSSPIIFSCSREVGLRCLHLC
                    EPSSQPTIPIVGIIAGLVLFGAVITGAVVAAVMWRRKSSDRKGGSYSQAASSDSAQGS
                    EPSSQPTIPIVGIIAGLVLFGAVITGAVVAAVMWRRKSSDRKGGSYSQAASSDSAQGS
                    EPSSQPTIPIVGIIAGLVLFGAVITGAVVAAVMWRRKSSDRKGGSYSQAASSDSAQGS
                    EPSSQPTIPIVGIIAGLVLFGAVITGAVVAAVMWRRKSSDRKGGSYSQAASSDSAQGS
                    EPSSQPTIPIVGIIAGLVLFGAVITGAVVAAVMWRRKSSDRKGGSYSQAASSDSAQGS
                    EPSSQPTIPIVGIIAGLVLFGAVITGAVVAAVMWRRKSSDRKGGSYSQAASSDSAQGS
                    EPSSQPTIPIVGIIAGLVLFGAVITGAVVAAVMWRRKSSDRKGGSYSQAASSLYSVRQ
                    EPSSQPTIPIVGIIAGLVLFGAVITGAVVAAVMWRRKSSDRKGGKSCSCPSLC~~~~
                    EPSSQPTIPIVGIIAGLVLFGAVITGAVVAAVMWRRKSSPIIFPVPERWG*~~~~~
                    EPSSQPTIPIVGIIAGLVLFGAVITGAVVAAVMWRRKSSDR*~~~~~~~~~~~~~~~
                    CWPGSLWSCDWSCGRCCDVEEEELR*~~~~~~~~~~~~~~~~~~~~~~~~~~~~~~
                    EPSSQPTIPIVASLLAWFSLEL*~~~~~~~~~~~~~~~~~~~~~~~~~~~~~~~~~

EPSSQPTIPIVGIVAGLAVLAVLAVLGAVVAVVWCRRKSSGGKGGSCSQAASSNSAQG
                    EPSSQPTIPIVGIVAGLAVLAVLAVLGAVVAVVWCRRKSSGGKGGSCSQAASSNSAQG
                    EPSSQPTIPIVGIVAGLAVLAVLAVLGAVMAVVWCRRKSSGGKGGSCSQAASSNSAQG
                    EPSSQPTIPIVGIVAGLAVLAVLAVLGAVVAVVWCRRKSSGGKGGSCSQAASSNSAQG
                    EPSSQPTIPIVGIVAGLAVLAVLAVLGAVVAVVWCRRKSSGGKGGSCSQAASSNSAQG
                    EPSSQPTIPIVGIVAGLAVLAVLAVLGAVVAVVWCRRKSSGGKGGSCSQAASSNSAQG
                    EPSSQPTIPIVGIVAGLAVLAVLAVLGAVVAVVWCRRKSSGGKGGSCSQAASSNSAQG
                    ~~~~~~~~~~~~~~~~~~~~~~~~~~~~~~~~~~~~~~~~~GGKGGSCSQAASSNSAQG
                    EPSSQPTIPIVGIVAGLAVLAVLAVLGAVVAVVWCRRKSSGGKGGELLSVWD*~~~
                    EPSSQPTIPIVGIVAGLAVLAVLAVLGAVVAVVWCRRKSSGGKGFLHTSPL*~~~~
                    EPSSQPTIPIVGIVAGLAVLAVLAVLGAVVAVVWCRRKSPPPCPP*~~~~~~~~~~
                    EPSSQPTIPINLSCSREVGLDYSISVSNSWCTELQLLTSLMKLRT*~~~~~~~~~~

KSIRQLEVWD*~~~~~~~~~~~~~~~~~~~~~~~~~~~~~~~~~~~~~~~~~~~~~
                    EPSSQPTIPIVASLLAWLSWLS*~~~~~~~~~~~~~~~~~~~~~~~~~~~~~~~~~

FVTSRASGISFCKGT*~~~~~~~~~~~~~~~~~~~~~~~~~~~~~~~~~~~~~~~~
```

LNFMVH*
DVSLTACKV*
DVSLTACKV*

DVSLTACKV*
DVSLTACKV*
DVSLTACKV*
DVSLTACKV*
LPCVGLRGKSCSCPSLCDLKNPDFVSAKAPACVCVRVGIM*
                 DLKNPDFVSAKAPACVCVRVGIM*

SDESLIACKA*
SDESLIACKA*
SDESLIACKA-
SDESLIACKA*
SDESLIACKA*
SDESLIACKA*
SDESLIACKA*
SDESLIACKA*
SDESLIACKA*

SEQUENCE LISTING

```
<160> NUMBER OF SEQ ID NOS: 122

<210> SEQ ID NO 1
<211> LENGTH: 206
<212> TYPE: PRT
<213> ORGANISM: Homo sapiens

<400> SEQUENCE: 1

Met Gly Lys Glu Lys Thr His Ile Asn Ile Val Val Ile Gly His Val
1               5                   10                  15

Asp Ser Gly Lys Ser Thr Thr Thr Gly His Leu Ile Tyr Lys Cys Gly
            20                  25                  30

Gly Ile Asp Lys Arg Thr Ile Glu Lys Phe Glu Lys Glu Ala Ala Glu
        35                  40                  45

Met Gly Lys Gly Ser Phe Lys Tyr Ala Trp Val Leu Asp Lys Leu Lys
    50                  55                  60

Ala Glu Arg Glu Arg Gly Ile Thr Ile Asp Ile Ser Leu Trp Lys Phe
65                  70                  75                  80

Glu Thr Ser Lys Tyr Tyr Val Thr Ile Ile Asp Ala Pro Gly His Arg
                85                  90                  95

Asp Phe Ile Lys Asn Met Ile Thr Gly Thr Ser Gln Ala Asp Cys Ala
            100                 105                 110

Val Leu Ile Val Ala Ala Gly Val Gly Glu Phe Glu Ala Gly Ile Ser
        115                 120                 125

Lys Asn Gly Gln Thr Arg Glu His Ala Leu Leu Ala Tyr Thr Leu Gly
    130                 135                 140

Val Lys Gln Leu Ile Val Gly Val Asn Lys Met Asp Ser Thr Glu Pro
145                 150                 155                 160

Pro Tyr Ser Gln Lys Arg Tyr Glu Glu Ile Val Lys Glu Val Ser Thr
                165                 170                 175

Tyr Ile Lys Lys Ile Gly Tyr Asn Pro Asp Thr Val Ala Phe Val Pro
            180                 185                 190

Ile Ser Gly Trp Asn Gly Asp Lys His Ala Gly Ala Lys Cys
        195                 200                 205

<210> SEQ ID NO 2
<211> LENGTH: 260
<212> TYPE: PRT
<213> ORGANISM: Homo sapiens

<400> SEQUENCE: 2

Met Gly Lys Glu Lys Thr His Ile Asn Ile Val Val Ile Gly His Val
1               5                   10                  15

Asp Ser Gly Lys Ser Thr Thr Thr Gly His Leu Ile Tyr Lys Cys Gly
            20                  25                  30

Gly Ile Asp Lys Arg Thr Ile Glu Lys Phe Glu Lys Glu Ala Ala Glu
        35                  40                  45
```

```
Met Gly Lys Gly Ser Phe Lys Tyr Ala Trp Val Leu Asp Lys Leu Lys
            50                  55                  60

Ala Glu Arg Glu Arg Gly Ile Thr Ile Asp Ile Ser Leu Trp Lys Phe
 65                  70                  75                  80

Glu Thr Ser Lys Tyr Tyr Val Thr Ile Ile Asp Ala Pro Gly His Arg
                 85                  90                  95

Asp Phe Ile Lys Asn Met Ile Thr Gly Thr Ser Gln Ala Asp Cys Ala
                100                 105                 110

Val Leu Ile Val Ala Ala Gly Val Gly Glu Phe Glu Ala Gly Ile Ser
            115                 120                 125

Lys Asn Gly Gln Thr Arg Glu His Ala Leu Leu Ala Tyr Thr Leu Gly
130                 135                 140

Val Lys Gln Leu Ile Val Gly Val Asn Lys Met Asp Ser Thr Glu Pro
145                 150                 155                 160

Pro Tyr Ser Gln Lys Arg Tyr Glu Glu Ile Val Lys Glu Val Ser Thr
                165                 170                 175

Tyr Ile Lys Lys Ile Gly Tyr Asn Pro Asp Thr Val Ala Phe Val Pro
                180                 185                 190

Ile Ser Gly Trp Asn Gly Asp Asn Met Leu Glu Pro Ser Ala Asn Met
            195                 200                 205

Pro Trp Phe Lys Gly Trp Lys Val Thr Arg Lys Asp Gly Asn Ala Ser
210                 215                 220

Gly Thr Thr Leu Leu Glu Ala Leu Asp Trp Cys Ser Gln Thr Arg Tyr
225                 230                 235                 240

Gly Gly His Leu Cys Ser Ser Gln Arg Tyr Asn Gly Ser Lys Ile Cys
                245                 250                 255

Arg Asn Ala Pro
            260

<210> SEQ ID NO 3
<211> LENGTH: 109
<212> TYPE: PRT
<213> ORGANISM: Homo sapiens

<400> SEQUENCE: 3

Met Gly Lys Glu Lys Thr His Ile Asn Ile Val Val Ile Gly His Val
 1               5                  10                  15

Asp Ser Gly Lys Ser Thr Thr Thr Gly His Leu Ile Tyr Lys Cys Gly
                20                  25                  30

Gly Ile Asp Lys Arg Thr Ile Glu Lys Phe Glu Lys Glu Ala Ala Glu
            35                  40                  45

Met Gly Lys Gly Ser Phe Lys Tyr Ala Trp Val Leu Asp Lys Leu Thr
 50                  55                  60

Ser Pro Cys Ala Cys Leu Ser Arg Met Ser Thr Lys Leu Val Val Leu
 65                  70                  75                  80

Val Leu Phe Leu Leu Ala Glu Trp Arg Leu Val Phe Ser Asn Pro Val
                 85                  90                  95

Trp Trp Ser Pro Leu Leu Gln Ser Thr Leu Gln Arg Lys
            100                 105

<210> SEQ ID NO 4
<211> LENGTH: 137
<212> TYPE: PRT
<213> ORGANISM: Homo sapiens

<400> SEQUENCE: 4
```

```
Met Asp Ser Thr Glu Pro Pro Tyr Ser Gln Lys Arg Tyr Glu Asp Gly
1               5                   10                  15

Asn Ala Ser Gly Thr Thr Leu Leu Glu Ala Leu Asp Cys Ile Leu His
                20                  25                  30

Gln Leu Val Gln Leu Thr Ser Pro Cys Ala Cys Leu Ser Arg Met Ser
            35                  40                  45

Thr Lys Leu Val Val Leu Val Leu Phe Leu Leu Ala Glu Trp Arg Leu
        50                  55                  60

Val Phe Ser Asn Arg Tyr Gly Gly His Leu Cys Ser Ser Gln Arg Tyr
65                  70                  75                  80

Asn Glu Val Lys Ser Val Glu Met His His Glu Ala Leu Ser Glu Ala
                85                  90                  95

Leu Pro Gly Asp Asn Val Gly Phe Asn Val Lys Asn Val Ser Val Lys
            100                 105                 110

Asp Val Arg Arg Gly Asn Val Ala Gly Asp Ser Lys Asn Asp His Gln
        115                 120                 125

Trp Lys Gln Leu Ala Ser Leu Leu Arg
    130                 135

<210> SEQ ID NO 5
<211> LENGTH: 284
<212> TYPE: PRT
<213> ORGANISM: Homo sapiens

<400> SEQUENCE: 5

Met Gly Lys Glu Lys Thr His Ile Asn Ile Val Val Ile Gly His Val
1               5                   10                  15

Asp Ser Gly Lys Ser Thr Thr Thr Gly His Leu Ile Tyr Lys Cys Gly
                20                  25                  30

Gly Ile Asp Lys Arg Thr Ile Glu Lys Phe Glu Lys Glu Ala Ala Glu
            35                  40                  45

Met Gly Lys Gly Ser Phe Lys Tyr Ala Trp Val Leu Asp Lys Leu Lys
        50                  55                  60

Ala Glu Arg Glu Arg Gly Ile Thr Ile Asp Ile Ser Leu Trp Lys Phe
65                  70                  75                  80

Glu Thr Ser Lys Tyr Tyr Val Thr Ile Ile Asp Ala Pro Gly His Arg
                85                  90                  95

Asp Phe Ile Lys Asn Met Ile Thr Gly Thr Ser Gln Ala Asp Cys Ala
            100                 105                 110

Val Leu Ile Val Ala Ala Gly Val Met Leu Glu Pro Ser Ala Asn Met
        115                 120                 125

Pro Trp Phe Lys Gly Trp Lys Val Thr Arg Lys Asp Gly Asn Ala Ser
    130                 135                 140

Gly Thr Thr Leu Leu Glu Ala Leu Asp Cys Ile Leu Pro Pro Thr Arg
145                 150                 155                 160

Pro Thr Asp Lys Pro Leu Arg Leu Pro Leu Gly Val Leu Lys Pro Gly
                165                 170                 175

Met Val Val Thr Phe Ala Pro Val Asn Val Thr Thr Glu Val Lys Ser
            180                 185                 190

Val Glu Met His His Glu Ala Leu Ser Glu Ala Leu Pro Gly Asp Asn
        195                 200                 205

Val Gly Phe Asn Val Lys Asn Val Ser Val Lys Asp Val Arg Arg Gly
    210                 215                 220

Asn Val Ala Gly Asp Ser Lys Asn Asp Pro Pro Met Glu Ala Ala Gly
```

```
               225                 230                 235                 240

Phe Thr Ala Gln Val Ile Ile Leu Asn His Pro Gly Gln Ile Ser Ala
                        245                 250                 255

Gly Tyr Ala Pro Val Leu Asp Cys His Thr Ala His Ile Ala Cys Lys
                        260                 265                 270

Phe Ala Glu Leu Lys Glu Lys Ile Asp Arg Cys Ser
                        275                 280

<210> SEQ ID NO 6
<211> LENGTH: 297
<212> TYPE: PRT
<213> ORGANISM: Homo sapiens

<400> SEQUENCE: 6

Met Gly Lys Glu Ile Val Lys Glu Val Ser Thr Tyr Ile Lys Lys Ile
        1               5                   10                  15

Gly Tyr Asn Pro Asp Thr Val Ala Phe Val Pro Ile Ser Gly Trp Asn
                        20                  25                  30

Gly Asp Asn Met Leu Glu Pro Ser Ala Asn Met Pro Trp Phe Lys Gly
                        35                  40                  45

Trp Lys Val Thr Arg Lys Asp Gly Asn Ala Ser Gly Thr Thr Leu Leu
        50                  55                  60

Glu Ala Leu Asp Cys Ile Leu Pro Pro Thr Arg Pro Thr Asp Lys Pro
        65                  70                  75                  80

Leu Arg Leu Pro Leu Gln Asp Val Tyr Lys Ile Gly Ile Gly Ile Thr
                        85                  90                  95

Val Pro Val Gly Arg Val Glu Thr Gly Val Leu Lys Pro Gly Met Val
                        100                 105                 110

Val Thr Phe Ala Pro Val Asn Val Thr Thr Glu Val Lys Ser Val Glu
                        115                 120                 125

Met His His Glu Ala Leu Ser Glu Ala Leu Pro Gly Asp Asn Val Gly
        130                 135                 140

Phe Asn Val Lys Asn Val Ser Val Lys Asp Val Arg Arg Gly Asn Val
        145                 150                 155                 160

Ala Gly Asp Ser Lys Asn Asp Pro Pro Met Glu Ala Ala Gly Phe Thr
                        165                 170                 175

Ala Gln Val Ile Ile Leu Asn His Pro Gly Gln Ile Ser Ala Gly Tyr
                        180                 185                 190

Ala Pro Val Leu Asp Cys His Thr Ala His Ile Ala Cys Lys Phe Ala
                        195                 200                 205

Glu Leu Lys Glu Lys Ile Asp Arg Arg Ser Gly Lys Lys Leu Glu Asp
                        210                 215                 220

Gly Pro Lys Phe Leu Lys Ser Gly Asp Ala Ala Ile Val Asp Met Val
        225                 230                 235                 240

Pro Gly Lys Pro Met Cys Val Glu Ser Phe Ser Asp Tyr Pro Pro Leu
                        245                 250                 255

Gly Arg Phe Ala Val Arg Asp Met Arg Gln Thr Val Ala Val Val Val
                        260                 265                 270

Ile Lys Ala Val Asp Lys Lys Ala Ala Gly Ala Gly Lys Val Thr Lys
                        275                 280                 285

Ser Ala Gln Lys Ala Gln Lys Ala Lys
                        290                 295

<210> SEQ ID NO 7
<211> LENGTH: 359
```

```
<212> TYPE: PRT
<213> ORGANISM: Homo sapiens

<400> SEQUENCE: 7

Met Gly Lys Glu Lys Thr His Ile Asn Ile Val Val Ile Gly His Val
1               5                   10                  15

Asp Ser Gly Lys Ser Thr Thr Thr Gly His Leu Ile Tyr Lys Cys Gly
                20                  25                  30

Gly Ile Asp Lys Arg Thr Ile Glu Lys Phe Glu Lys Glu Ala Ala Glu
            35                  40                  45

Met Gly Lys Gly Ser Phe Lys Tyr Ala Trp Val Leu Asp Lys Leu Lys
50                  55                  60

Ala Glu Arg Glu Arg Gly Ile Thr Ile Asp Ile Ser Leu Trp Lys Phe
65                  70                  75                  80

Glu Thr Ser Lys Tyr Tyr Val Thr Ile Ile Asp Ala Pro Gly His Arg
                85                  90                  95

Asp Phe Ile Lys Asn Met Ile Thr Gly Thr Ser Gln Ala Asp Cys Ala
            100                 105                 110

Val Leu Ile Val Ala Ala Gly Val Gly Glu Phe Glu Ala Gly Ile Ser
        115                 120                 125

Lys Asn Gly Gln Thr Arg Glu His Ala Leu Leu Ala Tyr Thr Leu Gly
130                 135                 140

Val Lys Gln Leu Ile Val Gly Val Asn Lys Met Asp Ser Thr Glu Pro
145                 150                 155                 160

Pro Tyr Ser Gln Lys Arg Tyr Glu Glu Ile Val Lys Glu Val Ser Thr
                165                 170                 175

Tyr Ile Lys Lys Ile Gly Tyr Asn Pro Asp Thr Val Ala Phe Val Pro
            180                 185                 190

Ile Ser Gly Trp Asn Gly Asp Asn Met Leu Glu Pro Ser Ala Asn Met
        195                 200                 205

Pro Trp Phe Lys Gly Trp Lys Val Thr Arg Lys Asp Gly Asn Ala Ser
210                 215                 220

Gly Thr Thr Leu Leu Glu Ala Leu Asp Cys Ile Leu Pro Pro Thr Arg
225                 230                 235                 240

Pro Thr Asp Lys Pro Leu Arg Leu Pro Leu Gln Asp Val Tyr Lys Ile
                245                 250                 255

Gly Gly Ile Gly Thr Val Pro Val Gly Arg Val Glu Thr Gly Val Leu
            260                 265                 270

Lys Pro Gly Met Val Val Thr Phe Ala Pro Val Asn Val Thr Thr Glu
275                 280                 285

Val Lys Ser Val Glu Met His His Glu Ala Leu Ser Glu Ala Leu Pro
290                 295                 300

Gly Asp Asn Val Gly Phe Asn Val Lys Asn Val Ser Val Lys Asp Val
305                 310                 315                 320

Arg Arg Gly Asn Val Ala Gly Asp Ser Lys Asn Asp Pro Pro Met Glu
                325                 330                 335

Ala Val Asp Lys Lys Ala Ala Gly Ala Gly Lys Val Thr Lys Ser Ala
            340                 345                 350

Gln Lys Ala Gln Lys Ala Lys
        355

<210> SEQ ID NO 8
<211> LENGTH: 380
<212> TYPE: PRT
<213> ORGANISM: Homo sapiens
```

<400> SEQUENCE: 8

```
Met Gly Lys Glu Lys Thr His Ile Asn Ile Val Val Ile Gly His Val
1               5                   10                  15

Asp Ser Gly Lys Ser Thr Thr Thr Gly His Leu Ile Tyr Lys Cys Gly
            20                  25                  30

Gly Ile Asp Lys Arg Thr Ile Glu Lys Phe Glu Lys Glu Ala Ala Glu
        35                  40                  45

Met Gly Lys Gly Ser Phe Lys Tyr Ala Trp Val Leu Asp Lys Leu Lys
50                  55                  60

Ala Glu Arg Glu Arg Gly Ile Thr Ile Asp Ile Ser Leu Trp Lys Phe
65                  70                  75                  80

Glu Thr Ser Lys Tyr Tyr Val Thr Ile Ile Asp Ala Pro Gly His Arg
                85                  90                  95

Asp Phe Ile Lys Asn Met Ile Thr Gly Thr Ser Gln Ala Asp Cys Ala
            100                 105                 110

Val Leu Ile Val Ala Ala Gly Val Gly Glu Phe Glu Ala Gly Ile Ser
        115                 120                 125

Lys Asn Gly Gln Thr Arg Glu His Ala Leu Leu Ala Tyr Thr Leu Gly
130                 135                 140

Val Lys Gln Leu Ile Val Gly Val Asn Lys Met Asp Ser Thr Glu Pro
145                 150                 155                 160

Pro Tyr Ser Gln Lys Arg Tyr Glu Glu Ile Val Lys Glu Val Ser Thr
                165                 170                 175

Tyr Ile Lys Lys Ile Gly Tyr Asn Pro Asp Thr Val Ala Phe Val Pro
            180                 185                 190

Ile Ser Gly Trp Asn Gly Asp Asn Met Leu Glu Pro Ser Ala Asn Met
        195                 200                 205

Pro Trp Phe Lys Gly Trp Lys Val Thr Arg Lys Asp Gly Asn Ala Ser
210                 215                 220

Gly Thr Thr Leu Leu Glu Ala Leu Asp Cys Ile Leu Pro Pro Thr Arg
225                 230                 235                 240

Pro Thr Asp Lys Pro Leu Arg Leu Pro Leu Gln Asp Val Tyr Lys Ile
                245                 250                 255

Gly Gly Ile Gly Thr Val Pro Val Gly Arg Val Glu Thr Gly Val Leu
            260                 265                 270

Lys Pro Gly Met Val Val Thr Phe Ala Pro Val Asn Val Thr Thr Glu
        275                 280                 285

Val Lys Ser Val Glu Met His His Glu Ala Leu Ser Glu Ala Leu Pro
290                 295                 300

Gly Asp Asn Val Gly Phe Asn Val Lys Asn Val Ser Val Lys Asp Val
305                 310                 315                 320

Arg Arg Gly Asn Val Ala Gly Asp Ser Lys Asn Asp Pro Pro Met Glu
                325                 330                 335

Ala Ala Gly Phe Thr Ala Gln Val Ile Ile Leu Asn His Pro Gly Gln
            340                 345                 350

Ile Ser Ala Gly Tyr Ala Pro Val Leu Asp Cys His Thr Ala His Ile
        355                 360                 365

Ala Cys Lys Ser Ala Gln Lys Ala Gln Lys Ala Lys
370                 375                 380
```

<210> SEQ ID NO 9
<211> LENGTH: 425
<212> TYPE: PRT

<213> ORGANISM: Homo sapiens

<400> SEQUENCE: 9

```
Met Gly Lys Glu Lys Thr His Ile Asn Ile Val Val Ile Gly His Val
1               5                   10                  15
Asp Ser Gly Lys Ser Thr Thr Thr Gly His Leu Ile Tyr Lys Cys Gly
            20                  25                  30
Gly Ile Asp Lys Arg Thr Ile Glu Lys Phe Glu Lys Glu Ala Ala Glu
        35                  40                  45
Met Gly Lys Gly Ser Phe Lys Tyr Ala Trp Val Leu Asp Lys Leu Lys
50                  55                  60
Ala Glu Arg Glu Arg Gly Ile Thr Ile Asp Ile Ser Leu Trp Lys Phe
65                  70                  75                  80
Glu Thr Ser Lys Tyr Tyr Val Thr Ile Ile Asp Ala Pro Gly His Arg
                85                  90                  95
Asp Phe Ile Lys Asn Met Ile Thr Gly Thr Ser Gln Ala Asp Cys Ala
            100                 105                 110
Val Leu Ile Val Ala Ala Gly Val Gly Glu Phe Glu Ala Gly Ile Ser
        115                 120                 125
Lys Asn Gly Gln Thr Arg Glu His Ala Leu Leu Ala Tyr Thr Leu Gly
130                 135                 140
Val Lys Gln Leu Ile Val Gly Val Asn Lys Met Asp Ser Thr Glu Pro
145                 150                 155                 160
Pro Tyr Ser Gln Lys Arg Tyr Glu Glu Ile Val Lys Glu Val Ser Thr
                165                 170                 175
Tyr Ile Lys Lys Ile Gly Tyr Asn Pro Asp Thr Val Ala Phe Val Pro
            180                 185                 190
Ile Ser Gly Trp Asn Gly Asp Asn Met Leu Glu Pro Ser Ala Asn Met
        195                 200                 205
Pro Trp Phe Lys Gly Trp Lys Val Thr Arg Lys Asp Gly Asn Ala Ser
210                 215                 220
Gly Thr Thr Leu Leu Glu Ala Leu Asp Cys Ile Leu Pro Pro Thr Arg
225                 230                 235                 240
Pro Thr Asp Lys Pro Leu Arg Leu Pro Leu Gln Asp Val Tyr Lys Ile
                245                 250                 255
Gly Gly Ile Gly Thr Val Pro Val Gly Arg Val Glu Thr Gly Val Leu
            260                 265                 270
Lys Pro Gly Met Val Val Thr Phe Ala Pro Val Asn Val Thr Thr Glu
        275                 280                 285
Val Lys Ser Val Glu Asn Asp Pro Pro Met Glu Ala Ala Gly Phe Thr
290                 295                 300
Ala Gln Val Ile Ile Leu Asn His Pro Gly Gln Ile Ser Ala Gly Tyr
305                 310                 315                 320
Ala Pro Val Leu Asp Cys His Thr Ala His Ile Ala Cys Lys Phe Ala
                325                 330                 335
Glu Leu Lys Glu Lys Ile Asp Arg Arg Ser Gly Lys Lys Leu Glu Asp
            340                 345                 350
Gly Pro Lys Phe Leu Lys Ser Gly Asp Ala Ala Ile Val Asp Met Val
        355                 360                 365
Pro Gly Lys Pro Met Cys Val Glu Ser Phe Ser Asp Tyr Pro Pro Leu
370                 375                 380
Gly Arg Phe Ala Val Arg Asp Met Arg Gln Thr Val Ala Val Gly Val
385                 390                 395                 400
```

Ile Lys Ala Val Asp Lys Lys Ala Ala Gly Ala Lys Val Thr Lys
                405                 410                 415

Ser Ala Gln Lys Ala Gln Lys Ala Lys
            420                 425

<210> SEQ ID NO 10
<211> LENGTH: 399
<212> TYPE: PRT
<213> ORGANISM: Homo sapiens

<400> SEQUENCE: 10

Met Gly Lys Glu Lys Thr His Ile Thr Ile Asp Ile Ser Leu Trp Lys
1               5                   10                  15

Phe Glu Thr Ser Lys Tyr Tyr Val Thr Ile Ile Asp Ala Pro Gly His
                20                  25                  30

Arg Asp Phe Ile Lys Asn Met Ile Thr Gly Thr Ser Gln Ala Asp Cys
            35                  40                  45

Ala Val Leu Ile Val Ala Ala Gly Val Gly Glu Phe Glu Ala Gly Ile
        50                  55                  60

Ser Lys Asn Gly Gln Thr Arg Glu His Ala Leu Leu Ala Tyr Thr Leu
65              70                  75                  80

Gly Val Lys Gln Leu Ile Val Gly Val Asn Lys Met Asp Ser Thr Glu
                85                  90                  95

Pro Pro Tyr Ser Gln Lys Arg Tyr Glu Glu Ile Val Lys Glu Val Ser
            100                 105                 110

Thr Tyr Ile Lys Lys Ile Gly Tyr Asn Pro Asp Thr Val Ala Phe Val
        115                 120                 125

Pro Ile Ser Gly Trp Asn Gly Asp Asn Met Leu Glu Pro Ser Ala Asn
130                 135                 140

Met Pro Trp Phe Lys Gly Trp Lys Val Thr Arg Lys Asp Gly Asn Ala
145                 150                 155                 160

Ser Gly Thr Thr Leu Leu Glu Ala Leu Asp Cys Ile Leu Pro Pro Thr
                165                 170                 175

Arg Pro Thr Asp Lys Pro Leu Arg Leu Pro Leu Gln Asp Val Tyr Lys
            180                 185                 190

Ile Gly Gly Ile Gly Thr Val Pro Val Gly Arg Val Glu Thr Gly Val
        195                 200                 205

Leu Lys Pro Gly Met Val Val Thr Phe Ala Pro Val Asn Val Thr Thr
210                 215                 220

Glu Val Lys Ser Val Glu Met His His Glu Ala Leu Ser Glu Ala Leu
225                 230                 235                 240

Pro Gly Asp Asn Val Gly Phe Asn Val Lys Asn Val Ser Val Lys Asp
                245                 250                 255

Val Arg Arg Gly Asn Val Ala Gly Asp Ser Lys Asn Asp Pro Pro Met
            260                 265                 270

Glu Ala Ala Gly Phe Thr Ala Gln Val Ile Ile Leu Asn His Pro Gly
        275                 280                 285

Gln Ile Ser Ala Gly Tyr Ala Pro Val Leu Asp Cys His Thr Ala His
290                 295                 300

Ile Ala Cys Lys Phe Ala Glu Leu Lys Glu Lys Ile Asp Arg Arg Ser
305                 310                 315                 320

Gly Lys Lys Leu Glu Asp Gly Pro Lys Phe Leu Lys Ser Gly Asp Ala
                325                 330                 335

Ala Ile Val Asp Met Val Pro Gly Lys Pro Met Cys Val Glu Ser Phe
            340                 345                 350

Ser Asp Tyr Pro Pro Leu Gly Arg Phe Ala Val Arg Asp Met Arg Gln
        355                 360                 365

Thr Val Ala Val Gly Val Ile Lys Ala Val Asp Lys Lys Ala Ala Gly
        370                 375                 380

Ala Gly Lys Val Thr Lys Ser Ala Gln Lys Ala Gln Lys Ala Lys
385                 390                 395

<210> SEQ ID NO 11
<211> LENGTH: 155
<212> TYPE: PRT
<213> ORGANISM: Homo sapiens

<400> SEQUENCE: 11

Met Gly Lys Glu Lys Thr His Ile Asn Ile Val Val Ile Gly His Val
1               5                   10                  15

Asp Ser Gly Lys Ser Thr Thr Thr Gly His Leu Ile Tyr Lys Cys Gly
            20                  25                  30

Gly Ile Asp Lys Arg Thr Ile Glu Lys Phe Glu Lys Glu Ala Ala Glu
        35                  40                  45

Met Gly Lys Gly Ser Phe Lys Tyr Ala Trp Val Leu Asp Lys Leu Lys
50                  55                  60

Ala Glu Arg Glu Arg Gly Ile Thr Ile Asp Ile Ser Leu Trp Lys Phe
65                  70                  75                  80

Glu Thr Ser Lys Tyr Tyr Val Thr Ile Ile Asp Ala Ala Ile Val Asp
                85                  90                  95

Met Val Pro Gly Lys Pro Met Cys Val Glu Ser Phe Ser Asp Tyr Pro
            100                 105                 110

Pro Leu Gly Arg Phe Ala Val Arg Asp Met Arg Gln Thr Val Ala Val
        115                 120                 125

Gly Val Ile Lys Ala Val Asp Lys Lys Ala Ala Gly Ala Gly Lys Val
    130                 135                 140

Thr Lys Ser Ala Gln Lys Ala Gln Lys Ala Lys
145                 150                 155

<210> SEQ ID NO 12
<211> LENGTH: 43
<212> TYPE: PRT
<213> ORGANISM: Homo sapiens

<400> SEQUENCE: 12

Met Gly Lys Glu Lys Thr His Ile Asn Ile Val Val Ile Gly His Val
1               5                   10                  15

Asp Ser Gly Lys Ser Thr Thr Thr Gly His Leu Ile Tyr Lys Cys Gly
            20                  25                  30

Gly Ile Asp Lys Ser Ser Leu Ala Trp Ile Asn
        35                  40

<210> SEQ ID NO 13
<211> LENGTH: 62
<212> TYPE: PRT
<213> ORGANISM: Homo sapiens

<400> SEQUENCE: 13

Met Gly Lys Glu Lys Thr His Ile Asn Ile Val Val Ile Gly His Val
1               5                   10                  15

Asp Ser Gly Lys Ser Thr Thr Thr Gly His Leu Ile Tyr Lys Cys Gly
            20                  25                  30

```
Gly Ile Asp Lys Arg Thr Ile Glu Lys Phe Lys Glu Ala Ala Glu
             35                  40                  45

Met Gly Lys Gly Ser Phe Lys Tyr Ala Trp Ser Trp Ile Asn
 50                  55                  60
```

<210> SEQ ID NO 14
<211> LENGTH: 462
<212> TYPE: PRT
<213> ORGANISM: Homo sapiens

<400> SEQUENCE: 14

```
Met Gly Lys Glu Lys Thr His Ile Asn Ile Val Val Ile Gly His Val
 1               5                  10                  15

Asp Ser Gly Lys Ser Thr Thr Thr Gly His Leu Ile Tyr Lys Cys Gly
             20                  25                  30

Gly Ile Asp Lys Arg Thr Ile Glu Lys Phe Glu Lys Glu Ala Ala Glu
             35                  40                  45

Met Gly Lys Gly Ser Phe Lys Tyr Ala Trp Val Leu Asp Lys Leu Lys
 50                  55                  60

Ala Glu Arg Glu Arg Gly Ile Thr Ile Asp Ile Ser Leu Trp Lys Phe
 65                  70                  75                  80

Glu Thr Ser Lys Tyr Tyr Val Thr Ile Ile Asp Ala Pro Gly His Arg
                 85                  90                  95

Asp Phe Ile Lys Asn Met Ile Thr Gly Thr Ser Gln Ala Asp Cys Ala
            100                 105                 110

Val Leu Ile Val Ala Ala Gly Val Gly Glu Phe Glu Ala Gly Ile Ser
        115                 120                 125

Lys Asn Gly Gln Thr Arg Glu His Ala Leu Leu Ala Tyr Thr Leu Gly
    130                 135                 140

Val Lys Gln Leu Ile Val Gly Val Asn Lys Met Asp Ser Thr Glu Pro
145                 150                 155                 160

Pro Tyr Ser Gln Lys Arg Tyr Glu Glu Ile Val Lys Glu Val Ser Thr
                165                 170                 175

Tyr Ile Lys Lys Ile Gly Tyr Asn Pro Asp Thr Val Ala Phe Val Pro
            180                 185                 190

Ile Ser Gly Trp Asn Gly Asp Asn Met Leu Glu Pro Ser Ala Asn Met
        195                 200                 205

Pro Trp Phe Lys Gly Trp Lys Val Thr Arg Lys Asp Gly Asn Ala Ser
    210                 215                 220

Gly Thr Thr Leu Leu Glu Ala Leu Asp Cys Ile Leu Pro Pro Thr Arg
225                 230                 235                 240

Pro Thr Asp Lys Pro Leu Arg Leu Pro Leu Gln Asp Val Tyr Lys Ile
                245                 250                 255

Gly Gly Ile Gly Thr Val Pro Val Gly Arg Val Glu Thr Gly Val Leu
            260                 265                 270

Lys Pro Gly Met Val Val Thr Phe Ala Pro Val Asn Val Thr Thr Glu
        275                 280                 285

Val Lys Ser Val Glu Met His His Glu Ala Leu Ser Glu Ala Leu Pro
    290                 295                 300

Gly Asp Asn Val Gly Phe Asn Val Lys Asn Val Ser Val Lys Asp Val
305                 310                 315                 320

Arg Arg Gly Asn Val Ala Gly Asp Ser Lys Asn Asp Pro Pro Met Glu
                325                 330                 335

Ala Ala Gly Phe Thr Ala Gln Val Ile Ile Leu Asn His Pro Gly Gln
            340                 345                 350
```

Ile Ser Ala Gly Tyr Ala Pro Val Leu Asp Cys His Thr Ala His Ile
        355                 360                 365

Ala Cys Lys Phe Ala Glu Leu Lys Glu Lys Ile Asp Arg Arg Ser Gly
370                 375                 380

Lys Lys Leu Glu Asp Gly Pro Lys Phe Leu Lys Ser Gly Asp Ala Ala
385                 390                 395                 400

Ile Val Asp Met Val Pro Gly Lys Pro Met Cys Val Glu Ser Phe Ser
                405                 410                 415

Asp Tyr Pro Pro Leu Gly Arg Phe Ala Val Arg Asp Met Arg Gln Thr
            420                 425                 430

Val Ala Val Gly Val Ile Lys Ala Val Asp Lys Ala Ala Gly Ala
        435                 440                 445

Gly Lys Val Thr Lys Ser Ala Gln Lys Ala Gln Lys Ala Lys
    450                 455                 460

<210> SEQ ID NO 15
<211> LENGTH: 225
<212> TYPE: PRT
<213> ORGANISM: Homo sapiens

<400> SEQUENCE: 15

Gly His Val Asp Ser Gly Lys Ser Thr Thr Thr Gly His Leu Ile Tyr
1               5                   10                  15

Lys Cys Gly Gly Ile Asp Lys Arg Thr Ile Glu Lys Phe Glu Lys Glu
                20                  25                  30

Ala Ala Glu Met Gly Lys Gly Ser Phe Lys Tyr Ala Trp Val Leu Asp
            35                  40                  45

Lys Leu Lys Ala Glu Arg Glu Arg Gly Ile Thr Ile Asp Ile Ser Leu
    50                  55                  60

Trp Lys Phe Glu Thr Ser Lys Tyr Tyr Val Thr Ile Ile Asp Ala Pro
65                  70                  75                  80

Gly His Arg Asp Phe Ile Lys Asn Met Ile Thr Gly Thr Ser Gln Ala
                85                  90                  95

Asp Cys Ala Val Leu Ile Val Ala Ala Gly Val Gly Glu Phe Glu Ala
            100                 105                 110

Gly Ile Ser Lys Asn Gly Gln Thr Arg Glu His Ala Leu Leu Ala Tyr
        115                 120                 125

Thr Leu Gly Val Lys Gln Leu Ile Val Gly Val Asn Lys Met Asp Ser
    130                 135                 140

Thr Glu Pro Pro Tyr Ser Gln Lys Arg Tyr Glu Glu Ile Val Lys Glu
145                 150                 155                 160

Val Ser Thr Tyr Ile Lys Lys Ile Gly Tyr Asn Pro Asp Thr Val Ala
                165                 170                 175

Phe Val Pro Ile Ser Gly Trp Asn Gly Asp Asn Met Leu Glu Pro Ser
            180                 185                 190

Ala Asn Met Pro Trp Phe Lys Gly Trp Lys Val Thr Arg Lys Asp Gly
        195                 200                 205

Asn Ala Ser Gly Thr Thr Leu Leu Glu Ala Leu Asp Cys Ile Leu Pro
    210                 215                 220

Pro
225

<210> SEQ ID NO 16
<211> LENGTH: 70
<212> TYPE: PRT

<213> ORGANISM: Homo sapiens

<400> SEQUENCE: 16

Gly Thr Val Pro Val Gly Arg Val Glu Thr Gly Val Leu Lys Pro Gly
1               5                   10                  15
Met Val Val Thr Phe Ala Pro Val Asn Val Thr Thr Glu Val Lys Ser
            20                  25                  30
Val Glu Met His His Glu Ala Leu Ser Glu Ala Leu Pro Gly Asp Asn
        35                  40                  45
Val Gly Phe Asn Val Lys Asn Val Ser Val Lys Asp Val Arg Arg Gly
    50                  55                  60
Asn Val Ala Gly Asp Ser
65                  70

<210> SEQ ID NO 17
<211> LENGTH: 90
<212> TYPE: PRT
<213> ORGANISM: Homo sapiens

<400> SEQUENCE: 17

Pro Pro Met Glu Ala Ala Gly Phe Thr Ala Gln Val Ile Ile Leu Asn
1               5                   10                  15
His Pro Gly Gln Ile Ser Ala Gly Tyr Ala Pro Val Leu Asp Cys His
            20                  25                  30
Thr Ala His Ile Ala Cys Lys Phe Ala Glu Leu Lys Glu Lys Ile Asp
        35                  40                  45
Arg Arg Ser Gly Lys Lys Leu Glu Asp Gly Pro Lys Phe Leu Lys Ser
    50                  55                  60
Gly Asp Ala Ala Ile Val Asp Met Val Pro Gly Lys Pro Met Cys Val
65                  70                  75                  80
Glu Ser Phe Ser Asp Tyr Pro Pro Leu Gly
                85                  90

<210> SEQ ID NO 18
<211> LENGTH: 62
<212> TYPE: PRT
<213> ORGANISM: Homo sapiens

<400> SEQUENCE: 18

Met Gly Lys Glu Lys Thr His Ile Asn Ile Val Val Ile Gly His Val
1               5                   10                  15
Asp Ser Gly Lys Ser Thr Thr Thr Gly His Leu Ile Tyr Lys Cys Gly
            20                  25                  30
Gly Ile Asp Lys Arg Thr Ile Glu Lys Phe Glu Lys Glu Ala Ala Glu
        35                  40                  45
Met Gly Lys Gly Ser Phe Lys Tyr Ala Trp Val Trp Ile Asn
    50                  55                  60

<210> SEQ ID NO 19
<211> LENGTH: 59
<212> TYPE: PRT
<213> ORGANISM: Homo sapiens

<400> SEQUENCE: 19

Met Val Pro Gly Lys Pro Met Cys Val Glu Ser Phe Ser Asp Tyr Pro
1               5                   10                  15
Pro Leu Gly Arg Phe Ala Val Arg Asp Met Arg Gln Thr Val Ala Val
            20                  25                  30

```
Gly Val Ile Lys Ala Val Asp Lys Ala Ala Gly Ala Gly Lys Val
         35                  40                  45

Thr Lys Ser Ala Gln Lys Ala Gln Lys Ala Lys
     50                  55
```

<210> SEQ ID NO 20
<211> LENGTH: 88
<212> TYPE: PRT
<213> ORGANISM: Homo sapiens

<400> SEQUENCE: 20

```
Met Gly Lys Glu Lys Thr His Ile Asn Ile Val Val Ile Gly His Val
 1               5                  10                  15

Asp Ser Gly Lys Ser Thr Thr Thr Gly His Leu Ile Tyr Lys Cys Gly
                20                  25                  30

Gly Ile Asp Lys Arg Thr Ile Glu Lys Phe Glu Lys Glu Ala Ala Glu
             35                  40                  45

Met Gly Lys Gly Ser Phe Lys Tyr Ala Trp Val Leu Asp Lys Leu Lys
         50                  55                  60

Ala Glu Cys Val Asn Val Val Arg Ser Ile Asn Gln Leu Ile Asn Leu
 65                  70                  75                  80

Leu Ser Val Val Gly Asn Phe Glu
                     85
```

<210> SEQ ID NO 21
<211> LENGTH: 455
<212> TYPE: PRT
<213> ORGANISM: Homo sapiens

<400> SEQUENCE: 21

```
Met Gly Lys Glu Lys Thr His Ile Asn Ile Val Val Ile Gly His Val
 1               5                  10                  15

Asp Ser Gly Lys Ser Thr Thr Thr Gly His Leu Ile Tyr Lys Cys Gly
                20                  25                  30

Gly Ile Asp Lys Arg Thr Ile Glu Lys Phe Glu Lys Glu Ala Ala Glu
             35                  40                  45

Met Gly Lys Gly Ser Phe Lys Tyr Ala Trp Val Leu Asp Lys Leu Lys
         50                  55                  60

Ala Glu Arg Glu Arg Gly Ile Thr Ile Asp Ile Ser Leu Trp Lys Phe
 65                  70                  75                  80

Glu Thr Ser Lys Tyr Tyr Val Thr Ile Ile Asp Ala Pro Gly His Arg
                     85                  90                  95

Asp Phe Ile Lys Asn Met Ile Thr Gly Thr Ser Gln Ala Asp Cys Ala
                100                 105                 110

Val Leu Ile Val Ala Ala Gly Val Gly Glu Phe Glu Ala Gly Ile Ser
            115                 120                 125

Lys Asn Gly Gln Thr Arg Glu His Ala Leu Leu Ala Tyr Thr Leu Gly
        130                 135                 140

Val Lys Gln Leu Ile Val Gly Val Asn Lys Met Asp Ser Thr Glu Pro
145                 150                 155                 160

Pro Tyr Ser Gln Lys Arg Tyr Glu Glu Ile Val Lys Glu Val Ser Thr
                    165                 170                 175

Tyr Ile Lys Lys Ile Gly Tyr Asn Pro Asp Thr Val Ala Phe Val Pro
                180                 185                 190

Ile Ser Gly Trp Asn Gly Asp Asn Met Pro Trp Phe Lys Gly Trp Lys
            195                 200                 205
```

```
Val Thr Arg Lys Asp Gly Asn Ala Ser Gly Thr Thr Leu Leu Glu Ala
    210                 215                 220

Leu Asp Cys Ile Leu Pro Pro Thr Arg Pro Thr Asp Lys Pro Leu Arg
225                 230                 235                 240

Leu Pro Leu Gln Asp Val Tyr Lys Ile Gly Ile Gly Thr Val Pro
                245                 250                 255

Val Gly Arg Val Glu Thr Gly Val Leu Lys Pro Gly Met Val Val Thr
            260                 265                 270

Phe Ala Pro Val Asn Val Thr Thr Glu Val Lys Ser Val Glu Met His
            275                 280                 285

His Glu Ala Leu Ser Glu Ala Leu Pro Gly Asp Asn Val Gly Phe Asn
290                 295                 300

Val Lys Asn Val Ser Val Lys Asp Val Arg Arg Gly Asn Val Ala Gly
305                 310                 315                 320

Asp Ser Lys Asn Asp Pro Pro Met Glu Ala Ala Gly Phe Thr Ala Gln
                325                 330                 335

Val Ile Ile Leu Asn His Pro Gly Gln Ile Ser Ala Gly Tyr Ala Pro
            340                 345                 350

Val Leu Asp Cys His Thr Ala His Ile Ala Cys Lys Phe Ala Glu Leu
            355                 360                 365

Lys Glu Lys Ile Asp Arg Arg Ser Gly Lys Lys Leu Glu Asp Gly Pro
370                 375                 380

Lys Phe Leu Lys Ser Gly Asp Ala Ala Ile Val Asp Met Val Pro Gly
385                 390                 395                 400

Lys Pro Met Cys Val Glu Ser Phe Ser Asp Tyr Pro Pro Leu Gly Arg
                405                 410                 415

Phe Ala Val Arg Asp Met Arg Gln Thr Val Ala Val Gly Val Ile Lys
            420                 425                 430

Ala Val Asp Lys Lys Ala Ala Gly Ala Gly Lys Val Thr Lys Ser Ala
            435                 440                 445

Gln Lys Ala Gln Lys Ala Lys
    450                 455

<210> SEQ ID NO 22
<211> LENGTH: 415
<212> TYPE: PRT
<213> ORGANISM: Homo sapiens

<400> SEQUENCE: 22

Met Gly Lys Glu Lys Thr His Ile Asn Ile Val Val Ile Gly His Val
1               5                   10                  15

Asp Ser Gly Lys Ser Thr Thr Thr Gly His Leu Ile Tyr Lys Cys Gly
            20                  25                  30

Gly Ile Asp Lys Arg Thr Ile Glu Lys Phe Glu Lys Glu Ala Ala Glu
        35                  40                  45

Met Gly Lys Gly Ser Phe Lys Tyr Ala Trp Val Leu Asp Lys Leu Lys
    50                  55                  60

Ala Glu Arg Glu Arg Gly Ile Thr Ile Asp Ile Ser Leu Trp Lys Phe
65                  70                  75                  80

Glu Thr Ser Lys Tyr Tyr Val Thr Ile Ile Asp Ala Pro Gly His Arg
                85                  90                  95

Asp Phe Ile Lys Asn Met Ile Thr Gly Thr Ser Gln Ala Asp Cys Ala
            100                 105                 110

Val Leu Ile Val Ala Ala Gly Val Gly Glu Phe Glu Ala Gly Ile Ser
        115                 120                 125
```

Lys Asn Gly Gln Thr Arg Glu His Ala Leu Leu Ala Tyr Thr Leu Gly
            130                 135                 140

Val Lys Gln Leu Ile Val Gly Val Asn Lys Met Asp Ser Thr Glu Pro
145                 150                 155                 160

Pro Tyr Ser Gln Lys Arg Tyr Glu Glu Ile Val Lys Asp Gly Asn Ala
                165                 170                 175

Ser Gly Thr Thr Leu Leu Glu Ala Leu Asp Cys Ile Leu Pro Pro Thr
            180                 185                 190

Arg Pro Thr Asp Lys Pro Leu Arg Leu Pro Leu Gln Asp Val Tyr Lys
                195                 200                 205

Ile Gly Gly Ile Gly Thr Val Pro Val Gly Arg Val Glu Thr Gly Val
210                 215                 220

Leu Lys Pro Gly Met Val Val Thr Phe Ala Pro Val Asn Val Thr Thr
225                 230                 235                 240

Glu Val Lys Ser Val Glu Met His His Glu Ala Leu Ser Glu Ala Leu
                245                 250                 255

Pro Gly Asp Asn Val Gly Phe Asn Val Lys Asn Val Ser Val Lys Asp
            260                 265                 270

Val Arg Arg Gly Asn Val Ala Gly Asp Ser Lys Asn Asp Pro Pro Met
            275                 280                 285

Glu Ala Ala Gly Phe Thr Ala Gln Val Ile Ile Leu Asn His Pro Gly
290                 295                 300

Gln Ile Ser Ala Gly Tyr Ala Pro Val Leu Asp Cys His Thr Ala His
305                 310                 315                 320

Ile Ala Cys Lys Phe Ala Glu Leu Lys Glu Lys Ile Asp Arg Arg Ser
                325                 330                 335

Gly Lys Lys Leu Glu Asp Gly Pro Lys Phe Leu Lys Ser Gly Asp Ala
            340                 345                 350

Ala Ile Val Asp Met Val Pro Gly Lys Pro Met Cys Val Glu Ser Phe
355                 360                 365

Ser Asp Tyr Pro Pro Leu Gly Arg Phe Ala Val Arg Asp Met Arg Gln
370                 375                 380

Thr Val Ala Val Gly Val Ile Lys Ala Val Asp Lys Lys Ala Ala Gly
385                 390                 395                 400

Ala Gly Lys Val Thr Lys Ser Ala Gln Lys Ala Gln Lys Ala Lys
                405                 410                 415

<210> SEQ ID NO 23
<211> LENGTH: 222
<212> TYPE: PRT
<213> ORGANISM: Homo sapiens

<400> SEQUENCE: 23

Met Gly Lys Glu Lys Thr His Ile Asn Ile Val Val Ile Gly His Val
1               5                   10                  15

Asp Ser Gly Lys Ser Thr Thr Thr Gly His Leu Ile Tyr Lys Cys Gly
            20                  25                  30

Gly Ile Asp Lys Arg Thr Ile Glu Lys Phe Glu Lys Glu Leu Leu Arg
        35                  40                  45

Trp Glu Arg Ala Pro Ser Ser Met Pro Trp Phe Lys Gly Trp Lys Val
    50                  55                  60

Thr Arg Lys Asp Gly Asn Ala Ser Gly Thr Thr Leu Leu Glu Ala Leu
65                  70                  75                  80

Asp Cys Ile Leu Pro Pro Thr Arg Pro Thr Asp Lys Pro Leu Arg Leu

```
                         85                  90                  95
Pro Leu Gln Asp Val Tyr Lys Ile Gly Gly Ile Gly Thr Val Pro Val
                100                 105                 110
Gly Arg Val Glu Thr Gly Val Leu Lys Pro Gly Met Val Val Thr Phe
            115                 120                 125
Ala Pro Val Asn Val Thr Thr Glu Val Lys Ser Val Glu Met His His
        130                 135                 140
Glu Ala Leu Ser Glu Ala Leu Pro Gly Asp Asn Val Gly Phe Asn Val
145                 150                 155                 160
Lys Asn Val Ser Val Lys Asp Val Arg Arg Gly Asn Val Ala Gly Asp
                165                 170                 175
Ser Lys Asn Asp Pro Pro Met Glu Ala Ala Gly Phe Thr Ala Gln Val
                180                 185                 190
Ile Ile Leu Asn His Pro Gly Gln Ile Ser Ala Gly Tyr Ala Leu Tyr
                195                 200                 205
Trp Ile Ala Thr Arg Leu Thr Leu His Ala Ser Leu Leu Ser
        210                 215                 220

<210> SEQ ID NO 24
<211> LENGTH: 190
<212> TYPE: PRT
<213> ORGANISM: Homo sapiens

<400> SEQUENCE: 24

Met Gly Lys Glu Lys Thr His Ile Asn Ile Val Val Ile Gly His Val
1               5                   10                  15
Asp Ser Gly Lys Ser Thr Thr Thr Gly His Leu Ile Tyr Lys Cys Gly
                20                  25                  30
Gly Ile Asp Lys Arg Thr Ile Glu Lys Phe Glu Lys Glu Ala Ala Glu
            35                  40                  45
Met Gly Lys Gly Ser Phe Lys Tyr Ser Trp Val Leu Asp Lys Leu Lys
        50                  55                  60
Ala Glu Arg Glu Arg Gly Ile Thr Ile Asp Ile Ser Leu Trp Lys Phe
65                  70                  75                  80
Glu Thr Ser Lys Tyr Tyr Val Thr Ile Ile Asp Ala Pro Gly His Ile
                85                  90                  95
Ala Cys Lys Phe Ala Glu Leu Lys Glu Lys Ile Asp Arg Arg Ser Gly
                100                 105                 110
Lys Lys Leu Glu Asp Gly Pro Lys Phe Leu Lys Ser Gly Asp Ala Ala
            115                 120                 125
Ile Val Asp Met Val Pro Gly Lys Pro Met Cys Val Glu Ser Phe Ser
        130                 135                 140
Asp Tyr Pro Pro Leu Gly Arg Phe Ala Val Arg Asp Met Arg Gln Thr
145                 150                 155                 160
Val Ala Val Gly Val Ile Lys Ala Val Asp Lys Lys Ala Ala Gly Ala
                165                 170                 175
Gly Lys Val Thr Lys Ser Ala Gln Lys Ala Gln Lys Ala Lys
                180                 185                 190

<210> SEQ ID NO 25
<211> LENGTH: 459
<212> TYPE: PRT
<213> ORGANISM: Homo sapiens

<400> SEQUENCE: 25

Met Gly Lys Glu Lys Thr His Ile Asn Ile Val Val Ile Gly His Val
```

-continued

```
1               5                   10                  15
Asp Ser Gly Lys Ser Thr Thr Thr Gly His Leu Ile Tyr Lys Cys Gly
                20                  25                  30
Gly Ile Asp Lys Arg Thr Ile Glu Lys Phe Glu Lys Glu Ala Ala Glu
                35                  40                  45
Met Gly Lys Gly Ser Phe Lys Tyr Ala Trp Val Leu Asp Lys Leu Lys
 50                  55                  60
Ala Glu Arg Glu Arg Gly Ile Thr Ile Asp Ile Ser Leu Trp Lys Phe
 65                  70                  75                  80
Glu Thr Ser Lys Tyr Tyr Val Thr Ile Ile Asp Ala Pro Gly His Arg
                85                  90                  95
Asp Phe Ile Lys Asn Met Ile Thr Gly Thr Ser Gln Ala Asp Cys Ala
                100                 105                 110
Val Leu Ile Val Ala Ala Gly Val Gly Glu Phe Glu Ala Gly Ile Ser
                115                 120                 125
Lys Asn Gly Gln Thr Arg Glu His Ala Leu Leu Ala Tyr Thr Leu Gly
                130                 135                 140
Val Lys Gln Leu Ile Val Gly Val Asn Lys Met Asp Ser Thr Glu Pro
145                 150                 155                 160
Pro Tyr Ser Gln Lys Arg Tyr Glu Glu Ile Val Lys Glu Val Ser Thr
                165                 170                 175
Tyr Ile Lys Lys Ile Gly Tyr Asn Pro Asp Thr Val Ala Phe Val Pro
                180                 185                 190
Ile Ser Gly Trp Asn Gly Asp Asn Met Leu Glu Pro Ser Ala Asn Met
                195                 200                 205
Pro Trp Phe Lys Gly Trp Lys Val Thr Arg Lys Asp Gly Asn Ala Ser
                210                 215                 220
Gly Thr Thr Leu Leu Glu Ala Leu Thr Ala Ser Tyr Thr Asn Ser Ser
225                 230                 235                 240
Thr Asp Asn Leu Ala Pro Ala Ser Pro Gly Cys Leu Gln Asn Val Tyr
                245                 250                 255
Trp Tyr Cys Ser Cys Trp Pro Ser Glu Thr Gly Val Leu Lys Pro Gly
                260                 265                 270
Met Val Val Thr Phe Ala Pro Val Asn Val Thr Thr Glu Val Lys Ser
                275                 280                 285
Val Glu Met His His Glu Ala Leu Ser Glu Ala Leu Pro Gly Asp Asn
                290                 295                 300
Val Gly Phe Asn Val Lys Asn Val Ser Val Lys Asp Val Arg Arg Gly
305                 310                 315                 320
Asn Val Ala Gly Asp Ser Lys Asn Asp Pro Pro Met Glu Ala Ala Gly
                325                 330                 335
Phe Thr Ala Gln Val Ile Ile Leu Asn His Pro Gly Gln Ile Ser Ala
                340                 345                 350
Gly Tyr Ala Pro Val Leu Asp Cys His Thr Ala His Ile Ala Cys Lys
                355                 360                 365
Phe Ala Glu Leu Lys Glu Lys Ile Asp Arg Arg Ser Gly Lys Lys Leu
                370                 375                 380
Glu Asp Gly Pro Lys Phe Leu Lys Ser Gly Asp Ala Ala Ile Val Asp
385                 390                 395                 400
Met Val Pro Gly Lys Pro Met Cys Val Glu Ser Phe Ser Asp Tyr Pro
                405                 410                 415
Pro Leu Gly Arg Phe Ala Val Arg Asp Met Arg Gln Thr Val Ala Val
                420                 425                 430
```

Gly Val Ile Lys Ala Val Asp Lys Ala Gly Ala Gly Lys Val
            435                 440                 445

Thr Lys Ser Ala Gln Lys Ala Gln Lys Ala Lys
        450                 455

<210> SEQ ID NO 26
<211> LENGTH: 296
<212> TYPE: PRT
<213> ORGANISM: Homo sapiens

<400> SEQUENCE: 26

Met Gly Lys Glu Lys Thr His Ile Asn Ile Val Val Ile Gly His Val
1               5                   10                  15

Asp Ser Gly Lys Ser Thr Thr Thr Gly His Leu Ile Tyr Lys Cys Gly
                20                  25                  30

Gly Ile Asp Lys Arg Thr Ile Glu Lys Phe Glu Lys Glu Ala Ala Glu
            35                  40                  45

Met Gly Lys Gly Ser Phe Lys Tyr Ala Trp Val Leu Asp Lys Leu Lys
        50                  55                  60

Ala Glu Arg Glu Arg Gly Ile Thr Ile Asp Ile Ser Leu Trp Lys Phe
65                  70                  75                  80

Glu Thr Ser Lys Tyr Tyr Val Thr Ile Lys Asn Met Ile Thr Gly Thr
                85                  90                  95

Ser Gln Ala Asp Cys Ala Val Leu Ile Val Ala Ala Gly Val Gly Glu
                100                 105                 110

Phe Glu Ala Gly Ile Ser Lys Asn Gly Gln Thr Arg Glu His Ala Leu
            115                 120                 125

Leu Ala Tyr Thr Leu Gly Val Lys Gln Leu Ile Val Gly Val Asn Lys
        130                 135                 140

Met Asp Ser Thr Glu Pro Pro Tyr Ser Gln Lys Arg Tyr Glu Glu Ile
145                 150                 155                 160

Val Lys Glu Val Ser Thr Tyr Ile Lys Lys Ile Gly Tyr Asn Pro Asp
                165                 170                 175

Thr Val Ala Phe Val Pro Ile Ser Gly Trp Asn Gly Asp Asn Met Leu
            180                 185                 190

Glu Pro Ser Ala Asn Met Pro Trp Phe Lys Gly Trp Lys Val Thr Val
        195                 200                 205

Arg Met Ala Met Pro Val Glu Pro Arg Cys Leu Arg Leu Trp Thr Ala
210                 215                 220

Ser Tyr His Gln Leu Val Gln Leu Thr Ser Pro Cys Ala Cys Leu Ser
225                 230                 235                 240

Arg Met Ser Thr Lys Leu Val Val Leu Val Leu Phe Leu Leu Ala Glu
                245                 250                 255

Trp Arg Leu Val Phe Ser Asn Pro Val Trp Trp Ser Pro Leu Leu Gln
            260                 265                 270

Ser Thr Leu Gln Cys Gly Leu Gln Cys Gln Cys Val Cys Gln Gly
        275                 280                 285

Cys Ser Ser Trp Gln Arg Cys Trp
    290                 295

<210> SEQ ID NO 27
<211> LENGTH: 205
<212> TYPE: PRT
<213> ORGANISM: Homo sapiens

<400> SEQUENCE: 27

```
Met Gly Lys Glu Lys Thr His Ile Asn Ile Val Val Ile Gly His Val
1               5                   10                  15

Asp Ser Gly Lys Ser Thr Thr Thr Gly His Leu Ile Tyr Lys Cys Gly
                20                  25                  30

Gly Ile Asp Lys Arg Thr Ile Glu Lys Phe Glu Lys Glu Ala Ala Glu
            35                  40                  45

Met Gly Lys Gly Ser Phe Lys Tyr Ala Trp Val Leu Asp Lys Leu Lys
    50                  55                  60

Ala Glu Arg Glu Arg Gly Ile Thr Ile Asp Ile Ser Leu Trp Lys Phe
65                  70                  75                  80

Glu Thr Ser Lys Tyr Tyr Val Ile Ile Leu Asn His Pro Gly Gln Ile
                85                  90                  95

Ser Ala Gly Tyr Ala Pro Val Leu Asp Cys His Thr Ala His Ile Ala
            100                 105                 110

Cys Lys Phe Ala Glu Leu Lys Glu Lys Ile Asp Arg Arg Ser Gly Lys
        115                 120                 125

Lys Leu Glu Asp Gly Pro Lys Phe Leu Lys Ser Gly Asp Ala Ala Ile
130                 135                 140

Val Asp Met Val Pro Gly Lys Pro Met Cys Val Glu Ser Phe Ser Asp
145                 150                 155                 160

Tyr Pro Pro Leu Gly Arg Phe Ala Val Arg Asp Met Arg Gln Thr Val
                165                 170                 175

Ala Val Gly Val Ile Lys Ala Val Asp Lys Lys Ala Ala Gly Ala Gly
            180                 185                 190

Lys Val Thr Lys Ser Ala Gln Lys Ala Gln Lys Ala Lys
        195                 200                 205

<210> SEQ ID NO 28
<211> LENGTH: 208
<212> TYPE: PRT
<213> ORGANISM: Homo sapiens

<400> SEQUENCE: 28

Met Gly Lys Glu Lys Thr His Ile Asn Ile Val Val Ile Gly His Val
1               5                   10                  15

Asp Ser Gly Lys Ser Thr Thr Thr Gly His Leu Ile Tyr Lys Cys Gly
                20                  25                  30

Gly Ile Asp Lys Arg Thr Ile Glu Lys Phe Glu Lys Glu Ala Ala Glu
            35                  40                  45

Met Gly Lys Gly Ser Phe Lys Tyr Ala Trp Val Leu Asp Lys Leu Lys
    50                  55                  60

Ala Glu Arg Glu Arg Gly Ile Thr Ile Asp Ile Ser Leu Trp Lys Phe
65                  70                  75                  80

Glu Thr Ser Lys Tyr Tyr Val Thr Ile Ile Asp Ala Pro Gly His Arg
                85                  90                  95

Asp Phe Ile Lys Asn Met Ile Thr Gly Thr Ser Gln Ala Asp Cys Ala
            100                 105                 110

Val Leu Ile Val Ala Ala Gly Val Gly Glu Phe Glu Ala Gly Ile Ser
        115                 120                 125

Lys Asn Gly Gln Thr Arg Glu His Ala Leu Leu Ala Tyr Thr Leu Gly
130                 135                 140

Val Lys Gln Leu Ile Val Gly Val Asn Lys Met Asp Ser Thr Glu Pro
145                 150                 155                 160

Pro Tyr Ser Gln Lys Arg Tyr Glu Glu Ile Val Lys Glu Lys Ile Asp
```

```
                     165                 170                 175
Arg Arg Ser Gly Lys Lys Leu Glu Asp Gly Pro Lys Phe Leu Lys Ser
            180                 185                 190

Gly Asp Ala Ala Ile Val Asp Met Val Ser Trp Gln Ala His Val Cys
            195                 200                 205

<210> SEQ ID NO 29
<211> LENGTH: 375
<212> TYPE: PRT
<213> ORGANISM: Homo sapiens

<400> SEQUENCE: 29

Met Gly Lys Glu Lys Thr His Ile Asn Ile Val Val Ile Gly His Val
1               5                   10                  15

Asp Ser Gly Lys Ser Thr Thr Thr Gly His Leu Ile Tyr Lys Cys Gly
            20                  25                  30

Gly Ile Asp Lys Arg Thr Ile Glu Lys Phe Glu Lys Glu Ala Ala Glu
        35                  40                  45

Met Gly Lys Gly Ser Phe Lys Tyr Ala Trp Val Leu Asp Lys Leu Lys
    50                  55                  60

Ala Glu Arg Glu Arg Gly Ile Thr Ile Asp Ile Ser Leu Trp Lys Phe
65                  70                  75                  80

Glu Thr Ser Lys Tyr Tyr Val Thr Ile Ile Asp Ala Pro Gly His Arg
                85                  90                  95

Asp Phe Ile Lys Asn Met Ile Thr Gly Thr Ser Gln Ala Asp Cys Ala
            100                 105                 110

Val Leu Ile Val Ala Ala Gly Val Gly Glu Phe Glu Ala Gly Ile Ser
        115                 120                 125

Lys Asn Gly Gln Thr Arg Glu His Ala Leu Leu Ala Tyr Thr Leu Gly
    130                 135                 140

Val Lys Gln Leu Ile Val Gly Val Asn Lys Met Asp Ser Thr Glu Pro
145                 150                 155                 160

Pro Tyr Ser Gln Lys Arg Tyr Glu Glu Ile Val Lys Glu Val Ser Thr
                165                 170                 175

Tyr Ile Lys Lys Ile Gly Tyr Asn Pro Asp Thr Val Ala Phe Val Pro
            180                 185                 190

Ile Ser Gly Trp Asn Gly Asp Asn Met Leu Glu Pro Ser Ala Asn Met
        195                 200                 205

Pro Trp Phe Lys Gly Trp Lys Val Thr Arg Lys Asp Gly Asn Ala Ser
    210                 215                 220

Gly Thr Thr Leu Leu Glu Ala Leu Asp Cys Ile Leu Pro Pro Thr Arg
225                 230                 235                 240

Pro Thr Asp Lys Pro Leu Arg Leu Pro Leu Gln Asp Val Tyr Lys Ile
                245                 250                 255

Gly Gly Ile Gly Thr Val Pro Val Gly Arg Val Glu Thr Gly Val Leu
            260                 265                 270

Lys Pro Gly Met Val Val Thr Phe Ala Pro Val Asn Val Thr Thr Glu
        275                 280                 285

Val Lys Ser Val Glu Met His His Glu Ala Leu Ser Glu Ala Leu Pro
    290                 295                 300

Gly Asp Asn Val Gly Phe Asn Val Lys Asn Val Ser Val Lys Asp Val
305                 310                 315                 320

Arg Arg Gly Asn Val Ala Gly Asp Ser Lys Asn Asp Pro Pro Met Glu
                325                 330                 335
```

```
Ala Ala Gly Phe Thr Ala Gln Val Ile Ile Leu Asn His Pro Gly Gln
            340                 345                 350

Ile Ser Ala Gly Tyr Ala Pro Val Leu Asp Cys His Thr Ala His Ile
        355                 360                 365

Ala Cys Lys Phe Ala Glu Leu
    370                 375

<210> SEQ ID NO 30
<211> LENGTH: 140
<212> TYPE: PRT
<213> ORGANISM: Homo sapiens

<400> SEQUENCE: 30

Met Gly Lys Glu Lys Thr His Ile Asn Ile Val Val Ile Gly His Val
1               5                   10                  15

Asp Ser Gly Lys Ser Thr Thr Thr Gly His Leu Ile Tyr Lys Cys Gly
            20                  25                  30

Gly Ile Asp Lys Arg Thr Ile Glu Lys Phe Glu Lys Glu Ala Ala Glu
        35                  40                  45

Met Gly Lys Gly Ser Phe Lys Tyr Ala Trp Val Leu Asp Lys Leu Lys
    50                  55                  60

Ala Glu Arg Glu Arg Gly Ile Thr Ile Asp Ile Ser Leu Trp Lys Phe
65                  70                  75                  80

Glu Thr Ser Lys Tyr Tyr Val Thr Ile Ile Asp Ala Pro Gly His Arg
                85                  90                  95

Asp Phe Ile Lys Asn Met Ile Thr Gly Thr Ser Gln Ala Asp Cys Ala
            100                 105                 110

Val Leu Ile Val Ala Ala Gly Val Gly Glu Phe Glu Ala Gly Ile Ser
        115                 120                 125

Lys Asn Gly Gln Thr Arg Glu His Ala Leu Asn Ser
    130                 135                 140

<210> SEQ ID NO 31
<211> LENGTH: 29
<212> TYPE: PRT
<213> ORGANISM: Homo sapiens

<400> SEQUENCE: 31

Met Gly Lys Gly Lys Asp Ser Tyr Gln His Cys Arg His Trp Thr Arg
1               5                   10                  15

Arg Phe Gly Gln Val His His Tyr Trp Pro Ser Asp Leu
            20                  25

<210> SEQ ID NO 32
<211> LENGTH: 108
<212> TYPE: PRT
<213> ORGANISM: Homo sapiens

<400> SEQUENCE: 32

Met Gly Lys Glu Lys Thr His Ile Asn Ile Val Val Ile Gly His Val
1               5                   10                  15

Asp Ser Gly Lys Ser Thr Thr Thr Gly His Leu Ile Tyr Lys Cys Gly
            20                  25                  30

Gly Ile Asp Lys Arg Thr Ile Glu Lys Phe Glu Lys Glu Ala Ala Glu
        35                  40                  45

Met Gly Lys Gly Ser Phe Lys Tyr Ala Trp Val Leu Asp Lys Leu Lys
    50                  55                  60

Ala Glu Arg Glu Arg Gly Ile Thr Ile Asp Ile Ser Leu Trp Lys Phe
```

```
                65                  70                  75                  80
Glu Thr Ser Lys Tyr Tyr Val Thr Ile Ile Asp Ala Gln Asp Thr Glu
                    85                  90                  95

Thr Leu Ser Lys His Asp Tyr Arg Asp Ile Ser Gly
                100                 105
```

<210> SEQ ID NO 33
<211> LENGTH: 87
<212> TYPE: PRT
<213> ORGANISM: Homo sapiens

<400> SEQUENCE: 33

```
Met Gly Lys Glu Lys Thr His Ile Asn Ile Val Val Ile Gly His Val
1               5                   10                  15

Asp Ser Gly Lys Ser Thr Thr Thr Gly His Leu Ile Tyr Lys Cys Gly
                20                  25                  30

Gly Ile Asp Lys Arg Thr Ile Glu Lys Phe Glu Lys Glu Ala Ala Glu
                35                  40                  45

Met Gly Lys Gly Ser Phe Lys Tyr Ala Trp Val Leu Asp Lys Leu Lys
        50                  55                  60

Thr Arg Tyr Gly Gly His Leu Cys Ser Ser Gln Arg Tyr Asn Gly Ser
65                  70                  75                  80

Lys Ile Cys Arg Asn Ala Pro
                85
```

<210> SEQ ID NO 34
<211> LENGTH: 86
<212> TYPE: PRT
<213> ORGANISM: Homo sapiens

<400> SEQUENCE: 34

```
Met Gly Lys Glu Lys Thr His Ile Asn Ile Val Val Ile Gly His Val
1               5                   10                  15

Asp Ser Gly Lys Ser Thr Thr Thr Gly His Leu Ile Tyr Lys Cys Gly
                20                  25                  30

Gly Ile Asp Lys Arg Thr Ile Glu Lys Phe Glu Lys Glu Ala Ala Glu
                35                  40                  45

Met Gly Lys Gly Ser Phe Lys Tyr Ala Trp Val Leu Asp Lys Leu Lys
        50                  55                  60

Ala Glu Arg Glu Arg Gly Ile Thr Ile Asp Ile Ser Leu Trp Lys Gln
65                  70                  75                  80

Leu Ala Ser Leu Leu Arg
                85
```

<210> SEQ ID NO 35
<211> LENGTH: 83
<212> TYPE: PRT
<213> ORGANISM: Homo sapiens

<400> SEQUENCE: 35

```
Met Gly Lys Glu Lys Thr His Ile Asn Ile Val Val Ile Gly His Val
1               5                   10                  15

Asp Ser Gly Lys Ser Thr Thr Thr Gly His Leu Ile Tyr Lys Cys Gly
                20                  25                  30

Gly Ile Asp Lys Arg Thr Ile Glu Lys Phe Glu Lys Glu Ala Ala Glu
                35                  40                  45

Met Gly Lys Gly Ser Phe Lys Tyr Ala Trp Val Leu Asp Lys Leu Lys
        50                  55                  60
```

Ala Glu Arg Glu Arg Gly Ile Thr Ile Asp Ile Ser Leu Trp Lys Phe
65                  70                  75                  80

Glu Thr Lys

<210> SEQ ID NO 36
<211> LENGTH: 218
<212> TYPE: PRT
<213> ORGANISM: Homo sapiens

<400> SEQUENCE: 36

Met Gly Lys Gly Ser Phe Lys Tyr Ala Trp Val Leu Asp Lys Leu Lys
1               5                   10                  15

Ala Glu Arg Glu Arg Gly Val Leu Lys Pro Gly Met Val Val Thr Phe
                20                  25                  30

Ala Pro Val Asn Val Thr Thr Glu Val Lys Ser Val Glu Met His His
                35                  40                  45

Glu Ala Leu Ser Glu Ala Leu Pro Gly Asp Asn Val Gly Phe Asn Val
            50                  55                  60

Lys Asn Val Ser Val Lys Asp Val Arg Arg Gly Asn Val Ala Gly Asp
65                  70                  75                  80

Ser Lys Asn Asp Pro Pro Met Glu Ala Ala Gly Phe Thr Ala Gln Val
                    85                  90                  95

Ile Ile Leu Asn His Pro Gly Gln Ile Ser Ala Gly Tyr Ala Pro Val
                100                 105                 110

Leu Asp Cys His Thr Ala His Ile Ala Cys Lys Phe Ala Glu Leu Lys
            115                 120                 125

Glu Lys Ile Asp Arg Arg Ser Gly Lys Lys Leu Glu Asp Gly Pro Lys
            130                 135                 140

Phe Leu Lys Ser Gly Asp Ala Ala Ile Val Asp Met Val Pro Gly Lys
145                 150                 155                 160

Pro Met Cys Val Glu Ser Phe Ser Asp Tyr Pro Pro Leu Gly Arg Phe
                165                 170                 175

Ala Val Arg Asp Met Arg Gln Thr Val Ala Val Gly Val Ile Lys Ala
                180                 185                 190

Val Asp Lys Lys Ala Ala Gly Ala Gly Lys Val Thr Lys Ser Ala Arg
            195                 200                 205

Lys Leu Arg Arg Leu Asn Glu Tyr Tyr Pro
            210                 215

<210> SEQ ID NO 37
<211> LENGTH: 149
<212> TYPE: PRT
<213> ORGANISM: Homo sapiens

<400> SEQUENCE: 37

Met Ile Thr Gly Thr Ser Gln Ala Asp Cys Ala Val Leu Ile Val Ala
1               5                   10                  15

Ala Gly Val Gly Glu Phe Glu Ala Ala Gly Phe Thr Ala Gln Val Ile
                20                  25                  30

Ile Leu Asn His Pro Gly Gln Ile Ser Ala Gly Tyr Ala Pro Val Leu
                35                  40                  45

Asp Cys His Thr Ala His Ile Ala Cys Lys Phe Ala Glu Leu Lys Glu
            50                  55                  60

Lys Ile Asp Arg Arg Ser Gly Lys Lys Leu Glu Asp Gly Pro Lys Phe
65                  70                  75                  80

```
Leu Lys Ser Gly Asp Ala Ala Ile Val Asp Met Val Pro Gly Lys Pro
                85                  90                  95

Met Cys Val Glu Ser Phe Ser Asp Tyr Pro Pro Leu Gly Arg Phe Ala
            100                 105                 110

Val Arg Asp Met Arg Gln Thr Val Ala Val Gly Val Ile Lys Ala Val
        115                 120                 125

Asp Lys Lys Ala Ala Gly Ala Gly Lys Val Thr Lys Ser Ala Gln Lys
    130                 135                 140

Ala Gln Lys Ala Lys
145

<210> SEQ ID NO 38
<211> LENGTH: 75
<212> TYPE: PRT
<213> ORGANISM: Homo sapiens

<400> SEQUENCE: 38

Met Leu Glu Pro Ser Ala Asn Met Pro Trp Phe Lys Gly Trp Lys Val
1               5                   10                  15

Thr Val Arg Met Ala Met Pro Val Glu Pro Arg Cys Leu Arg Leu Trp
            20                  25                  30

Thr Ala Ser Tyr His Gln Leu Val Gln Leu Thr Ser Leu Ala Pro Ala
        35                  40                  45

Ser Pro Gly Cys Leu Gln Asn Leu Val Phe Ser Asn Pro Val Trp Trp
    50                  55                  60

Ser Pro Leu Leu Gln Ser Thr Leu Gln Arg Lys
65                  70                  75

<210> SEQ ID NO 39
<211> LENGTH: 108
<212> TYPE: PRT
<213> ORGANISM: Homo sapiens

<400> SEQUENCE: 39

Met Ala Met Val Ser Glu Phe Leu Lys Gln Ala Trp Phe Ile Glu Asn
1               5                   10                  15

Glu Glu Gln Glu Tyr Val Gln Thr Val Lys Ser Ser Lys Gly Gly Pro
            20                  25                  30

Gly Ser Ala Val Ser Pro Tyr Pro Thr Phe Asn Pro Ser Ser Asp Val
        35                  40                  45

Ala Ala Leu His Lys Ala Ile Met Val Lys Gly Val Asp Glu Ala Thr
    50                  55                  60

Ile Ile Asp Ile Leu Thr Lys Arg Asn Asn Ala Gln Arg Gln Gln Ile
65                  70                  75                  80

Lys Ala Ala Tyr Leu Gln Glu Thr Gly Lys Pro Leu Asp Glu Thr Leu
            85                  90                  95

Lys Lys Ala Leu Gln Val Thr Leu Arg Arg Leu Phe
        100                 105

<210> SEQ ID NO 40
<211> LENGTH: 113
<212> TYPE: PRT
<213> ORGANISM: Homo sapiens

<400> SEQUENCE: 40

Met Ala Met Val Ser Glu Phe Leu Lys Gln Ala Trp Phe Ile Glu Asn
1               5                   10                  15

Glu Glu Gln Glu Tyr Val Gln Thr Val Lys Ser Ser Lys Gly Gly Pro
```

-continued

```
                20                  25                  30

Gly Ser Ala Val Ser Pro Tyr Pro Thr Phe Asn Pro Ser Ser Asp Val
            35                  40                  45

Ala Ala Leu His Lys Ala Ile Met Val Lys Gly Val Asp Glu Ala Thr
50                  55                  60

Ile Ile Asp Ile Leu Thr Lys Arg Asn Asn Ala Gln Arg Gln Gln Ile
65                  70                  75                  80

Lys Ala Ala Tyr Leu Gln Glu Thr Gly Lys Pro Leu Asp Glu Thr Leu
                85                  90                  95

Lys Lys Ala Leu Thr Gly His Leu Glu Glu Lys Gly Glu Arg Gly Gln
            100                 105                 110

Thr
```

<210> SEQ ID NO 41
<211> LENGTH: 127
<212> TYPE: PRT
<213> ORGANISM: Homo sapiens

<400> SEQUENCE: 41

```
Met Ala Met Val Ser Glu Phe Leu Lys Gln Ala Trp Phe Ile Glu Asn
1               5                   10                  15

Glu Glu Gln Glu Tyr Val Gln Thr Val Lys Ser Ser Lys Gly Gly Pro
                20                  25                  30

Gly Ser Ala Val Ser Pro Tyr Pro Thr Phe Asn Pro Ser Ser Asp Val
            35                  40                  45

Ala Ala Leu His Lys Ala Ile Met Val Lys Gly Val Asp Glu Ala Thr
50                  55                  60

Ile Ile Asp Ile Leu Thr Lys Arg Asn Asn Ala Gln Arg Gln Gln Ile
65                  70                  75                  80

Lys Ala Ala Tyr Leu Gln Glu Thr Gly Lys Pro Leu Asp Glu Thr Leu
                85                  90                  95

Lys Lys Ala Leu Thr Gly His Leu Glu Glu Val Val Leu Ala Leu Leu
            100                 105                 110

Lys Thr Lys Lys Ser Glu Thr Leu Thr Gly Ser Thr Glu Arg Asn
        115                 120                 125
```

<210> SEQ ID NO 42
<211> LENGTH: 131
<212> TYPE: PRT
<213> ORGANISM: Homo sapiens

<400> SEQUENCE: 42

```
Met Ala Met Val Ser Glu Phe Leu Lys Gln Ala Trp Phe Ile Glu Asn
1               5                   10                  15

Glu Glu Gln Glu Tyr Val Gln Thr Val Lys Ser Ser Lys Gly Gly Pro
                20                  25                  30

Gly Ser Ala Val Ser Pro Tyr Pro Thr Phe Asn Pro Ser Ser Asp Val
            35                  40                  45

Ala Ala Leu His Lys Ala Ile Met Val Lys Gly Val Asp Glu Ala Thr
50                  55                  60

Ile Ile Asp Ile Leu Thr Lys Arg Asn Asn Ala Gln Arg Gln Gln Ile
65                  70                  75                  80

Lys Ala Ala Tyr Leu Gln Glu Thr Gly Lys Pro Leu Asp Glu Thr Leu
                85                  90                  95

Lys Lys Ala Leu Thr Gly His Leu Glu Glu Val Val Leu Ala Leu Leu
            100                 105                 110
```

```
Lys Thr Pro Ala Gln Phe Asp Ala Asp Glu Leu Arg Ala Ala Met Lys
            115                 120                 125

Gly Leu Val
    130

<210> SEQ ID NO 43
<211> LENGTH: 183
<212> TYPE: PRT
<213> ORGANISM: Homo sapiens

<400> SEQUENCE: 43

Met Ala Met Val Ser Glu Phe Leu Lys Gln Ala Trp Phe Ile Glu Asn
1               5                   10                  15

Glu Glu Gln Glu Tyr Val Gln Thr Val Lys Ser Ser Lys Gly Gly Pro
            20                  25                  30

Gly Ser Ala Val Ser Pro Tyr Pro Thr Phe Asn Pro Ser Ser Asp Val
        35                  40                  45

Ala Ala Leu His Lys Ala Ile Met Val Lys Gly Val Asp Glu Ala Thr
    50                  55                  60

Ile Ile Asp Ile Leu Thr Lys Arg Asn Asn Ala Gln Arg Gln Gln Ile
65                  70                  75                  80

Lys Ala Ala Tyr Leu Gln Glu Thr Gly Lys Pro Leu Asp Glu Thr Leu
                85                  90                  95

Lys Lys Ala Leu Thr Gly His Leu Glu Val Val Leu Ala Leu Leu
            100                 105                 110

Lys Thr Pro Ala Gln Phe Asp Ala Asp Glu Leu Arg Ala Ala Met Lys
            115                 120                 125

Gly Leu Gly Thr Asp Glu Asp Thr Leu Ile Glu Ile Leu Ala Ser Arg
    130                 135                 140

Thr Lys Gln Ser Arg Arg Lys Glu Lys Gly Asp Arg Arg Lys Arg Val
145                 150                 155                 160

Gln Tyr His Pro Tyr His Gln Lys Leu Ser Thr Thr Ser Gln Ser Val
                165                 170                 175

Ser Glu Ile His Gln Val Gln
            180

<210> SEQ ID NO 44
<211> LENGTH: 92
<212> TYPE: PRT
<213> ORGANISM: Homo sapiens

<400> SEQUENCE: 44

Met Ala Met Val Ser Glu Phe Leu Lys Gln Ala Trp Phe Ile Glu Asn
1               5                   10                  15

Glu Glu Gln Glu Tyr Val Gln Thr Val Lys Ser Ser Lys Gly Gly Pro
            20                  25                  30

Gly Ser Ala Val Ser Pro Tyr Pro Thr Phe Asn Pro Ser Ser Asp Val
        35                  40                  45

Ala Ala Leu His Lys Ala Ile Met Val Lys Gly Val Asp Glu Ala Thr
    50                  55                  60

Ile Ile Asp Ile Leu Thr Lys Arg Asn Asn Ala Gln Arg Gln Gln Ile
65                  70                  75                  80

Lys Ala Ala Tyr Leu Gln Glu Thr Gly Lys Val Ser
                85                  90

<210> SEQ ID NO 45
```

```
<211> LENGTH: 297
<212> TYPE: PRT
<213> ORGANISM: Homo sapiens

<400> SEQUENCE: 45

Met Ala Met Val Ser Glu Phe Leu Lys Gln Ala Trp Phe Ile Glu Asn
1               5                   10                  15

Glu Glu Gln Glu Tyr Val Gln Thr Val Lys Ser Ser Lys Gly Gly Pro
            20                  25                  30

Gly Ser Ala Val Ser Pro Tyr Pro Thr Phe Asn Pro Ser Ser Asp Val
        35                  40                  45

Ala Ala Leu His Lys Ala Ile Met Val Lys Gly Val Asp Glu Ala Thr
    50                  55                  60

Ile Ile Asp Ile Leu Thr Lys Arg Asn Asn Ala Gln Arg Gln Gln Ile
65                  70                  75                  80

Lys Ala Ala Tyr Leu Gln Glu Thr Gly Lys Pro Leu Asp Glu Thr Leu
                85                  90                  95

Lys Lys Ala Leu Thr Gly His Leu Glu Glu Val Val Leu Ala Leu Leu
            100                 105                 110

Lys Thr Pro Ala Gln Phe Asp Ala Asp Glu Leu Arg Ala Ala Met Lys
        115                 120                 125

Gly Leu Gly Thr Asp Glu Asp Thr Leu Ile Glu Ile Leu Ala Ser Arg
    130                 135                 140

Thr Asn Lys Glu Ile Arg Asp Ile Asn Arg Val Tyr Arg Glu Glu Leu
145                 150                 155                 160

Lys Arg Asp Leu Ala Lys Asp Ile Thr Ser Asp Thr Ser Gly Asp Phe
                165                 170                 175

Arg Asn Ala Leu Leu Ser Leu Ala Lys Gly Asp Arg Ser Glu Asp Phe
            180                 185                 190

Gly Val Asn Glu Asp Leu Ala Asp Ser Asp Ala Arg Ala Leu Tyr Glu
        195                 200                 205

Ala Gly Glu Arg Arg Lys Gly Thr Asp Val Asn Val Phe Asn Thr Ile
    210                 215                 220

Leu Thr Thr Arg Ser Tyr Pro Gln Leu Arg Arg Val Phe Gln Lys Tyr
225                 230                 235                 240

Thr Lys Tyr Ser Lys His Asp Met Asn Lys Val Leu Asp Leu Glu Leu
                245                 250                 255

Lys Gly Asp Ile Glu Lys Cys Leu Thr Ala Ile Val Lys Cys Ala Thr
            260                 265                 270

Ser Lys Pro Ala Phe Phe Ala Glu Lys Leu His Gln Ala Met Lys Val
        275                 280                 285

Cys Thr Ile Leu Leu Ile Cys Pro Ala
    290                 295

<210> SEQ ID NO 46
<211> LENGTH: 254
<212> TYPE: PRT
<213> ORGANISM: Homo sapiens

<400> SEQUENCE: 46

Met Ala Met Val Ser Glu Phe Leu Lys Gln Ala Trp Phe Ile Glu Asn
1               5                   10                  15

Glu Glu Gln Glu Tyr Val Gln Thr Val Lys Ser Ser Lys Gly Gly Pro
            20                  25                  30

Gly Ser Ala Val Ser Pro Tyr Pro Thr Phe Asn Pro Ser Ser Asp Val
        35                  40                  45
```

```
Ala Ala Leu His Lys Ala Ile Met Val Lys Gly Val Asp Glu Ala Thr
        50                  55                  60

Ile Ile Asp Ile Leu Thr Lys Arg Asn Asn Ala Gln Arg Gln Gln Ile
 65                  70                  75                  80

Lys Ala Ala Tyr Leu Gln Glu Thr Gly Lys Pro Leu Asp Glu Thr Leu
                85                  90                  95

Lys Lys Ala Leu Thr Gly His Leu Glu Glu Val Val Leu Ala Leu Leu
                100                 105                 110

Lys Thr Pro Ala Gln Phe Asp Ala Asp Glu Leu Arg Ala Ala Met Lys
                115                 120                 125

Gly Leu Gly Thr Asp Glu Asp Thr Leu Ile Glu Ile Leu Ala Ser Arg
        130                 135                 140

Thr Asn Lys Glu Ile Arg Asp Ile Asn Arg Val Tyr Arg Glu Glu Leu
145                 150                 155                 160

Lys Arg Asp Leu Ala Lys Asp Ile Thr Ser Asp Thr Ser Gly Asp Phe
                165                 170                 175

Arg Asn Ala Leu Leu Ser Leu Ala Lys Gly Asp Arg Ser Glu Asp Phe
                180                 185                 190

Gly Val Asn Glu Asp Leu Ala Asp Ser Asp Ala Arg Ala Leu Tyr Glu
                195                 200                 205

Ala Gly Glu Arg Arg Lys Gly Thr Asp Val Asn Val Phe Asn Thr Ile
        210                 215                 220

Leu Thr Thr Arg Ser Tyr Pro Gln Leu Arg Arg Gly Asn Asn Lys Phe
225                 230                 235                 240

Leu Phe Leu Glu Ser Val Tyr Gly Arg Cys Asn Phe Leu Phe
                245                 250

<210> SEQ ID NO 47
<211> LENGTH: 212
<212> TYPE: PRT
<213> ORGANISM: Homo sapiens

<400> SEQUENCE: 47

Met Ala Met Val Ser Glu Phe Leu Lys Gln Ala Trp Phe Ile Glu Asn
  1               5                  10                  15

Glu Glu Gln Glu Tyr Val Gln Thr Val Lys Ser Ser Lys Gly Gly Pro
                20                  25                  30

Gly Ser Ala Val Ser Pro Tyr Pro Thr Phe Asn Pro Ser Ser Asp Val
                35                  40                  45

Ala Ala Leu His Lys Ala Ile Met Val Lys Gly Val Asn Glu Asp Leu
        50                  55                  60

Ala Asp Ser Asp Ala Arg Ala Leu Tyr Glu Ala Gly Glu Arg Arg Lys
 65                  70                  75                  80

Gly Thr Asp Val Asn Val Phe Asn Thr Ile Leu Thr Thr Arg Ser Tyr
                85                  90                  95

Pro Gln Leu Arg Arg Val Phe Gln Lys Tyr Thr Lys Tyr Ser Lys His
                100                 105                 110

Asp Met Asn Lys Val Leu Asp Leu Glu Leu Lys Gly Asp Ile Glu Lys
                115                 120                 125

Cys Leu Thr Ala Ile Val Lys Cys Ala Thr Ser Lys Pro Ala Phe Phe
        130                 135                 140

Ala Glu Lys Leu His Gln Ala Met Lys Gly Val Gly Thr Arg His Lys
145                 150                 155                 160

Ala Leu Ile Arg Ile Met Val Ser Arg Ser Glu Ile Asp Met Asn Asp
```

```
            165                 170                 175
Ile Lys Ala Phe Tyr Gln Lys Met Tyr Gly Ile Ser Leu Cys Gln Ala
            180                 185                 190
Ile Leu Asp Glu Thr Lys Gly Asp Tyr Glu Lys Ile Leu Val Ala Leu
            195                 200                 205
Cys Gly Gly Asn
            210

<210> SEQ ID NO 48
<211> LENGTH: 306
<212> TYPE: PRT
<213> ORGANISM: Homo sapiens

<400> SEQUENCE: 48

Met Ala Met Val Ser Glu Phe Leu Lys Gln Ala Trp Phe Ile Glu Asn
1               5                   10                  15
Glu Glu Gln Glu Tyr Val Gln Thr Val Lys Ser Ser Lys Gly Gly Pro
            20                  25                  30
Gly Ser Ala Val Ser Pro Tyr Pro Thr Phe Asn Pro Ser Ser Asp Val
            35                  40                  45
Ala Ala Leu His Lys Ala Ile Met Val Lys Gly Val Asp Glu Ala Thr
        50                  55                  60
Ile Ile Asp Ile Leu Thr Lys Arg Asn Asn Ala Gln Arg Gln Gln Ile
65                  70                  75                  80
Lys Ala Ala Tyr Leu Gln Glu Thr Gly Lys Pro Leu Asp Glu Asp Thr
                85                  90                  95
Leu Ile Glu Ile Leu Ala Ser Arg Thr Asn Lys Glu Ile Arg Asp Ile
            100                 105                 110
Asn Arg Val Tyr Arg Glu Glu Leu Lys Arg Asp Leu Ala Lys Asp Ile
            115                 120                 125
Thr Ser Asp Thr Ser Gly Asp Phe Arg Asn Ala Leu Leu Ser Leu Ala
        130                 135                 140
Lys Gly Asp Arg Ser Glu Asp Phe Gly Val Asn Glu Asp Leu Ala Asp
145                 150                 155                 160
Ser Asp Ala Arg Ala Leu Tyr Glu Ala Gly Glu Arg Arg Lys Gly Thr
                165                 170                 175
Asp Val Asn Val Phe Asn Thr Ile Leu Thr Thr Arg Ser Tyr Pro Gln
            180                 185                 190
Leu Arg Arg Val Phe Gln Lys Tyr Thr Lys Tyr Ser Lys His Asp Met
            195                 200                 205
Asn Lys Val Leu Asp Leu Glu Leu Lys Gly Asp Ile Glu Lys Cys Leu
        210                 215                 220
Thr Ala Ile Val Lys Cys Ala Thr Ser Lys Pro Ala Phe Phe Ala Glu
225                 230                 235                 240
Lys Leu His Gln Ala Met Lys Gly Val Gly Thr Arg His Lys Ala Leu
                245                 250                 255
Ile Arg Ile Met Val Ser Arg Ser Glu Ile Asp Met Asn Asp Ile Lys
            260                 265                 270
Ala Phe Tyr Gln Lys Met Tyr Gly Ile Ser Leu Cys Gln Ala Ile Leu
            275                 280                 285
Asp Glu Thr Lys Gly Asp Tyr Glu Lys Ile Leu Val Ala Leu Cys Gly
        290                 295                 300
Gly Asn
305
```

<210> SEQ ID NO 49
<211> LENGTH: 269
<212> TYPE: PRT
<213> ORGANISM: Homo sapiens

<400> SEQUENCE: 49

```
Met Ala Met Val Ser Glu Phe Leu Lys Gln Ala Trp Phe Ile Glu Asn
1               5                   10                  15

Glu Glu Gln Glu Tyr Val Gln Thr Val Lys Ser Ser Lys Gly Gly Pro
            20                  25                  30

Gly Ser Ala Val Ser Pro Tyr Pro Thr Phe Asn Pro Ser Ser Asp Val
        35                  40                  45

Ala Ala Leu His Lys Ala Ile Met Val Lys Gly Val Asp Glu Ala Thr
    50                  55                  60

Ile Ile Asp Ile Leu Thr Lys Arg Asn Asn Ala Gln Arg Gln Gln Ile
65                  70                  75                  80

Lys Ala Ala Tyr Leu Gln Glu Thr Gly Lys Pro Leu Asp Glu Thr Leu
                85                  90                  95

Lys Lys Ala Leu Thr Gly His Leu Glu Glu Val Val Leu Ala Leu Leu
            100                 105                 110

Lys Thr Pro Ala Gln Phe Asp Ala Asp Glu Leu Arg Ala Ala Met Lys
        115                 120                 125

Gly Leu Gly Thr Asp Glu Asp Thr Leu Ile Glu Ile Leu Ala Ser Arg
    130                 135                 140

Thr Asn Lys Glu Ile Arg Asp Ile Asn Arg Val Tyr Arg Glu Glu Leu
145                 150                 155                 160

Lys Arg Asp Leu Ala Lys Asp Ile Thr Ser Asp Thr Ser Gly Asp Phe
                165                 170                 175

Arg Asn Ala Leu Leu Ser Leu Ala Lys Gly Asp Arg Ser Glu Asp Phe
            180                 185                 190

Gly Val Asn Glu Asp Leu Ala Asp Ser Asp Ala Arg Ala Leu Tyr Glu
        195                 200                 205

Ala Gly Glu Arg Arg Lys Gly Thr Asp Val Asn Val Phe Asn Thr Ile
    210                 215                 220

Leu Thr Thr Arg Ser Tyr Pro Gln Leu Arg Arg Val Phe Gln Lys Tyr
225                 230                 235                 240

Thr Lys Tyr Ser Lys His Asp Met Asn Lys Val Leu Asp Leu Glu Leu
                245                 250                 255

Lys Gly Asp Ile Glu Lys Cys Leu Thr Ala Ile Gly Met
            260                 265
```

<210> SEQ ID NO 50
<211> LENGTH: 284
<212> TYPE: PRT
<213> ORGANISM: Homo sapiens

<400> SEQUENCE: 50

```
Met Ala Met Val Ser Glu Phe Leu Lys Gln Ala Trp Phe Ile Glu Asn
1               5                   10                  15

Glu Glu Gln Glu Tyr Val Gln Thr Val Lys Ser Ser Lys Gly Gly Pro
            20                  25                  30

Gly Ser Ala Val Ser Pro Tyr Pro Thr Phe Asn Pro Ser Ser Asp Val
        35                  40                  45

Ala Ala Leu His Lys Ala Ile Met Val Lys Gly Val Asp Glu Ala Thr
    50                  55                  60
```

Ile Ile Asp Ile Leu Thr Lys Arg Asn Asn Ala Gln Arg Gln Gln Ile
65                  70                  75                  80

Lys Ala Ala Tyr Leu Gln Glu Thr Gly Lys Pro Leu Asp Glu Thr Leu
                85                  90                  95

Lys Lys Ala Leu Thr Gly His Leu Glu Glu Val Val Leu Ala Leu Leu
            100                 105                 110

Lys Thr Pro Ala Gln Phe Asp Ala Asp Glu Leu Arg Ala Ala Met Lys
            115                 120                 125

Gly Leu Gly Thr Asp Glu Asp Leu Ala Asp Ser Asp Ala Arg Ala Leu
            130                 135                 140

Tyr Glu Ala Gly Glu Arg Arg Lys Gly Thr Asp Val Asn Val Phe Asn
145                 150                 155                 160

Thr Ile Leu Thr Thr Arg Ser Tyr Pro Gln Leu Arg Arg Val Phe Gln
                165                 170                 175

Lys Tyr Thr Lys Tyr Ser Lys His Asp Met Asn Lys Val Leu Asp Leu
            180                 185                 190

Glu Leu Lys Gly Asp Ile Glu Lys Cys Leu Thr Ala Ile Val Lys Cys
            195                 200                 205

Ala Thr Ser Lys Pro Ala Phe Phe Ala Glu Lys Leu His Gln Ala Met
210                 215                 220

Lys Gly Val Gly Thr Arg His Lys Ala Leu Ile Arg Ile Met Val Ser
225                 230                 235                 240

Arg Ser Glu Ile Asp Met Asn Asp Ile Lys Ala Phe Tyr Gln Lys Met
                245                 250                 255

Tyr Gly Ile Ser Leu Cys Gln Ala Ile Leu Asp Glu Thr Lys Gly Asp
            260                 265                 270

Tyr Glu Lys Ile Leu Val Ala Leu Cys Gly Gly Asn
            275                 280

<210> SEQ ID NO 51
<211> LENGTH: 282
<212> TYPE: PRT
<213> ORGANISM: Homo sapiens

<400> SEQUENCE: 51

Met Ala Met Val Ser Glu Phe Leu Lys Gln Ala Trp Phe Ile Glu Asn
1               5                   10                  15

Glu Glu Gln Glu Tyr Val Gln Thr Val Lys Ser Ser Lys Gly Gly Pro
                20                  25                  30

Gly Ser Ala Val Ser Pro Tyr Pro Thr Phe Asn Pro Ser Ser Asp Val
            35                  40                  45

Ala Ala Leu His Lys Ala Ile Met Val Lys Gly Val Asp Glu Ala Thr
50                  55                  60

Ile Ile Asp Ile Leu Thr Lys Arg Asn Asn Ala Gln Arg Gln Gln Ile
65                  70                  75                  80

Lys Ala Ala Tyr Leu Gln Glu Thr Gly Lys Pro Leu Asp Glu Thr Leu
                85                  90                  95

Lys Arg Asp Leu Ala Lys Asp Ile Thr Ser Asp Ser Gly Asp Phe
            100                 105                 110

Arg Asn Ala Leu Leu Ser Leu Ala Lys Gly Asp Arg Ser Glu Asp Phe
            115                 120                 125

Gly Val Asn Glu Asp Leu Ala Asp Ser Asp Ala Arg Ala Leu Tyr Glu
            130                 135                 140

Ala Gly Glu Arg Arg Lys Gly Thr Asp Val Asn Val Phe Asn Thr Ile
145                 150                 155                 160

Leu Thr Thr Arg Ser Tyr Pro Gln Leu Arg Arg Val Phe Gln Lys Tyr
            165                 170                 175

Thr Lys Tyr Ser Lys His Asp Met Asn Lys Val Leu Asp Leu Glu Leu
        180                 185                 190

Lys Gly Asp Ile Glu Lys Cys Leu Thr Ala Ile Val Lys Cys Ala Thr
    195                 200                 205

Ser Lys Pro Ala Phe Phe Ala Glu Lys Leu His Gln Ala Met Lys Gly
210                 215                 220

Val Gly Thr Arg His Lys Ala Leu Ile Arg Ile Met Val Ser Arg Ser
225                 230                 235                 240

Glu Ile Asp Met Asn Asp Ile Lys Ala Phe Tyr Gln Lys Met Tyr Gly
                245                 250                 255

Ile Ser Leu Cys Gln Ala Ile Leu Asp Glu Thr Lys Gly Asp Tyr Glu
            260                 265                 270

Lys Ile Leu Val Ala Leu Cys Gly Gly Asn
        275                 280

<210> SEQ ID NO 52
<211> LENGTH: 220
<212> TYPE: PRT
<213> ORGANISM: Homo sapiens

<400> SEQUENCE: 52

Met Lys Gly Leu Gly Thr Asp Glu Asp Thr Leu Ile Glu Ile Leu Ala
1               5                   10                  15

Ser Arg Thr Asn Lys Glu Ile Arg Asp Ile Asn Arg Val Tyr Arg Glu
            20                  25                  30

Glu Leu Lys Arg Asp Leu Ala Lys Asp Ile Thr Ser Asp Thr Ser Gly
        35                  40                  45

Asp Phe Arg Asn Ala Leu Leu Ser Leu Ala Lys Gly Asp Arg Ser Glu
    50                  55                  60

Asp Phe Gly Val Asn Glu Asp Leu Ala Asp Ser Asp Ala Arg Ala Leu
65                  70                  75                  80

Tyr Glu Ala Gly Glu Arg Arg Lys Gly Thr Asp Val Asn Val Phe Asn
                85                  90                  95

Thr Ile Leu Thr Thr Arg Ser Tyr Pro Gln Leu Arg Arg Val Phe Gln
            100                 105                 110

Lys Tyr Thr Lys Tyr Ser Lys His Asp Met Asn Lys Val Leu Asp Leu
        115                 120                 125

Glu Leu Lys Gly Asp Ile Glu Lys Cys Leu Thr Ala Ile Val Lys Cys
    130                 135                 140

Ala Thr Ser Lys Pro Ala Phe Phe Ala Glu Lys Leu His Gln Ala Met
145                 150                 155                 160

Lys Gly Val Gly Thr Arg His Lys Ala Leu Ile Arg Ile Met Val Ser
                165                 170                 175

Arg Ser Glu Ile Asp Met Asn Asp Ile Lys Ala Phe Tyr Gln Lys Met
            180                 185                 190

Tyr Gly Ile Ser Leu Cys Gln Ala Ile Leu Asp Glu Thr Lys Gly Asp
        195                 200                 205

Tyr Glu Lys Ile Leu Val Ala Leu Cys Gly Gly Asn
    210                 215                 220

<210> SEQ ID NO 53
<211> LENGTH: 99
<212> TYPE: PRT

```
<213> ORGANISM: Homo sapiens

<400> SEQUENCE: 53

Met Asn Lys Val Leu Asp Leu Glu Leu Lys Gly Asp Ile Glu Lys Cys
1               5                   10                  15

Leu Thr Ala Ile Val Lys Cys Ala Thr Ser Lys Pro Ala Phe Phe Ala
            20                  25                  30

Glu Lys Leu His Gln Ala Met Lys Gly Val Gly Thr Arg His Lys Ala
        35                  40                  45

Leu Ile Arg Ile Met Val Ser Arg Ser Glu Ile Asp Met Asn Asp Ile
    50                  55                  60

Lys Ala Phe Tyr Gln Lys Met Tyr Gly Ile Ser Leu Cys Gln Ala Ile
65                  70                  75                  80

Leu Asp Glu Thr Lys Gly Asp Tyr Glu Lys Ile Leu Val Ala Leu Cys
                85                  90                  95

Gly Gly Asn

<210> SEQ ID NO 54
<211> LENGTH: 346
<212> TYPE: PRT
<213> ORGANISM: Homo sapiens

<400> SEQUENCE: 54

Met Ala Met Val Ser Glu Phe Leu Lys Gln Ala Trp Phe Ile Glu Asn
1               5                   10                  15

Glu Glu Gln Glu Tyr Val Gln Thr Val Lys Ser Ser Lys Gly Gly Pro
            20                  25                  30

Gly Ser Ala Val Ser Pro Tyr Pro Thr Phe Asn Pro Ser Ser Asp Val
        35                  40                  45

Ala Ala Leu His Lys Ala Ile Met Val Lys Gly Val Asp Glu Ala Thr
    50                  55                  60

Ile Ile Asp Ile Leu Thr Lys Arg Asn Asn Ala Gln Arg Gln Gln Ile
65                  70                  75                  80

Lys Ala Ala Tyr Leu Gln Glu Thr Gly Lys Pro Leu Asp Glu Thr Leu
                85                  90                  95

Lys Lys Ala Leu Thr Gly His Leu Glu Glu Val Val Leu Ala Leu Leu
                100                 105                 110

Lys Thr Pro Ala Gln Phe Asp Ala Asp Glu Leu Arg Ala Ala Met Lys
            115                 120                 125

Gly Leu Gly Thr Asp Glu Asp Thr Leu Ile Glu Ile Leu Ala Ser Arg
        130                 135                 140

Thr Asn Lys Glu Ile Arg Asp Ile Asn Arg Val Tyr Arg Glu Glu Leu
145                 150                 155                 160

Lys Arg Asp Leu Ala Lys Asp Ile Thr Ser Asp Thr Ser Gly Asp Phe
                165                 170                 175

Arg Asn Ala Leu Leu Ser Leu Ala Lys Gly Asp Arg Ser Glu Asp Phe
            180                 185                 190

Gly Val Asn Glu Asp Leu Ala Asp Ser Asp Ala Arg Ala Leu Tyr Glu
        195                 200                 205

Ala Gly Glu Arg Arg Lys Gly Thr Asp Val Asn Val Phe Asn Thr Ile
    210                 215                 220

Leu Thr Thr Arg Ser Tyr Pro Gln Leu Arg Arg Val Phe Gln Lys Tyr
225                 230                 235                 240

Thr Lys Tyr Ser Lys His Asp Met Asn Lys Val Leu Asp Leu Glu Leu
                245                 250                 255
```

```
Lys Gly Asp Ile Glu Lys Cys Leu Thr Ala Ile Val Lys Cys Ala Thr
                260                 265                 270

Ser Lys Pro Ala Phe Phe Ala Glu Lys Leu His Gln Ala Met Lys Gly
            275                 280                 285

Val Gly Thr Arg His Lys Ala Leu Ile Arg Ile Met Val Ser Arg Ser
290                 295                 300

Glu Ile Asp Met Asn Asp Ile Lys Ala Phe Tyr Gln Lys Met Tyr Gly
305                 310                 315                 320

Ile Ser Leu Cys Gln Ala Ile Leu Asp Glu Thr Lys Gly Asp Tyr Glu
                325                 330                 335

Lys Ile Leu Val Ala Leu Cys Gly Gly Asn
                340                 345

<210> SEQ ID NO 55
<211> LENGTH: 61
<212> TYPE: PRT
<213> ORGANISM: Homo sapiens

<400> SEQUENCE: 55

Leu His Lys Ala Ile Met Val Lys Gly Val Asp Glu Ala Thr Ile Ile
1               5                   10                  15

Asp Ile Leu Thr Lys Arg Asn Asn Ala Gln Arg Gln Gln Ile Lys Ala
                20                  25                  30

Ala Tyr Leu Gln Glu Thr Gly Lys Pro Leu Asp Glu Thr Leu Lys Lys
            35                  40                  45

Ala Leu Thr Gly His Leu Glu Glu Val Val Leu Ala Leu
        50                  55                  60

<210> SEQ ID NO 56
<211> LENGTH: 61
<212> TYPE: PRT
<213> ORGANISM: Homo sapiens

<400> SEQUENCE: 56

Leu Arg Ala Ala Met Lys Gly Leu Gly Thr Asp Glu Asp Thr Leu Ile
1               5                   10                  15

Glu Ile Leu Ala Ser Arg Thr Asn Lys Glu Ile Arg Asp Ile Asn Arg
                20                  25                  30

Val Tyr Arg Glu Glu Leu Lys Arg Asp Leu Ala Lys Asp Ile Thr Ser
            35                  40                  45

Asp Thr Ser Gly Asp Phe Arg Asn Ala Leu Leu Ser Leu
        50                  55                  60

<210> SEQ ID NO 57
<211> LENGTH: 61
<212> TYPE: PRT
<213> ORGANISM: Homo sapiens

<400> SEQUENCE: 57

Tyr Glu Ala Gly Glu Arg Arg Lys Gly Thr Asp Val Asn Val Phe Asn
1               5                   10                  15

Thr Ile Leu Thr Thr Arg Ser Tyr Pro Gln Leu Arg Arg Val Phe Gln
                20                  25                  30

Lys Tyr Thr Lys Tyr Ser Lys His Asp Met Asn Lys Val Leu Asp Leu
            35                  40                  45

Glu Leu Lys Gly Asp Ile Glu Lys Cys Leu Thr Ala Ile
        50                  55                  60
```

<210> SEQ ID NO 58
<211> LENGTH: 61
<212> TYPE: PRT
<213> ORGANISM: Homo sapiens

<400> SEQUENCE: 58

Leu His Gln Ala Met Lys Gly Val Gly Thr Arg His Lys Ala Leu Ile
1               5                   10                  15

Arg Ile Met Val Ser Arg Ser Glu Ile Asp Met Asn Asp Ile Lys Ala
            20                  25                  30

Phe Tyr Gln Lys Met Tyr Gly Ile Ser Leu Cys Gln Ala Ile Leu Asp
        35                  40                  45

Glu Thr Lys Gly Asp Tyr Glu Lys Ile Leu Val Ala Leu
    50                  55                  60

<210> SEQ ID NO 59
<211> LENGTH: 294
<212> TYPE: PRT
<213> ORGANISM: Homo sapiens

<400> SEQUENCE: 59

Met Ala Met Val Ser Glu Phe Leu Lys Gln Ala Trp Phe Ile Glu Asn
1               5                   10                  15

Glu Glu Gln Glu Tyr Val Gln Thr Val Lys Ser Ser Lys Gly Gly Pro
            20                  25                  30

Gly Ser Ala Val Ser Pro Tyr Pro Thr Phe Asn Pro Ser Ser Asp Val
        35                  40                  45

Ala Ala Leu His Lys Ala Ile Met Val Lys Gly Val Asp Glu Ala Thr
    50                  55                  60

Ile Ile Asp Ile Leu Thr Lys Arg Asn Asn Ala Gln Arg Gln Gln Ile
65                  70                  75                  80

Lys Ala Ala Tyr Leu Gln Glu Thr Gly Lys Pro Leu Asp Glu Thr Leu
                85                  90                  95

Lys Lys Ala Leu Thr Gly His Leu Glu Glu Glu Leu Lys Arg Asp Leu
            100                 105                 110

Ala Lys Asp Ile Thr Ser Asp Thr Ser Gly Asp Phe Arg Asn Ala Leu
        115                 120                 125

Leu Ser Leu Ala Lys Gly Asp Arg Ser Glu Asp Phe Gly Val Asn Glu
    130                 135                 140

Asp Leu Ala Asp Ser Asp Ala Arg Ala Leu Tyr Glu Ala Gly Glu Arg
145                 150                 155                 160

Arg Lys Gly Thr Asp Val Asn Val Phe Asn Thr Ile Leu Thr Thr Arg
                165                 170                 175

Ser Tyr Pro Gln Leu Arg Arg Val Phe Gln Lys Tyr Thr Lys Tyr Ser
            180                 185                 190

Lys His Asp Met Asn Lys Val Leu Asp Leu Glu Leu Lys Gly Asp Ile
        195                 200                 205

Glu Lys Cys Leu Thr Ala Ile Val Lys Cys Ala Thr Ser Lys Pro Ala
    210                 215                 220

Phe Phe Ala Glu Lys Leu His Gln Ala Met Lys Gly Val Gly Thr Arg
225                 230                 235                 240

His Lys Ala Leu Ile Arg Ile Met Val Ser Arg Ser Glu Ile Asp Met
                245                 250                 255

Asn Asp Ile Lys Ala Phe Tyr Gln Lys Met Tyr Gly Ile Ser Leu Cys
            260                 265                 270

Gln Ala Ile Leu Asp Glu Thr Lys Gly Asp Tyr Glu Lys Ile Leu Val
            275                 280                 285

Ala Leu Cys Gly Gly Asn
            290

<210> SEQ ID NO 60
<211> LENGTH: 171
<212> TYPE: PRT
<213> ORGANISM: Homo sapiens

<400> SEQUENCE: 60

Met Lys Gly Leu Gly Thr Asp Glu Asp Thr Leu Ile Glu Ile Leu Ala
1               5                   10                  15

Ser Arg Thr Asn Lys Glu Ile Arg Asp Ile Asn Arg Val Tyr Arg Glu
            20                  25                  30

Glu Leu Lys Arg Asp Leu Ala Lys Asp Ile Thr Ser Asp Thr Ser Gly
        35                  40                  45

Asp Phe Arg Asn Ala Leu Leu Ser Leu Ala Lys Gly Asp Arg Ser Glu
    50                  55                  60

Asp Phe Gly Val Asn Glu Asp Leu Ala Asp Ser Asp Ala Arg Ala Leu
65                  70                  75                  80

Tyr Glu Ala Gly Glu Arg Arg Lys Gly Thr Asp Val Asn Val Phe Asn
                85                  90                  95

Thr Ile Leu Thr Thr Arg Ser Tyr Pro Gln Leu Arg Arg Val Phe Gln
            100                 105                 110

Lys Tyr Thr Lys Tyr Ser Lys His Asp Met Asn Lys Val Leu Asp Leu
        115                 120                 125

Glu Leu Lys Gly Asp Ile Glu Lys Cys Leu Thr Ala Ile Val Lys Cys
    130                 135                 140

Ala Thr Ser Lys Pro Ala Phe Phe Ala Glu Lys Leu His Gln Ala Met
145                 150                 155                 160

Lys Val Cys Thr Ile Leu Leu Ile Cys Pro Ala
                165                 170

<210> SEQ ID NO 61
<211> LENGTH: 140
<212> TYPE: PRT
<213> ORGANISM: Homo sapiens

<400> SEQUENCE: 61

Met Ala Met Val Ser Glu Phe Leu Lys Gln Ala Trp Phe Ile Glu Asn
1               5                   10                  15

Glu Glu Gln Glu Tyr Val Gln Thr Val Lys Ser Ser Lys Gly Gly Pro
            20                  25                  30

Gly Ser Ala Val Ser Pro Tyr Pro Thr Phe Asn Pro Ser Ser Asp Val
        35                  40                  45

Ala Ala Leu His Lys Ala Ile Met Val Lys Gly Val Asp Glu Ala Thr
    50                  55                  60

Ile Ile Asp Ile Leu Thr Lys Arg Asn Asn Ala Pro Ala Ser Thr Asp
65                  70                  75                  80

Glu Asp Thr Leu Ile Glu Ile Leu Ala Ser Arg Thr Asn Lys Glu Ile
                85                  90                  95

Arg Asp Ile Asn Arg Val Tyr Arg Glu Glu Leu Lys Arg Asp Leu Ala
            100                 105                 110

Lys Asp Ile Thr Gln Thr His Leu Glu Ile Phe Gly Thr Leu Cys Phe
        115                 120                 125

```
Leu Leu Leu Arg Val Thr Asp Leu Arg Thr Leu Val
    130                 135                 140
```

<210> SEQ ID NO 62
<211> LENGTH: 95
<212> TYPE: PRT
<213> ORGANISM: Homo sapiens

<400> SEQUENCE: 62

```
Met Ala Met Val Ser Glu Phe Leu Lys Gln Ala Trp Phe Ile Glu Asn
1               5                   10                  15

Glu Glu Gln Glu Tyr Val Gln Thr Val Lys Ser Ser Lys Gly Gly Pro
                20                  25                  30

Gly Ser Ala Val Ser Pro Tyr Pro Thr Phe Asn Pro Ser Ser Asp Val
            35                  40                  45

Ala Ala Leu His Lys Ala Ile Met Val Lys Gly Val Asp Glu Ala Thr
        50                  55                  60

Ile Ile Asp Ile Leu Thr Lys Arg Asn Asn Ala Gln Arg Gln Gln Ile
65                  70                  75                  80

Lys Ala Ala Tyr Leu Gln Glu Thr Gly Lys Pro Trp Met Lys His
                85                  90                  95
```

<210> SEQ ID NO 63
<211> LENGTH: 87
<212> TYPE: PRT
<213> ORGANISM: Homo sapiens

<400> SEQUENCE: 63

```
Met Ala Met Val Ser Glu Phe Leu Lys Gln Ala Trp Phe Ile Glu Asn
1               5                   10                  15

Glu Glu Gln Glu Tyr Val Gln Thr Val Lys Ser Ser Lys Gly Gly Pro
                20                  25                  30

Gly Ser Ala Val Ser Pro Tyr Pro Thr Phe Asn Pro Ser Ser Asp Val
            35                  40                  45

Ala Ala Leu His Lys Ala Ile Met Val Lys Gly Val Asp Glu Ala Thr
        50                  55                  60

Ile Ile Asp Ile Leu Thr Lys Arg Asn Asn Ala Gln Arg Gln Gln Ile
65                  70                  75                  80

Lys Gly Glu Arg Gly Gln Thr
                85
```

<210> SEQ ID NO 64
<211> LENGTH: 70
<212> TYPE: PRT
<213> ORGANISM: Homo sapiens

<400> SEQUENCE: 64

```
Met Ala Met Val Ser Glu Phe Leu Lys Gln Ala Trp Phe Ile Glu Asn
1               5                   10                  15

Glu Glu Gln Glu Tyr Val Gln Thr Val Lys Ser Ser Lys Gly Gly Pro
                20                  25                  30

Gly Ser Ala Val Ser Pro Tyr Pro Thr Phe Asn Pro Ser Ser Asp Val
            35                  40                  45

Ala Ala Leu His Lys Ala Ile Met Val Lys Gly Val Asp Glu Ala Thr
        50                  55                  60

Ile Ile Glu His Ser Asn
65                  70
```

```
<210> SEQ ID NO 65
<211> LENGTH: 54
<212> TYPE: PRT
<213> ORGANISM: Homo sapiens

<400> SEQUENCE: 65

Met Ala Met Val Ser Glu Phe Leu Lys Gln Ala Trp Phe Ile Glu Asn
1               5                   10                  15

Glu Glu Gln Glu Tyr Val Gln Thr Val Lys Ser Ser Lys Gly Gly Pro
            20                  25                  30

Gly Ser Ala Val Ser Pro Ile Leu Pro Ser Ile His Pro Arg Met Ser
        35                  40                  45

Leu Pro Cys Ile Arg Pro
    50

<210> SEQ ID NO 66
<211> LENGTH: 253
<212> TYPE: PRT
<213> ORGANISM: Homo sapiens

<400> SEQUENCE: 66

Met His Ser Trp Glu Arg Leu Ala Val Leu Val Leu Leu Gly Ala Ala
1               5                   10                  15

Ala Cys Ala Ala Pro Pro Arg Gly Arg Ile Leu Gly Gly Arg Glu Ala
            20                  25                  30

Glu Ala His Ala Arg Pro Tyr Met Ala Ser Val Gln Leu Asn Gly Ala
        35                  40                  45

His Leu Cys Gly Gly Val Leu Val Ala Glu Gln Trp Val Leu Ser Ala
    50                  55                  60

Ala His Cys Leu Glu Asp Ala Ala Asp Gly Lys Val Gln Val Leu Leu
65                  70                  75                  80

Gly Ala His Ser Leu Ser Gln Pro Glu Pro Ser Lys Arg Leu Tyr Asp
                85                  90                  95

Val Leu Arg Ala Val Pro His Pro Asp Ser Gln Pro Asp Thr Ile Asp
            100                 105                 110

His Asp Leu Leu Leu Leu Gln Leu Ser Glu Lys Ala Thr Leu Gly Pro
        115                 120                 125

Ala Val Arg Pro Leu Pro Trp Gln Arg Val Asp Arg Asp Val Ala Pro
    130                 135                 140

Gly Thr Leu Cys Asp Val Ala Gly Trp Gly Ile Val Asn His Ala Gly
145                 150                 155                 160

Arg Arg Pro Asp Ser Leu Gln His Val Leu Leu Pro Val Leu Asp Arg
                165                 170                 175

Ala Thr Cys Asn Arg Arg Thr His His Asp Gly Ala Ile Thr Glu Arg
            180                 185                 190

Leu Met Cys Ala Glu Ser Asn Arg Arg Asp Ser Cys Lys Gly Asp Ser
        195                 200                 205

Gly Gly Pro Leu Val Cys Gly Val Leu Glu Gly Val Val Thr Ser
    210                 215                 220

Gly Ser Arg Val Cys Gly Asn Arg Lys Lys Pro Gly Ile Tyr Thr Arg
225                 230                 235                 240

Val Ala Ser Tyr Ala Ala Trp Ile Asp Ser Val Leu Ala
                245                 250

<210> SEQ ID NO 67
<211> LENGTH: 214
<212> TYPE: PRT
```

<213> ORGANISM: Homo sapiens

<400> SEQUENCE: 67

```
Met Val Ser Leu Gln Leu Arg Gly Gly His Phe Cys Gly Ala Thr Leu
1               5                   10                  15
Ile Ala Pro Asn Phe Val Met Ser Ala Ala His Cys Val Ala Asn Val
                20                  25                  30
Ala Asp Gly Lys Val Gln Val Leu Leu Gly Ala His Ser Leu Ser Gln
            35                  40                  45
Pro Glu Pro Ser Lys Arg Leu Tyr Asp Val Leu Arg Ala Val Pro His
    50                  55                  60
Pro Asp Ser Gln Pro Asp Thr Ile Asp His Asp Leu Leu Leu Leu Gln
65                  70                  75                  80
Leu Ser Glu Lys Ala Thr Leu Gly Pro Ala Val Arg Pro Leu Pro Trp
                85                  90                  95
Gln Arg Val Asp Arg Asp Val Ala Pro Gly Thr Leu Cys Asp Val Ala
                100                 105                 110
Gly Trp Gly Ile Val Asn His Ala Gly Arg Arg Pro Asp Ser Leu Gln
            115                 120                 125
His Val Leu Leu Pro Val Leu Asp Arg Ala Thr Cys Asn Arg Arg Thr
    130                 135                 140
His His Asp Gly Ala Ile Thr Glu Arg Leu Met Cys Ala Glu Ser Asn
145                 150                 155                 160
Arg Arg Asp Ser Cys Lys Gly Asp Ser Gly Gly Pro Leu Val Cys Gly
                165                 170                 175
Gly Val Leu Glu Gly Val Val Thr Ser Gly Ser Arg Val Cys Gly Asn
                180                 185                 190
Arg Lys Lys Pro Gly Ile Tyr Thr Arg Val Ala Ser Tyr Ala Ala Trp
            195                 200                 205
Ile Asp Ser Val Leu Ala
        210
```

<210> SEQ ID NO 68
<211> LENGTH: 195
<212> TYPE: PRT
<213> ORGANISM: Homo sapiens

<400> SEQUENCE: 68

```
Met Val Ser Leu Gln Leu Arg Gly Gly His Phe Cys Gly Ala Thr Leu
1               5                   10                  15
Ile Ala Pro Asn Phe Val Met Ser Ala Ala His Cys Val Ala Asn Val
                20                  25                  30
Asn Val Arg Ala Val Arg Val Val Leu Gly Ala His Asn Leu Ser Arg
            35                  40                  45
Arg Glu Pro Thr Arg Gln Val Phe Ala Val Gln Arg Ile Phe Glu Asn
    50                  55                  60
Gly Tyr Asp Pro Val Asn Leu Leu Asn Asp Ile Val Ile Leu Gln Leu
65                  70                  75                  80
Asn Gly Ser Ala Thr Ile Asn Ala Asn Val Gln Val Ala Gln Leu Pro
                85                  90                  95
Ala Gln Gly Arg Arg Leu Gly Asn Gly Val Gln Cys Leu Ala Met Gly
                100                 105                 110
Trp Gly Leu Leu Gly Arg Asn Arg Gly Ile Ala Ser Val Leu Gln Glu
            115                 120                 125
Leu Asn Val Thr Val Val Thr Ser Leu Cys Arg Arg Ser Asn Val Cys
```

```
                130                 135                 140
Thr Leu Val Arg Gly Arg Gln Ala Gly Val Cys Phe Gly Asp Ser Gly
145                 150                 155                 160

Ser Pro Leu Val Cys Asn Gly Leu Ile His Gly Ile Ala Ser Phe Val
                165                 170                 175

Arg Gly Gly Cys Ala Ser Gly Leu Tyr Pro Met Pro Leu Pro Arg Trp
                180                 185                 190

His Ser Leu
        195

<210> SEQ ID NO 69
<211> LENGTH: 143
<212> TYPE: PRT
<213> ORGANISM: Homo sapiens

<400> SEQUENCE: 69

Met Gly Lys Leu Arg Pro Gly Glu Gly Arg Val Ile Ile Thr Ala Pro
1               5                   10                  15

Cys Asp Ala Leu Thr Ile Cys Pro His Arg His Ser Ser Thr Gly Arg
                20                  25                  30

Pro Pro Ser Thr Pro Thr Cys Arg Cys Pro Ala Ala Gly Ser Gly Thr
            35                  40                  45

Pro Pro Gly Gln Arg Val Gln Cys Leu Ala Met Gly Trp Gly Leu Leu
        50                  55                  60

Gly Arg Asn Arg Gly Ile Ala Ser Val Leu Gln Glu Leu Asn Val Thr
65                  70                  75                  80

Val Val Thr Ser Leu Cys Arg Arg Ser Asn Val Cys Thr Leu Val Arg
                85                  90                  95

Gly Arg Gln Ala Gly Val Cys Phe Gly Asp Ser Gly Ser Pro Leu Val
                100                 105                 110

Cys Asn Gly Leu Ile His Gly Ile Ala Ser Phe Val Arg Glu Ala Ala
            115                 120                 125

Pro Gln Gly Ser Thr Pro Met Pro Leu Pro Arg Trp His Ser Leu
        130                 135                 140

<210> SEQ ID NO 70
<211> LENGTH: 267
<212> TYPE: PRT
<213> ORGANISM: Homo sapiens

<400> SEQUENCE: 70

Met Thr Leu Gly Arg Arg Leu Ala Cys Leu Phe Leu Ala Cys Val Leu
1               5                   10                  15

Pro Ala Leu Leu Leu Gly Gly Thr Ala Leu Ala Ser Glu Ile Val Gly
                20                  25                  30

Gly Arg Arg Ala Arg Pro His Ala Trp Pro Phe Met Val Ser Leu Gln
            35                  40                  45

Leu Arg Gly Gly His Phe Cys Gly Ala Thr Leu Ile Ala Pro Asn Phe
        50                  55                  60

Val Met Ser Ala Ala His Cys Val Ala Asn Val Asn Val Arg Ala Val
65                  70                  75                  80

Arg Val Val Leu Gly Ala His Asn Leu Ser Arg Arg Glu Pro Thr Arg
                85                  90                  95

Gln Val Phe Ala Val Gln Arg Ile Phe Glu Asn Gly Tyr Asp Pro Val
                100                 105                 110

Asn Leu Leu Asn Asp Ile Val Ile Leu Gln Leu Asn Gly Ser Ala Thr
```

```
                115                 120                 125
Ile Asn Ala Asn Val Gln Val Ala Gln Leu Pro Ala Gln Gly Arg Arg
            130                 135                 140

Leu Gly Asn Gly Val Gln Cys Leu Ala Met Gly Trp Gly Leu Leu Gly
145                 150                 155                 160

Arg Asn Arg Gly Ile Ala Ser Val Leu Gln Glu Leu Asn Val Thr Val
                165                 170                 175

Val Thr Ser Leu Cys Arg Arg Ser Asn Val Cys Thr Leu Val Arg Gly
            180                 185                 190

Arg Gln Ala Gly Val Cys Phe Gly Asp Ser Gly Ser Pro Leu Val Cys
        195                 200                 205

Asn Gly Leu Ile His Gly Ile Ala Ser Phe Val Arg Gly Gly Cys Ala
        210                 215                 220

Ser Gly Leu Tyr Pro Asp Ala Phe Ala Pro Val Ala Gln Phe Val Asn
225                 230                 235                 240

Trp Ile Asp Ser Ile Ile Gln Arg Ser Glu Asp Asn Pro Cys Pro His
                245                 250                 255

Pro Arg Asp Pro Asp Pro Ala Ser Arg Thr His
            260                 265

<210> SEQ ID NO 71
<211> LENGTH: 342
<212> TYPE: PRT
<213> ORGANISM: Homo sapiens

<400> SEQUENCE: 71

Met Thr Leu Gly Arg Arg Leu Ala Cys Leu Phe Leu Ala Cys Val Leu
1               5                   10                  15

Pro Ala Leu Leu Leu Gly Gly Thr Ala Leu Ala Ser Glu Ile Val Gly
            20                  25                  30

Gly Arg Arg Ala Arg Pro His Ala Trp Pro Phe Met Val Ser Leu Gln
        35                  40                  45

Leu Arg Gly Gly His Phe Cys Gly Ala Thr Leu Ile Ala Pro Asn Phe
    50                  55                  60

Val Met Ser Ala Ala His Cys Val Ala Asn Val Asn Val Arg Ala Val
65                  70                  75                  80

Arg Val Val Leu Gly Ala His Asn Leu Ser Arg Arg Glu Pro Thr Arg
                85                  90                  95

Gln Val Phe Ala Val Gln Arg Ile Phe Glu Asn Gly Tyr Asp Pro Val
            100                 105                 110

Asn Leu Leu Asn Asp Ile Val Ile Leu Gln Leu Asn Gly Ser Ala Thr
        115                 120                 125

Ile Asn Ala Asn Val Gln Val Ala Gln Leu Pro Ala Gln Gly Arg Arg
    130                 135                 140

Leu Gly Asn Gly Val Gln Cys Leu Ala Met Gly Trp Gly Leu Leu Gly
145                 150                 155                 160

Arg Asn Arg Gly Ile Ala Ser Val Leu Gln Glu Leu Asn Val Thr Val
                165                 170                 175

Val Thr Ser Leu Cys Arg Arg Ser Asn Val Cys Thr Leu Val Arg Gly
            180                 185                 190

Arg Gln Ala Gly Val Cys Phe Val Arg Ala Leu Gly Val Pro Leu Leu
        195                 200                 205

Pro Thr Arg Ser Gln Pro Gly Leu Gln Gln Ala Pro Trp Leu Asp
    210                 215                 220
```

Pro Arg Arg Asp Phe Pro Thr Leu Thr Gly Gly Gln Val Gly Arg
225                 230                 235                 240

Ala Ser Gln Ser Ser Phe Pro Thr Leu Ser Ala Ser Thr Gly Gly Leu
            245                 250                 255

Arg Gln Pro Leu Gly Leu Gln Arg Ala Asn Pro Arg Asn Cys Leu Leu
        260                 265                 270

Arg Pro Gly Arg Leu Arg Leu Arg Ala Leu Pro Arg Cys Leu Cys Pro
    275                 280                 285

Gly Gly Thr Val Cys Lys Leu Asp Arg Leu Tyr His Pro Thr Leu Arg
290                 295                 300

Gly Gln Pro Leu Ser Pro Pro Gly Pro Gly Pro Gly Gln Gln Asp
305                 310                 315                 320

Pro Leu Arg Arg Ala Ala Arg Val Thr Ser Ala Ala His Thr His Thr
                325                 330                 335

Leu Gln His Leu Ala Gln
            340

<210> SEQ ID NO 72
<211> LENGTH: 176
<212> TYPE: PRT
<213> ORGANISM: Homo sapiens

<400> SEQUENCE: 72

Met Gly Thr Arg Leu Ala Gly Ala Arg Trp Ala Gln Arg Val Gly His
1               5                   10                  15

His Gln Arg Gln Arg Ala Gly Gly Pro Ala Ala Gly Ser Gly Thr Pro
            20                  25                  30

Pro Gly Gln Arg Gly Ala Val Pro Gly His Gly Leu Gly Pro Ser Gly
        35                  40                  45

Gln Glu Pro Trp Asp Arg Gln Arg Pro Ala Gly Ala Gln Arg Asp Gly
    50                  55                  60

Gly Asp Val Pro Leu Pro Ser Gln Gln Arg Leu His Ser Arg Glu Gly
65                  70                  75                  80

Pro Ala Gly Arg Arg Leu Phe Arg Gly Leu Arg Gln Pro Leu Gly Leu
                85                  90                  95

Gln Arg Ala Asn Pro Arg Asn Cys Leu Leu Arg Pro Gly Arg Leu Arg
            100                 105                 110

Leu Arg Ala Leu Pro Arg Cys Leu Cys Pro Gly Gly Thr Val Cys Lys
        115                 120                 125

Leu Asp Arg Leu Tyr His Pro Thr Leu Arg Gly Gln Pro Leu Ser Pro
    130                 135                 140

Pro Pro Gly Pro Gly Pro Gly Gln Gln Asp Pro Leu Arg Arg Ala Ala
145                 150                 155                 160

Arg Val Thr Ser Ala Ala His Thr His Thr Leu Gln His Leu Ala Gln
                165                 170                 175

<210> SEQ ID NO 73
<211> LENGTH: 114
<212> TYPE: PRT
<213> ORGANISM: Homo sapiens

<400> SEQUENCE: 73

Met Gly Trp Gly Leu Leu Gly Arg Asn Arg Gly Ile Ala Ser Val Leu
1               5                   10                  15

Gln Glu Leu Asn Val Thr Val Thr Ser Leu Cys Arg Arg Ser Asn
            20                  25                  30

```
Val Cys Thr Leu Val Arg Gly Arg Gln Ala Gly Val Cys Phe Gly Asp
            35                  40                  45

Ser Gly Ser Pro Leu Val Cys Asn Gly Leu Ile His Gly Ile Ala Ser
 50                  55                  60

Phe Val Arg Gly Gly Cys Ala Ser Gly Leu Tyr Pro Asp Ala Phe Ala
 65                  70                  75                  80

Pro Val Ala Gln Phe Val Asn Trp Ile Asp Ser Ile Gln Arg Ser
                 85                  90                  95

Glu Asp Asn Pro Cys Pro His Pro Arg Asp Pro Asp Pro Ala Ser Arg
                100                 105                 110

Thr His
```

<210> SEQ ID NO 74
<211> LENGTH: 257
<212> TYPE: PRT
<213> ORGANISM: Homo sapiens

<400> SEQUENCE: 74

```
Met Thr Leu Gly Arg Arg Leu Ala Cys Leu Phe Leu Ala Cys Val Leu
 1               5                  10                  15

Pro Ala Leu Leu Leu Gly Gly Thr Ala Leu Ala Ser Glu Ile Val Gly
                20                  25                  30

Gly Arg Arg Ala Arg Pro His Ala Trp Pro Phe Met Val Ser Leu Gln
             35                  40                  45

Leu Arg Gly Gly His Phe Cys Gly Ala Thr Leu Ile Ala Pro Asn Phe
 50                  55                  60

Val Met Ser Ala Ala His Cys Val Ala Asn Val Asn Val Arg Ala Val
 65                  70                  75                  80

Arg Val Val Leu Gly Ala His Asn Leu Ser Arg Arg Glu Pro Thr Arg
                 85                  90                  95

Gln Val Phe Ala Val Gln Arg Ile Phe Glu Asn Gly Tyr Asp Pro Val
                100                 105                 110

Asn Leu Leu Asn Asp Ile Val Ile Leu Gln Gly Arg Arg Glu Gly Ala
                115                 120                 125

Gly Ser Pro Gly Arg Ala Leu Pro Val Ala Ala Gly Ala Leu Gln Ala
130                 135                 140

Pro Val Arg Arg Ala Pro Arg Ser Ala Pro Pro Gly Gln Pro Ala Arg
145                 150                 155                 160

His His Arg Pro Arg Pro Ala Ala Thr Ala Val Gly Glu Gly His
                165                 170                 175

Thr Gly Pro Cys Cys Ala Pro Pro Leu Ala Ala Arg Gly Pro Arg
                180                 185                 190

Arg Gly Thr Gly Asn Ser Leu Arg Arg Gly Arg Leu Gly His Ser Gln
                195                 200                 205

Pro Arg Gly Pro Pro Gly Gln Pro Ala Ala Arg Ala Leu Ala Ser
210                 215                 220

Ala Gly Pro Arg His Leu Gln Pro Ala His Ala Pro Arg Arg Arg His
225                 230                 235                 240

His Arg Ala Leu Asp Val Arg Gly Glu Gln Ser Pro Gly Gln Leu Gln
                245                 250                 255

Gly
```

<210> SEQ ID NO 75
<211> LENGTH: 209
<212> TYPE: PRT

-continued

<213> ORGANISM: Homo sapiens

<400> SEQUENCE: 75

Met Thr Leu Gly Arg Arg Leu Ala Val Phe Ser Ser Pro Val Ser Cys
1               5                   10                  15

Arg Pro Cys Cys Trp Gly His Arg Ala Gly Leu Gly Asp Cys Gly Gly
            20                  25                  30

Pro Ala Ser Ala Ala Pro Arg Val Ala Leu His Gly Val Pro Ala Ala
        35                  40                  45

Ala Arg Arg Pro Leu Leu Arg Arg His Pro Asp Cys Ala Gln Leu Arg
    50                  55                  60

His Val Gly Arg Ala Leu Arg Gly Glu Cys Gly Arg Arg Glu Gly Ala
65                  70                  75                  80

Gly Ser Pro Gly Arg Ala Leu Pro Val Ala Ala Gly Ala Leu Gln Ala
                85                  90                  95

Pro Val Arg Arg Ala Pro Arg Ser Ala Pro Pro Gly Gln Pro Ala Arg
            100                 105                 110

His His Arg Pro Arg Pro Ala Ala Thr Ala Val Gly Glu Gly His
        115                 120                 125

Thr Gly Pro Cys Cys Ala Pro Pro Ala Leu Ala Ala Arg Gly Pro Arg
    130                 135                 140

Arg Gly Thr Gly Asn Ser Leu Arg Arg Gly Arg Leu Gly His Ser Gln
145                 150                 155                 160

Pro Arg Gly Pro Pro Pro Gly Gln Pro Ala Ala Arg Ala Leu Ala Ser
                165                 170                 175

Ala Gly Pro Arg His Leu Gln Pro Ala His Ala Pro Arg Arg Arg His
            180                 185                 190

His Arg Ala Leu Asp Val Arg Gly Glu Gln Ser Pro Gly Gln Leu Gln
        195                 200                 205

Gly

<210> SEQ ID NO 76
<211> LENGTH: 75
<212> TYPE: PRT
<213> ORGANISM: Homo sapiens

<400> SEQUENCE: 76

Met Ala Val Met Ala Pro Pro Asn Pro Arg Pro Ala Thr Leu Gly Ala
1               5                   10                  15

Leu Ala Leu Thr Gln Thr Trp Ala Gly Ser His Ser Met Arg Tyr Phe
            20                  25                  30

Phe Thr Ser Val Ser Arg Pro Gly Arg Gly Ser Pro Ala Ser Ser Gln
        35                  40                  45

Trp Ala Thr Trp Thr Thr Arg Ser Ser Cys Gly Ser Thr Ala Thr Pro
    50                  55                  60

Arg Ala Arg Gly Trp Ser Arg Gly Arg Gly
65                  70                  75

<210> SEQ ID NO 77
<211> LENGTH: 75
<212> TYPE: PRT
<213> ORGANISM: Homo sapiens

<400> SEQUENCE: 77

Met Ala Val Met Ala Pro Arg Thr Leu Val Leu Leu Leu Ser Gly Ala
1               5                   10                  15

-continued

Leu Ala Leu Thr Gln Thr Trp Ala Gly Ser His Ser Met Arg Tyr Phe
            20                  25                  30

Phe Thr Ser Val Ser Arg Pro Gly Arg Gly Pro Ala Ser Ser Gln
        35                  40                  45

Trp Ala Thr Trp Thr Thr Arg Ser Ser Cys Gly Ser Thr Ala Thr Pro
50                  55                  60

Arg Ala Arg Gly Trp Ser Arg Gly Arg Gly
65                  70                  75

<210> SEQ ID NO 78
<211> LENGTH: 179
<212> TYPE: PRT
<213> ORGANISM: Homo sapiens

<400> SEQUENCE: 78

Met Ala Val Met Ala Pro Arg Thr Leu Val Leu Leu Leu Ser Gly Ala
1               5                   10                  15

Leu Ala Leu Thr Gln Thr Trp Ala Gly Ser His Ser Met Arg Tyr Phe
            20                  25                  30

Phe Thr Ser Val Ser Arg Pro Gly Arg Gly Glu Pro Arg Phe Ile Ala
        35                  40                  45

Val Gly Tyr Val Asp Asp Thr Gln Phe Val Arg Phe Asp Ser Asp Ala
50                  55                  60

Ala Ser Gln Arg Met Glu Pro Arg Ala Pro Trp Ile Glu Gln Glu Gly
65                  70                  75                  80

Pro Glu Tyr Trp Asp Gly Glu Thr Arg Lys Val Lys Ala His Ser Gln
                85                  90                  95

Thr His Arg Val Asp Leu Gly Thr Leu Arg Gly Tyr Tyr Asn Gln Ser
                100                 105                 110

Glu Ala Gly Ser His Thr Val Gln Arg Met Tyr Gly Cys Asp Val Gly
            115                 120                 125

Ser Asp Trp Arg Phe Leu Arg Gly Tyr His Gln Tyr Ala Tyr Asp Gly
        130                 135                 140

Lys Asp Tyr Ile Ala Leu Lys Glu Asp Leu Arg Ser Trp Thr Ala Ala
145                 150                 155                 160

Asp Met Ala Ala Gln Thr Thr Lys His Lys Trp Glu Ala Ala Met Trp
                165                 170                 175

Arg Ser Ser

<210> SEQ ID NO 79
<211> LENGTH: 362
<212> TYPE: PRT
<213> ORGANISM: Homo sapiens

<400> SEQUENCE: 79

Met Ala Val Met Ala Pro Arg Thr Leu Val Leu Leu Leu Ser Gly Ala
1               5                   10                  15

Leu Ala Leu Thr Gln Thr Trp Ala Gly Ser His Ser Met Arg Tyr Phe
            20                  25                  30

Phe Thr Ser Val Ser Arg Pro Gly Arg Gly Glu Pro Arg Phe Ile Ala
        35                  40                  45

Val Gly Tyr Val Asp Asp Thr Gln Phe Val Arg Phe Asp Ser Asp Ala
50                  55                  60

Ala Ser Gln Arg Met Glu Pro Arg Ala Pro Trp Ile Glu Gln Glu Gly
65                  70                  75                  80

Pro Glu Tyr Trp Asp Gly Glu Thr Arg Lys Val Lys Ala His Ser Gln

Thr His Arg Val Asp Leu Gly Thr Leu Arg Gly Tyr Tyr Asn Gln Ser
              85                  90                  95

Glu Ala Gly Ser His Thr Val Gln Arg Met Tyr Gly Cys Asp Val Gly
            100                 105                 110

Ser Asp Trp Arg Phe Leu Arg Gly Tyr His Gln Tyr Ala Tyr Asp Gly
        115                 120                 125

Lys Asp Tyr Ile Ala Leu Lys Glu Asp Leu Arg Ser Trp Thr Ala Ala
130                 135                 140

Asp Met Ala Ala Gln Thr Thr Lys His Lys Trp Glu Ala Ala His Val
145                 150                 155                 160

Ala Glu Gln Leu Arg Ala Tyr Leu Glu Gly Thr Cys Val Glu Trp Leu
                165                 170                 175

Arg Arg Tyr Leu Glu Asn Gly Lys Glu Thr Leu Gln Arg Thr Asp Ala
            180                 185                 190

Pro Lys Thr His Met Thr His His Ala Val Ser Asp His Glu Ala Thr
        195                 200                 205

Leu Arg Cys Trp Ala Leu Ser Phe Tyr Pro Ala Glu Ile Thr Leu Thr
210                 215                 220

Trp Gln Arg Asp Gly Glu Asp Gln Thr Gln Asp Thr Glu Leu Val Glu
225                 230                 235                 240

Thr Arg Pro Ala Gly Asp Gly Thr Phe Gln Lys Trp Ala Ala Val Val
                245                 250                 255

Val Pro Ser Gly Gln Glu Gln Arg Tyr Thr Cys His Val Gln His Glu
            260                 265                 270

Gly Leu Pro Lys Pro Leu Thr Leu Arg Trp Glu Pro Ser Ser Gln Pro
        275                 280                 285

Thr Ile Pro Ile Val Gly Ile Ile Ala Gly Leu Val Leu Phe Gly Ala
290                 295                 300

Val Ile Thr Gly Ala Val Val Ala Ala Val Met Trp Arg Arg Lys Ser
305                 310                 315                 320

Ser Ser Pro Ile Ile Phe Ser Cys Ser Arg Glu Val Gly Leu Arg Cys
                325                 330                 335

Leu His Leu Cys Leu Asn Phe Met Val His
            340                 345                 350

<210> SEQ ID NO 80
<211> LENGTH: 365
<212> TYPE: PRT
<213> ORGANISM: Homo sapiens

<400> SEQUENCE: 80

Met Ala Val Met Ala Pro Arg Thr Leu Val Leu Leu Leu Ser Gly Ala
1               5                   10                  15

Leu Ala Leu Thr Gln Thr Trp Ala Gly Ser His Ser Met Arg Tyr Phe
            20                  25                  30

Phe Thr Ser Val Ser Arg Pro Gly Arg Gly Glu Pro Arg Phe Ile Ala
        35                  40                  45

Val Gly Tyr Val Asp Asp Thr Gln Phe Val Arg Phe Asp Ser Asp Ala
    50                  55                  60

Ala Ser Gln Arg Met Glu Pro Arg Ala Pro Trp Ile Glu Gln Glu Gly
65                  70                  75                  80

Pro Glu Tyr Trp Asp Gly Glu Thr Arg Lys Val Lys Ala His Ser Gln
                85                  90                  95

Thr His Arg Val Asp Leu Gly Thr Leu Arg Gly Tyr Tyr Asn Gln Ser
            100                 105                 110

Glu Ala Gly Ser His Thr Val Gln Arg Met Tyr Gly Cys Asp Val Gly
        115                 120                 125

Ser Asp Trp Arg Phe Leu Arg Gly Tyr His Gln Tyr Ala Tyr Asp Gly
    130                 135                 140

Lys Asp Tyr Ile Ala Leu Lys Glu Asp Leu Arg Ser Trp Thr Ala Ala
145                 150                 155                 160

Asp Met Ala Ala Gln Thr Thr Lys His Lys Trp Glu Ala Ala His Val
                165                 170                 175

Ala Glu Gln Leu Arg Ala Tyr Leu Glu Gly Thr Cys Val Glu Trp Leu
            180                 185                 190

Arg Arg Tyr Leu Glu Asn Gly Lys Glu Thr Leu Gln Arg Thr Asp Ala
        195                 200                 205

Pro Lys Thr His Met Thr His His Ala Val Ser Asp His Glu Ala Thr
    210                 215                 220

Leu Arg Cys Trp Ala Leu Ser Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ala Val Val
            260                 265                 270

Val Pro Ser Gly Gln Glu Gln Arg Tyr Thr Cys His Val Gln His Glu
        275                 280                 285

Gly Leu Pro Lys Pro Leu Thr Leu Arg Trp Glu Pro Ser Ser Gln Pro
    290                 295                 300

Thr Ile Pro Ile Val Gly Ile Ile Ala Gly Leu Val Leu Phe Gly Ala
305                 310                 315                 320

Val Ile Thr Gly Ala Val Val Ala Ala Val Met Trp Arg Arg Lys Ser
                325                 330                 335

Ser Asp Arg Lys Gly Gly Ser Tyr Ser Gln Ala Ala Ser Ser Asp Ser
            340                 345                 350

Ala Gln Gly Ser Asp Val Ser Leu Thr Ala Cys Lys Val
        355                 360                 365

<210> SEQ ID NO 81
<211> LENGTH: 194
<212> TYPE: PRT
<213> ORGANISM: Homo sapiens

<400> SEQUENCE: 81

Met Arg Tyr Phe Phe Thr Ser Val Ser Arg Pro Gly Arg Gly Glu Pro
1               5                   10                  15

Arg Phe Ile Ala Val Gly Tyr Val Asp Asp Thr Gln Phe Val Arg Phe
            20                  25                  30

Asp Ser Asp Ala Ala Ser Gln Arg Met Glu Pro Arg Ala Pro Trp Ile
        35                  40                  45

Glu Gln Glu Gly Pro Glu Tyr Trp Asp Gly Glu Thr Arg Lys Val Lys
    50                  55                  60

Ala His Ser Gln Thr His Arg Val Asp Leu Gly Thr Leu Arg Gly Tyr
65                  70                  75                  80

Tyr Asn Gln Ser Glu Ala Gly Ser His Thr Val Gln Arg Met Tyr Gly
                85                  90                  95

Cys Asp Val Gly Ser Asp Trp Arg Phe Leu Arg Gly Tyr His Gln Tyr
            100                 105                 110

Ala Tyr Asp Gly Lys Asp Tyr Ile Ala Leu Lys Glu Asp Leu Arg Ser
            115                 120                 125

Trp Thr Ala Ala Asp Met Ala Ala Gln Thr Thr Lys His Lys Trp Glu
130                 135                 140

Ala Ala His Val Ala Glu Gln Leu Arg Ala Tyr Leu Glu Gly Thr Cys
145                 150                 155                 160

Val Glu Trp Leu Arg Arg Tyr Leu Glu Asn Gly Lys Glu Thr Leu Gln
            165                 170                 175

Arg Thr Asp Ala Pro Lys Thr His Met Thr His His Ala Val Ser His
            180                 185                 190

Ser Leu

<210> SEQ ID NO 82
<211> LENGTH: 297
<212> TYPE: PRT
<213> ORGANISM: Homo sapiens

<400> SEQUENCE: 82

Met Glu Pro Arg Ala Pro Trp Ile Glu Gln Glu Gly Pro Glu Tyr Trp
1               5                   10                  15

Asp Gly Glu Thr Arg Lys Val Lys Ala His Ser Gln Thr His Arg Val
            20                  25                  30

Asp Leu Gly Thr Leu Arg Gly Tyr Tyr Asn Gln Ser Glu Ala Gly Ser
        35                  40                  45

His Thr Val Gln Arg Met Tyr Gly Cys Asp Val Gly Ser Asp Trp Arg
    50                  55                  60

Phe Leu Arg Gly Tyr His Gln Tyr Ala Tyr Asp Gly Lys Asp Tyr Ile
65                  70                  75                  80

Ala Leu Lys Glu Asp Leu Arg Ser Trp Thr Ala Ala Asp Met Ala Ala
                85                  90                  95

Gln Thr Thr Lys His Lys Trp Glu Ala Ala His Val Ala Glu Gln Leu
            100                 105                 110

Arg Ala Tyr Leu Glu Gly Thr Cys Val Glu Trp Leu Arg Arg Tyr Leu
        115                 120                 125

Glu Asn Gly Lys Glu Thr Leu Gln Arg Thr Asp Ala Pro Lys Thr His
    130                 135                 140

Met Thr His His Ala Val Ser Asp His Glu Ala Thr Leu Arg Cys Trp
145                 150                 155                 160

Ala Leu Ser Phe Tyr Pro Ala Glu Ile Thr Leu Thr Trp Gln Arg Asp
                165                 170                 175

Gly Glu Asp Gln Thr Gln Asp Thr Glu Leu Val Glu Thr Arg Pro Ala
            180                 185                 190

Gly Asp Gly Thr Phe Gln Lys Trp Ala Ala Val Val Val Pro Ser Gly
        195                 200                 205

Gln Glu Gln Arg Tyr Thr Cys His Val Gln His Glu Gly Leu Pro Lys
    210                 215                 220

Pro Leu Thr Leu Arg Trp Glu Pro Ser Ser Gln Pro Thr Ile Pro Ile
225                 230                 235                 240

Val Gly Ile Ile Ala Gly Leu Val Leu Phe Gly Ala Val Ile Thr Gly
                245                 250                 255

Ala Val Val Ala Ala Val Met Trp Arg Arg Lys Ser Ser Asp Arg Lys
            260                 265                 270

Gly Gly Ser Tyr Ser Gln Ala Ala Ser Ser Asp Ser Ala Gln Gly Ser
        275                 280                 285

```
Asp Val Ser Leu Thr Ala Cys Lys Val
    290                 295
```

```
<210> SEQ ID NO 83
<211> LENGTH: 153
<212> TYPE: PRT
<213> ORGANISM: Homo sapiens

<400> SEQUENCE: 83

Met Thr His His Ala Val Ser Asp His Glu Ala Thr Leu Arg Cys Trp
1               5                   10                  15

Ala Leu Ser Phe Tyr Pro Ala Glu Ile Thr Leu Thr Trp Gln Arg Asp
            20                  25                  30

Gly Glu Asp Gln Thr Gln Asp Thr Glu Leu Val Glu Thr Arg Pro Ala
        35                  40                  45

Gly Asp Gly Thr Phe Gln Lys Trp Ala Ala Val Val Val Pro Ser Gly
    50                  55                  60

Gln Glu Gln Arg Tyr Thr Cys His Val Gln His Glu Gly Leu Pro Lys
65                  70                  75                  80

Pro Leu Thr Leu Arg Trp Glu Pro Ser Ser Gln Pro Thr Ile Pro Ile
                85                  90                  95

Val Gly Ile Ile Ala Gly Leu Val Leu Phe Gly Ala Val Ile Thr Gly
            100                 105                 110

Ala Val Val Ala Ala Val Met Trp Arg Arg Lys Ser Ser Asp Arg Lys
        115                 120                 125

Gly Gly Ser Tyr Ser Gln Ala Ala Ser Ser Asp Ser Ala Gln Gly Ser
    130                 135                 140

Asp Val Ser Leu Thr Ala Cys Lys Val
145                 150
```

```
<210> SEQ ID NO 84
<211> LENGTH: 300
<212> TYPE: PRT
<213> ORGANISM: Homo sapiens

<400> SEQUENCE: 84

Met Ala Val Met Glu Pro Arg Ala Pro Trp Ile Glu Gln Glu Gly Pro
1               5                   10                  15

Glu Tyr Trp Asp Gly Glu Thr Arg Lys Val Lys Ala His Ser Gln Thr
            20                  25                  30

His Arg Val Asp Leu Gly Thr Leu Arg Gly Tyr Tyr Asn Gln Ser Glu
        35                  40                  45

Ala Gly Ser His Thr Val Gln Arg Met Tyr Gly Cys Asp Val Gly Ser
    50                  55                  60

Asp Trp Arg Phe Leu Arg Gly Tyr His Gln Tyr Ala Tyr Asp Gly Lys
65                  70                  75                  80

Asp Tyr Ile Ala Leu Lys Glu Asp Leu Arg Ser Trp Thr Ala Ala Asp
                85                  90                  95

Met Ala Ala Gln Thr Thr Lys His Lys Trp Glu Ala Ala His Val Ala
            100                 105                 110

Glu Gln Leu Arg Ala Tyr Leu Glu Gly Thr Cys Val Glu Trp Leu Arg
        115                 120                 125

Arg Tyr Leu Glu Asn Gly Lys Glu Thr Leu Gln Arg Thr Asp Ala Pro
    130                 135                 140

Lys Thr His Met Thr His His Ala Val Ser Asp His Glu Ala Thr Leu
145                 150                 155                 160
```

```
Arg Cys Trp Ala Leu Ser Phe Tyr Pro Ala Glu Ile Thr Leu Thr Trp
                165                 170                 175

Gln Arg Asp Gly Glu Asp Gln Thr Gln Asp Thr Glu Leu Val Glu Thr
            180                 185                 190

Arg Pro Ala Gly Asp Gly Thr Phe Gln Lys Trp Ala Ala Val Val Val
        195                 200                 205

Pro Ser Gly Gln Glu Gln Arg Tyr Thr Cys His Val Gln His Glu Gly
    210                 215                 220

Leu Pro Lys Pro Leu Thr Leu Arg Trp Glu Pro Ser Ser Gln Pro Thr
225                 230                 235                 240

Ile Pro Ile Val Gly Ile Ile Ala Gly Leu Val Leu Phe Gly Ala Val
                245                 250                 255

Ile Thr Gly Ala Val Val Ala Ala Val Met Trp Arg Arg Lys Ser Ser
            260                 265                 270

Asp Arg Lys Gly Gly Ser Tyr Ser Gln Ala Ala Ser Ser Asp Ser Ala
        275                 280                 285

Gln Gly Ser Asp Val Ser Leu Thr Ala Cys Lys Val
    290                 295                 300

<210> SEQ ID NO 85
<211> LENGTH: 396
<212> TYPE: PRT
<213> ORGANISM: Homo sapiens

<400> SEQUENCE: 85

Met Ala Val Met Ala Pro Arg Thr Leu Val Leu Leu Leu Ser Gly Ala
1               5                   10                  15

Leu Ala Leu Thr Gln Thr Trp Ala Gly Ser His Ser Met Arg Tyr Phe
            20                  25                  30

Phe Thr Ser Val Ser Arg Pro Gly Arg Gly Glu Pro Arg Phe Ile Ala
        35                  40                  45

Val Gly Tyr Val Asp Asp Thr Gln Phe Val Arg Phe Asp Ser Asp Ala
    50                  55                  60

Ala Ser Gln Arg Met Glu Pro Arg Ala Pro Trp Ile Glu Gln Glu Gly
65                  70                  75                  80

Pro Glu Tyr Trp Asp Gly Glu Thr Arg Lys Val Lys Ala His Ser Gln
                85                  90                  95

Thr His Arg Val Asp Leu Gly Thr Leu Arg Gly Tyr Tyr Asn Gln Ser
            100                 105                 110

Glu Ala Gly Ser His Thr Val Gln Arg Met Tyr Gly Cys Asp Val Gly
        115                 120                 125

Ser Asp Trp Arg Phe Leu Arg Gly Tyr His Gln Tyr Ala Tyr Asp Gly
    130                 135                 140

Lys Asp Tyr Ile Ala Leu Lys Glu Asp Leu Arg Ser Trp Thr Ala Ala
145                 150                 155                 160

Asp Met Ala Ala Gln Thr Thr Lys His Lys Trp Glu Ala Ala His Val
                165                 170                 175

Ala Glu Gln Leu Arg Ala Tyr Leu Glu Gly Thr Cys Val Glu Trp Leu
            180                 185                 190

Arg Arg Tyr Leu Glu Asn Gly Lys Glu Thr Leu Gln Arg Thr Asp Ala
        195                 200                 205

Pro Lys Thr His Met Thr His His Ala Val Ser Asp His Glu Ala Thr
    210                 215                 220

Leu Arg Cys Trp Ala Leu Ser Phe Tyr Pro Ala Glu Ile Thr Leu Thr
```

```
                225                 230                 235                 240
Trp Gln Arg Asp Gly Glu Asp Gln Thr Gln Asp Thr Glu Leu Val Glu
                    245                 250                 255

Thr Arg Pro Ala Gly Asp Gly Thr Phe Gln Lys Trp Ala Ala Val Val
                    260                 265                 270

Val Pro Ser Gly Gln Glu Gln Arg Tyr Thr Cys His Val Gln His Glu
                    275                 280                 285

Gly Leu Pro Lys Pro Leu Thr Leu Arg Trp Glu Pro Ser Ser Gln Pro
                    290                 295                 300

Thr Ile Pro Ile Val Gly Ile Ile Ala Gly Leu Val Leu Phe Gly Ala
305                 310                 315                 320

Val Ile Thr Gly Ala Val Val Ala Ala Val Met Trp Arg Arg Lys Ser
                    325                 330                 335

Ser Asp Arg Lys Gly Gly Ser Tyr Ser Gln Ala Ala Ser Ser Leu Tyr
                    340                 345                 350

Ser Val Arg Gln Leu Pro Cys Val Gly Leu Arg Gly Lys Ser Cys Ser
                    355                 360                 365

Cys Pro Ser Leu Cys Asp Leu Lys Asn Pro Asp Phe Val Ser Ala Lys
                    370                 375                 380

Ala Pro Ala Cys Val Cys Val Arg Val Gly Ile Met
385                 390                 395

<210> SEQ ID NO 86
<211> LENGTH: 306
<212> TYPE: PRT
<213> ORGANISM: Homo sapiens

<400> SEQUENCE: 86

Met Glu Pro Arg Ala Pro Trp Ile Glu Gln Glu Gly Pro Glu Tyr Trp
1               5                   10                  15

Asp Gly Glu Thr Arg Lys Val Lys Ala His Ser Gln Thr His Arg Val
                20                  25                  30

Asp Leu Gly Thr Leu Arg Gly Tyr Tyr Asn Gln Ser Glu Ala Ala Ser
            35                  40                  45

His Thr Val Gln Arg Met Tyr Gly Cys Asp Val Gly Ser Asp Trp Arg
        50                  55                  60

Phe Leu Arg Gly Tyr His Gln Tyr Ala Tyr Asp Gly Lys Asp Tyr Ile
65                  70                  75                  80

Ala Leu Lys Glu Asp Leu Arg Ser Trp Thr Ala Ala Asp Met Ala Ala
                85                  90                  95

Gln Thr Thr Lys His Lys Trp Glu Ala Ala His Val Ala Glu Gln Leu
                100                 105                 110

Arg Ala Tyr Leu Glu Gly Thr Cys Val Glu Trp Leu Arg Arg Tyr Leu
            115                 120                 125

Glu Asn Gly Lys Glu Thr Leu Gln Arg Thr Asp Ala Pro Lys Thr His
        130                 135                 140

Met Thr His His Ala Val Ser Asp His Glu Ala Thr Leu Arg Cys Trp
145                 150                 155                 160

Ala Leu Ser Phe Tyr Pro Ala Glu Ile Thr Leu Thr Trp Gln Arg Asp
                165                 170                 175

Gly Glu Asp Gln Thr Gln Asp Thr Glu Leu Val Glu Thr Arg Pro Ala
                180                 185                 190

Gly Asp Gly Thr Phe Gln Lys Trp Ala Ala Val Val Val Pro Ser Gly
            195                 200                 205
```

-continued

```
Gln Glu Gln Arg Tyr Thr Cys His Val Gln His Glu Gly Leu Pro Lys
    210                 215                 220

Pro Leu Thr Leu Arg Trp Glu Pro Ser Ser Gln Pro Thr Ile Pro Ile
225                 230                 235                 240

Val Gly Ile Ile Ala Gly Leu Val Leu Phe Gly Ala Val Ile Thr Gly
                245                 250                 255

Ala Val Val Ala Ala Val Met Trp Arg Arg Lys Ser Ser Asp Arg Lys
            260                 265                 270

Gly Gly Lys Ser Cys Ser Cys Pro Ser Leu Cys Asp Leu Lys Asn Pro
        275                 280                 285

Asp Phe Val Ser Ala Lys Ala Pro Ala Cys Val Cys Val Arg Val Gly
290                 295                 300

Ile Met
305

<210> SEQ ID NO 87
<211> LENGTH: 348
<212> TYPE: PRT
<213> ORGANISM: Homo sapiens

<400> SEQUENCE: 87

Met Ala Val Met Ala Pro Arg Thr Leu Val Leu Leu Leu Ser Gly Ala
1               5                   10                  15

Leu Ala Leu Thr Gln Thr Trp Ala Gly Ser His Ser Met Arg Tyr Phe
                20                  25                  30

Phe Thr Ser Val Ser Arg Pro Gly Arg Gly Glu Pro Arg Phe Ile Ala
            35                  40                  45

Val Gly Tyr Val Asp Asp Thr Gln Phe Val Arg Phe Asp Ser Asp Ala
50                  55                  60

Ala Ser Gln Arg Met Glu Pro Arg Ala Pro Trp Ile Glu Gln Glu Gly
65                  70                  75                  80

Pro Glu Tyr Trp Asp Gly Glu Thr Arg Lys Val Lys Ala His Ser Gln
                85                  90                  95

Thr His Arg Val Asp Leu Gly Thr Leu Arg Gly Tyr Tyr Asn Gln Ser
            100                 105                 110

Glu Ala Gly Ser His Thr Val Gln Arg Met Tyr Gly Cys Asp Val Gly
        115                 120                 125

Ser Asp Trp Arg Phe Leu Arg Gly Tyr His Gln Tyr Ala Tyr Asp Gly
    130                 135                 140

Lys Asp Tyr Ile Ala Leu Lys Glu Asp Leu Arg Ser Trp Thr Ala Ala
145                 150                 155                 160

Asp Met Ala Ala Gln Thr Thr Lys His Lys Trp Glu Ala Ala His Val
                165                 170                 175

Ala Glu Gln Leu Arg Ala Tyr Leu Glu Gly Thr Cys Val Glu Trp Leu
            180                 185                 190

Arg Arg Tyr Leu Glu Asn Gly Lys Glu Thr Leu Gln Arg Thr Asp Ala
        195                 200                 205

Pro Lys Thr His Met Thr His His Ala Val Ser Asp His Glu Ala Thr
    210                 215                 220

Leu Arg Cys Trp Ala Leu Ser Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ala Val Val
            260                 265                 270
```

```
Val Pro Ser Gly Gln Glu Gln Arg Tyr Thr Cys His Val Gln His Glu
        275                 280                 285

Gly Leu Pro Lys Pro Leu Thr Leu Arg Trp Glu Pro Ser Ser Gln Pro
        290                 295                 300

Thr Ile Pro Ile Val Gly Ile Ile Ala Gly Leu Val Leu Phe Gly Ala
305                 310                 315                 320

Val Ile Thr Gly Ala Val Val Ala Ala Val Met Trp Arg Arg Lys Ser
                325                 330                 335

Ser Pro Ile Ile Phe Pro Val Pro Glu Arg Trp Gly
                340                 345

<210> SEQ ID NO 88
<211> LENGTH: 339
<212> TYPE: PRT
<213> ORGANISM: Homo sapiens

<400> SEQUENCE: 88

Met Ala Val Met Ala Pro Arg Thr Leu Val Leu Leu Leu Ser Gly Ala
1               5                   10                  15

Leu Ala Leu Thr Gln Thr Trp Ala Gly Ser His Ser Met Arg Tyr Phe
            20                  25                  30

Phe Thr Ser Val Ser Arg Pro Gly Arg Gly Glu Pro Arg Phe Ile Ala
        35                  40                  45

Val Gly Tyr Val Asp Asp Thr Gln Phe Val Arg Phe Asp Ser Asp Ala
    50                  55                  60

Ala Ser Gln Arg Met Glu Pro Arg Ala Pro Trp Ile Glu Gln Glu Gly
65                  70                  75                  80

Pro Glu Tyr Trp Asp Gly Glu Thr Arg Lys Val Lys Ala His Ser Gln
                85                  90                  95

Thr His Arg Val Asp Leu Gly Thr Leu Arg Gly Tyr Tyr Asn Gln Ser
            100                 105                 110

Glu Ala Gly Ser His Thr Val Gln Arg Met Tyr Gly Cys Asp Val Gly
        115                 120                 125

Ser Asp Trp Arg Phe Leu Arg Gly Tyr His Gln Tyr Ala Tyr Asp Gly
    130                 135                 140

Lys Asp Tyr Ile Ala Leu Lys Glu Asp Leu Arg Ser Trp Thr Ala Ala
145                 150                 155                 160

Asp Met Ala Ala Gln Thr Thr Lys His Lys Trp Glu Ala Ala His Val
                165                 170                 175

Ala Glu Gln Leu Arg Ala Tyr Leu Glu Gly Thr Cys Val Glu Trp Leu
            180                 185                 190

Arg Arg Tyr Leu Glu Asn Gly Lys Glu Thr Leu Gln Arg Thr Asp Ala
        195                 200                 205

Pro Lys Thr His Met Thr His His Ala Val Ser Asp His Glu Ala Thr
    210                 215                 220

Leu Arg Cys Trp Ala Leu Ser Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ala Val Val
            260                 265                 270

Val Pro Ser Gly Gln Glu Gln Arg Tyr Thr Cys His Val Gln His Glu
        275                 280                 285

Gly Leu Pro Lys Pro Leu Thr Leu Arg Trp Glu Pro Ser Ser Gln Pro
```

```
                290                 295                 300
Thr Ile Pro Ile Val Gly Ile Ala Gly Leu Val Leu Phe Gly Ala
305                 310                 315                 320

Val Ile Thr Gly Ala Val Val Ala Ala Val Met Trp Arg Arg Lys Ser
                325                 330                 335

Ser Asp Arg

<210> SEQ ID NO 89
<211> LENGTH: 324
<212> TYPE: PRT
<213> ORGANISM: Homo sapiens

<400> SEQUENCE: 89

Met Ala Val Met Ala Pro Arg Thr Leu Val Leu Leu Ser Gly Ala
1               5                   10                  15

Leu Ala Leu Thr Gln Thr Trp Ala Gly Ser His Ser Met Arg Tyr Phe
                20                  25                  30

Phe Thr Ser Val Ser Arg Pro Gly Arg Gly Glu Pro Arg Phe Ile Ala
                35                  40                  45

Val Gly Tyr Val Asp Asp Thr Gln Phe Val Arg Phe Asp Ser Asp Ala
50                  55                  60

Ala Ser Gln Arg Met Glu Pro Arg Ala Pro Trp Ile Glu Gln Glu Gly
65                  70                  75                  80

Pro Glu Tyr Trp Asp Gly Glu Thr Arg Lys Val Lys Ala His Ser Gln
                85                  90                  95

Thr His Arg Val Asp Leu Gly Thr Leu Arg Gly Tyr Tyr Asn Gln Ser
                100                 105                 110

Glu Ala Gly Ser His Thr Val Gln Arg Met Tyr Gly Cys Asp Val Gly
                115                 120                 125

Ser Asp Trp Arg Phe Leu Arg Gly Tyr His Gln Tyr Ala Tyr Asp Gly
                130                 135                 140

Lys Asp Tyr Ile Ala Leu Lys Glu Asp Leu Arg Ser Trp Thr Ala Ala
145                 150                 155                 160

Asp Met Ala Ala Gln Thr Thr Lys His Lys Trp Glu Ala Ala His Val
                165                 170                 175

Ala Glu Gln Leu Arg Ala Tyr Leu Glu Gly Thr Cys Val Glu Trp Leu
                180                 185                 190

Arg Arg Tyr Leu Glu Asn Gly Lys Glu Thr Leu Gln Arg Thr Asp Ala
                195                 200                 205

Pro Lys Thr His Met Thr His His Ala Val Ser Asp His Glu Ala Thr
                210                 215                 220

Leu Arg Cys Trp Ala Leu Ser Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ala Val Val
                260                 265                 270

Val Pro Ser Gly Gln Glu Gln Arg Tyr Thr Cys His Val Gln His Glu
                275                 280                 285

Gly Leu Pro Lys Pro His Arg Gly His His Cys Trp Pro Gly Ser Leu
                290                 295                 300

Trp Ser Cys Asp His Trp Ser Cys Gly Arg Cys Cys Asp Val Glu Glu
305                 310                 315                 320

Glu Glu Leu Arg
```

<210> SEQ ID NO 90
<211> LENGTH: 252
<212> TYPE: PRT
<213> ORGANISM: Homo sapiens

<400> SEQUENCE: 90

Met Glu Pro Arg Ala Pro Trp Ile Glu Gln Glu Gly Pro Glu Tyr Trp
1               5                   10                  15

Asp Gly Glu Thr Arg Lys Val Lys Ala His Ser Gln Thr His Arg Val
                20                  25                  30

Asp Leu Gly Thr Leu Arg Gly Tyr Tyr Asn Gln Ser Glu Ala Gly Ser
            35                  40                  45

His Thr Val Gln Arg Met Tyr Gly Cys Asp Val Gly Ser Asp Trp Arg
    50                  55                  60

Phe Leu Arg Gly Tyr His Gln Tyr Ala Tyr Asp Gly Lys Asp Tyr Ile
65                  70                  75                  80

Ala Leu Lys Glu Asp Leu Arg Ser Trp Thr Ala Ala Asp Met Ala Ala
                85                  90                  95

Gln Thr Thr Lys His Lys Trp Glu Ala Ala His Val Ala Glu Gln Leu
            100                 105                 110

Arg Ala Tyr Leu Glu Gly Thr Cys Val Glu Trp Leu Arg Arg Tyr Leu
        115                 120                 125

Glu Asn Gly Lys Glu Thr Leu Gln Arg Thr Asp Ala Pro Lys Thr His
    130                 135                 140

Met Thr His His Ala Val Ser Asp His Glu Ala Thr Leu Arg Cys Trp
145                 150                 155                 160

Ala Leu Ser Phe Tyr Pro Ala Glu Ile Thr Leu Thr Trp Gln Arg Asp
                165                 170                 175

Gly Glu Asp Gln Thr Gln Asp Thr Glu Leu Val Glu Thr Arg Pro Ala
            180                 185                 190

Gly Asp Gly Thr Phe Gln Lys Trp Ala Ala Val Val Val Pro Ser Gly
        195                 200                 205

Gln Glu Gln Arg Tyr Thr Cys His Val Gln His Glu Gly Leu Pro Lys
    210                 215                 220

Pro Leu Thr Leu Arg Trp Glu Pro Ser Ser Gln Pro Thr Ile Pro Ile
225                 230                 235                 240

Val Ala Ser Leu Leu Ala Trp Phe Ser Leu Glu Leu
                245                 250

<210> SEQ ID NO 91
<211> LENGTH: 281
<212> TYPE: PRT
<213> ORGANISM: Homo sapiens

<400> SEQUENCE: 91

Met Ala Val Met Ala Pro Arg Thr Leu Val Leu Leu Leu Ser Gly Ala
1               5                   10                  15

Leu Ala Leu Thr Gln Thr Trp Ala Gly Ser His Ser Met Arg Tyr Phe
                20                  25                  30

Phe Thr Ser Val Ser Arg Pro Gly Arg Gly Glu Pro Arg Phe Ile Ala
            35                  40                  45

Val Gly Tyr Val Asp Asp Thr Gln Phe Val Arg Phe Asp Ser Asp Ala
    50                  55                  60

Ala Ser Gln Arg Met Glu Pro Arg Ala Pro Trp Ile Glu Gln Glu Gly
65                  70                  75                  80

```
Pro Glu Tyr Trp Asp Gly Glu Thr Arg Lys Val Lys Ala His Ser Gln
                85                  90                  95

Thr His Arg Val Asp Leu Gly Thr Leu Arg Gly Tyr Tyr Asn Gln Ser
            100                 105                 110

Glu Ala Gly Ser His Thr Val Gln Arg Met Tyr Gly Cys Asp Val Gly
        115                 120                 125

Ser Asp Trp Arg Phe Leu Arg Gly Tyr His Gln Tyr Ala Tyr Asp Gly
    130                 135                 140

Lys Asp Tyr Ile Ala Leu Lys Glu Asp Leu Arg Ser Trp Thr Ala Ala
145                 150                 155                 160

Asp Met Ala Ala Gln Thr Thr Lys His Lys Trp Glu Ala Ala His Val
                165                 170                 175

Ala Glu Gln Leu Arg Ala Tyr Leu Glu Gly Thr Cys Val Glu Trp Leu
            180                 185                 190

Arg Arg Tyr Leu Glu Asn Gly Lys Glu Thr Leu Gln Arg Thr Asp Ala
        195                 200                 205

Pro Lys Thr His Met Thr His His Ala Val Ser Asp His Glu Ala Thr
    210                 215                 220

Leu Arg Cys Trp Ala Leu Ser Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Ser Arg Asp Thr Pro Ala Met Cys Ser
            260                 265                 270

Met Arg Val Cys Pro Ser Pro Ser Pro
        275                 280

<210> SEQ ID NO 92
<211> LENGTH: 187
<212> TYPE: PRT
<213> ORGANISM: Homo sapiens

<400> SEQUENCE: 92

Met Glu Pro Arg Ala Pro Trp Ile Glu Gln Glu Gly Pro Glu Tyr Trp
1               5                   10                  15

Asp Gly Glu Thr Arg Lys Val Lys Ala His Ser Gln Thr His Arg Val
            20                  25                  30

Asp Leu Gly Thr Leu Arg Gly Tyr Tyr Asn Gln Ser Glu Ala Gly Ser
        35                  40                  45

His Thr Val Gln Arg Met Tyr Gly Cys Asp Val Gly Ser Asp Trp Arg
    50                  55                  60

Phe Leu Arg Gly Tyr His Gln Tyr Ala Tyr Asp Gly Lys Asp Tyr Ile
65                  70                  75                  80

Ala Leu Lys Glu Asp Leu Arg Ser Trp Thr Ala Ala Asp Met Ala Ala
                85                  90                  95

Gln Thr Thr Lys His Lys Trp Glu Ala Ala His Val Ala Glu Gln Leu
            100                 105                 110

Arg Ala Tyr Leu Glu Gly Thr Cys Val Glu Trp Leu Arg Arg Tyr Leu
        115                 120                 125

Glu Asn Gly Lys Glu Thr Leu Gln Arg Thr Asp Ala Pro Lys Thr His
    130                 135                 140

Met Thr His His Ala Val Ser Asp His Glu Ala Thr Leu Arg Cys Trp
145                 150                 155                 160

Ala Leu Ser Phe Tyr Pro Ala Glu Ile Thr Leu Thr Trp Gln Arg Asp
```

165                 170                 175

Gly Glu Asp Gln Thr Gln Asp Thr Glu Leu Arg
            180                 185

<210> SEQ ID NO 93
<211> LENGTH: 212
<212> TYPE: PRT
<213> ORGANISM: Homo sapiens

<400> SEQUENCE: 93

Met Ala Val Met Ala Pro Arg Thr Leu Val Leu Leu Leu Ser Gly Ala
1               5                   10                  15

Leu Ala Leu Thr Gln Thr Trp Ala Gly Ser His Ser Met Arg Tyr Phe
            20                  25                  30

Phe Thr Ser Val Ser Arg Pro Gly Arg Gly Glu Pro Arg Phe Ile Ala
        35                  40                  45

Val Gly Tyr Val Asp Asp Thr Gln Phe Val Arg Phe Asp Ser Asp Ala
    50                  55                  60

Ala Ser Gln Arg Met Glu Pro Arg Ala Pro Trp Ile Glu Gln Glu Gly
65                  70                  75                  80

Pro Glu Tyr Trp Asp Gly Glu Thr Arg Lys Val Lys Ala His Ser Gln
                85                  90                  95

Thr His Arg Val Asp Leu Gly Thr Leu Arg Gly Tyr Tyr Asn Gln Ser
            100                 105                 110

Glu Ala Gly Ser His Thr Val Gln Arg Met Tyr Gly Cys Asp Val Gly
        115                 120                 125

Ser Asp Trp Arg Phe Leu Arg Gly Tyr His Gln Tyr Ala Tyr Asp Gly
    130                 135                 140

Lys Asp Tyr Ile Ala Leu Lys Glu Asp Leu Arg Ser Trp Thr Ala Ala
145                 150                 155                 160

Asp Met Ala Ala Gln Ile Glu Lys Glu Gly Ala Thr Leu Arg Leu Gln
                165                 170                 175

Ala Val Ala Val Pro Arg Ala Leu Met Cys Leu Ser Gln Leu Val Lys
            180                 185                 190

Cys Glu Thr Ala Ala Leu Cys Gly Thr Glu Arg Gln Glu Leu Phe Leu
        195                 200                 205

Pro Phe Pro Leu
    210

<210> SEQ ID NO 94
<211> LENGTH: 96
<212> TYPE: PRT
<213> ORGANISM: Homo sapiens

<400> SEQUENCE: 94

Met Arg Val Met Ala Pro Arg Thr Leu Leu Leu Leu Leu Ser Gly Ala
1               5                   10                  15

Leu Ala Leu Thr Glu Thr Trp Ala Cys Ser His Ser Met Arg Tyr Phe
            20                  25                  30

Asp Thr Ala Cys Pro Gly Pro Ala Ala Glu Ser Pro Thr Ser Ser Gln
        35                  40                  45

Trp Ala Thr Trp Thr Thr Arg Ser Ser Cys Gly Ser Thr Ala Thr Pro
    50                  55                  60

Arg Val Gln Glu Gly Ser Arg Gly Ala Val Gly Gly Ala Gly Gly Ala
65                  70                  75                  80

Gly Val Leu Gly Pro Gly Asp Thr Glu Val Gln Ala Pro Gly Thr Asp

-continued

```
                    85                  90                  95

<210> SEQ ID NO 95
<211> LENGTH: 110
<212> TYPE: PRT
<213> ORGANISM: Homo sapiens

<400> SEQUENCE: 95

Met Arg Val Met Ala Pro Arg Thr Leu Leu Leu Leu Ser Gly Ala
1               5                   10                  15

Leu Ala Leu Thr Glu Thr Trp Ala Cys Ser His Ser Met Arg Tyr Phe
                20                  25                  30

Tyr Thr Ala Val Ser Arg Pro Ser Arg Gly Glu Pro His Phe Ile Ala
            35                  40                  45

Val Gly Tyr Val Asp Asp Thr Gln Phe Val Arg Phe Asp Ser Asp Ala
    50                  55                  60

Ala Ser Pro Arg Gly Ser Arg Gly Arg Gly Trp Ser Arg Arg Gly
65                  70                  75                  80

Arg Ser Ile Gly Thr Gly Arg His Arg Ser Thr Ser Ala Ser Ser Ala
                85                  90                  95

Gly Met Thr Ser Pro Pro Thr Thr Ala Arg Ile Thr Ser Pro
                100                 105                 110

<210> SEQ ID NO 96
<211> LENGTH: 291
<212> TYPE: PRT
<213> ORGANISM: Homo sapiens

<400> SEQUENCE: 96

Met Arg Val Met Ala Pro Arg Thr Leu Leu Leu Leu Ser Gly Ala
1               5                   10                  15

Leu Ala Leu Thr Glu Thr Trp Ala Cys Ser His Ser Met Arg Tyr Phe
                20                  25                  30

Tyr Thr Ala Val Ser Arg Pro Ser Arg Gly Glu His His Phe Ile Ala
            35                  40                  45

Val Gly Tyr Val Asp Asp Thr Gln Phe Val Arg Phe Asp Ser Asp Ala
    50                  55                  60

Ala Ser Pro Arg Gly Glu Pro Arg Ala Pro Trp Val Glu Gln Glu Gly
65                  70                  75                  80

Pro Glu Tyr Trp Asp Arg Glu Thr Gln Lys Tyr Lys Arg Gln Ala Gln
                85                  90                  95

Thr Asp Arg Val Asn Leu Arg Lys Leu Arg Gly Tyr Tyr Asn Gln Ser
                100                 105                 110

Glu Ala Gly Ser His Thr Leu Gln Arg Met Tyr Gly Cys Asp Leu Gly
            115                 120                 125

Pro Asp Gly Arg Leu Leu Arg Gly Tyr Asp Gln Ser Ala Tyr Asp Gly
        130                 135                 140

Lys Asp Tyr Ile Ala Leu Asn Glu Asp Leu Arg Ser Trp Thr Ala Ala
145                 150                 155                 160

Asp Thr Ala Ala Gln Ile Thr Gln Arg Lys Trp Glu Ala Ala Arg Glu
                165                 170                 175

Ala Glu Gln Trp Arg Ala Tyr Leu Glu Gly Glu Cys Val Glu Trp Leu
            180                 185                 190

Arg Arg Tyr Leu Glu Asn Gly Lys Glu Thr Leu Gln Arg Ala Glu His
        195                 200                 205

Pro Lys Thr His Val Thr His His Pro Val Ser Asp His Glu Ala Thr
```

```
                210                 215                 220
Leu Arg Cys Trp Ala Leu Gly Phe Tyr Pro Thr Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Arg Gly Ser Val Gly Ala
                260                 265                 270

Ser Gly Glu Ser Arg Ile His Val Pro Cys Ala Ala Arg Gly Arg Arg
                275                 280                 285

Ala Leu Thr
    290

<210> SEQ ID NO 97
<211> LENGTH: 293
<212> TYPE: PRT
<213> ORGANISM: Homo sapiens

<400> SEQUENCE: 97

Met Arg Val Met Ala Pro Arg Thr Leu Leu Leu Leu Ser Gly Ala
1               5                   10                  15

Leu Ala Leu Thr Glu Thr Trp Ala Cys Ser His Ser Met Arg Tyr Phe
                20                  25                  30

Tyr Thr Ala Val Ser Arg Pro Ser Arg Gly Glu Pro His Phe Ile Ala
                35                  40                  45

Val Gly Tyr Val Asp Asp Thr Gln Phe Val Arg Phe Asp Ser Asp Ala
                50                  55                  60

Ala Ser Pro Arg Gly Glu Pro Arg Ala Pro Trp Val Glu Gln Glu Gly
65                  70                  75                  80

Pro Glu Tyr Trp Asp Arg Glu Thr Gln Lys Tyr Lys Arg Gln Ala Gln
                85                  90                  95

Thr Asp Arg Val Asn Leu Arg Lys Leu Arg Gly Tyr Tyr Asn Gln Ser
                100                 105                 110

Glu Ala Gly Ser His Thr Leu Gln Arg Met Tyr Gly Cys Asp Leu Gly
                115                 120                 125

Pro Asp Gly Arg Leu Leu Arg Gly Tyr Asp Gln Ser Ala Tyr Asp Gly
                130                 135                 140

Lys Asp Tyr Ile Ala Leu Asn Glu Asp Leu Arg Ser Trp Thr Ala Ala
145                 150                 155                 160

Asp Thr Ala Ala Gln Ile Thr Gln Arg Lys Trp Glu Ala Ala Arg Glu
                165                 170                 175

Ala Glu Gln Trp Arg Ala Tyr Leu Glu Gly Glu Cys Val Glu Trp Leu
                180                 185                 190

Arg Arg Tyr Leu Glu Asn Gly Lys Glu Thr Leu Gln Arg Ala Glu His
                195                 200                 205

Pro Lys Thr His Val Thr His His Pro Val Ser Asp His Glu Ala Thr
                210                 215                 220

Leu Arg Cys Trp Ala Leu Gly Phe Tyr Pro Thr Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ala Val Val
                260                 265                 270

Val Pro Ser Gly Cys Pro Gly Cys Pro Ser Cys Pro Arg Ser Cys Gly
                275                 280                 285
```

Gly Cys Cys Asp Val
            290

<210> SEQ ID NO 98
<211> LENGTH: 245
<212> TYPE: PRT
<213> ORGANISM: Homo sapiens

<400> SEQUENCE: 98

Met Tyr Gly Cys Asp Leu Gly Pro Asp Gly Arg Leu Leu Arg Gly Tyr
1               5                   10                  15

Asp Gln Ser Ala Tyr Asp Gly Lys Asp Tyr Ile Ala Leu Asn Glu Asp
            20                  25                  30

Leu Arg Ser Trp Thr Ala Ala Asp Thr Ala Ala Gln Ile Thr Gln Arg
        35                  40                  45

Lys Trp Glu Ala Ala Arg Glu Ala Glu Gln Trp Arg Ala Tyr Leu Glu
    50                  55                  60

Gly Glu Cys Val Glu Trp Leu Arg Arg Tyr Leu Glu Asn Gly Lys Glu
65                  70                  75                  80

Thr Leu Gln Arg Ala Glu His Pro Lys Thr His Val Thr His His Pro
                85                  90                  95

Val Ser Asp His Glu Ala Thr Leu Arg Cys Trp Ala Leu Gly Phe Tyr
            100                 105                 110

Pro Thr Glu Ile Thr Leu Thr Trp Gln Arg Asp Gly Glu Asp Gln Thr
        115                 120                 125

Gln Asp Thr Glu Leu Val Glu Thr Arg Pro Ala Gly Asp Gly Thr Phe
    130                 135                 140

Gln Lys Trp Ala Ala Val Val Val Pro Ser Gly Glu Glu Gln Arg Tyr
145                 150                 155                 160

Thr Cys His Val Gln His Glu Gly Leu Pro Glu Pro Leu Thr Leu Arg
                165                 170                 175

Trp Glu Pro Ser Ser Gln Pro Thr Ile Pro Ile Val Gly Ile Val Ala
            180                 185                 190

Gly Leu Ala Val Leu Ala Val Leu Ala Val Leu Gly Ala Val Val Ala
        195                 200                 205

Val Val Met Cys Arg Arg Lys Ser Ser Gly Gly Lys Gly Gly Ser Cys
    210                 215                 220

Ser Gln Ala Ala Ser Ser Asn Ser Ala Gln Gly Ser Asp Glu Ser Leu
225                 230                 235                 240

Ile Ala Cys Lys Ala
            245

<210> SEQ ID NO 99
<211> LENGTH: 366
<212> TYPE: PRT
<213> ORGANISM: Homo sapiens

<400> SEQUENCE: 99

Met Arg Val Met Ala Pro Arg Thr Leu Leu Leu Leu Leu Ser Gly Ala
1               5                   10                  15

Leu Ala Leu Thr Glu Thr Trp Ala Cys Ser His Ser Met Arg Tyr Phe
            20                  25                  30

Tyr Thr Ala Val Ser Arg Pro Ser Arg Gly Glu Pro His Phe Ile Ala
        35                  40                  45

Val Gly Tyr Val Asp Asp Thr Gln Phe Val Arg Phe Asp Ser Asp Ala
    50                  55                  60

Ala Ser Pro Arg Gly Glu Pro Arg Ala Pro Trp Val Glu Gln Glu Gly
65                  70                  75                  80

Pro Glu Tyr Trp Asp Arg Glu Thr Gln Lys Tyr Lys Arg Gln Ala Gln
                85                  90                  95

Thr Asp Arg Val Asn Leu Arg Lys Leu Arg Gly Tyr Tyr Asn Gln Ser
            100                 105                 110

Glu Ala Gly Ser His Thr Leu Gln Arg Met Tyr Gly Cys Asp Leu Gly
        115                 120                 125

Pro Asp Gly Arg Leu Leu Arg Gly Tyr Asp Gln Ser Ala Tyr Asp Gly
    130                 135                 140

Lys Asp Tyr Ile Ala Leu Asn Glu Asp Leu Arg Ser Trp Thr Ala Ala
145                 150                 155                 160

Asp Thr Ala Ala Gln Ile Thr Gln Arg Lys Trp Glu Ala Ala Arg Glu
                165                 170                 175

Ala Glu Gln Trp Arg Ala Tyr Leu Glu Gly Glu Cys Val Glu Trp Leu
            180                 185                 190

Arg Arg Tyr Leu Glu Asn Gly Lys Glu Thr Leu Gln Arg Ala Glu His
        195                 200                 205

Pro Lys Thr His Val Thr His His Pro Val Ser Asp His Glu Ala Thr
    210                 215                 220

Leu Arg Cys Trp Ala Leu Gly Phe Tyr Pro Thr Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Glu Pro Leu Thr Leu Arg Trp Glu Pro Ser Ser Gln Pro
    290                 295                 300

Thr Ile Pro Ile Val Gly Ile Val Ala Gly Leu Ala Val Leu Ala Val
305                 310                 315                 320

Leu Ala Val Leu Gly Ala Val Val Ala Val Val Met Cys Arg Arg Lys
                325                 330                 335

Ser Ser Gly Gly Lys Gly Gly Ser Cys Ser Gln Ala Ala Ser Ser Asn
            340                 345                 350

Ser Ala Gln Gly Ser Asp Glu Ser Leu Ile Ala Cys Lys Ala
        355                 360                 365

<210> SEQ ID NO 100
<211> LENGTH: 366
<212> TYPE: PRT
<213> ORGANISM: Homo sapiens

<400> SEQUENCE: 100

Met Arg Val Met Ala Pro Arg Thr Leu Ile Leu Leu Leu Ser Gly Ala
1               5                   10                  15

Leu Ala Leu Thr Glu Thr Trp Ala Cys Ser His Ser Met Arg Tyr Phe
            20                  25                  30

Asp Thr Ala Val Ser Arg Pro Gly Arg Gly Glu Pro Arg Phe Ile Ser
        35                  40                  45

Val Gly Tyr Val Asp Asp Thr Gln Phe Val Arg Phe Asp Ser Asp Ala
    50                  55                  60

Ala Ser Pro Arg Gly Glu Pro Arg Ala Pro Trp Val Glu Gln Glu Gly
65                  70                  75                  80

```
Pro Glu Tyr Trp Asp Arg Glu Thr Gln Lys Tyr Lys Arg Gln Ala Gln
                85                  90                  95

Ala Asp Arg Val Asn Leu Arg Lys Leu Arg Gly Tyr Tyr Asn Gln Ser
            100                 105                 110

Glu Asp Gly Ser His Thr Leu Gln Trp Met Tyr Gly Cys Asp Leu Gly
        115                 120                 125

Pro Asp Gly Arg Leu Leu Arg Gly Tyr Asp Gln Ser Ala Tyr Asp Gly
    130                 135                 140

Lys Asp Tyr Ile Ala Leu Asn Glu Asp Leu Arg Ser Trp Thr Ala Ala
145                 150                 155                 160

Asp Thr Ala Ala Gln Ile Thr Gln Arg Lys Trp Glu Ala Ala Arg Glu
                165                 170                 175

Ala Glu Gln Trp Arg Ala Tyr Leu Glu Gly Thr Cys Val Glu Trp Leu
            180                 185                 190

Arg Arg Tyr Leu Glu Asn Gly Lys Glu Thr Leu Gln Arg Ala Glu His
        195                 200                 205

Pro Lys Thr His Val Thr His His Pro Val Ser Asp His Glu Ala Thr
    210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Glu Pro Leu Thr Leu Arg Trp Glu Pro Ser Ser Gln Pro
    290                 295                 300

Thr Ile Pro Ile Val Gly Ile Val Ala Gly Leu Ala Val Leu Ala Val
305                 310                 315                 320

Leu Ala Val Leu Gly Ala Val Met Ala Val Val Met Cys Arg Arg Lys
                325                 330                 335

Ser Ser Gly Gly Lys Gly Gly Ser Cys Ser Gln Ala Ala Ser Ser Asn
            340                 345                 350

Ser Ala Gln Gly Ser Asp Glu Ser Leu Ile Ala Cys Lys Ala
        355                 360                 365

<210> SEQ ID NO 101
<211> LENGTH: 327
<212> TYPE: PRT
<213> ORGANISM: Homo sapiens

<400> SEQUENCE: 101

Met Arg Val Met Ala Pro Arg Thr Leu Leu Leu Leu Leu Ser Gly Ala
1               5                   10                  15

Leu Ala Leu Thr Glu Thr Trp Ala Cys Ser His Ser Met Arg Tyr Phe
                20                  25                  30

Tyr Thr Ala Val Ser Arg Pro Ser Arg Gly Glu Pro His Phe Ile Ala
            35                  40                  45

Val Gly Tyr Val Asp Asp Thr Gln Phe Val Arg Phe Asp Ser Asp Ala
        50                  55                  60

Ala Ser Pro Arg Gly Glu Pro Arg Ala Pro Trp Val Glu Gln Glu Gly
65                  70                  75                  80

Pro Glu Tyr Trp Asp Arg Glu Thr Gln Lys Tyr Lys Arg Gln Ala Gln
```

```
                        85                  90                  95
Thr Asp Arg Val Asn Leu Arg Lys Leu Arg Gly Tyr Tyr Asn Gln Ser
            100                 105                 110

Glu Ala Gly Ser His Thr Leu Gln Arg Met Tyr Gly Cys Asp Leu Gly
            115                 120                 125

Pro Asp Gly Arg Leu Leu Arg Gly Tyr Asp Gln Ser Ala Tyr Asp Gly
            130                 135                 140

Lys Asp Tyr Ile Ala Leu Asn Glu Asp Leu Arg Ser Trp Thr Ala Ala
145                 150                 155                 160

Asp Thr Ala Ala Gln Ile Thr Gln Arg Lys Trp Glu Ala Ala Arg Glu
            165                 170                 175

Ala Glu Gln Trp Arg Ala Tyr Leu Glu Gly Glu Cys Trp Ala Leu Gly
            180                 185                 190

Phe Tyr Pro Thr Glu Ile Thr Leu Thr Trp Gln Arg Asp Gly Glu Asp
            195                 200                 205

Gln Thr Gln Asp Thr Glu Leu Val Glu Thr Arg Pro Ala Gly Asp Gly
            210                 215                 220

Thr Phe Gln Lys Trp Ala Ala Val Val Val Pro Ser Gly Glu Glu Gln
225                 230                 235                 240

Arg Tyr Thr Cys His Val Gln His Glu Gly Leu Pro Glu Pro Leu Thr
            245                 250                 255

Leu Arg Trp Glu Pro Ser Ser Gln Pro Thr Ile Pro Ile Val Gly Ile
            260                 265                 270

Val Ala Gly Leu Ala Val Leu Ala Val Leu Ala Val Leu Gly Ala Val
            275                 280                 285

Val Ala Val Val Met Cys Arg Arg Lys Ser Ser Gly Gly Lys Gly Gly
            290                 295                 300

Ser Cys Ser Gln Ala Ala Ser Ser Asn Ser Ala Gln Gly Ser Asp Glu
305                 310                 315                 320

Ser Leu Ile Ala Cys Lys Ala
            325

<210> SEQ ID NO 102
<211> LENGTH: 352
<212> TYPE: PRT
<213> ORGANISM: Homo sapiens

<400> SEQUENCE: 102

Met Arg Val Met Ala Pro Arg Thr Leu Ala Cys Ser His Ser Met Arg
1               5                   10                  15

Tyr Phe Tyr Thr Ala Val Ser Arg Pro Ser Arg Gly Glu Pro His Phe
            20                  25                  30

Ile Ala Val Gly Tyr Val Asp Asp Thr Gln Phe Val Arg Phe Asp Ser
            35                  40                  45

Asp Ala Ala Ser Pro Arg Gly Glu Pro Arg Ala Pro Trp Val Glu Gln
            50                  55                  60

Glu Gly Pro Glu Tyr Trp Asp Arg Glu Thr Gln Lys Tyr Lys Arg Gln
65                  70                  75                  80

Ala Gln Thr Asp Arg Val Asn Leu Arg Lys Leu Arg Gly Tyr Tyr Asn
            85                  90                  95

Gln Ser Glu Ala Gly Ser His Thr Leu Gln Arg Met Tyr Gly Cys Asp
            100                 105                 110

Leu Gly Pro Asp Gly Arg Leu Leu Arg Gly Tyr Asp Gln Ser Ala Tyr
            115                 120                 125
```

```
Asp Gly Lys Asp Tyr Ile Ala Leu Asn Glu Asp Leu Arg Ser Trp Thr
    130                 135                 140

Ala Ala Asp Thr Ala Ala Gln Ile Thr Gln Arg Lys Trp Glu Ala Ala
145                 150                 155                 160

Arg Glu Ala Glu Gln Trp Arg Ala Tyr Leu Glu Gly Glu Cys Val Glu
                165                 170                 175

Trp Leu Arg Arg Tyr Leu Glu Asn Gly Lys Glu Thr Leu Gln Arg Ala
                180                 185                 190

Glu His Pro Lys Thr His Val Thr His Pro Val Ser Asp His Glu
                195                 200                 205

Ala Thr Leu Arg Cys Trp Ala Leu Gly Phe Tyr Pro Thr Glu Ile Thr
    210                 215                 220

Leu Thr Trp Gln Arg Asp Gly Glu Asp Gln Thr Gln Asp Thr Glu Leu
225                 230                 235                 240

Val Glu Thr Arg Pro Ala Gly Asp Gly Thr Phe Gln Lys Trp Ala Ala
                245                 250                 255

Val Val Val Pro Ser Gly Glu Glu Gln Arg Tyr Thr Cys His Val Gln
                260                 265                 270

His Glu Gly Leu Pro Glu Pro Leu Thr Leu Arg Trp Glu Pro Ser Ser
    275                 280                 285

Gln Pro Thr Ile Pro Ile Val Gly Ile Val Ala Gly Leu Ala Val Leu
    290                 295                 300

Ala Val Leu Ala Val Leu Gly Ala Val Val Ala Val Met Cys Arg
305                 310                 315                 320

Arg Lys Ser Ser Gly Gly Lys Gly Gly Ser Cys Ser Gln Ala Ala Ser
                325                 330                 335

Ser Asn Ser Ala Gln Gly Ser Asp Glu Ser Leu Ile Ala Cys Lys Ala
                340                 345                 350

<210> SEQ ID NO 103
<211> LENGTH: 338
<212> TYPE: PRT
<213> ORGANISM: Homo sapiens

<400> SEQUENCE: 103

Met Arg Tyr Phe Tyr Thr Ala Val Ser Arg Pro Ser Arg Gly Glu Pro
1               5                   10                  15

His Phe Ile Ala Val Gly Tyr Val Asp Asp Thr Gln Phe Val Arg Phe
                20                  25                  30

Asp Ser Asp Ala Ala Ser Pro Arg Gly Glu Pro Arg Ala Pro Trp Val
            35                  40                  45

Glu Gln Glu Gly Pro Glu Tyr Trp Asp Arg Glu Thr Gln Lys Tyr Lys
50                  55                  60

Arg Gln Ala Gln Thr Asp Arg Val Asn Leu Arg Lys Leu Arg Gly Tyr
65                  70                  75                  80

Tyr Asn Gln Ser Glu Ala Gly Ser His Thr Leu Gln Arg Met Tyr Gly
                85                  90                  95

Cys Asp Leu Gly Pro Asp Gly Arg Leu Leu Arg Gly Tyr Asp Gln Ser
                100                 105                 110

Ala Tyr Asp Gly Lys Asp Tyr Ile Ala Leu Asn Glu Asp Leu Arg Ser
            115                 120                 125

Trp Thr Ala Ala Asp Thr Ala Ala Gln Ile Thr Gln Arg Lys Trp Glu
    130                 135                 140

Ala Ala Arg Glu Ala Glu Gln Trp Arg Ala Tyr Leu Glu Gly Glu Cys
145                 150                 155                 160
```

```
Val Glu Trp Leu Arg Arg Tyr Leu Glu Asn Gly Lys Glu Thr Leu Gln
                165                 170                 175

Arg Ala Glu His Pro Lys Thr His Val Thr His His Pro Val Ser Asp
            180                 185                 190

His Glu Ala Thr Leu Arg Cys Trp Ala Leu Gly Phe Tyr Pro Thr Glu
        195                 200                 205

Ile Thr Leu Thr Trp Gln Arg Asp Gly Glu Asp Gln Thr Gln Asp Thr
    210                 215                 220

Glu Leu Val Glu Thr Arg Pro Ala Gly Asp Gly Thr Phe Gln Lys Trp
225                 230                 235                 240

Ala Ala Val Val Val Pro Ser Gly Glu Glu Gln Arg Tyr Thr Cys His
                245                 250                 255

Val Gln His Glu Gly Leu Pro Glu Pro Leu Thr Leu Arg Trp Glu Pro
            260                 265                 270

Ser Ser Gln Pro Thr Ile Pro Ile Val Gly Ile Val Ala Gly Leu Ala
        275                 280                 285

Val Leu Ala Val Leu Ala Val Leu Gly Ala Val Val Ala Val Val Met
    290                 295                 300

Cys Arg Arg Lys Ser Ser Gly Gly Lys Gly Gly Ser Cys Ser Gln Ala
305                 310                 315                 320

Ala Ser Ser Asn Ser Ala Gln Gly Ser Asp Glu Ser Leu Ile Ala Cys
                325                 330                 335

Lys Ala

<210> SEQ ID NO 104
<211> LENGTH: 326
<212> TYPE: PRT
<213> ORGANISM: Homo sapiens

<400> SEQUENCE: 104

Met Arg Val Met Ala Pro Arg Thr Leu Leu Leu Leu Leu Ser Gly Ala
1               5                   10                  15

Leu Ala Leu Thr Glu Thr Trp Ala Cys Ser His Ser Met Arg Tyr Phe
                20                  25                  30

Tyr Thr Ala Val Ser Arg Pro Ser Arg Gly Glu Pro His Phe Ile Ala
            35                  40                  45

Val Gly Tyr Val Asp Asp Thr Gln Phe Val Arg Phe Asp Ser Asp Ala
        50                  55                  60

Ala Ser Pro Arg Gly Glu Pro Arg Ala Pro Trp Val Glu Gln Glu Gly
65                  70                  75                  80

Pro Glu Tyr Trp Asp Arg Glu Thr Gln Lys Tyr Lys Arg Gln Ala Gln
                85                  90                  95

Thr Asp Arg Val Asn Leu Arg Lys Leu Arg Gly Tyr Tyr Asn Gln Ser
            100                 105                 110

Glu Ala Gly Ser His Thr Leu Gln Arg Met Tyr Gly Cys Asp Leu Gly
        115                 120                 125

Pro Asp Gly Arg Leu Leu Arg Gly Tyr Asp Gln Ser Ala Tyr Asp Gly
    130                 135                 140

Lys Asp Tyr Ile Ala Leu Asn Glu Asp Leu Arg Ser Trp Thr Ala Ala
145                 150                 155                 160

Asp Thr Ala Ala Gln Ile Thr Gln Arg Lys Trp Glu Ala Ala Arg Glu
                165                 170                 175

Ala Glu Gln Trp Arg Ala Tyr Leu Glu Gly Glu Cys Val Glu Trp Leu
            180                 185                 190
```

-continued

Arg Arg Tyr Leu Glu Asn Gly Lys Glu Thr Leu Gln Arg Ala Glu His
        195                 200                 205

Pro Lys Thr His Val Thr His His Pro Val Ser Asp His Glu Ala Thr
210                 215                 220

Leu Arg Cys Trp Ala Leu Gly Phe Tyr Pro Thr Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Glu Pro Leu Thr Leu Arg Trp Gly Gly Lys Gly Ser
    290                 295                 300

Cys Ser Gln Ala Ala Ser Ser Asn Ser Ala Gln Gly Ser Asp Glu Ser
305                 310                 315                 320

Leu Ile Ala Cys Lys Ala
                325

<210> SEQ ID NO 105
<211> LENGTH: 350
<212> TYPE: PRT
<213> ORGANISM: Homo sapiens

<400> SEQUENCE: 105

Met Arg Val Met Ala Pro Arg Thr Leu Leu Leu Leu Leu Ser Gly Ala
1               5                   10                  15

Leu Ala Leu Thr Glu Thr Trp Ala Cys Ser His Ser Met Arg Tyr Phe
            20                  25                  30

Tyr Thr Ala Val Ser Arg Pro Ser Arg Gly Glu Pro His Phe Ile Ala
        35                  40                  45

Val Gly Tyr Val Asp Asp Thr Gln Phe Val Arg Phe Asp Ser Asp Ala
    50                  55                  60

Ala Ser Pro Arg Gly Glu Pro Arg Ala Pro Trp Val Glu Gln Glu Gly
65                  70                  75                  80

Pro Glu Tyr Trp Asp Arg Glu Thr Gln Lys Tyr Lys Arg Gln Ala Gln
                85                  90                  95

Thr Asp Arg Val Asn Leu Arg Lys Leu Arg Gly Tyr Tyr Asn Gln Ser
            100                 105                 110

Glu Ala Gly Ser His Thr Leu Gln Arg Met Tyr Gly Cys Asp Leu Gly
        115                 120                 125

Pro Asp Gly Arg Leu Leu Arg Gly Tyr Asp Gln Ser Ala Tyr Asp Gly
    130                 135                 140

Lys Asp Tyr Ile Ala Leu Asn Glu Asp Leu Arg Ser Trp Thr Ala Ala
145                 150                 155                 160

Asp Thr Ala Ala Gln Ile Thr Gln Arg Lys Trp Glu Ala Ala Arg Glu
                165                 170                 175

Ala Glu Gln Trp Arg Ala Tyr Leu Glu Gly Glu Cys Val Glu Trp Leu
            180                 185                 190

Arg Arg Tyr Leu Glu Asn Gly Lys Glu Thr Leu Gln Arg Ala Glu His
        195                 200                 205

Pro Lys Thr His Val Thr His His Pro Val Ser Asp His Glu Ala Thr
    210                 215                 220

Leu Arg Cys Trp Ala Leu Gly Phe Tyr Pro Thr Glu Ile Thr Leu Thr

```
                225                 230                 235                 240
Trp Gln Arg Asp Gly Glu Asp Gln Thr Gln Asp Thr Glu Leu Val Glu
                    245                 250                 255

Thr Arg Pro Ala Gly Asp Gly Thr Phe Gln Lys Trp Ala Ala Val Val
                260                 265                 270

Val Pro Ser Gly Glu Glu Gln Arg Tyr Thr Cys His Val Gln His Glu
            275                 280                 285

Gly Leu Pro Glu Pro Leu Thr Leu Arg Trp Glu Pro Ser Ser Gln Pro
        290                 295                 300

Thr Ile Pro Ile Val Gly Ile Val Ala Gly Leu Ala Val Leu Ala Val
305                 310                 315                 320

Leu Ala Val Leu Gly Ala Val Val Ala Val Val Met Cys Arg Arg Lys
                325                 330                 335

Ser Ser Gly Gly Lys Gly Gly Glu Leu Leu Ser Val Trp Asp
                340                 345                 350

<210> SEQ ID NO 106
<211> LENGTH: 228
<212> TYPE: PRT
<213> ORGANISM: Homo sapiens

<400> SEQUENCE: 106

Met Tyr Gly Cys Asp Leu Gly Pro Asp Gly Arg Leu Leu Arg Gly Tyr
1               5                   10                  15

Asp Gln Ser Ala Tyr Asp Gly Lys Asp Tyr Ile Ala Leu Asn Glu Asp
                20                  25                  30

Leu Arg Ser Trp Thr Ala Ala Asp Thr Ala Ala Gln Ile Thr Gln Arg
            35                  40                  45

Lys Trp Glu Ala Ala Arg Glu Ala Glu Gln Trp Arg Ala Tyr Leu Glu
        50                  55                  60

Gly Glu Cys Val Glu Trp Leu Arg Arg Tyr Leu Glu Asn Gly Lys Glu
65                  70                  75                  80

Thr Leu Gln Arg Ala Glu His Pro Lys Thr His Val Thr His His Pro
                85                  90                  95

Val Ser Asp His Glu Ala Thr Leu Arg Cys Trp Ala Leu Gly Phe Tyr
                100                 105                 110

Pro Thr Glu Ile Thr Leu Thr Trp Gln Arg Asp Gly Glu Asp Gln Thr
            115                 120                 125

Gln Asp Thr Glu Leu Val Glu Thr Arg Pro Ala Gly Asp Gly Thr Phe
        130                 135                 140

Gln Lys Trp Ala Ala Val Val Val Pro Ser Gly Glu Glu Gln Arg Tyr
145                 150                 155                 160

Thr Cys His Val Gln His Glu Gly Leu Pro Glu Pro Leu Thr Leu Arg
                165                 170                 175

Trp Glu Pro Ser Ser Gln Pro Thr Ile Pro Ile Val Gly Ile Val Ala
                180                 185                 190

Gly Leu Ala Val Leu Ala Val Leu Ala Val Leu Gly Ala Val Val Ala
            195                 200                 205

Val Val Met Cys Arg Arg Lys Ser Ser Gly Gly Lys Gly Phe Leu His
        210                 215                 220

Thr Ser Pro Leu
225

<210> SEQ ID NO 107
<211> LENGTH: 343
```

<212> TYPE: PRT
<213> ORGANISM: Homo sapiens

<400> SEQUENCE: 107

Met Arg Val Met Ala Pro Arg Thr Leu Leu Leu Leu Ser Gly Ala
1               5                   10                  15

Leu Ala Leu Thr Glu Thr Trp Ala Cys Ser His Ser Met Arg Tyr Phe
            20                  25                  30

Tyr Thr Ala Val Ser Arg Pro Ser Arg Gly Glu Pro His Phe Ile Ala
            35                  40                  45

Val Gly Tyr Val Asp Asp Thr Gln Phe Val Arg Phe Asp Ser Asp Ala
        50                  55                  60

Ala Ser Pro Arg Gly Glu Pro Arg Ala Pro Trp Val Glu Gln Glu Gly
65                  70                  75                  80

Pro Glu Tyr Trp Asp Arg Glu Thr Gln Lys Tyr Lys Arg Gln Ala Gln
                85                  90                  95

Thr Asp Arg Val Asn Leu Arg Lys Leu Arg Gly Tyr Tyr Asn Gln Ser
            100                 105                 110

Glu Ala Gly Ser His Thr Leu Gln Arg Met Tyr Gly Cys Asp Leu Gly
        115                 120                 125

Pro Asp Gly Arg Leu Leu Arg Gly Tyr Asp Gln Ser Ala Tyr Asp Gly
    130                 135                 140

Lys Asp Tyr Ile Ala Leu Asn Glu Asp Leu Arg Ser Trp Thr Ala Ala
145                 150                 155                 160

Asp Thr Ala Ala Gln Ile Thr Gln Arg Lys Trp Glu Ala Ala Arg Glu
                165                 170                 175

Ala Glu Gln Trp Arg Ala Tyr Leu Glu Gly Glu Cys Val Glu Trp Leu
            180                 185                 190

Arg Arg Tyr Leu Glu Asn Gly Lys Glu Thr Leu Gln Arg Ala Glu His
        195                 200                 205

Pro Lys Thr His Val Thr His His Pro Val Ser Asp His Glu Ala Thr
    210                 215                 220

Leu Arg Cys Trp Ala Leu Gly Phe Tyr Pro Thr Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Glu Pro Leu Thr Leu Arg Trp Glu Pro Ser Ser Gln Pro
    290                 295                 300

Thr Ile Pro Ile Val Gly Ile Val Ala Gly Leu Ala Val Leu Ala Val
305                 310                 315                 320

Leu Ala Val Leu Gly Ala Val Val Ala Val Val Met Cys Arg Arg Lys
                325                 330                 335

Ser Pro Pro Pro Cys Pro Pro
            340

<210> SEQ ID NO 108
<211> LENGTH: 343
<212> TYPE: PRT
<213> ORGANISM: Homo sapiens

<400> SEQUENCE: 108

```
Met Arg Val Met Ala Pro Arg Ala Leu Leu Leu Leu Ser Gly Gly
1               5                   10                  15

Leu Ala Leu Thr Glu Thr Trp Ala Cys Ser His Ser Met Arg Tyr Phe
            20                  25                  30

Asp Thr Ala Val Ser Arg Pro Gly Arg Gly Glu Pro Arg Phe Ile Ser
            35                  40                  45

Val Gly Tyr Val Asp Asp Thr Gln Phe Val Arg Phe Asp Ser Asp Ala
50                  55                  60

Ala Ser Pro Arg Gly Glu Pro Arg Ala Pro Trp Val Glu Gln Glu Gly
65                  70                  75                  80

Pro Glu Tyr Trp Asp Arg Glu Thr Gln Lys Tyr Lys Arg Gln Ala Gln
                85                  90                  95

Ala Asp Arg Val Ser Leu Arg Asn Leu Arg Gly Tyr Tyr Asn Gln Ser
            100                 105                 110

Glu Asp Gly Ser His Thr Leu Gln Arg Met Ser Gly Cys Asp Leu Gly
            115                 120                 125

Pro Asp Gly Arg Leu Leu Arg Gly Tyr Asp Gln Ser Ala Tyr Asp Gly
            130                 135                 140

Lys Asp Tyr Ile Ala Leu Asn Glu Asp Leu Arg Ser Trp Thr Ala Ala
145                 150                 155                 160

Asp Thr Ala Ala Gln Ile Thr Gln Arg Lys Leu Glu Ala Ala Arg Ala
                165                 170                 175

Ala Glu Gln Leu Arg Ala Tyr Leu Glu Gly Thr Cys Val Glu Trp Leu
            180                 185                 190

Arg Arg Tyr Leu Glu Asn Gly Lys Glu Thr Leu Gln Arg Ala Glu Pro
            195                 200                 205

Pro Lys Thr His Val Thr His His Pro Leu Ser Asp His Glu Ala Thr
            210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ala Val Val
            260                 265                 270

Val Pro Ser Gly Gln Glu Gln Arg Tyr Thr Cys His Met Gln His Glu
            275                 280                 285

Gly Leu Gln Glu Pro Leu Thr Leu Ser Trp Glu Pro Ser Ser Gln Pro
            290                 295                 300

Thr Ile Pro Asp His Leu Ser Cys Ser Arg Glu Val Gly Leu Asp Val
305                 310                 315                 320

Ser Ile Ser Val Ser Asn Ser Trp Cys Thr Glu Leu Gln Leu Leu Thr
                325                 330                 335

Ser Leu Met Lys Leu Arg Thr
            340

<210> SEQ ID NO 109
<211> LENGTH: 174
<212> TYPE: PRT
<213> ORGANISM: Homo sapiens

<400> SEQUENCE: 109

Met Ser Gly Cys Asp Leu Gly Pro Asp Gly Arg Leu Leu Arg Gly Tyr
1               5                   10                  15

Asp Gln Ser Ala Tyr Asp Gly Lys Asp Tyr Ile Ala Leu Asn Glu Asp
            20                  25                  30
```

```
Leu Arg Ser Trp Thr Ala Ala Asp Thr Ala Ala Gln Ile Thr Gln Arg
            35                  40                  45

Lys Leu Glu Ala Ala Arg Ala Ala Glu Gln Leu Arg Ala Tyr Leu Glu
    50                  55                  60

Gly Thr Cys Val Glu Trp Leu Arg Arg Tyr Leu Glu Asn Gly Lys Glu
65                  70                  75                  80

Thr Leu Gln Arg Ala Glu Pro Pro Lys Thr His Val Thr His His Pro
                85                  90                  95

Leu Ser Asp His Glu Ala Thr Leu Arg Cys Trp Ala Leu Gly Phe Tyr
                100                 105                 110

Pro Ala Glu Ile Thr Leu Thr Trp Gln Arg Asp Gly Glu Asp Gln Thr
                115                 120                 125

Gln Asp Thr Glu Leu Val Glu Thr Arg Pro Ala Gly Asp Gly Thr Phe
130                 135                 140

Gln Lys Trp Ala Ala Val Val Val Pro Ser Gly Gln Glu Gln Arg Tyr
145                 150                 155                 160

Thr Cys His Met Gln His Glu Gly Cys Lys Ser Pro Ser Pro
                165                 170

<210> SEQ ID NO 110
<211> LENGTH: 308
<212> TYPE: PRT
<213> ORGANISM: Homo sapiens

<400> SEQUENCE: 110

Met Arg Val Met Ala Pro Arg Thr Leu Leu Leu Leu Leu Ser Gly Ala
1               5                   10                  15

Leu Ala Leu Thr Glu Thr Trp Ala Cys Ser His Ser Met Arg Tyr Phe
                20                  25                  30

Tyr Thr Ala Val Ser Arg Pro Ser Arg Gly Glu Pro His Phe Ile Ala
            35                  40                  45

Val Gly Tyr Val Asp Asp Thr Gln Phe Val Arg Phe Asp Ser Asp Ala
    50                  55                  60

Ala Ser Pro Arg Gly Glu Pro Arg Ala Pro Trp Val Glu Gln Glu Gly
65                  70                  75                  80

Pro Glu Tyr Trp Asp Arg Glu Thr Gln Lys Tyr Lys Arg Gln Ala Gln
                85                  90                  95

Thr Asp Arg Val Asn Leu Arg Lys Leu Arg Gly Tyr Tyr Asn Gln Ser
                100                 105                 110

Glu Ala Gly Ser His Thr Leu Gln Arg Met Tyr Gly Cys Asp Leu Gly
                115                 120                 125

Pro Asp Gly Arg Leu Leu Arg Gly Tyr Asp Gln Ser Ala Tyr Asp Gly
130                 135                 140

Lys Asp Tyr Ile Ala Pro Asn Glu Asp Leu Arg Ser Trp Thr Ala Ala
145                 150                 155                 160

Asp Thr Ala Ala Gln Ile Thr Gln Arg Lys Trp Glu Ala Ala Arg Glu
                165                 170                 175

Ala Glu Gln Trp Arg Ala Tyr Leu Glu Gly Glu Cys Val Glu Trp Leu
                180                 185                 190

Arg Arg Tyr Leu Glu Asn Gly Lys Glu Thr Leu Gln Arg Ala Glu His
                195                 200                 205

Pro Lys Thr His Val Thr His His Pro Val Ser Asp His Glu Ala Thr
                210                 215                 220

Leu Arg Cys Trp Ala Leu Gly Phe Tyr Pro Thr Glu Ile Thr Leu Thr
```

```
                225                 230                 235                 240
Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ala Val Val
                260                 265                 270

Val Pro Ser Gly Glu Glu Gln Arg Tyr Thr Cys His Val Gln His Glu
                275                 280                 285

Gly Leu Pro Glu Pro Leu Thr Leu Arg Trp Lys Ser Leu Arg Gln Leu
                290                 295                 300

Pro Val Trp Asp
305

<210> SEQ ID NO 111
<211> LENGTH: 181
<212> TYPE: PRT
<213> ORGANISM: Homo sapiens

<400> SEQUENCE: 111

Met Tyr Gly Cys Asp Leu Gly Pro Asp Gly Arg Leu Leu Arg Gly Tyr
1               5                   10                  15

Asp Gln Ser Ala Tyr Asp Gly Lys Asp Tyr Ile Ala Leu Asn Glu Asp
                20                  25                  30

Leu Arg Ser Trp Thr Ala Ala Asp Thr Ala Ala Gln Ile Thr Gln Arg
            35                  40                  45

Lys Trp Glu Ala Ala Arg Arg Tyr Leu Glu Asn Gly Lys Glu Thr Leu
        50                  55                  60

Gln Arg Ala Glu His Pro Lys Thr His Val Thr His His Pro Val Ser
65                  70                  75                  80

Asp His Glu Ala Thr Leu Arg Cys Trp Ala Leu Gly Phe Tyr Pro Thr
                85                  90                  95

Glu Ile Thr Leu Thr Trp Gln Arg Asp Gly Glu Asp Gln Thr Gln Asp
                100                 105                 110

Thr Glu Leu Val Glu Thr Arg Pro Ala Gly Asp Gly Thr Phe Gln Lys
            115                 120                 125

Trp Ala Ala Val Val Val Pro Ser Gly Glu Glu Gln Arg Tyr Thr Cys
        130                 135                 140

His Val Gln His Glu Gly Leu Pro Glu Pro Leu Thr Leu Arg Trp Glu
145                 150                 155                 160

Pro Ser Ser Gln Pro Thr Ile Pro Ile Val Ala Ser Leu Leu Ala Trp
                165                 170                 175

Leu Ser Trp Leu Ser
            180

<210> SEQ ID NO 112
<211> LENGTH: 83
<212> TYPE: PRT
<213> ORGANISM: Homo sapiens

<400> SEQUENCE: 112

Met Arg Val Met Ala Pro Arg Thr Leu Leu Leu Leu Gly Arg Arg Ala
1               5                   10                  15

Leu Ala Leu Thr Glu Thr Gln Lys Tyr Lys Arg Gln Ala Gln Thr Asp
                20                  25                  30

Arg Val Asn Leu Arg Lys Leu Arg Gly Tyr Tyr Asn Gln Ser Glu Ala
            35                  40                  45

Gly Ser His Thr Leu Gln Arg Met Tyr Gly Cys Asp Leu Gly Pro Thr
```

```
                    50                  55                  60
Gly Ala Ser Ser Ala Gly Met Thr Ser Pro Thr Thr Ala Arg Ile
 65                  70                  75                  80

Thr Ser Pro

<210> SEQ ID NO 113
<211> LENGTH: 154
<212> TYPE: PRT
<213> ORGANISM: Homo sapiens

<400> SEQUENCE: 113

Met Arg Tyr Phe Asp Thr Ala Val Ser Arg Pro Gly Arg Gly Glu Pro
 1               5                  10                  15

Arg Phe Ile Ser Val Gly Tyr Val Asp Asp Thr Gln Phe Val Arg Phe
                20                  25                  30

Asp Ser Asp Ala Ala Ser Pro Arg Gly Glu Pro Arg Ala Pro Trp Val
            35                  40                  45

Glu Gln Glu Gly Pro Glu Tyr Trp Asp Arg Glu Thr Gln Lys Tyr Lys
        50                  55                  60

Arg Gln Ala Gln Ala Asp Arg Val Ser Leu Arg Asn Leu Arg Gly Tyr
 65                  70                  75                  80

Tyr Asn Gln Ser Glu Asp Gly Ser His Thr Leu Gln Arg Met Ser Gly
                85                  90                  95

Cys Asp Leu Gly Pro Asp Gly Arg Leu Leu Arg Gly Tyr Asp Gln Ser
            100                 105                 110

Ala Tyr Asp Gly Lys Asp Tyr Ile Ala Leu Asn Glu Asp Leu Arg Ser
        115                 120                 125

Trp Thr Ala Ala Asp Thr Ala Ala Gln Ile Thr Gln Arg Lys Leu Glu
    130                 135                 140

Ala Ala Arg Ala Ala Glu Gln Leu Arg Ala
145                 150

<210> SEQ ID NO 114
<211> LENGTH: 169
<212> TYPE: PRT
<213> ORGANISM: Homo sapiens

<400> SEQUENCE: 114

Met Arg Val Met Ala Pro Arg Thr Leu Leu Leu Leu Leu Ser Gly Ala
 1               5                  10                  15

Leu Ala Leu Thr Glu Thr Trp Ala Cys Ser His Ser Met Arg Tyr Phe
                20                  25                  30

Tyr Thr Ala Val Ser Arg Pro Ser Arg Gly Glu Pro His Phe Ile Ala
            35                  40                  45

Val Gly Tyr Val Asp Asp Thr Gln Phe Val Arg Phe Asp Ser Asp Ala
        50                  55                  60

Ala Ser Pro Arg Gly Glu Pro Arg Ala Pro Trp Val Glu Gln Glu Gly
 65                  70                  75                  80

Pro Glu Tyr Trp Asp Arg Glu Thr Gln Lys Tyr Lys Arg Gln Ala Gln
                85                  90                  95

Thr Asp Arg Val Asn Leu Arg Lys Leu Arg Gly Tyr Tyr Asn Gln Ser
            100                 105                 110

Glu Ala Gly Ser His Thr Leu Gln Arg Met Tyr Gly Cys Asp Leu Gly
        115                 120                 125

Pro Asp Gly Arg Leu Leu Arg Leu Arg Arg Gln Gly Leu His Arg Pro
    130                 135                 140
```

Glu Arg Gly Pro Ala Leu Leu Asp Arg Arg Gly His Ser Gly Ser Asp
145                 150                 155                 160

His Pro Ala Gln Val Gly Gly Pro
                165

<210> SEQ ID NO 115
<211> LENGTH: 313
<212> TYPE: PRT
<213> ORGANISM: Homo sapiens

<400> SEQUENCE: 115

Met Arg Val Met Ala Pro Arg Ala Leu Leu Leu Leu Leu Ser Gly Gly
1               5                   10                  15

Leu Ala Leu Thr Glu Thr Trp Ala Cys Ser His Ser Met Arg Tyr Phe
            20                  25                  30

Asp Thr Ala Val Ser Arg Pro Gly Arg Gly Glu Pro Arg Phe Ile Ser
        35                  40                  45

Val Gly Tyr Val Asp Asp Thr Gln Phe Val Arg Phe Asp Ser Asp Ala
    50                  55                  60

Ala Ser Pro Arg Gly Glu Pro Arg Ala Pro Trp Val Glu Gln Glu Gly
65                  70                  75                  80

Pro Glu Tyr Trp Asp Arg Glu Thr Gln Lys Tyr Lys Arg Gln Ala Gln
                85                  90                  95

Ala Asp Arg Val Ser Leu Arg Asn Leu Arg Gly Tyr Tyr Asn Gln Ser
            100                 105                 110

Glu Asp Gly Ser His Thr Leu Gln Arg Met Ser Gly Cys Asp Leu Gly
        115                 120                 125

Pro Asp Gly Arg Leu Leu Arg Gly Tyr Asp Gln Ser Ala Tyr Asp Gly
    130                 135                 140

Lys Asp Tyr Ile Ala Leu Asn Glu Asp Leu Arg Ser Trp Thr Ala Ala
145                 150                 155                 160

Asp Thr Ala Ala Gln Ile Thr Gln Arg Lys Leu Glu Ala Ala Arg Ala
                165                 170                 175

Ala Glu Gln Leu Arg Ala Tyr Leu Glu Gly Thr Cys Val Glu Trp Leu
            180                 185                 190

Arg Arg Tyr Leu Glu Asn Gly Lys Glu Thr Leu Gln Arg Ala Glu Pro
        195                 200                 205

Pro Lys Ile His Val Pro Tyr Ala Ala Arg Gly Ala Ala Arg Ala Pro
    210                 215                 220

His Pro Glu Leu Gly Ala Ile Phe Pro Ala His His Pro His His Gly
225                 230                 235                 240

His Arg Cys Trp Pro Gly Cys Pro Gly Cys Pro Ser Cys Pro Trp Ser
                245                 250                 255

Cys Gly His Arg Tyr Asp Val Val Thr Ala Thr Val Pro Arg Ala Leu
            260                 265                 270

Met Ser Leu Ser Ser Leu Val Lys Pro Glu Thr Ala Ala Cys Val Gly
        275                 280                 285

Leu Arg Cys Arg Ile Ser Ser His Leu Ser Phe Val Thr Ser Arg Ala
    290                 295                 300

Ser Gly Ile Ser Phe Cys Lys Gly Thr
305                 310

<210> SEQ ID NO 116
<211> LENGTH: 258
<212> TYPE: PRT

<213> ORGANISM: Homo sapiens

<400> SEQUENCE: 116

Met Arg Val Met Ala Pro Arg Thr Leu Leu Leu Leu Ser Gly Ala
1               5                   10                  15

Leu Ala Leu Thr Glu Thr Trp Ala Cys Ser His Ser Met Arg Tyr Phe
            20                  25                  30

Tyr Thr Ala Val Ser Arg Pro Ser Arg Gly Glu Pro His Phe Ile Ala
        35                  40                  45

Val Gly Tyr Val Asp Asp Thr Gln Phe Val Arg Phe Asp Ser Asp Ala
    50                  55                  60

Ala Ser Pro Arg Gly Glu Pro Arg Ala Pro Trp Val Glu Gln Glu Gly
65                  70                  75                  80

Pro Glu Tyr Trp Asp Arg Glu Thr Gln Lys Tyr Lys Arg Gln Ala Gln
                85                  90                  95

Thr Asp Arg Val Asn Leu Arg Lys Leu Arg Gly Tyr Tyr Asn Gln Ser
            100                 105                 110

Glu Ala Gly Ser His Thr Leu Gln Arg Met Tyr Gly Cys Asp Leu Gly
        115                 120                 125

Pro Asp Gly Arg Leu Leu Arg Gly Tyr Asp Gln Ser Ala Tyr Asp Gly
    130                 135                 140

Lys Asp Tyr Ile Ala Leu Asn Glu Asp Leu Arg Ser Trp Thr Ala Ala
145                 150                 155                 160

Asp Thr Ala Ala Gln Ile Thr Gln Arg Lys Trp Glu Ala Ala Arg Glu
                165                 170                 175

Ala Glu Gln Trp Arg Ala Tyr Leu Glu Gly Glu Cys Val Glu Trp Leu
            180                 185                 190

Arg Arg Tyr Leu Glu Asn Gly Lys Glu Thr Leu Gln Arg Ala Glu His
        195                 200                 205

Pro Lys Thr His Val Thr His His Pro Val Ser Asp His Glu Ala Thr
    210                 215                 220

Leu Arg Cys Trp Ala Leu Gly Phe Tyr Pro Thr Glu Ile Thr Leu Thr
225                 230                 235                 240

Trp Gln Arg Asp Gly Glu Asp Gln Thr Gln Asp Thr Glu Leu Trp Trp
                245                 250                 255

Leu Leu

<210> SEQ ID NO 117
<211> LENGTH: 28
<212> TYPE: PRT
<213> ORGANISM: Homo sapiens

<400> SEQUENCE: 117

Val Ile Ile Leu Asn His Pro Gly Gln Ile Ser Ala Gly Tyr Ala Pro
1               5                   10                  15

Val Leu Asp Cys His Thr Ala His Ile Ala Cys Lys
            20                  25

<210> SEQ ID NO 118
<211> LENGTH: 14
<212> TYPE: PRT
<213> ORGANISM: Homo sapiens

<400> SEQUENCE: 118

Phe Ile Ala Val Gly Tyr Val Asp Asp Thr Gln Phe Val Arg
1               5                   10

```
<210> SEQ ID NO 119
<211> LENGTH: 13
<212> TYPE: PRT
<213> ORGANISM: Homo sapiens

<400> SEQUENCE: 119

Ala Tyr Leu Glu Gly Glu Thr Cys Val Glu Trp Leu Arg
1               5                   10

<210> SEQ ID NO 120
<211> LENGTH: 24
<212> TYPE: PRT
<213> ORGANISM: Homo sapiens

<400> SEQUENCE: 120

Asp Gly Glu Asp Gln Thr Gln Asp Thr Glu Leu Val Glu Thr Arg Pro
1               5                   10                  15

Ala Gly Asp Gly Thr Phe Gln Lys
            20

<210> SEQ ID NO 121
<211> LENGTH: 13
<212> TYPE: PRT
<213> ORGANISM: Homo sapiens

<400> SEQUENCE: 121

Trp Ala Ala Val Val Val Pro Ser Gly Gln Glu Gln Arg
1               5                   10

<210> SEQ ID NO 122
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 122

His His His His His His
1               5
```

METHODS OF IDENTIFYING NOVEL PROTEINS AND ANTIGENS IN CANCER CELLS

CROSS-REFERENCE TO RELATED APPLICATIONS

This application is the National Stage entry under 35 U.S.C. § 371 of International Application No. PCT/US2017/045057 filed on Aug. 2, 2017, published on Feb. 8, 2018 under Publication Number WO 2018/026896, which claims the benefit of U.S. Provisional Application No. 62/370,020 filed on Aug. 2, 2016, the entireties of which are herein incorporated by reference.

STATEMENT REGARDING FEDERALLY SPONSORED RESEARCH OR DEVELOPMENT

This invention was made with government support under CA71508, CA51008, CA177'166, grant numbers CA051008, CA071508, CA113477, and CA177466 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Mar. 5, 2021, is named A376-52_1_SL.txt and is 224,362 bytes in size.

BACKGROUND OF THE INVENTION

Field of the Invention

The present invention provides methods of identifying neopeptides in abnormal cells, with the methods comprising sequencing long-read messenger RNA (mRNA) isolated from the abnormal cells, identifying splice variants that could be generated from the sequenced long-read mRNA, determining if the abnormal cells contain neopeptides that correlate with the identified splice variants. The methods may also comprise identifying at least one neoantigen on the neopeptides that are present in the abnormal cells.

Background of the Invention

Successful treatment of cancers with Immune Checkpoint Inhibitors (ICIs) has been associated with the mutational load of tumors. The biological rationale for this association between mutational load and ICI response is that neoantigens are generated by mutations in protein coding sequences that provide a steady flow of neoantigens to prime the immune system for the production of antigen-specific tumor-infiltrating lymphocytes (TILs). It is thought that mutant protein fragments will lead to altered MHC/peptide recognition and immune cell activation. Treatment of cancer with ICIs enhance TIL functionality.

Neoantigens are also relevant for an alternative, cell-based immunotherapeutic approach, i.e., Adoptive Cell Transfer (ACT). This concept of neoantigens derived from DNA mutations has led to an intense line of investigation to uncover relevant neoantigens. There has been, however, inconsistent findings and results using the current neoantigen discovery approach, which is based on DNA mutation analysis of tumor samples by exome sequencing of genomic DNA.

The concept of neoantigens derived from mutant DNA ignores an important alternative mechanism that can also generate neoantigens in cancers. Specifically, posttranscriptional editing of primary RNA may also involve pathologic alternative splicing, which will introduce new, immunogenic peptide sequences to the immune system. Indeed, malignant progression can generate alternatively spliced transcripts not present in normal tissues. In addition, DNA mutations in intronic sequences can also alter splicing of the primary transcripts due to changes in splice donor/acceptor sites, altered primary RNA transcript structure and RNA binding due to the mutated RNA sequence. The current methods of neoantigen identification involving sequencing of exonomic DNA for mutation are therefore limited as they cannot be used to detect mutations in RNA transcripts. What is needed are methods of identifying additional neoantigens or potential neoantigens that are generated at the RNA transcript level.

SUMMARY OF THE INVENTION

The present invention provides methods of identifying neopeptides in abnormal cells, with the methods comprising sequencing long-read messenger RNA (mRNA) isolated from the abnormal cells, identifying splice variants that could be generated from the sequenced long-read mRNA, determining if the abnormal cells contain neopeptides that correlate with the identified splice variants. The methods may also comprise identifying at least one neoantigen on the neopeptides that are present in the abnormal cells.

BRIEF DESCRIPTION OF THE DRAWINGS

FIG. 2 depicts mRNA isoforms of the EEF1A1 gene as an example of analyses. 2A shows the reference gene model from hg19. Arrows indicate direction of transcription. 2B-2E show isoforms and abundances (TPM) discovered in lineage-neg and total BM population by conventional short read (short-read) RNA-seq (2B, 2D) or by full length (long-read) RNA-seq (2C, 2E). Abbreviations: S, short read RNA-seq; C, canonical transcript and open reading frame (ORF); C*, transcripts with canonical ORF; ID #s of the isoforms are from the identifiers generated by the sequencing method. ORFs and a novel protein isoform (arrows) that was confirmed by mass spectrometry for a unique peptide are shown in FIG. 3.

FIG. 4 depicts mRNA isoforms of the ANXA1 gene. 4A shows the reference gene model from hg19. Arrows indicate direction of transcription. 4B-4E show results for lineage-neg and total BM from short read RNA-seq (4B, 4D) or full length (long-read) RNA-seq (4C, 4E). Isoforms and abundances (TPM) discovered in lineage-neg and total BM population by short read (4B, 4D) or full length RNA-seq (4C, 4E). Abbreviations: S, short read RNA-seq; C, canonical transcript and open reading frame (ORF); C*, transcript with canonical ORF; ID #s of the isoforms are from the identifiers generated by the sequencing methods. ORFs are shown in FIG. 6.

FIG. 7 discloses SEQ ID NOS 66, 66-70, and 70-75, respectively, in order of appearance.

FIG. 8 depicts multiple amino acid sequence alignment and mass spectrometry detected peptides for HLA-A, -B and -C transcripts. Sequences predicted from transcript isoforms of HLA-A, HLA-B and HLA-C are shown, in which SEQ ID NOS 76-80, 80-82, 80, 83-102, 99, 103, 99, 104-116, and 118-121 are disclosed, respectively, in order of appearance. The identifiers of the transcript isoforms are included. Canonical amino acid sequences are highlighted. Peptide fragments are identified by mass spectrometry analysis of tryptic fragments of proteins extracted from lin-neg bone marrow cells.

DETAILED DESCRIPTION OF THE INVENTION

Figure 1:
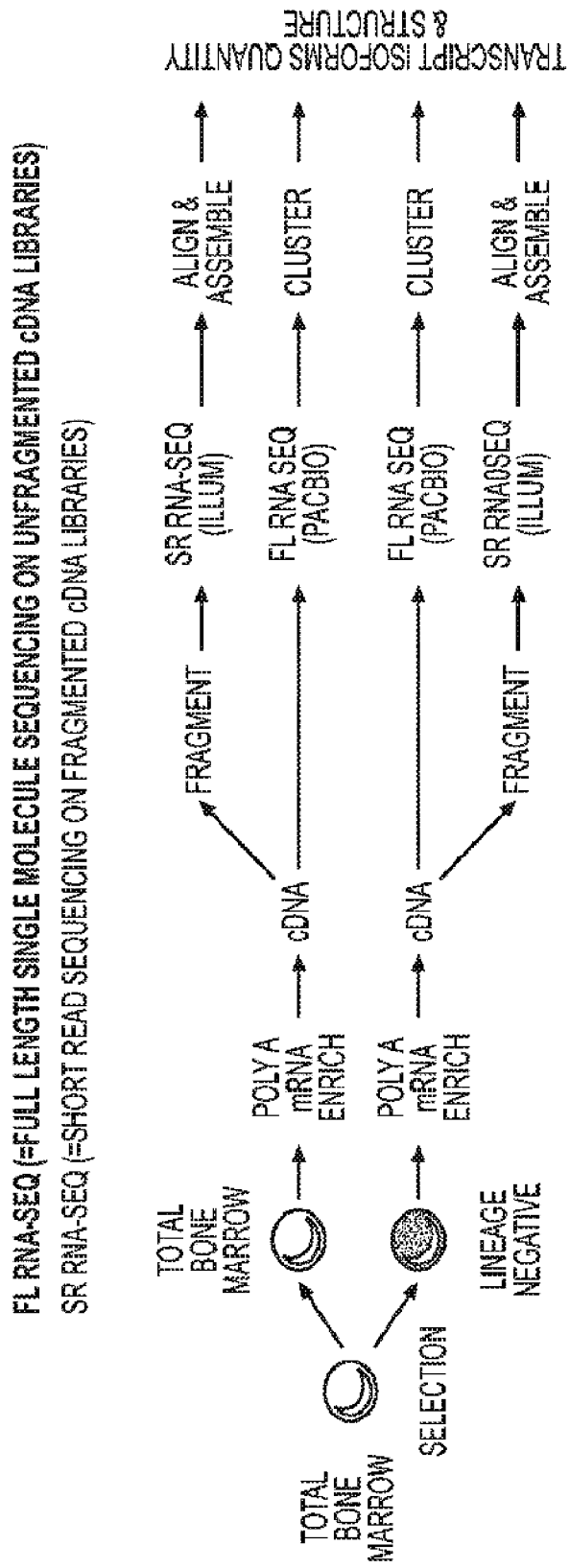
FIG. 1 depicts a transcriptome analysis of human bone marrow (BM) cells. Poly(A)+RNA was isolated from Total (T) or lineage-Negative BM cell populations (N). Lineage-negative (lin-neg) cells contain the stem cell population present in the bone marrow. Full length (long read) cDNA libraries were subjected to single molecule real-time RNA-seq (SMRT; PacBio platform) or conventional short read RNA-seq of fragmented cDNAs at 20 million (T) or 100 million (N) read depth (Illumina platform). Full length RNA-seq data were processed using the ToFU software generated at PacBio. Illumina reads were first aligned and then assembled using the Tuxedo suite. The efficiency of the double selection of lineage negative cells used here was confirmed by comparison of the abundance of standard markers of differentiated cells: CD14=6:1; CD16b=25:1; CD24=109:1; CD45=11:1; CD66b=16:1 expression ratio of lin-pos to lin-neg cells.

The present invention provides methods of identifying neopeptide and/or neoantigens in abnormal cells, with the methods comprising long-read sequencing of messenger RNA (mRNA) isolated from the abnormal cells, identifying splice variants that could be generated from the sequenced long-read mRNA, determining if the abnormal cells contain neopeptides that correlate with the identified splice variants. The methods may further comprise identifying at least one neoantigen on the neopeptides that are present in the abnormal cells.

As used herein, the term "neoantigen" is an antigen that is formed by peptides that are normally absent from the proteome of a cell. The term antigen is used herein as it is in art and means a molecule or portion thereof that induces the production of antibodies in an organism capable of antibody production. Not all antigens can elicit an immune response, thus the term "antigenic" is not synonymous with "immunogenic." Likewise, the term "antigen" is not synonymous with "immunogen." As used herein, the neoantigens that are discovered using the methods of the present invention may or may not be immunogenic. In one embodiment, the neoantigens discovered using the methods of the present invention are immunogenic. In another embodiment, the neoantigens discovered using the methods of the present invention are not immunogenic to one host, e.g., a human host, but can be used to generate antibodies in other hosts to target them therapeutically.

Typically, a "neoantigen" is used in art to indicate a new antigen that is produced when a genetic mutation occurs in the cell's DNA, thus forming a different protein when the mutant DNA is transcribed and subsequently translated. As used herein, the terms protein, peptide and polypeptide are interchangeable. The present invention, however, focuses on identifying neoantigens that are formed when an abnormal splice variant occurs to generate a protein that is normally not found in the cell's proteome. Thus, the term "neoantigen" as used herein does not imply or require the presence of a mutation in the cell's genome. Nonetheless, the methods of the present invention may also be used to identify neoantigens that result from a genetic mutation in the cell's DNA, provided, however, that the neoantigens are caused by an abnormal splice event. By way of a non-limiting example, if a genetic mutation in the cell's DNA generates an abnormal splice junction, and thus leading to an abnormal splice variant, the term "neoantigen" as used herein would apply and the methods of the present invention could be used to identify the neoantigen caused by the genetic mutation.

The neoantigens of the present invention can be specific for each individual population of cells. For example, a population of cells obtained from one subject may contain neoantigens that are different from neoantigens contained in a population of cells obtained from a different subject. Thus, while the cells' DNA may be identical or nearly identical between two cell populations taken from different subjects, the neoantigens contained in the cell populations could be different. Accordingly, the present invention can be applied to methods of personalized medicine.

Typically, the methods of the present invention can be applied to any cell or population of cells. In one embodiment, the cell or population of cells that are used in the methods of the present invention are abnormal cells or are suspected of being abnormal. As used herein, the term "abnormal cells" are cells that exhibit abnormal metabolism, growth patterns, protein expression patterns or morphology. For example, abnormal cells may be cells that do not undergo apoptosis at the appropriate time or they divide more than normal. By way of another example, abnormal cells may be cells that do not appear to be morphologically normal to a clinician, such as a pathologist or histologist. In one embodiment, the cells that are subjected to the methods of the present invention are known to be abnormal cells. In another embodiment, the cells that are subjected to the methods of the present invention are suspected of being abnormal prior to identifying the neoantigens. The methods of the present invention thus can be used to confirm that a population of cells is abnormal by detecting the presence of one or more neoantigens.

The methods of the present invention are generally performed on a population of cells. The population of cells need not be a pure population of cells. For example, the cells can be obtained from a biopsy and need not be separated and/or purified prior to obtaining the RNA from the cells. In another embodiment, the population of cells is a pure or substantially pure population of cells. For example, the cells may be obtained from a tissue sample and the tissue may be digested and the cells separated and placed in culture to expand the cell population prior to subjecting the cells to the methods of the present invention. The cells can be obtained from any animal that is capable of generating antibodies, such as but not limited to mammals and birds. In specific embodiments, the cells used in the present invention are cells obtained from a mouse, rat, rabbit, ferret, cat, dog, camel, horse, cow, human or non-human primate. Generally speaking, the cells upon which the methods of the present invention are performed are split into multiple subsets to ensure that the methods of the present invention can be completed on the population of cells. To that end, the subsets into which the cells are split need not be identical to one another, both in terms of number and purity. For example, if a biopsy is obtained from a patient, the tissue fragment may be split into multiple pieces and each piece could represent a "subset" of the population of cells without purifying the cells within each portion of the biopsy. In another example, cells may be obtained from a subject and expanded in culture, and the cultured cells may be split into multiple subsets of cells using routine passaging techniques.

In select embodiments, the population of abnormal cells is considered to be a population of cancer cells. As used herein, the term "cancer cell" refers to a cell or cells that are obtained from abnormal tissues or conditions such as, but not limited to, hypertrophy, neoplasia, hyperplasia, benign and malignant tumors. As used herein, the term "tumor" is a general term that includes hypertrophies, neoplasias, hyperplasias, benign cancers and malignant cancers. Accordingly, certain embodiments of the present invention are performed on cells isolated from a hypertrophy, a neoplasia, a hyperplasia, a benign or a malignant cancer in a subject. Other types of cancer cells include abnormal cells obtained from blood-born cancers (or non-solid tumors), such as lymphomas, leukemias and the like.

The cancer cells can be from any animal, including but not limited to any mammal, such as mouse, rat, canine, feline, bovine, equine, porcine, non-human and human primates. Mammalian cells particularly suitable for cultivation in the present media include cancer cells of human origin. In addition, transformed cells or established cell lines cancer cell lines can also be used. In one embodiment, the cells are primary or secondary cancer cells. In another embodiment, the cells are not primary cells, such as cells from an established cell line, transformed cells, thawed cells from a previously frozen collection and the like. Animal cells for culturing by the present invention may be obtained commercially, for example from ATCC (Rockville, Md.), Cell Systems, Inc. (Kirkland, Wash.), Clonetics Corporation (San Diego, Calif.), BioWhittaker (Walkersville, Md.) or Cascade Biologicals (Portland, Oreg.).

In other select embodiments, the cells are primary cancer cells of an abnormal tissue obtained from a subject, with the subset of cells being portions of the abnormal tissue. As used herein, primary cancer cells are cells that have been taken directly from living tissue, such as a biopsy, and have not been passaged or only passaged one time. Thus, primary cells have been freshly isolated, often through tissue digestion and plated. Provided the cells have been passaged one time or less, primary cells may or may not be frozen and then thawed at a later time. In addition, the tissue from which the primary cancer cells are isolated may or may not have been frozen or preserved in some other manner immediately prior to processing. By "cell culture" or "culture" is meant the maintenance of the cells in an artificial, in vitro environment. The term "cell culture" also encompasses cultivating individual cells and tissues.

As can be appreciated, obtaining RNA from cells will necessarily result in their destruction, thus the population of cells may be divided into two or more subsets of cells prior to subjecting the cells to the methods of the present invention. The subsets of cells need not be identical in size. Methods of isolating mRNA from cells are well known in the art, and the invention is not limited by the manner in which the mRNA is obtained from the cells. RNA quality can, but need not, be assessed prior to analysis by standard methods known to those skilled in the arts including capillary electrophoreses.

Generally, speaking the RNA that is obtained from the cells is cytosolic RNA. In one embodiment, the RNA that is obtained from the cells and sequenced is messenger RNA (mRNA). The mRNA may or may not be poly-adenylated (poly-A) as typically occurs when mRNA is properly processed after transcription.

As used herein, the term "long range RNA," or "long-read RNA" including "long range RNA" or "long-read mRNA," means that the RNA that is subject to sequencing is 70 nucleotides (nts) or longer in length. Ordinarily, RNA is sequenced in "short-read" batches of less than about 70 nts and then the sequence of the RNA is deduced by piecing together these short-read sequences in order using the known genome as a template. Recent evidence suggests, however, that such methods of short-read sequencing of RNAs, do not accurately provide a full picture of the sequence and structure of the long-read RNA as it occurs in the cell. The methods of the present invention therefor require long-read sequencing of RNA molecules that are about 70 nts or longer. In select embodiments, the long-read RNA molecules that are sequenced are between about 70 nts and about 150 nts in length, between about 150 nts and about 300 nts in length, between about 300 nts and about 500 nts, between about 500 nts and about 750 nts, between about 750 nts and about 1000 nts, between about 1000 nts and about 1250 nts, between about 1250 nts and about 1500 nts, between about 1500 nts and about 1750 nts, between about 1750 nts and about 2000 nts, between about 2000 nts and about 2250 nts, between about 2250 nts and about 2500 nts, between about 2500 nts and about 2750 nts, between about 2750 nts and about 3000 nts, between about 3000 nts and about 3250 nts, between about 3250 nts and about 3500 nts, between about 3500 nts and about 4000 nts, between about 4000 nts and about 4500 nts, between about 4500 nts and about 5000 nts, between about 5000 nts and about 5500 nts, between about 5500 nts and about 6000 nts, between about 6000 nts and about 6500 nts, between about 6500 nts and about 7000 nts, between about 7000 nts and about 7500 nts, between about 7500 nts and about 8000 nts, between about 8000 nts and about 8500 nts, between about 8500 nts and about 9000 nts, between about 9000 nts and about 9500 nts or between about 9500 nts and about 10000 nts. To obtain these long-read RNA molecules, the RNA is generally not fragmented during isolation and purification. The term "fragmented," with respect to RNA or DNA molecules is well understood in the art and means that the longer molecules are split into shorter pieces, sometimes with the use of enzymes. In select embodiments, the long-read RNA that is sequenced is not fragmented prior to sequencing.

Once isolated, the long-read RNA is sequenced. Protocols for sequencing long-read RNA molecules are well-known in the art and are disclosed in publications such as Tilgner, H. et al., *Proc. Nat'l Acad. Sci.*, USA, 111(27):9869-9874 (2014), Tseng, E. and Underwood, J., *J. Biomol. Techniques.*, 24 Supplement:545 (2013), Sharon, D., et al., *Nature Biotech.* 31(10):1009-1014 (2013), Pan. Q., et al., Nature Genetics, 40:1413-1415 (2008), Steijger, T., et al., *Nature Methods*, 10:1177-1184 (2013) and U.S. Pat. Nos. 8,192,961, 8,501,405 and 8,940,507, all of which are incorporated by reference. The invention is not limited to specific methods of sequencing long-read RNAs, provided that the RNAs that are sequenced are at least about 150 nts or more.

Once sequenced, the long-read RNA is then analyzed to determine potential splice variants that may occur in the long-read RNA. The term "splice variant" is well-understood and it used as it is in the art. In short, a splice variant is a "species" of a primary RNA, which is a direct copy of the cell's DNA, that the cell processes to exclude or include exons in the final mRNA that is transported from the nucleus to the cytosol and is then translated into a peptide. Accordingly, in one embodiment, the RNA that is obtained and sequenced during the methods of the present invention is cytosolic RNA, that is not tRNA or rRNA. In another embodiment, the RNA that is obtained and sequenced during the methods of the present invention is not nuclear RNA. A single primary RNA can thus be processed to provide multiple distinct mRNA molecules, based upon the inclusion or exclusion of specific exons from the primary RNA molecule. Each separate splice variant therefore correlates to a specific peptide, based on the amino acid sequence for that the processed mRNA codes. Because each specific splice variant results in a specific peptide, identifying potential splice variants can be used to determine if a potential peptide is present in the cell's proteome. The potential splice variants that are identified with the methods of the present invention may or may not be known splice variants of the peptide.

In one embodiment, the splice variant analysis of the long-read RNAs that are sequenced during the methods of the present invention are previously unknown splice variants, i.e., a novel splice variant, of the target RNA. Methods for determining if a splice variant is novel are well-known. In particular, one of skill in the art is well-aware of internet-based databases and collections of splice variants that are readily searchable. Examples of splice variant databases on the internet include but are not limited to Protein Information Resource (PIR) (pir.georgetown.edu), ExPASy (www-.expasy.org), EVDB (projects.insilico.us/SpliceMiner/), ECgene (genome.ewha.ac.kr/ECgene/), SpliceNest (splicenest.molgen.mpg.de/) and MAASE (maase.genomics.purdue.edu/), to name a few. The identified long read RNA sequence is matched to the genomic DNA sequences to determine if an interruption of the contiguous sequences could represent a splice event in which a portion of the primary RNA transcript is removed by polymerase reading of the genomic DNA. Such matching and review of the transcript to the genomic sequence is routine in the art and can be accomplished using blast search engines, which are publically available.

Once the splice variants are determined, a protein with a specific amino acid sequence can be then predicted from each of these splice variants. Each of these proteins, if novel, represents a potential set of novel neoantigens that may be present in or on the protein. As used herein, the term "neopeptide" means a peptide that is normally absent from the proteome of a cell. The term "neopeptide" as used herein does not imply or require the presence of a mutation in the cell's genome to produce the neopeptide. Nonetheless, the methods of the present invention may also be used to identify neopeptides that result from a genetic mutation in the cell's DNA, provided, however, that the neopeptides are caused by an abnormal splice event. By way of a non-limiting example, if a genetic mutation in the cell's DNA generates an abnormal splice junction, and thus leading to an abnormal splice variant, the term "neopeptide" as used herein would apply and the methods of the present invention could be used to identify the neopeptide caused by the genetic mutation.

The neopeptides of the present invention can be specific for each individual population of cells. For example, a population of cells obtained from one subject may contain neopeptides that are different from neopeptides contained in a population of cells obtained from a different subject. Thus, while the cells' DNA may be identical or nearly identical between two cell populations taken from different subjects, the neopeptides contained in the cell populations could be different.

Methods of determining the presence or absence of peptides that correspond to the identified splice variants are then carried out on the cells. Protein is extracted from the cells using standard protein extraction techniques. Obviously, the cells from which the proteins are extracted are not the identical cells from which the RNA is extracted for sequencing, thus protein is extracted from a second subset of cells, whereas RNA was extracted from a first subset of cells.

The identification of peptides that correspond to splice variants is routine in the art and the methods of the present invention are not limited by the manner in which the peptides are identified. For example, once the neopeptide is identified in the protein extract from the population of abnormal cells, mass spectrometry can then be employed on protein extracts obtained from normal cells of the same tissue origin. If the neopeptide is not present in the population of normal cells, the presence of the neopeptide can then be considered as a marker for abnormal cells and the neoantigen can, optionally, be further identified. In other words, the methods of the present invention may also include additional steps to determining in a population of normal cells the absence of the neopeptides that correlate with the identified splice variants. In other embodiments, performing additional assays on normal cells may not be necessary if it is already established in the art that a specific cell type does of or does not normally contain a specific protein within its proteome. In this instance, simply comparing the results of the proteomic analysis described herein with well-established standards will suffice for purposes of comparing proteomes in abnormal and normal populations of cells. If the presence of the neopeptide is detected in the population of abnormal cells and the absence of the neopeptide is confirmed in the normal cells, these results would indicate that the neopeptide is a marker for abnormal cells. In an additional embodiment, the confirmed neopeptide can then be used to generate an agent, e.g., an antibody or fragment thereof, that specifically binds to the neopeptide found in abnormal cells this identifying the neoantigen in the abnormal cells.

In one aspect of the present invention, determining the presence of the neopeptides comprises the use of mass spectrometry. Methods of using mass spectrometry to determine the presence of a specific protein in a sample are well known and have been reviewed in Aebersold, R. and Mann, M., Nature, 422:198-207 (2003), which is incorporated by reference.

Other methods of determining if neopeptides are present in a sample include chemically synthesizing the neopeptides and generating antibodies towards the neopeptides using standard immunological techniques to identify one or more neoantigens that are contained on the neopeptide. Once the antibodies are generated, they are applied to the protein extract obtained from the cells and the presence or absence of binding of the antibodies to the neopeptides, thus identifying a neoantigen, can then be assessed. Detecting the presence or absence of antibody binding can be achieved using routine binding assays, such as peptide arrays, ELISA, Western Blot, immunohistochemical assays and the like. One of skill in the art would be well-versed in methods of detecting antibody binding. In one aspect of the present invention, determining the presence of the neopeptides comprises generating antibodies capable of specifically binding the neopeptides and determining if the antibodies bind to the neopeptides.

As is readily appreciated, antigens can be formed not only through a linear chain of amino acids, but also through the three dimensional configuration of the peptide that it assumes in solution. Thus, any identified neopeptides can provide an array of neoantigens in a number of ways.

As used herein, the phrase "identifying a neoantigen" is not intended require the identification of a specific linear sequence of amino acids or a specific three dimensional arrangements of the neopeptides that create the neoantigen. Instead, "identifying a neoantigen" can mean generating an agent, such as an antibody or an antibody fragment, that specifically binds to the neopeptide. In other words, production of antibodies, either polyclonal or monoclonal, is included in the phrase "identifying a neoantigen."

Any of the antibodies can be, for example, polyclonal, monoclonal, bi-specific, multispecific, human or chimeric antibodies. The antibody molecules of the invention can be of any type, e.g., IgG, IgE, IgM, IgD, IgA and IgY, class, e.g., IgG1, IgG2, IgG3, IgG4, IgA1 and IgA2 or subclass of immunoglobulin molecule. In one embodiment, the antibody that is generated to bind to the neoantigen comprises, or alternatively consists of, a polypeptide having an amino acid sequence of a VH domain, at least one VH CDR, a VL domain, or at least one VL CDR.

The antibodies or antibody fragment that is generated to bind to the neoantigen may be monovalent, bivalent, trivalent or multivalent. For example, monovalent scFvs can be multimerized either chemically or by association with another protein or substance. An scFv that is fused to a hexahistidine tag (SEQ ID NO:122) or a Flag tag can be multimerized using Ni-NTA agarose (Qiagen) or using anti-Flag antibodies (Stratagene, Inc.).

The antibodies that are generated to bind to the neoantigens may be monospecific, bi-specific, trispecific or of greater multispecificity. Multispecific antibodies may be specific for different epitopes of the neopeptide or they may be specific for both the neopeptide and a heterologous epitope, such as a heterologous polypeptide or solid support material. See, e.g., PCT publications WO 93/17715; WO 92/08802; WO 91/00360; WO 92/05793; Tutt, et al, *J. Immunol.* 147:60 69 (1991); U.S. Pat. Nos. 4,474,893; 4,714,681; 4,925,648; 5,573,920; 5,601,819; Kostelny et al, *J. Immunol.* 148:1547-1553 (1992), which are incorporated by reference.

As used herein, an antibody fragment is a fragment of an antibody capable of specifically binding the same epitope that the intact antibody would bind. Examples of antibody fragments include but are not limited to Fab and F(ab') 2 fragments, Fd fragments, disulfide-linked Fvs (sdFvs), anti-idiotypic (anti-Id) antibodies, including but not limited to anti-Id antibodies to antibodies that is generated to bind to the neoantigen, and epitope-binding fragments of any of the above. Fab and F(ab')$_2$ fragments lack the Fc fragment of intact antibody and generally clear more rapidly from the circulation, and may have less non-specific tissue binding than that of an intact antibody (Wahl et al., *J. Nucl. Med.* 24:316-325 (1983)). Other types of antibody fragments include but are not limited to single chain Fv fragments (scFv) that are well-known in the art. Techniques described for the production of single chain antibodies (U.S. Pat. No. 4,946,778) can be adapted to produce single chain antibodies to specific neopeptides.

The antibodies or fragments of the present invention may be prepared by any of a variety of methods. For example, cells expressing the neopeptide can be administered to an animal to induce the production of sera containing polyclonal antibodies. In one method, a preparation of neopeptides is prepared and purified to render it substantially free of natural contaminants. Such a preparation is then introduced into an animal in order to produce polyclonal antisera of greater specific activity.

Polyclonal antibodies that are generated to bind to the neoantigens may be produced according to standard techniques by immunizing a suitable animal, e.g., rabbit, goat, etc., with an antigen comprising an antigenic portion of the neopeptide. Collecting immune serum from the animal and separating the polyclonal antibodies from the immune serum can be carried out in accordance with known procedures, and screening and isolating a polyclonal antibody specific for neopeptide can be carried out with well-known procedures and as described below. Methods for immunizing non-human animals such as mice, rats, sheep, goats, pigs, cattle and horses are well known in the art. See, e.g., Harlow and Lane, *Antibodies: A Laboratory Manual*, New York: Cold Spring Harbor Press, 1990, which is incorporated by reference.

The neoantigen may be the full length neopeptide or a portion thereof. In some embodiments the neoantigen is a peptide of from 7 to 20 amino acids in length, in particular from about 8 to 17 amino acids in length. In some embodiments, the neoantigen desirably will comprise about 3 to 8 amino acids. Neopeptides suitable for producing antibodies that are generated to bind to the neoantigens may be designed, constructed and employed in accordance with well-known techniques. See, e.g., Antibodies: A Laboratory Manual, Chapter 5, p. 75-76, Harlow & Lane Eds., Cold Spring Harbor Laboratory (1988); Czemik, Methods In Enzymology, 201: 264-283 (1991); Merrifield, *J. Am. Chem. Soc.* 85: 21-49 (1962), which are incorporated by reference.

In some embodiments the neopeptide is administered with an adjuvant. Suitable adjuvants will be well known to those of skill in the art. Exemplary adjuvants include complete or incomplete Freund's adjuvant, RIBI (muramyl dipeptides) or ISCOM (immunostimulating complexes).

When the above-described methods are used for producing polyclonal antibodies, following immunization, the polyclonal antibodies which secreted into the bloodstream can be recovered using known techniques. Purified forms of these antibodies can, of course, be readily prepared by standard purification techniques, such as for example, affinity chromatography with Protein A, anti-immunoglobulin, or the antigen itself. In any case, to monitor the success of immunization, the antibody levels with respect to the antigen in serum can be monitored using standard techniques such as ELISA, RIA and the like.

In one aspect of the present invention, the antibodies or fragments thereof that are generated to bind to the neoantigens on the neopeptides are monoclonal antibodies. Such monoclonal antibodies can be prepared using hybridoma technology (Kohler et al., Nature 256:495 (1975); Kohler et al., Eur. J. Immunol. 6:511 (1976); Kohler et al., Eur. J. Immunol. 6:292 (1976); Hammerling et al., In: Monoclonal Antibodies and T-Cell Hybridomas, Elsevier, N.Y., (1981) pp. 563-681). In general, such procedures involve immunizing an animal (for example a mouse) with a neopeptide. Suitable cells can be recognized by their capacity to bind anti-neopeptide antibody. Such cells may be cultured in any suitable tissue culture medium; however, it is desirable to culture cells in Earl's modified Eagle's medium supplemented with 10% fetal bovine serum (inactivated at about 56° C.), and supplemented with about 10 g/l of nonessential amino acids, about 1,000 U/ml of penicillin, and about 100 µg/ml of streptomycin. The splenocytes of such mice are extracted and fused with a suitable myeloma cell line. Any suitable myeloma cell line may be employed in accordance with the present invention; however, it is may be desirable to employ the parent myeloma cell line (SP$_2$O), available from the American Type Culture Collection, Rockville, Md. After fusion, the resulting hybridoma cells are selectively maintained in HAT medium, and then cloned by limiting dilution as described by Wands et al. (Gastroenterology 80:225-232 (1981)). The hybridoma cells obtained through such a selection are then assayed to identify clones which secrete antibodies capable of binding the neoantigen on the neopeptide. The secreted antibody may be recovered from tissue culture supernatant by conventional methods such as precipitation, ion exchange or affinity chromatography, or the like. Other methods of generating monoclonal antibodies include but are not limited to the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77-96).

Alternatively, additional antibodies capable of binding to the neoantigens may be produced in a two-step procedure through the use of anti-idiotypic antibodies. Such a method makes use of the fact that antibodies are themselves antigens, thus it is possible to obtain an antibody which binds to a second antibody. In accordance with this method, neopeptide specific antibodies are used to immunize an animal, for example a mouse. The splenocytes of such an animal are then used to produce hybridoma cells, and the hybridoma cells are screened to identify clones which produce an antibody whose ability to bind to neopeptide-specific antibody can be blocked by a neopeptide antigen, respectively. Such antibodies comprise anti-idiotypic antibodies to neopeptide-specific antibody and can be used to immunize an animal to induce formation of neopeptide-specific antibodies.

The invention also encompasses antibody-producing cells and cell lines, such as hybridomas, as described above.

Polyclonal or monoclonal antibodies may also be obtained through in vitro immunization. For example, phage display techniques can be used to provide libraries containing a repertoire of antibodies with varying affinities for a particular antigen. Techniques for the identification of high affinity human antibodies from such libraries are described by Griffiths et al., *EMBO J.*, 13:3245-3260 (1994); which is incorporated by reference.

The antibodies may be produced recombinantly using methods well known in the art for example, according to the methods disclosed in U.S. Pat. No. 4,349,893 or U.S. Pat. No. 4,816,567, which are incorporated by reference. The antibodies may also be chemically constructed by specific antibodies made according to the method disclosed in U.S. Pat. No. 4,676,980, which is incorporated by reference.

Once a desired neopeptide antibody is identified, polynucleotides encoding the antibody, such as heavy, light chains or both (or single chains in the case of a single chain antibody) or portions thereof such as those encoding the variable region, may be cloned and isolated from antibody-producing cells using means that are well known in the art. For example, the neoantigen binding site of the monoclonal antibody can be cloned by PCR and single-chain antibodies produced as phage-displayed recombinant antibodies or soluble antibodies in *E. coli*. See, e.g., Antibody Engineering Protocols, Humana Press, Sudhir Paul, Ed. (1995), which is incorporated by reference.

In another embodiment, identifying a neoantigen can also mean using the neopeptide to assay samples, e.g., serum, from a subject for the presence of binding agents, e.g, antibodies to that bind to the neopeptide. The presence of a binding agent that binds the neopeptide would indicate that the subject's immune system has recognized the neopeptide.

The neopeptides can also be used to monitor the presence or absence of binding agents, which bind to the neopeptide, in a subject. For example, the neopeptides can be used to assay samples from a subject taken at multiple time points. When there is a decrease the amount of binding agents that bind to the neopeptides over time, this decrease could be used as an indication that the number of abnormal cells is decreasing over time. Thus in one embodiment, the invention provides methods of monitoring the progression of an abnormal condition, with the methods comprising assessing in the subject the levels of the identified neopeptide or the agent that binds the neopeptide at more than one time point. For example, some embodiments of the methods of the present invention will comprise assessing in the subject the levels of the identified neopeptide or the agent that binds the neopeptide at two, three, four, five, six, seven, eight, nine, 10 or even more time points over a period of time, such as a year, two years, three, years, four years, five years, six years, seven years, eight years, nine years or even 10 years or longer.

In other words, the present invention also includes methods of monitoring the efficacy of treatment of an abnormal condition by assessing in the subject the levels of the identified neopeptide or the agent that binds the neopeptide over the course of the treatment and after the treatment. In specific embodiments, the methods of monitoring the efficacy of treatment comprise assessing in the subject the levels of the identified neopeptide or the agent that binds the neopeptide at at least one, two, three, four, five, six, seven, eight, nine or 10 or more different time points prior to the receipt of treatment for the abnormal condition and subsequently assessing in the subject the levels of the identified neopeptide or the agent that binds the neopeptide at at least one, two, three, four, five, six, seven, eight, nine or 10 or more different time points after beginning of treatment for the abnormal condition, and determining the changes, if any, in the subject the levels of the identified neopeptide or the agent that binds the neopeptide. The levels can be monitored, with, for example, the normalization or decline in the values of the profile over time being indicative that the treatment may showing efficacy.

In another embodiment, identifying a neoantigen can mean generating a nucleic acid molecule that encodes an antibody or fragment thereof that binds a neoantigen. Methods of determining a coding sequence of a protein, including an antibody, are well known in the art. In another aspect, identifying the specific linear antigenic sequence or specific antigenic configuration of the peptide is also included in the phrase "identifying a neoantigen."

The methods of present invention may optionally include administration of the agent used to identify the neoantigen ("identifying agent") to a population of cells suspected of being abnormal, such as cancer cells, as well as administering the identifying agent to a group of normal cells. If binding of the identifying agent is detected in the population of abnormal cells and binding of the identifying agent is not detected in the normal cells, this analysis can be used to confirm that the identified neoantigen can be used as a marker for abnormal cells.

The present invention also provides methods of identifying abnormal tissue in a subject. For example, once the neoantigens or neopeptides have been identified, the identifying agents can then be used to identify the presence or absence of the neoantigens in other samples. These "other samples" may or may not be from the same subject from which the original population of cells was obtained. Accordingly, in one embodiment, the methods of identifying abnormal tissue comprise the additional steps of administering a compound that specifically binds to the identified neoantigen and detecting the presence or absence of the binding of the component. In another embodiment, the methods of identifying abnormal tissue comprise determining the presence of the neopeptide, e.g., using mass spectroscopy, in a population of cells suspected of being abnormal.

EXAMPLES

Example 1— Methods of Determining Novel Splice Variants in Bone Marrow Mononuclear Cells Freshly harvested bone marrow tissues were collected from discarded healthy human bone marrow collection filters that had been de-identified. Mononuclear cells were isolated by Ficoll gradient centrifugation. To select for lineage-negative cells, bone marrow mononuclear cells were incubated with an antibody cocktail containing antibodies against CD2, CD3, CD11b, CD11C, CD14, CD16, CD19, CD24, CD5, CD61, CD66b, and Glycophorin A (Stemcell Technologies). Lineage-positive cells bound to the antibodies were removed by magnetic beads and lineage-negative cells obtained from the flow-through. To increase purity, lineage-negative cells were enriched two times.

Sequencing of fragmented (short-read) cDNAs. Briefly, the integrity and purity of total RNA isolated from the cells were assessed using Agilent Bioanalyzer by OD260/280 ratio. 5 µg of total RNA was subjected to rRNA depletion using the RiboZero Human/Mouse/Rat kit (Epicentre Biotechnologies). cDNA was generated from the depleted RNA using random hexamers or custom primers and Superscript III (Life Technologies, Carlsbad, CA USA, catalog #18080093). The resulting cDNA was purified and fragmented using a Covaris fragmentation kit (Covaris, Inc.), profiled using an Agilent Bioanalyzer, and Illumina libraries were prepared using NEBNext reagents (New England Biolabs). The quality, quantity and the size distribution of the Illumina libraries were determined using an Agilent Bioanalyzer 2100. The libraries were then submitted for Illumina HiSeq2000 sequencing. Paired-end 90 or 100 nucleotide reads were generated and checked for data quality using FASTQC (Babraham Institute), and DNAnexus (DNAnexus, Inc) was used on the platform provided by Center for Biotechnology and Computational Biology (University of Maryland) 17. 159,043,023 non-strand specific paired-end reads were collected for the total bone marrow sample (deep sequencing). 35,126,712 strand-specific paired-end reads were collected from the lineage-negative cell sample.

Sequencing of full length (long-read) cDNAs. The integrity and purity of total RNA were assessed using Agilent Bioanalyzer and OD260/280 prior to submission. Full length cDNA synthesis was done from polyA RNA using Clontech SMARTer PCR cDNA synthesis kit (Clontech Laboratories; 23). Libraries were prepared after size selection of cDNAs into bins that contain 1-2 kb, 2-3 kb and >3 kb cDNAs by the BluePippin size selection protocol. These fractions were converted to SMRTbell libraries. Full length cDNA libraries were produced from 1 ng of poly-A RNA. Non-fragmented long read RNA-seq followed. Total RNA was submitted to Pacific Biosciences (Menlo Park, CA) or Icahn School of Medicine at Mount Sinai (New York, NY). 17 SMRT cells (7 cells 1-2 kb, 5 cells 2-3 kb, 5 cells 3-6 kb) were used to sequence the total bone marrow cell population. 12 SMRT cells were used to sequence the lineage-negative population (5 cells 1-2 kb, 5 cells 2-3 kb, 2 cells 3-6 kb).

Peptide Analysis by Nano LC-MS/MS. Proteins were extracted using 0.1% Rapigest (Waters) in 25 mM ammonium bicarbonate extracted proteins were reduced with 5 mM DTT for 60 min at 60° C. and alkylated with 15 mM iodoacetamide for 30 min in the dark. Trypsin (Promega) digestion (2.5 ng/µL) was carried out at 37° C. in Barocycler NEP2320 (PressureBioSciences) for 1 h at 37° C. and then vacuum dried in Speed-vac (Labconco). Tryptic peptides were analyzed on a NanoAcquity UPLC (Waters) by RP chromatography on a Symmetry C18 (3 µm, 180 µm, 20 mm) trap column and UPLC capillary column (BEH 300A, 1.7 µm, 150 mm×0.75 µm) (Waters) interfaced with 5600 TripleTOF (AB Sciex). Separation was achieved by a 250 min gradient elution with ACN containing 0.1% formic acid. The chromatographic method was composed of 5 min trapping step using 2% ACN, 0.1% formic acid at 15 µL/min and chromatographic separation at 0.4 µL/min as follows:

starting conditions 2% ACN, 0.1% formic acid; 1-180 min, 2-60% ACN, 0.1% formic acid; 180-200 min, 60-95% ACN, 0.1% formic acid; 200-220 min 95% ACN, 0.1% formic acid followed by equilibration 2% ACN, 0.1% formic acid for an additional 30 min. For all runs, 5 µL of sample were injected directly after enzymatic digestion analysis used an Information Dependent Acquisition (IDA) work flow with one full scan (400-1500 m/z) and 50 MS/MS fragmentations of major multiply charged precursor ions with rolling collision energy. Mass spectra were recorded in the MS range of 400-1500 m/z and MS/MS spectra in the range of 100-1800 m/z with resolution of 30,000 and mass accuracy up to 2 ppm using the following experimental parameters: declustering potential, 80 V; curtain gas, 15; ion spray voltage, 2300 V; ion source gas 1, 20; interface heater, 180° C.; entrance potential, 10 V; collision exit potential, 11 V; exclusion time, 5 s; collision energy was set automatically according to m/z of the precursor (rolling collision energy). Data were processed using ProteinPilot 4.0 software (AB Sciex). For targeted measurement an inclusion parent mass list was created according to in-silico tryptic digest of interesting sequences.

Transcriptome alignment and assembly from Illumina data. Illumina reads were trimmed using Trimmomatic (www.usadellab.org/cms/?page=trimmomatic) with the default parameters and the reads then aligned and assembled according to the Tuxedo suite protocol as described in Trapnell, C. et al., Nat Protoc. 7, 562-578 (2012), which is incorporated by reference. The genome of reference used was GRCh37 (hg19). The genes.gtf from this reference was used to guide the read alignment during the Tophat 2 step and Cufflinks 2. Bowtie 2 indices were used for the genome reference. All computation was performed using Amazon Web Services and through the use of Starcluster software (star.mit.edu/cluster/) to manage the boxes. A Sun Grid Engine was employed to run the tasks. Reads were trimmed by Trimmomatic with the default parameters.

The conversion of ToFU abundance to TPMs was generated according to Li, B., et. al., Bioinformatics 26, 493-500 (2010), which is incorporated by reference.

Open Read Frame (ORF) predictions were generated using the ANGEL software package (github.com/PacificBiosciences/ANGEL), which publically available on github, and through the use of SerialCloner 2.6.1. ORFs accepted were the first ORFs and not necessarily the largest. In some cases both the first and the largest ORF were included and designated with letters a, b, etc., appended to the end of the name assigned.

Multiple Sequence Alignment was performed using Clustal Omega through the website (www.ebi.ac.uk/Tools/msa/clustalo). Sequence alignment was edited using BioEdit version 7.2.5. This Sequence Alignment Editor written for the windows environment was run on OS-X Yosemite on a Mac Book Pro through the use of the wine version 1.6.2, a windows emulator available for download and installation through Home Brew version 0.9.5. For figures herein, a simplification of the names generated by the cDNA Primer software was used creating a per figure unique nomenclature relating to the consensus deposited gene structures as well as using the uniprot deposited protein isoforms to unify results.

The full length sequence reads were aligned to hg19 reference genome using gsnap. The fragmented sequence reads were aligned to hg19 reference using Tophat 2 and the aligned and paired reads were assembled using Cufflinks 2 and genes.gtf also from hg19 annotation as a guide (Trapnell et al., 2012). Quantitation of transcripts was calculated as reported by Cufflinks in FPKMs and these were transformed to TPMs according to the methods described in Li et al, as previously described. Data structures using Bioconductor packages GRanges were used to unify the results.

Example 2— Results

Total human bone marrow cell population (T) dominated by differentiated cells was compared with a small (<1%) subpopulation of lineage-negative progenitor cells (N) using single-molecule, full length RNA-seq (FIG. 1). Samples were also analyzed at 20 and 100 million read depths by conventional RNA-seq that relies on the computational assembly of transcripts from short read sequences of fragmented cDNAs. The representative focus was on the analysis of two representative genes that are abundantly expressed in hematopoietic cells (EEF1A1 & ANXA1) to provide details of the analysis. Utilizing complete transcriptomes generated either by full length or short read RNA-seq, the composite results are described and then a comparison with protein fragments identified by mass spectrometry is also provided.

Eukaryotic translation elongation factor 1 alpha 1 (EEF1A1) is a highly abundant, conserved protein that delivers aminoacyl-tRNAs to the ribosome during protein synthesis but has also been found to contribute to additional cellular functions. The EEF1A1 gene spans 5.2 kb on chromosome 6q13 and results in a 3.5 kb transcript that contains six protein coding exons (RefSeq HG19). Short read (short-read) RNA-seq of total and lineage-negative bone marrow populations matched to the known reference transcripts and contained the Canonical open reading frame (ST1-C, ST2-C*, red; SN1-C, blue). One of the transcript isoforms, however, did not include the long 3' UTR (ST2-C*) and one novel isoform in lineage-negative cells (SN2-3) skipped four coding exons due to an alternative splice acceptor and did not contain the long 3' UTR in the RefSeq data base.

In contrast to this, the EEF1A1 transcript isoforms obtained from full length (long-read) RNA-seq (FIG. 2c) showed seven isoforms from lineage-negative (N4-C*, N9-C*, etc.) and one from the total bone marrow cell population (T2-C*) that contain the canonical open reading frame (P68104; see below FIG. 3a). An additional 34 novel transcript isoforms were identified, 14 of which were from the total and 28 from the lineage-negative cell populations. Exon-skipping was seen in 22, e.g., T9-28, exon-splitting in 2, T8-26, N13-10, and alternative donor/acceptor sites in 30 transcript isoforms, e.g., T7-25. No transcripts were found that contain the long 3' UTR included in the Refseq data base (FIG. 2c). Transcript abundance showed a 16-fold range amongst the isoforms identified with short read RNA-seq whereas full length RNA-seq revealed an approximately 1,700-fold dynamic range across the different isoforms (FIG. 2d, e). From these observations, full length (long-read) RNA-seq can uncover novel transcript isoforms that distinguish bone marrow cell subpopulations and captures a much broader range of transcript abundance.

Figures 3B, 3C, 3D:
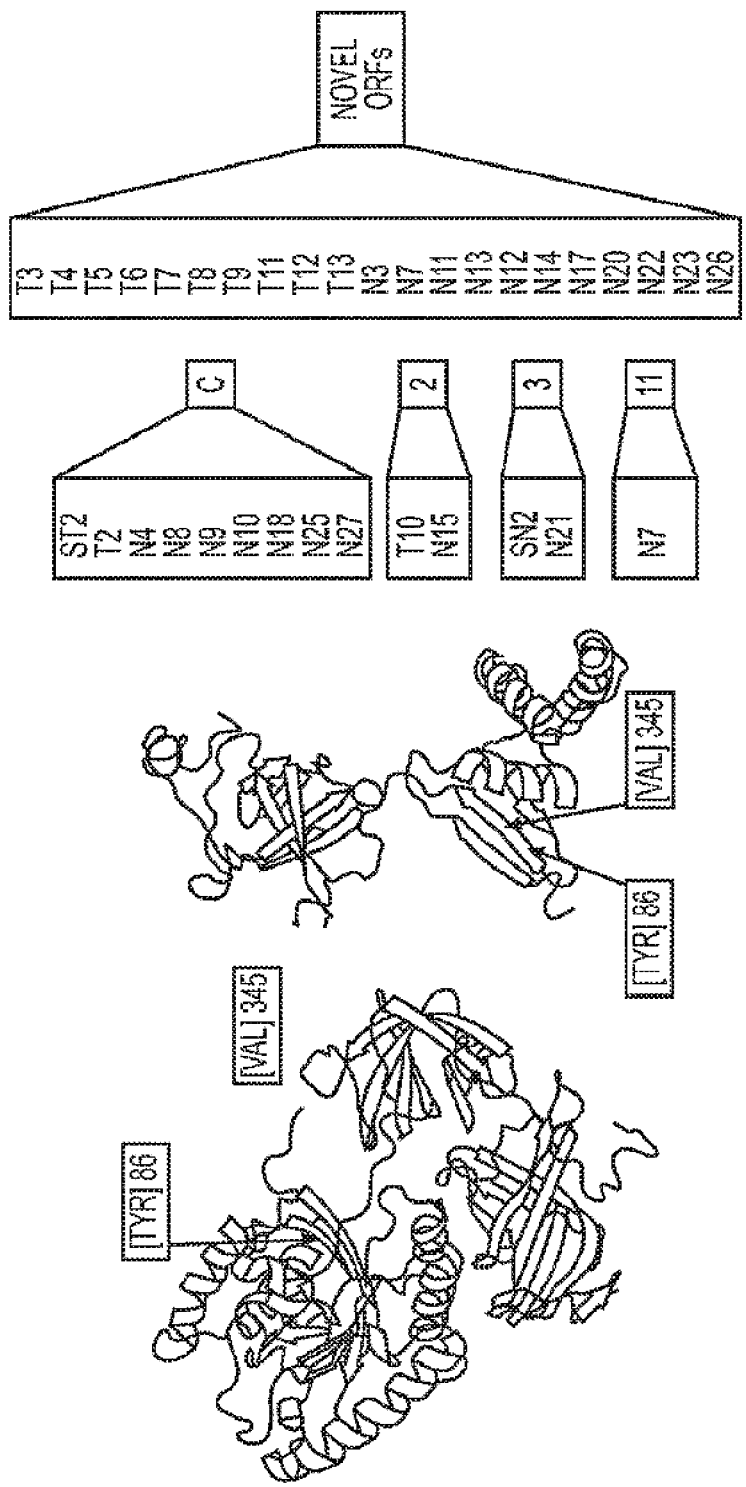
FIG. 3 depicts proteins predicted from the transcript isoforms identified for EEF1A1. 3A shows amino acid sequence alignments including the isoform identifiers. The protein predicted from the N7-24 transcript isoform (highlighted) was validated by mass spectrometry. The respective peptide identified after tryptic digest is shown with Y86 and V345 from the canonical protein flanking the novel junction site. 3A discloses SEQ ID NOS 1-14, 14, 14-17, 14, 14, 14, 14, 14, 14, 14, 18-19, 19-38, and 117, respectively, in order of appearance. 3B, 3C show protein structure models that were generated using the Phyre2 software. The predicted structure of the canonical EEF1A1 protein P68104 (3B) and of the new protein N7 (3C) are shown. For the canonical protein, the template c1g7ca covered 96% of the amino acids with >90% confidence. For the novel N7 protein the c1g7ca template covered 90% of the amino acids with >90% confidence. 3D shows higher magnification of ten transcript isoform identifiers that code for the canonical protein. Abbreviations: C, canonical, refseq derived transcripts. C*, previously unknown transcript isoforms that code for the canonical protein. Transcript isoforms SN2-3 and N21-3 predict the same protein.

Open reading frames predicted from the transcript isoforms of EEF1A1 were aligned to the canonical protein and overlayed with its 3D structure (FIG. 3a, b). Out of the 21 novel protein isoforms predicted from the transcriptome analysis (FIG. 3a, d) the N7 protein contained a unique peptide that was distinct from fragments of the canonical EEF1A1 protein and detectable by mass spectrometry. The N7 transcript is typically found in the lineage-negative cell population only at low abundance (21 TPM; see FIG. 2e) and is predicted to code for a 205 aa protein that lacks the central 258 amino acids of the EEF1A1 protein and thus joins Y86 with V345 (FIG. 3a, c). A unique peptide spanning Y86 to V345 was detected by mass spectrometry analysis of tryptic digests of proteins extracted from lineage-negative cells (FIG. 3a) and thus confirms that the N7 transcript is translated into a protein expressed at sufficient levels to be detectable by mass spectrometry.

Annexins are known as organizers of membrane dynamics that include binding proteins for endocytosis, exocytosis, and other localization functions. The ANXA1 gene spans 18 kb on chromosome 9q21 with 12 coding exons and results in an approximately 1.5 kb transcript. With the conventional short read (short-read) RNA-seq and computational transcript reconstruction only the canonical ANXA1 transcript was found in total bone marrow and in lineage-negative cell populations. In contrast, full length (long-read) RNA-seq identified 36 transcript isoforms in addition to the canonical transcript (FIG. 4c): 21 in the total and 17 in the lineage-negative cell population. Two of these novel isoforms predict the canonical protein, P04083 (T10-C*, N12-C*), while others contain distinct open reading frames generated by exon-skipping (25 isoforms; e.g., T16-.12, N7-12), alternative donor and acceptor sites (11 isoforms; e.g., T19-6, N10-2) and intron retentions (9 isoforms; e.g., T6-14, N11-13). The abundance of ANXA1 transcript expression was >10-fold lower in the lineage-negative cells when measured with short read RNA-seq (FIG. 4d). In contrast, full length RNA-seq revealed a 200-fold range of distinct expression levels of the different isoforms when comparing lineage-negative and total bone marrow cells (FIG. 4e).

Figure 6A:
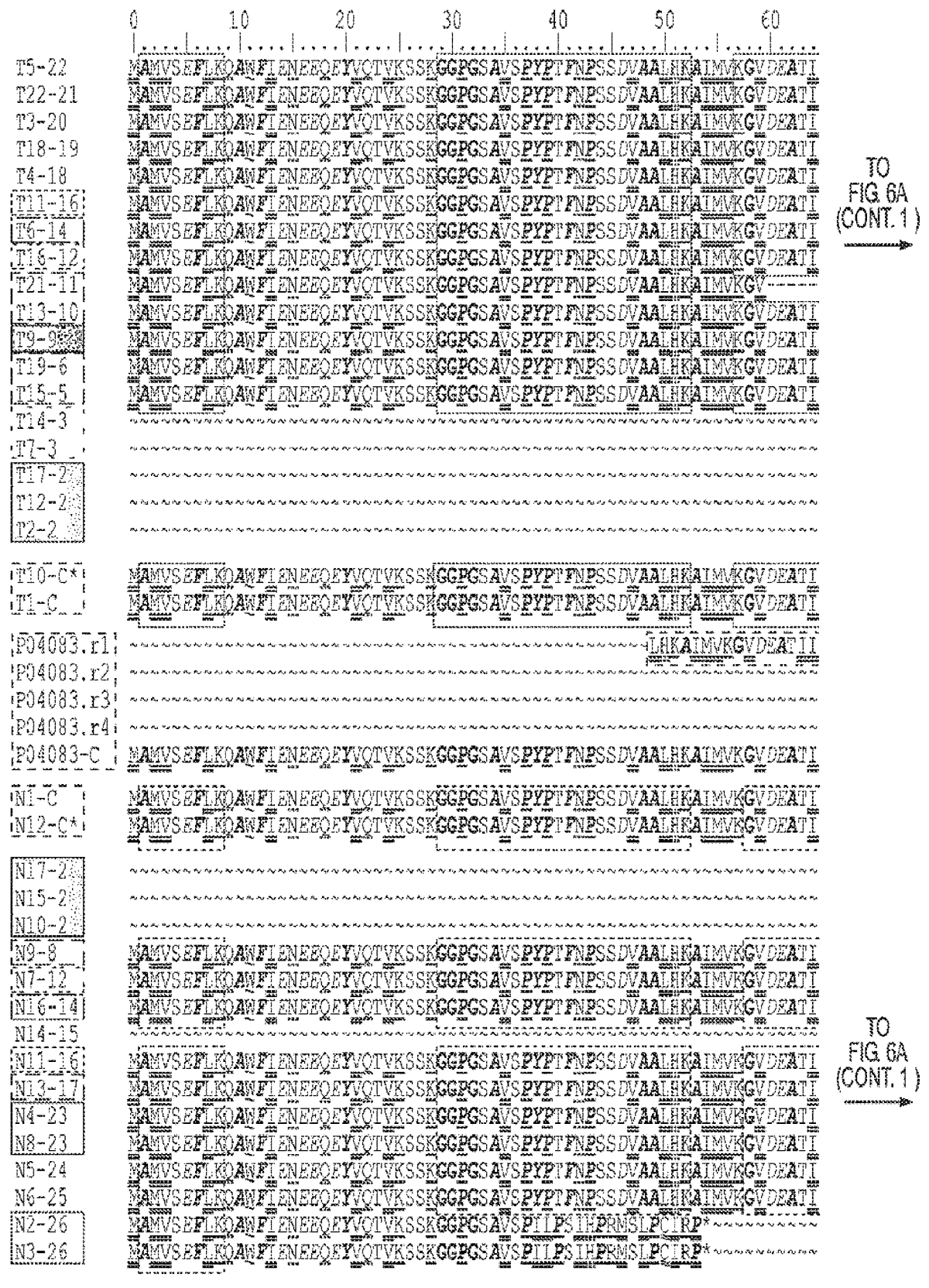
Figure 6A:
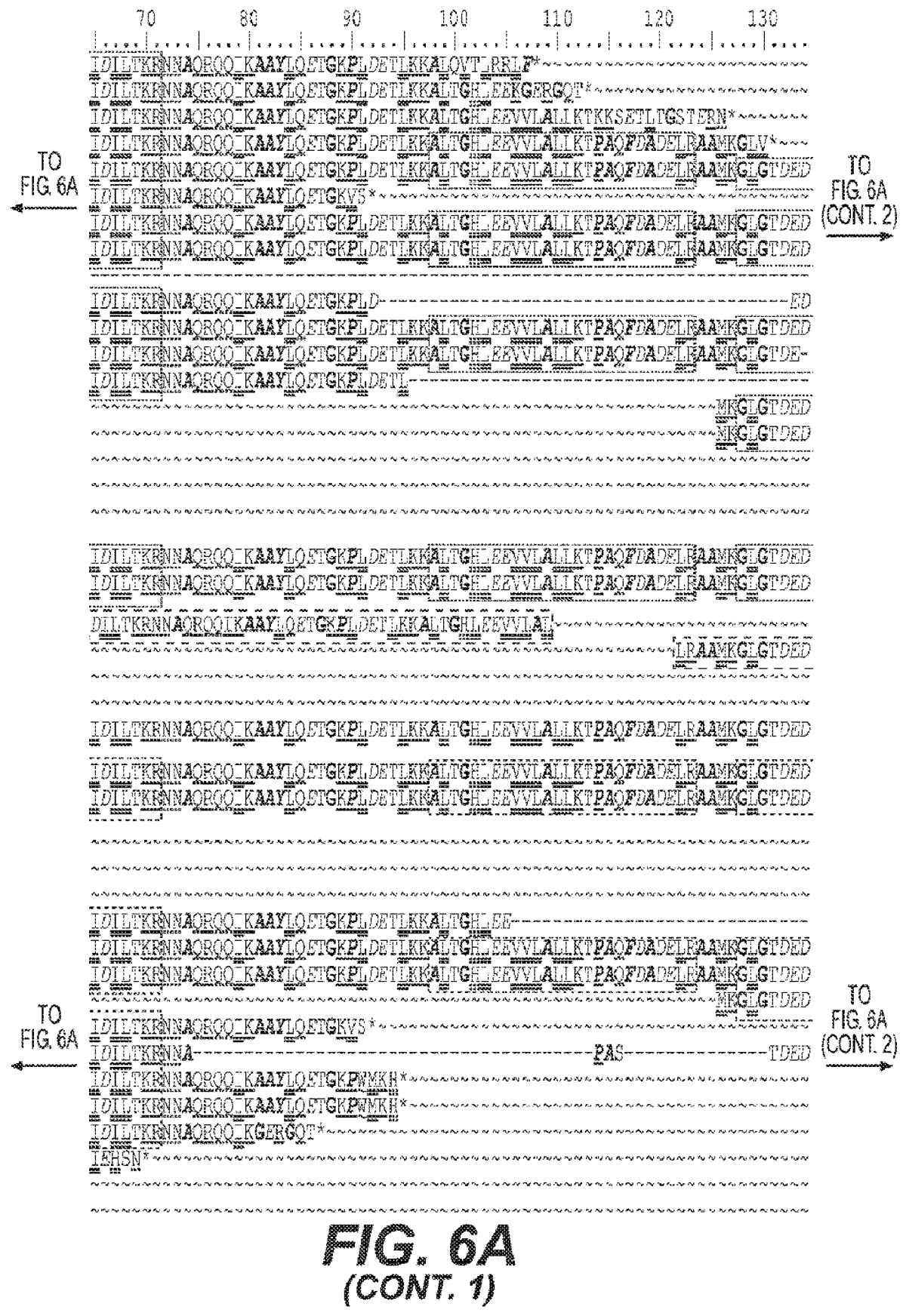
Figure 6A:
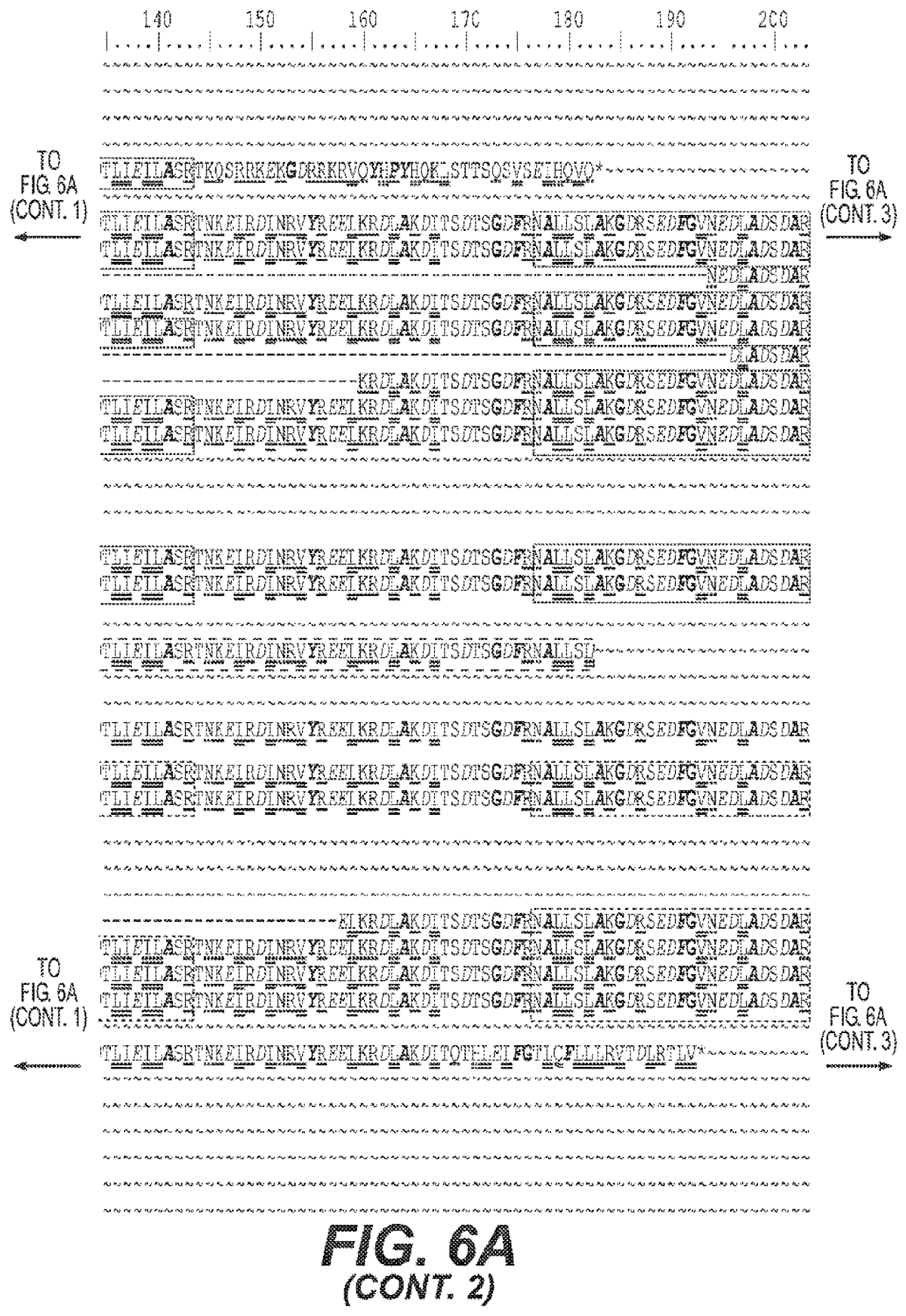
Figure 6A:
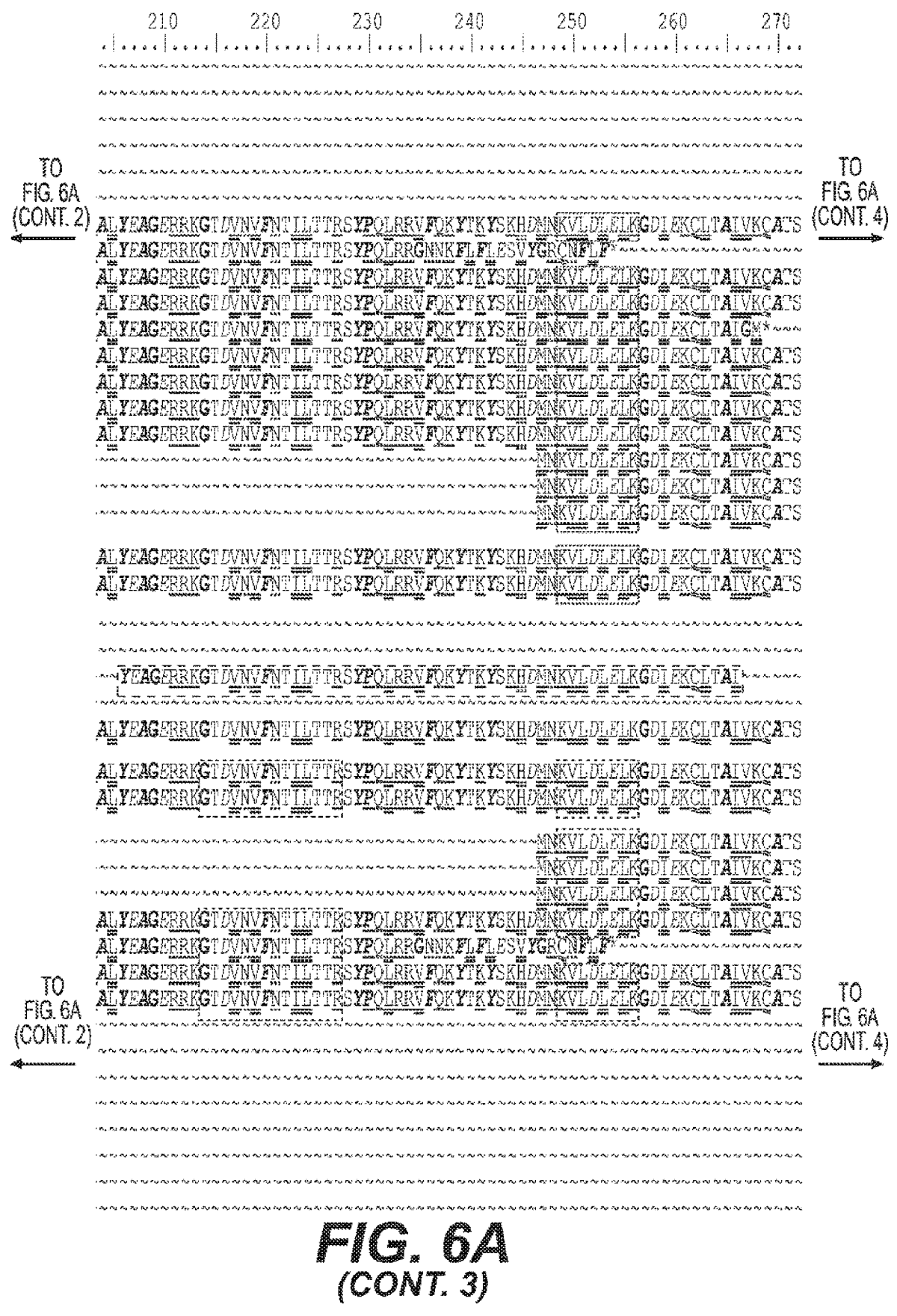
Figure 6A:
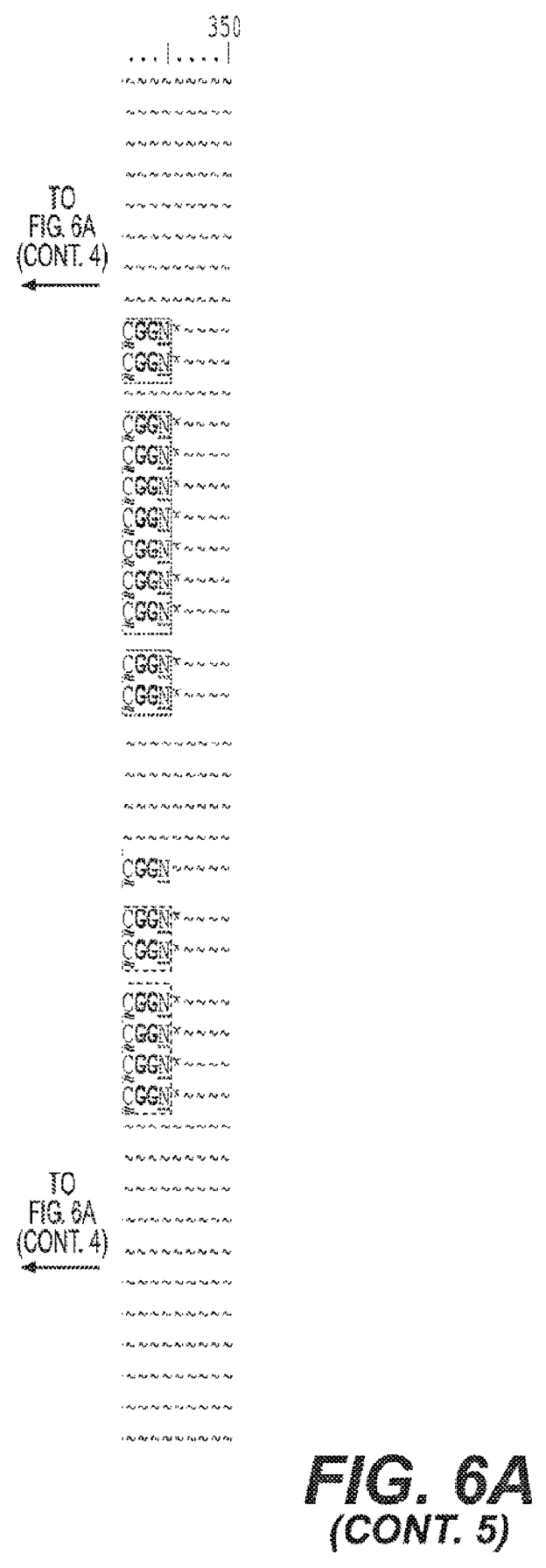
Figures 6B, 6C:
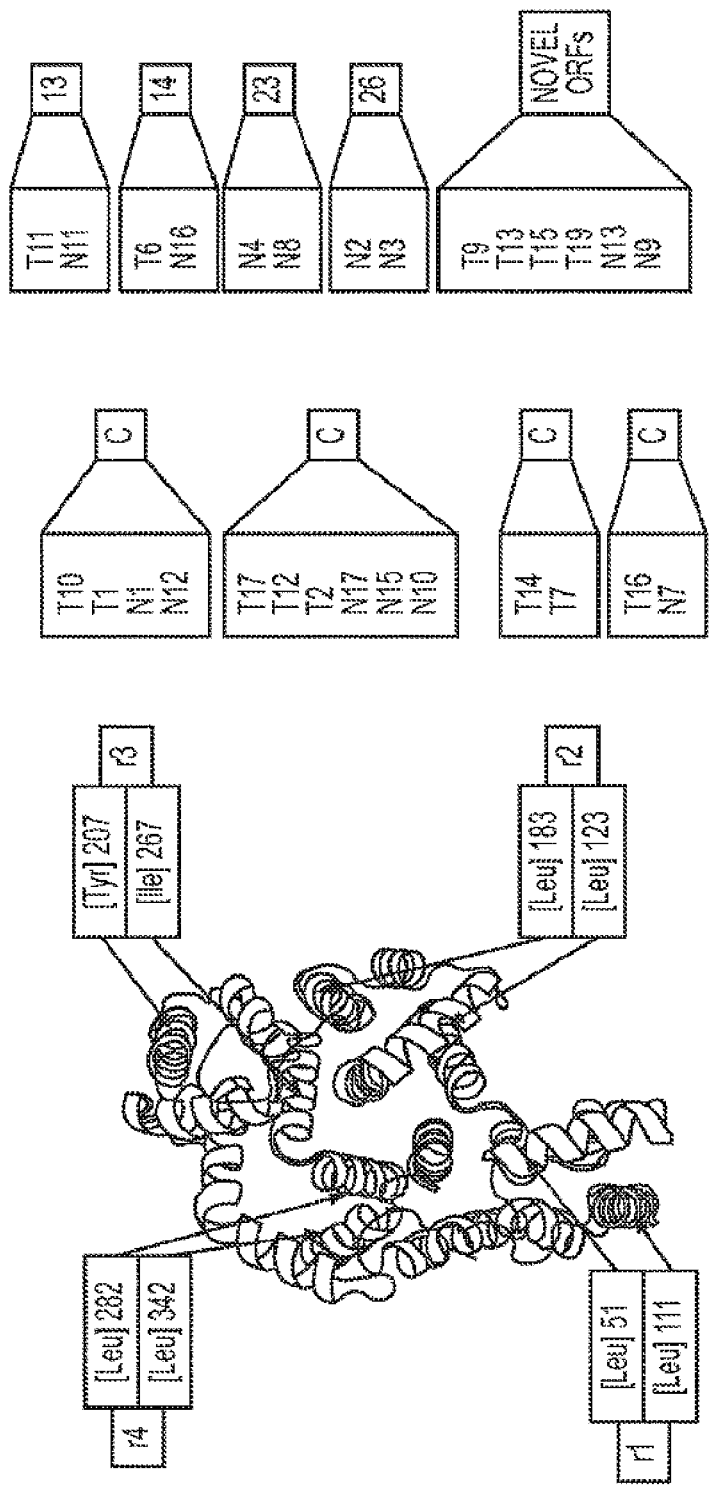
FIG. 6 depicts the amino acid sequence alignment and proteins predicted from the transcript isoforms identified for ANXA1. 6A shows the amino acid sequence alignments including the isoform identifiers. The canonical protein and conserved repeat domains r1-r4 are highlighted. ORFs coding for the same protein are also shown. Note: Solid lines connecting protein fragments indicate contiguous amino acid sequences predicted from the respective transcript isoform. 6A discloses SEQ ID NOS 39-52, 52-53, 53, 53-54, 54-58, 54, 54, 54, 53, 53, 53, 59, 46, 45, 60, 44, 61-62, 62-65, and 65, respectively, in order of appearance. 6B shows the predicted protein structure of the canonical ANXA1 protein P04083 with repeat domains r1 to r4 indicated. 6C shows the common predicted proteins for groups of transcript isoforms, ORFs 2, 3, 12, 13, 14, 23, 26 and the canonical ORF are listed and shown with the respective color from panel 6A. Novel ORFs are indicated.

The canonical ANXA1 protein contains four repeat regions (r1-r4) of approximately 70 amino acids, each with a motif for calcium binding. The sequences are highlighted and the alignment of the predicted ORFs from transcript isoforms in total and lineage-negative bone marrow cells shows the overlaps with the canonical protein and with each other (FIG. 6a, b). Mass spec analysis of the proteins confirmed the presence of peptides in both cell populations (FIG. 6a).

The canonical ANXA1 protein is predicted by 4 different transcript isoforms (T1-C, T10-C*, N1-C and N12-C*). The T10-C* and N12-C* transcripts are structurally different from T1-C and N1-C, each containing a novel exon in the 5' UTR (see FIG. 4c). ORF 2 matches with the r4 repeat and is contained in 7 different transcript isoforms whilst ORF 12, 13 and 14 matched with r1 to r3 repeats. These transcripts were detected in both cell populations. Additionally, ORF 3 (T14, T7), ORF 23 (N4, N8) and ORF 26 (N2,N3) are derived from two different transcript isoforms but typically found in only one of the cell populations (FIG. 6a, c). Finally, five novel exon-skipping proteins are predicted from transcript isoforms in total and lineage-negative cells (T13, T15, T19, N13 and N9). Full length (long rage) RNA-seq therefore shows a complex set of ANXA1 protein isoforms that distinguish bone marrow cell subpopulations.

As described above for ANXA1 and EEF1A1, full length (long-read) RNA-seq of bone marrow cell populations revealed an approximately 10-fold higher number of transcript isoforms than found by conventional short read RNA-seq. To investigate whether this is true for other genes, genes with <6 coding exons (UBC, KLF6, LYZ, SAT1) were evaluated and it was found that conventional short-read RNA-seq only found 1 to 4 isoforms, whereas long-read RNA-seq identified 12 to 36 isoforms. This was similar at loci with >6 coding exons where only 1 to 3 versus 31 to 43 transcript isoforms were identified by the two different RNA-seq approaches (FIG. 5a).

The analysis was extended by arranging genes by mean exon number and identifying the loci with the top five transcript isoform counts in each bin. The number of transcript isoforms identified by short read RNA-seq surprisingly plateaued at four isoforms irrespective of the number of exons in a given gene (FIG. 5b). In contrast, full length RNA-seq showed an increase in transcript isoform number with increasing complexity of genomic loci as indicated by their number of canonical exons (p=0.0014). An increase in sequencing depth for short read RNA-seq from 20 to 100 million reads did not impact this maximum significantly (p>0.05). Thus, the analysis supports the notion that the complexity of the transcriptome is underestimated by short-range RNA-seq irrespective of the complexity of genomic loci evaluated.

Figures 5A, 5B, 5C:
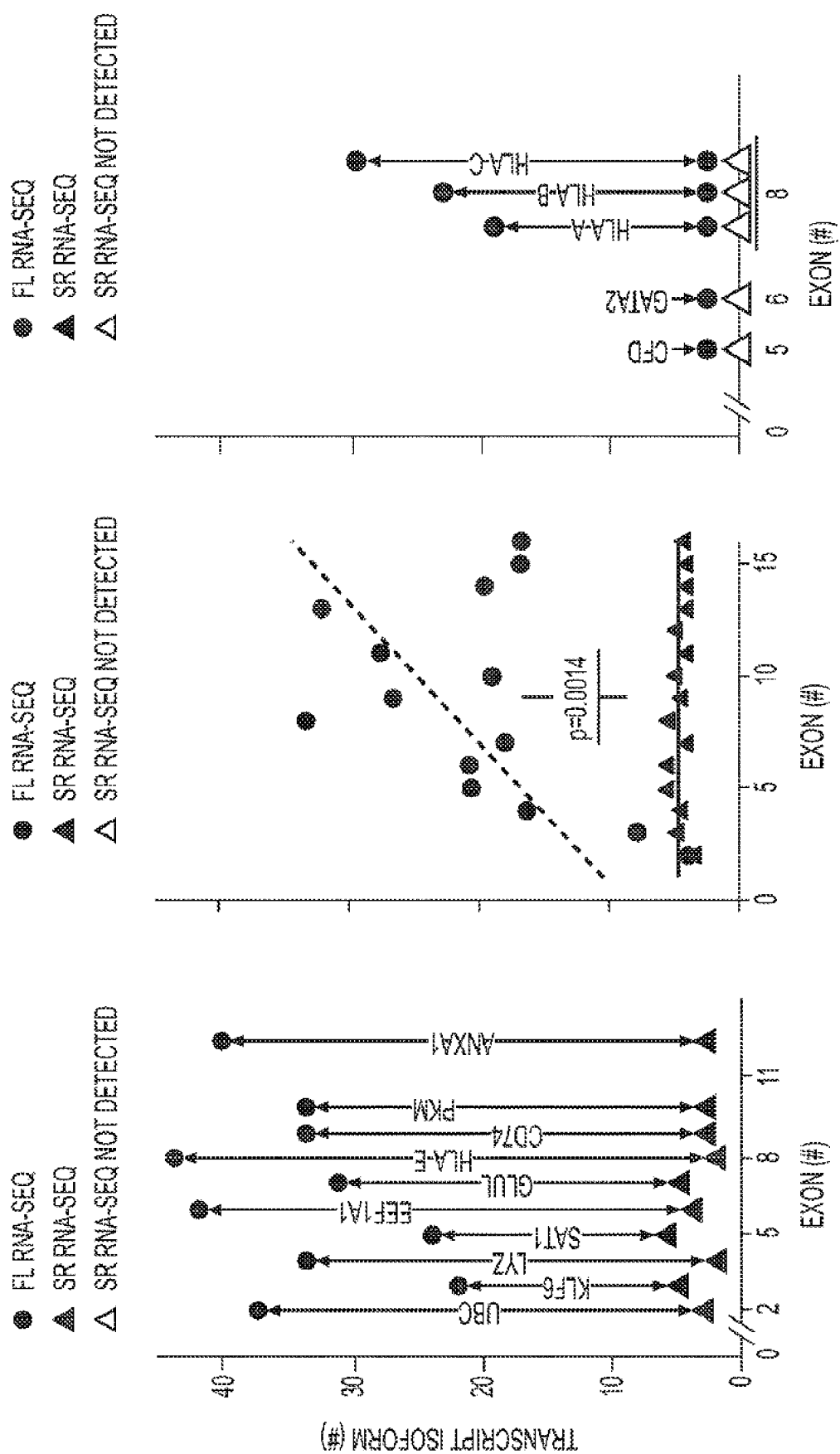
FIG. 5 depicts transcript isoforms from genomic loci of different complexity and redundancies. The number of canonical exons was obtained from the hg19 gene annotation. 5A shows representative genes with 3 to 13 canonical exons and the number of respective transcript isoforms detected. 5B shows the comparison of the mean of the top five transcript isoforms for genes with 2 to 16 exons from the analysis of all bone marrow cell populations (p=0.0014; Chi-sq. for trend short read (SR) RNA-seq vs full length (FL) RNA-seq). 5C shows the transcripts and isoforms identified only by full length (long-read) RNA-seq.
Figure 7:
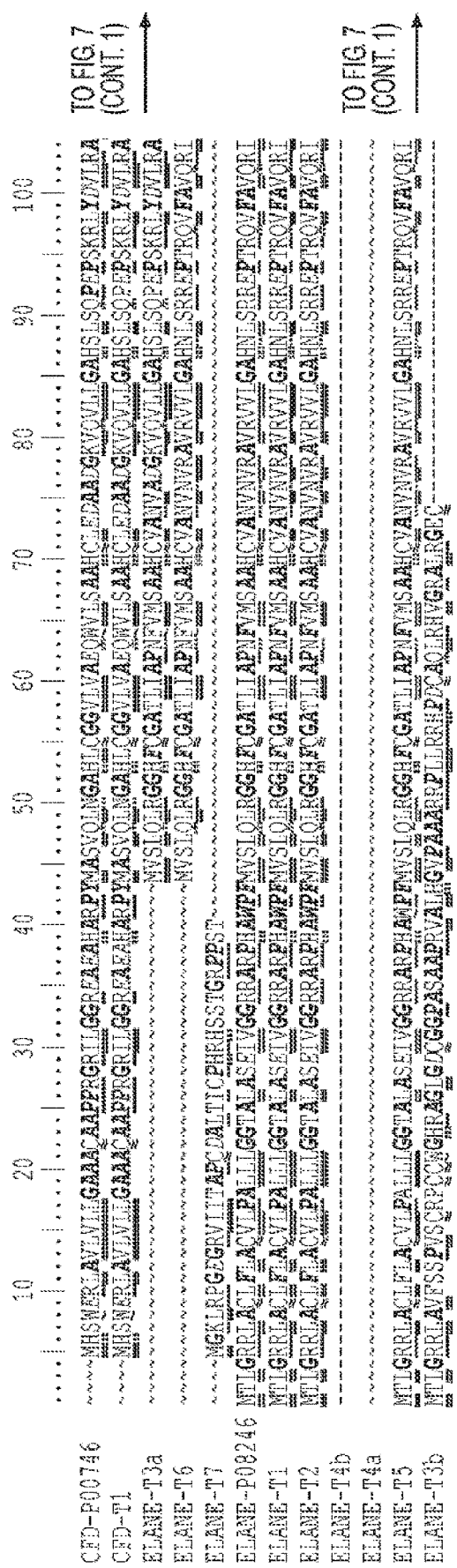
FIG. 7 depicts multiple amino acid sequence alignment predicted from transcript isoforms for ELANE and CFD. The identifiers of the transcript isoforms are included.

Additionally, full length (long-read) RNA-seq identified transcripts for CFD, GATA2, HLA-A, —B and -C that were missed by short read RNA-seq (FIG. 5c). The inability to detect or assign transcripts for these loci with short read RNA-seq may be explained by the paralogous nature of the genes involved: CFD is located on chr 19 with AZU1, PRTN3 and ELANE. These four genes rank second in the list of regions of homozygosity coldspots on human autosomes. Genes located in this run of homozygosity (ROH) region are under evolutionary pressure to remain heterozygous. Additionally, the ELANE and CFD proteins are 78% homologous (FIG. 7; canonical proteins).

Figure 8:
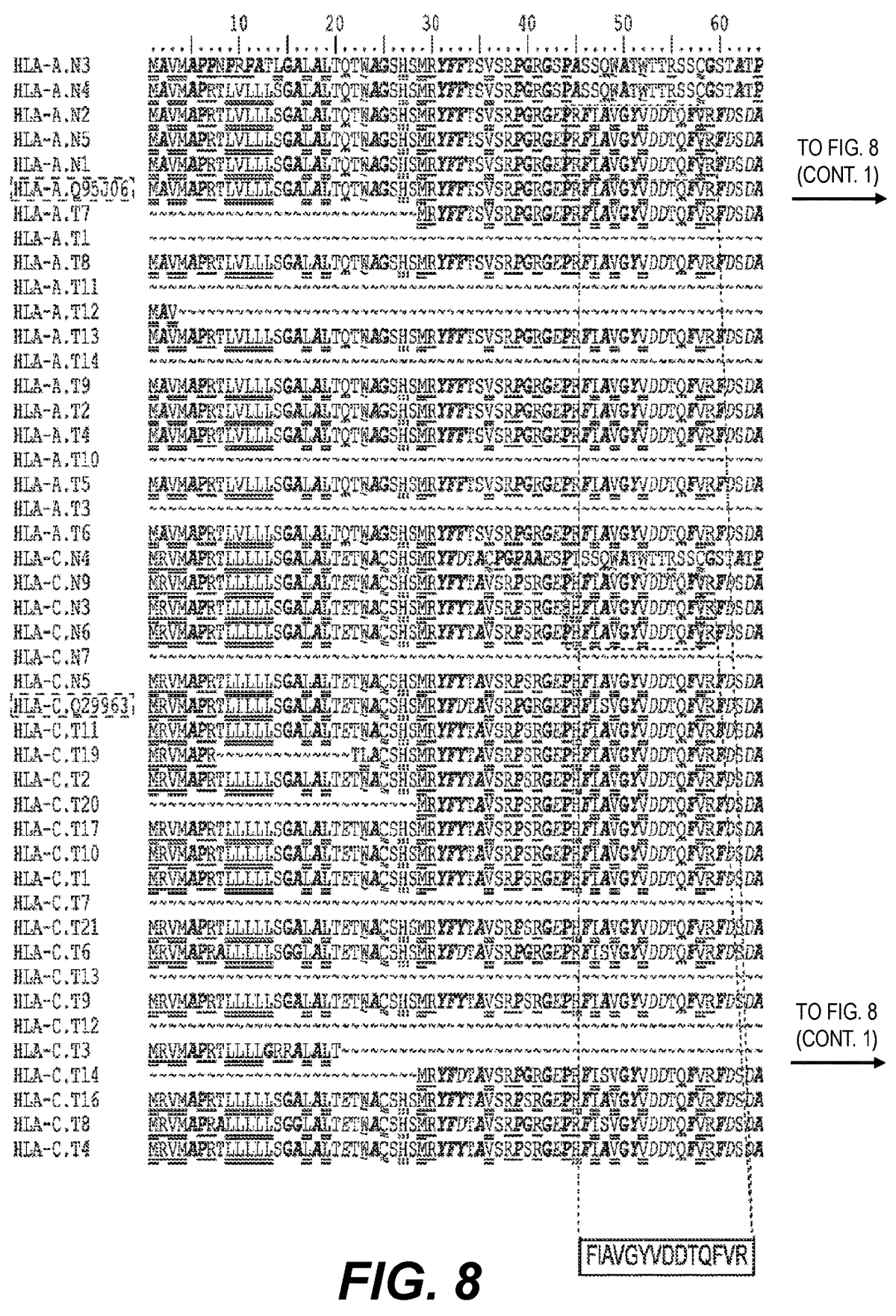
Figure 8:
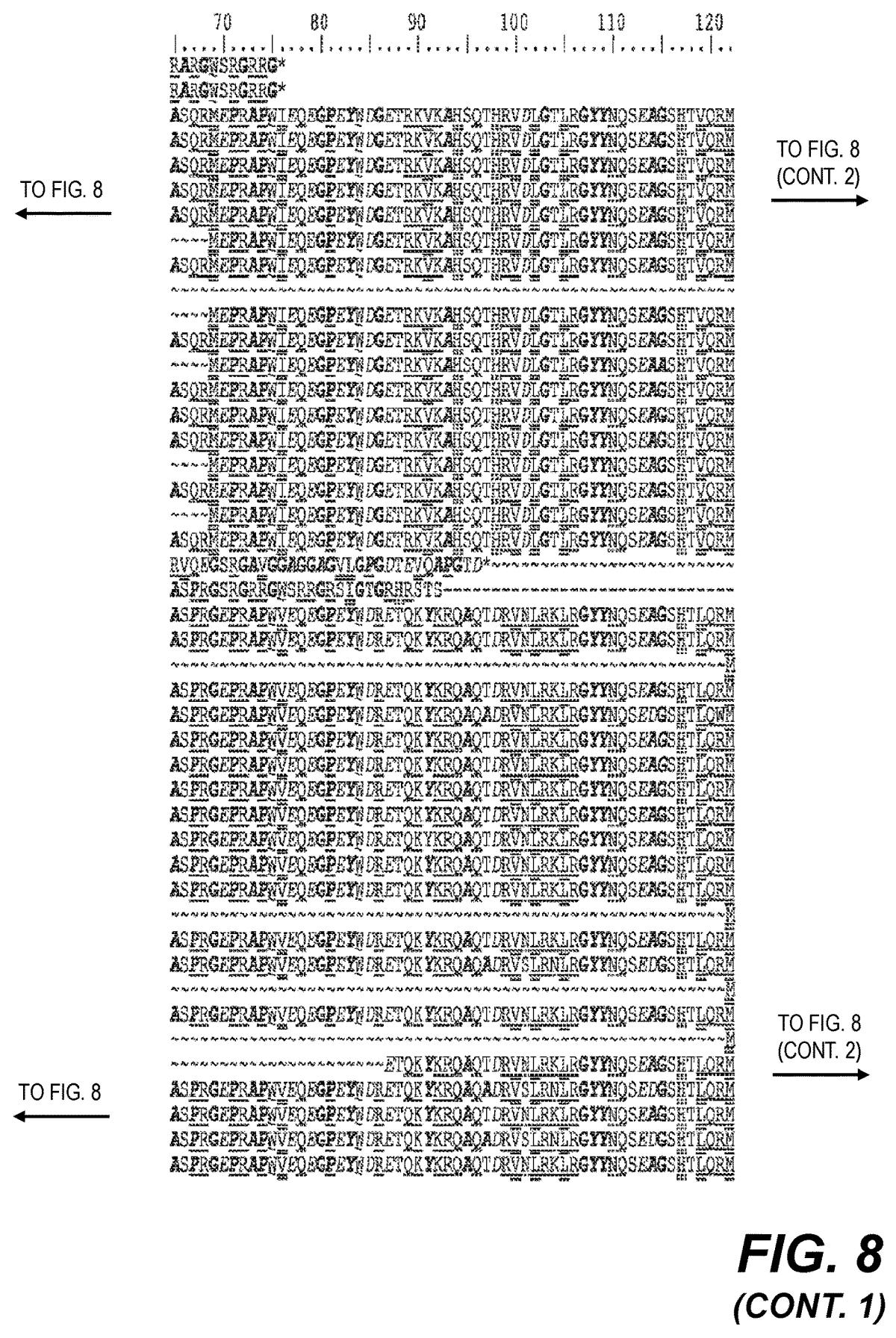
Figure 8:
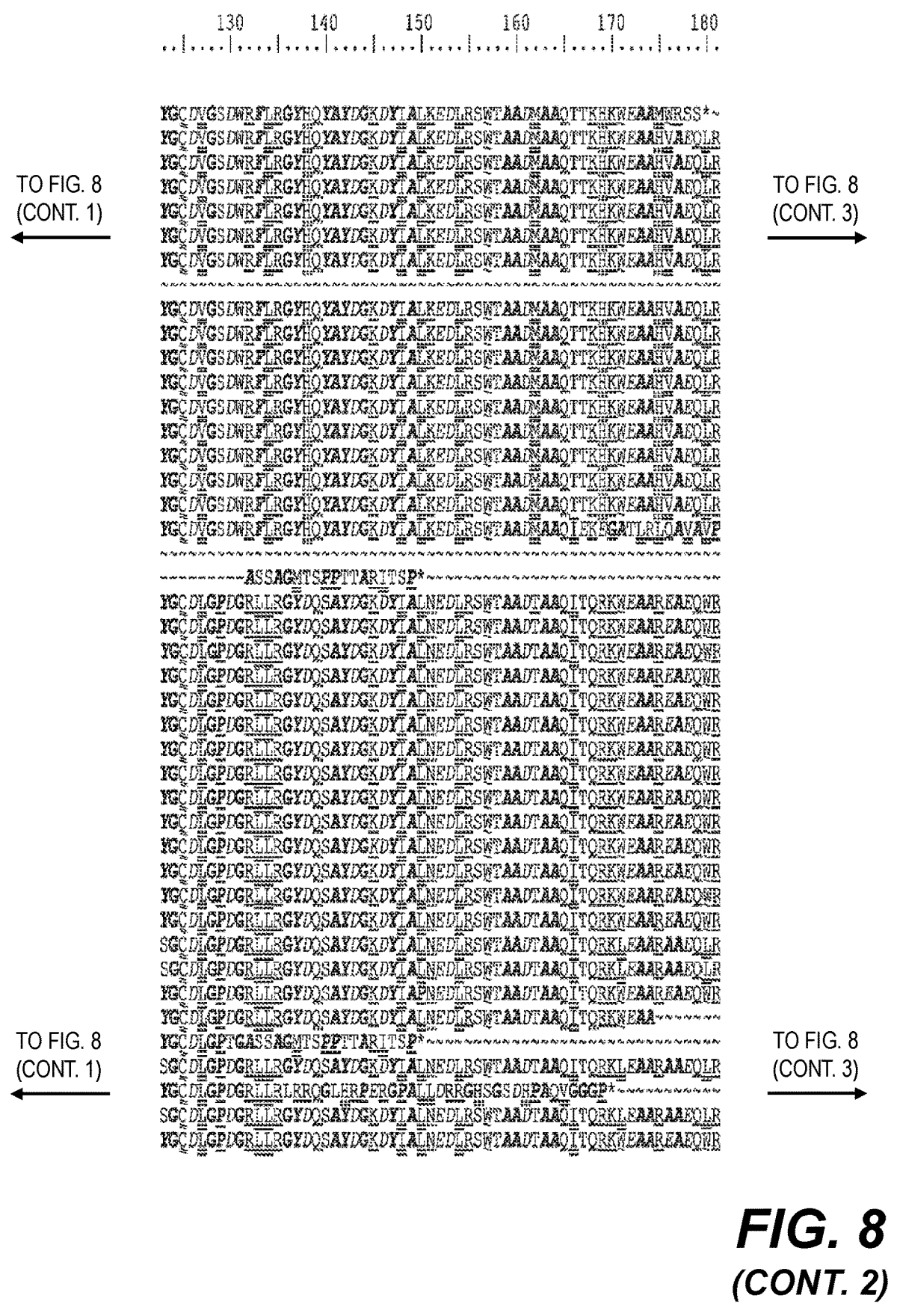
Figure 8:
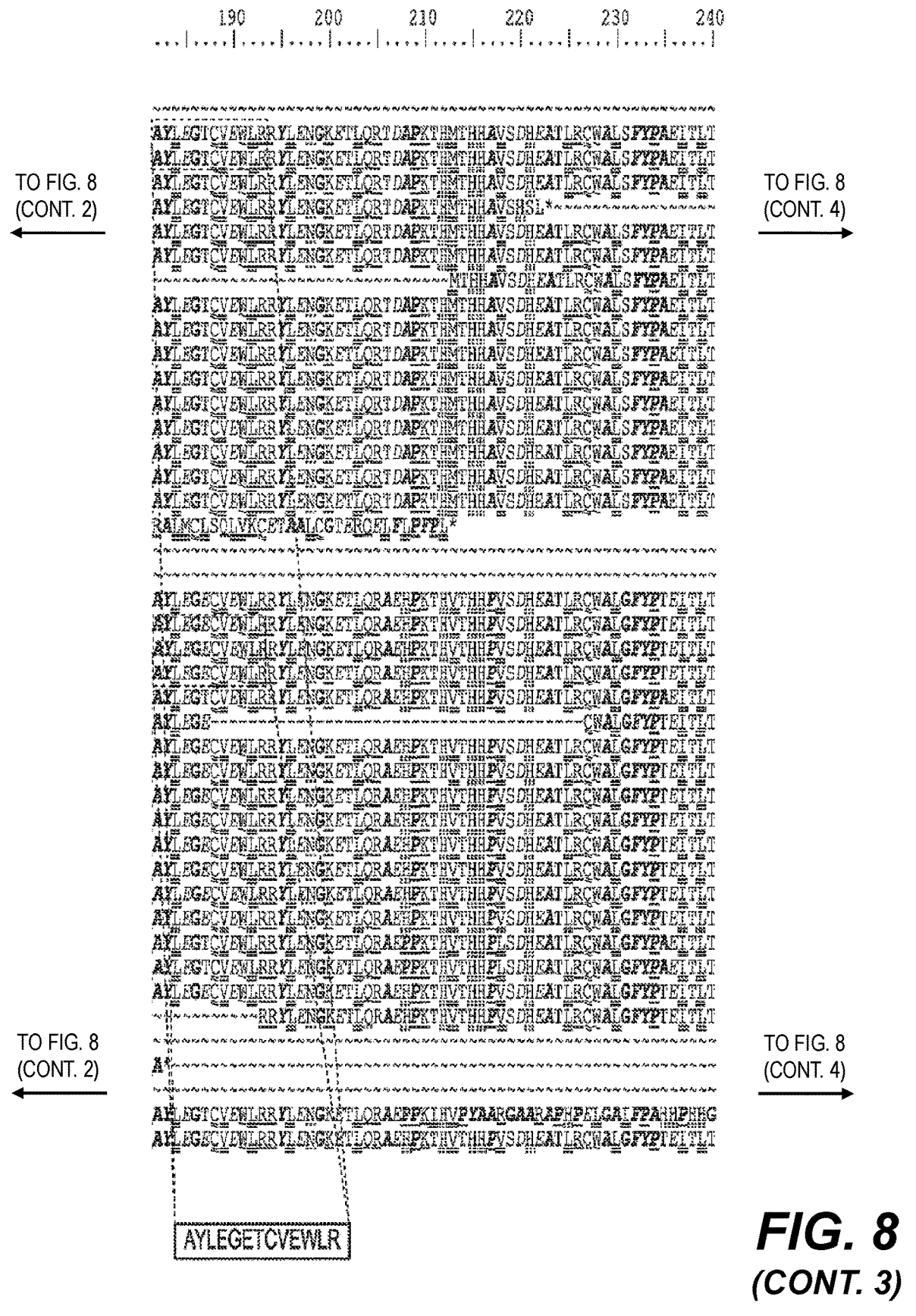
Figure 8:
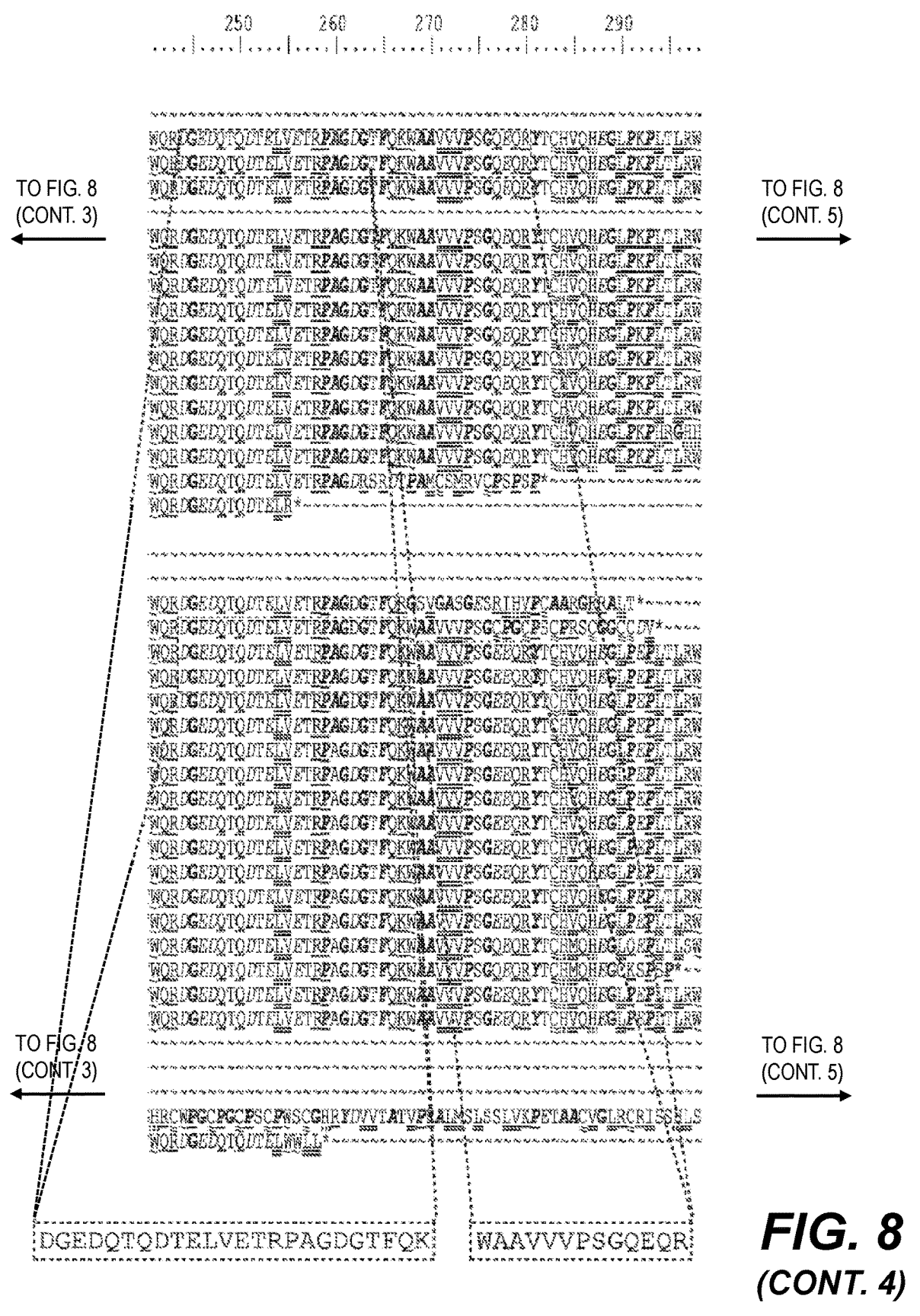

Short read RNA-seq uncovered transcripts from three of these four genes, but missed CFD, which is not surprising, because blastn analysis matched CFD fragment sequences to ELANE. Using full length RNA-seq, unique isoforms were identified for each of the genes in these regions of homozygosity. Similarly, HLA-A, HLA-B, and HLA-C are paralogs with >80% identity that cannot be mapped appropriately and detected by short read RNA-seq (FIGS. 5c and 8). These data suggest that the presence of transcripts from paralogs adds to the complexity of alignments and obfuscates transcript reconstruction from short reads as well as the estimate of transcript abundance.

To assess the biological relevance of the transcript isoforms found and their predicted open reading frames, detectable proteins were identified in the bone marrow cell populations by mass spectrometry. A range of genomic loci that contain between 2 and 16 exons was assessed and associated with the highest number of transcript isoforms. Peptides were confirmed for 52 of the 150 transcripts depicted in FIG. 5b.

As mentioned above, HLA-A, —B and -C transcript isoforms were only detected by full length RNA-seq (FIG. 5c). It is noteworthy that mass spectrometry identified 4 distinct peptides predicted from the HLA-A and HLA-C transcript isoforms that were detected (FIG. 8). This supports the relevance of these transcripts and the ORFs derived from the long-read RNA-sequencing.

For long-read RNA-sequencing, 56% of the transcripts mapped to loci with 4 or more exons and 31% mapped to loci with 8 or more exons. In contrast, short-range RNA sequencing mapped only 13% of transcripts to loci with >4 and 5% with >8 exons. Thus, full length RNA-seq provides a significant (p<0.0001) 4- to 6-fold gain in information. Given that over half of the detected transcripts are from multi-exon genes, the ability to span 2 exons with short reads may be inadequate to resolve a full length transcript successfully without the addition of longer reads. Also, ambiguous mapping of the short reads explains the high number of transcripts being mapped to genes with 1 or 2 exons. The data here also shows that short-read RNA sequencing reaches a maximum of approximately four transcript isoform even for complex loci 8, whereas long-read RNA sequencing shows a significant increase in transcript isoforms with increasing complexity of genomic loci (FIG. 5b).

To validate the sequences of the transcript isoforms described above, unfiltered raw reads from the short-read RNA sequencing were used. This complete set of raw reads was mapped against each of the respective transcript isoforms described above. Short reads with a full 100 base pair coverage were blasted against the individual transcript isoforms obtained from long-read RNA sequencing. Beyond that, long-read RNA sequencing with independent samples was used for additional validation of isoform reads not covered by the short-read RNA sequencing. From these approaches, 83% of the transcript isoforms reported above were confirmed (range 74% to 100%).

What is claimed is:

1. A method for identifying a neopeptide in or on a population of cells that is a marker of abnormal cells, the method comprising
   a) sequencing long-read messenger RNA (mRNA) isolated from a first subset of the population cells,
   b) identifying splice variants generated from the sequenced long-read mRNA,
   c) determining in a second subset of the population of cells presence of neopeptides that are translated from the identified splice variants and determining the presence of the neopeptide in a population of normal cells, wherein a single identified splice variant translates to a single neopeptide,
   wherein, the presence of the neopeptide in the second subset of the population cells and absence of the neopeptide in the normal cells is indicative that the neopeptide is a marker for abnormal cells;
   wherein the neopeptide comprises a novel splice variant; and
   wherein the population of cells is a population of cancer cells, and the population of normal cells is a population of non-cancer cells of the same tissue origin as the population of cells.

2. The method of claim 1, wherein the long-read mRNA is at least 70 nucleotides in length.

3. The method of claim 2, wherein the long-read mRNA is between about 150 nucleotides and 300 nucleotides in length.

4. The method of claim 3, wherein the long-read mRNA is between about 300 nucleotides and 10,000 nucleotides in length.

5. The method of claim 1, wherein the long-read mRNA has not been fragmented prior to sequencing.

6. The method of claim 1, wherein the isolated mRNA is cytosolic mRNA.

7. The method of claim 6, wherein the cytosolic mRNA comprises a poly-A tail.

8. The method of claim 1, wherein determining the presence of the neopeptides comprises mass spectrometry.

9. The method of claim 1, wherein determining the presence of the neopeptides comprises generating antibodies capable of specifically binding the neopeptides and determining if the antibodies bind to the neopeptides.

10. The method of claim 1, further comprising identifying at least one neoantigen on the neopeptide that is present in the second subset of the population of cells.

* * * * *